(12) United States Patent
Evans

(10) Patent No.: US 10,759,806 B2
(45) Date of Patent: Sep. 1, 2020

(54) ISOTOPOLOGUES OF ISOQUINOLINONE AND QUINAZOLINONE COMPOUNDS AND USES THEREOF AS PI3K KINASE INHIBITORS

(71) Applicant: Infinity Pharmaceuticals, Inc., Cambridge, MA (US)

(72) Inventor: Catherine A. Evans, Somerville, MA (US)

(73) Assignee: Infinity Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 16/085,536

(22) PCT Filed: Mar. 16, 2017

(86) PCT No.: PCT/US2017/022705
§ 371 (c)(1),
(2) Date: Sep. 14, 2018

(87) PCT Pub. No.: WO2017/161116
PCT Pub. Date: Sep. 21, 2017

(65) Prior Publication Data
US 2019/0202835 A1 Jul. 4, 2019

Related U.S. Application Data

(60) Provisional application No. 62/309,769, filed on Mar. 17, 2016.

(51) Int. Cl.
*A61K 31/519* (2006.01)
*C07D 487/04* (2006.01)
*A61P 37/00* (2006.01)
*A61P 35/00* (2006.01)

(52) U.S. Cl.
CPC ............ *C07D 487/04* (2013.01); *A61P 35/00* (2018.01); *A61P 37/00* (2018.01)

(58) Field of Classification Search
CPC .......................... A61K 31/519; C07D 487/04
USPC ........................................ 514/259.3; 544/281
See application file for complete search history.

(56) References Cited

U.S. PATENT DOCUMENTS

| | | |
|---|---|---|
| 4,547,508 A | 10/1985 | Konz et al. |
| 4,656,159 A | 4/1987 | McPherson et al. |
| 4,704,381 A | 11/1987 | Schaumann et al. |
| 4,795,627 A | 1/1989 | Fisher et al. |
| 4,981,856 A | 1/1991 | Hughes |
| 5,240,941 A | 8/1993 | Bruneau |
| 5,272,158 A | 12/1993 | Hartman et al. |
| 5,294,612 A | 3/1994 | Bacon et al. |
| 5,310,731 A | 5/1994 | Olsson et al. |
| 5,364,862 A | 11/1994 | Spada et al. |
| 5,409,930 A | 4/1995 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,504,103 A | 4/1996 | Bonjouklian et al. |
| 5,506,347 A | 4/1996 | Erion et al. |
| 5,527,811 A | 6/1996 | Natsugari et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |

(Continued)

FOREIGN PATENT DOCUMENTS

| | | |
|---|---|---|
| CA | 1338379 C | 6/1996 |
| CN | 1502608 | 6/2004 |

(Continued)

OTHER PUBLICATIONS

Kushner, et. al. Canadian Journal of Physiology and Pharmacology, (1999) 77,2, p. 79-88.*
Roger Tung, The Development of Deuterium-Containing Drugs (2010).*
Abdel-Rahman et al., "Synthesis of heterobicyclic quinazolinones derived from N-[2-(2-chloro-phenyl)-1-(6,8-dibromo-4-oxo-4H-benzo[d][1,3]oxazin-2-yl)-vinyl]-benzamide as antimicrobial agents," Egyptian Journal of Chemistry (2006), 49(4), 461-474.
Abdel-Rahman et al., "Synthesis, reactions and antifungal agents of 2-[benzoylamino-2-(naphthyl- and/or 2'-furyl)]vinyl-4-H-3,1-benzoxazin-4-ones derivatives," Egyptian Journal of Chemistry (2006), 49(2), 169-184.

(Continued)

*Primary Examiner* — Jeffrey H Murray
(74) *Attorney, Agent, or Firm* — Jones Day

(57) ABSTRACT

Provided are isotopologues of isoquinolinone and quinazolinone compounds of formula (AB') that modulate PI3 kinase activity, processes for the preparation of the compounds, pharmaceutical compositions comprising the compounds, and methods of treatment of diseases and disorders using the compounds or pharmaceutical compositions.

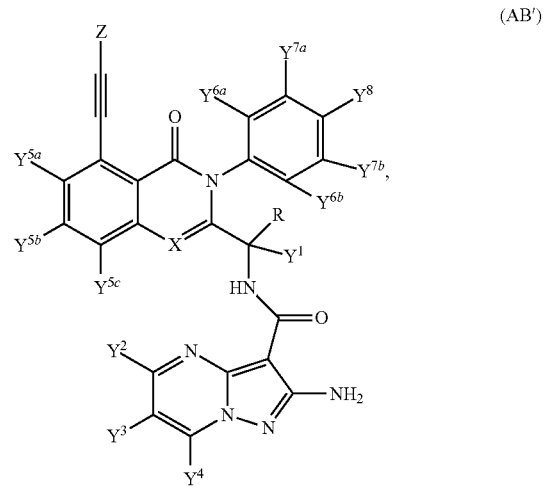

(AB')

22 Claims, No Drawings

(56) References Cited

U.S. PATENT DOCUMENTS

| | | |
|---|---|---|
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,679,677 A | 10/1997 | Pill et al. |
| 5,686,455 A | 11/1997 | Adams et al. |
| 5,736,554 A | 4/1998 | Spada et al. |
| 5,747,235 A | 5/1998 | Farid et al. |
| 5,756,502 A | 5/1998 | Padia |
| 5,756,711 A | 5/1998 | Zilch et al. |
| 5,763,596 A | 6/1998 | Boyer et al. |
| 5,763,597 A | 6/1998 | Ugarkar et al. |
| 5,763,608 A | 6/1998 | Bhattacharya et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,869,665 A | 2/1999 | Padia |
| 5,872,136 A | 2/1999 | Anthony et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,977,134 A | 11/1999 | Ciccarone et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,037,474 A | 3/2000 | Drauz et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,184,377 B1 | 2/2001 | Gao |
| 6,191,170 B1 | 2/2001 | Medina |
| 6,207,697 B1 | 3/2001 | Han et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,429,311 B2 | 8/2002 | Gao |
| 6,455,534 B2 | 9/2002 | Bridges et al. |
| 6,469,026 B2 | 10/2002 | Marlowe et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,004 B1 | 4/2003 | Finer et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,562,831 B1 | 5/2003 | Finer et al. |
| 6,583,161 B1 | 6/2003 | Medina |
| 6,596,497 B1 | 7/2003 | Jiang et al. |
| 6,596,718 B1 | 7/2003 | Flohr et al. |
| 6,596,723 B1 | 7/2003 | Watkins et al. |
| 6,613,798 B1 | 9/2003 | Porter et al. |
| 6,630,479 B1 | 10/2003 | Finer et al. |
| 6,630,495 B1 | 10/2003 | Cooke et al. |
| 6,632,789 B1 | 10/2003 | June |
| 6,645,989 B2 | 11/2003 | Adams et al. |
| 6,649,565 B1 | 11/2003 | Feucht et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,683,108 B1 | 1/2004 | Baxter et al. |
| 6,683,192 B2 | 1/2004 | Baxter et al. |
| 6,689,782 B2 | 2/2004 | Watkins et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,753,428 B2 | 6/2004 | Yao B et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,794,379 B2 | 9/2004 | Medina et al. |
| 6,800,620 B2 | 10/2004 | Sadhu et al. |
| 6,831,085 B1 | 12/2004 | Bergnes et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,870,055 B2 | 3/2005 | Claremon et al. |
| 6,900,219 B2 | 5/2005 | Ibrahim et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 6,964,967 B2 | 11/2005 | Medina et al. |
| 6,995,144 B2 | 2/2006 | Ozaki et al. |
| 7,009,049 B2 | 3/2006 | Bergnes et al. |
| 7,026,461 B1 | 4/2006 | Shokat |
| 7,038,048 B2 | 5/2006 | Dhanak et al. |
| 7,041,676 B2 | 5/2006 | McDonald et al. |
| 7,049,116 B2 | 5/2006 | Shokat |
| 7,049,312 B1 | 5/2006 | Rafferty et al. |
| 7,053,215 B2 | 5/2006 | Medina et al. |
| 7,053,216 B2 | 5/2006 | Sun et al. |
| 7,064,218 B2 | 6/2006 | Dyatkina et al. |
| 7,067,662 B2 | 6/2006 | Medina et al. |
| 7,071,355 B2 | 7/2006 | Leban et al. |
| 7,105,668 B1 | 9/2006 | Bergnes et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,214 B1 | 12/2006 | Janssens et al. |
| 7,157,487 B2 | 1/2007 | Nakayama et al. |
| 7,161,002 B2 | 1/2007 | Bergnes et al. |
| 7,166,293 B2 | 1/2007 | Teng et al. |
| 7,166,595 B2 | 1/2007 | Zhou et al. |
| 7,192,949 B2 | 3/2007 | Fraley et al. |
| 7,208,601 B2 | 4/2007 | Mjalli et al. |
| 7,214,800 B2 | 5/2007 | Feng et al. |
| 7,217,794 B2 | 5/2007 | Abdel-Meguid et al. |
| 7,230,000 B1 | 6/2007 | Finer et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,187 B2 | 8/2007 | Fraley et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,294,634 B2 | 11/2007 | Finer et al. |
| 7,329,765 B2 | 2/2008 | Burli et al. |
| 7,332,497 B2 | 2/2008 | Hirst et al. |
| 7,332,498 B2 | 2/2008 | Dhanak et al. |
| 7,345,046 B2 | 3/2008 | Wang et al. |
| 7,348,427 B2 | 3/2008 | Burli et al. |
| 7,365,094 B2 | 4/2008 | Leban et al. |
| 7,384,967 B2 | 6/2008 | Polisetti et al. |

(56) References Cited

U.S. PATENT DOCUMENTS

| | | |
|---|---|---|
| 7,396,836 B2 | 7/2008 | Harada et al. |
| 7,405,235 B2 | 7/2008 | Levy et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,528,137 B2 | 5/2009 | Feng et al. |
| 7,534,797 B2 | 5/2009 | Arnold et al. |
| 7,538,135 B2 | 5/2009 | Vedananda |
| 7,541,373 B2 | 6/2009 | Polisetti et al. |
| 7,550,590 B2 | 6/2009 | Feng et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,589,098 B2 | 9/2009 | Finer et al. |
| 7,608,594 B2 | 10/2009 | Blagg et al. |
| 7,615,552 B2 | 11/2009 | Ono et al. |
| 7,615,554 B2 | 11/2009 | Selliah et al. |
| 7,622,451 B2 | 11/2009 | Blagg et al. |
| 7,632,839 B2 | 12/2009 | Coleman et al. |
| 7,650,848 B2 | 1/2010 | Brennan et al. |
| 7,652,061 B2 | 1/2010 | Ksander et al. |
| 7,671,200 B2 | 3/2010 | Finer et al. |
| 7,678,803 B2 | 3/2010 | Huang et al. |
| 7,700,607 B2 | 4/2010 | Hu et al. |
| 7,705,018 B2 | 4/2010 | Chen et al. |
| 7,745,485 B2 | 6/2010 | Durden |
| 7,763,628 B2 | 7/2010 | Finer et al. |
| 7,799,795 B2 | 9/2010 | Bergeron et al. |
| 7,893,260 B2 | 2/2011 | Chong et al. |
| 7,932,260 B2 | 4/2011 | Fowler et al. |
| 7,939,538 B2 | 5/2011 | Fu et al. |
| 7,939,539 B2 | 5/2011 | Wang et al. |
| 8,013,003 B2 | 9/2011 | Sreet et al. |
| 8,030,318 B2 | 10/2011 | Simmen et al. |
| 8,106,146 B2 | 1/2012 | Benz et al. |
| 8,133,998 B2 | 3/2012 | Pajouhesh et al. |
| 8,193,182 B2 | 6/2012 | Ren et al. |
| 8,232,285 B2 | 7/2012 | Liu et al. |
| 8,236,808 B2 | 8/2012 | Collingwood et al. |
| 8,247,436 B2 | 8/2012 | Baettig et al. |
| 8,389,544 B2 | 3/2013 | Wong et al. |
| 8,399,483 B2 | 3/2013 | Allen et al. |
| 8,399,493 B2 | 3/2013 | Bolea et al. |
| 8,569,316 B2 | 10/2013 | Ettmayer et al. |
| 8,569,323 B2 | 10/2013 | Ren et al. |
| 8,586,619 B2 | 11/2013 | Wu et al. |
| 8,604,032 B2 | 12/2013 | Ren et al. |
| 8,637,666 B2 | 1/2014 | Charrier et al. |
| 8,642,609 B2 | 2/2014 | Makings et al. |
| 8,648,084 B2 | 2/2014 | Bunnelle et al. |
| 8,703,777 B2 | 4/2014 | Ren et al. |
| 8,716,297 B2 | 5/2014 | Woods et al. |
| 8,748,440 B2 | 6/2014 | Martin et al. |
| 8,785,470 B2 | 7/2014 | Castro et al. |
| 8,809,349 B2 | 8/2014 | Ren et al. |
| 8,809,530 B1 | 8/2014 | Wu et al. |
| 8,822,453 B2 | 9/2014 | Matsumura et al. |
| 8,901,133 B2 | 12/2014 | Ren et al. |
| 8,940,742 B2 | 1/2015 | Castro et al. |
| 8,969,363 B2 | 3/2015 | Castro et al. |
| 9,056,877 B2 | 6/2015 | Castro et al. |
| 9,115,141 B2 | 8/2015 | Castro et al. |
| 9,255,108 B2 | 2/2016 | Castro et al. |
| 9,359,365 B2 | 6/2016 | Castro et al. |
| 9,388,183 B2 | 7/2016 | Ren et al. |
| 10,329,299 B2 * | 6/2019 | Castro .................. C07D 403/12 |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0198236 A1 | 12/2002 | Baxter et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0144350 A1 | 7/2003 | Stevenson et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0220338 A1 | 11/2003 | Watkins et al. |
| 2003/0229097 A1 | 12/2003 | Watkins et al. |
| 2003/0232832 A1 | 12/2003 | Lombardo et al. |
| 2003/0232849 A1 | 12/2003 | Noe et al. |
| 2003/0235822 A1 | 12/2003 | Lokhov et al. |
| 2004/0023996 A1 | 2/2004 | Finer et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0082567 A1 | 4/2004 | McDonald et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0132732 A1 | 7/2004 | Han et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0242596 A1 | 12/2004 | Kim et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0065169 A1 | 3/2005 | Wang et al. |
| 2005/0070578 A1 | 3/2005 | Baxter et al. |
| 2005/0080138 A1 | 4/2005 | Guicherit et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0152940 A1 | 7/2005 | Hezi-Yamit et al. |
| 2005/0153997 A1 | 7/2005 | Simon et al. |
| 2005/0171148 A1 | 8/2005 | Mjalli et al. |
| 2005/0178286 A1 | 8/2005 | Brennan et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0203110 A1 | 9/2005 | Coleman et al. |
| 2005/0209254 A1 | 9/2005 | Wang et al. |

(56) References Cited

U.S. PATENT DOCUMENTS

| | | |
|---|---|---|
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282834 A1 | 12/2005 | Malik et al. |
| 2006/0019988 A1 | 1/2006 | McDonald et al. |
| 2006/0036093 A1 | 2/2006 | Lin et al. |
| 2006/0041128 A1 | 2/2006 | Aquila et al. |
| 2006/0063751 A1 | 3/2006 | Aquila et al. |
| 2006/0069034 A1 | 3/2006 | Burli et al. |
| 2006/0069106 A1 | 3/2006 | Fu et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0270849 A1 | 11/2006 | Nishino et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0021493 A1 | 1/2007 | Guicherit et al. |
| 2007/0027193 A1 | 2/2007 | Leban et al. |
| 2007/0032640 A1 | 2/2007 | Varghese et al. |
| 2007/0049593 A1 | 3/2007 | Oka et al. |
| 2007/0054915 A1 | 3/2007 | Arora et al. |
| 2007/0066632 A1 | 3/2007 | Hart et al. |
| 2007/0072897 A1 | 3/2007 | Mahaney et al. |
| 2007/0099871 A1 | 5/2007 | Davis et al. |
| 2007/0135454 A1 | 6/2007 | Hollingworth et al. |
| 2007/0142405 A1 | 6/2007 | Dong et al. |
| 2007/0155730 A1 | 7/2007 | Leit et al. |
| 2007/0161644 A1 | 7/2007 | Stockwell |
| 2007/0179151 A1 | 8/2007 | Chen et al. |
| 2007/0207996 A1 | 9/2007 | Auger et al. |
| 2007/0224672 A1 | 9/2007 | Leban et al. |
| 2007/0244133 A1 | 10/2007 | Bower et al. |
| 2007/0249598 A1 | 10/2007 | Wang et al. |
| 2007/0249680 A1 | 10/2007 | Illig et al. |
| 2007/0265231 A1 | 11/2007 | Hofmann et al. |
| 2007/0270452 A1 | 11/2007 | Blagg et al. |
| 2008/0004253 A1 | 1/2008 | Branstetter et al. |
| 2008/0032960 A1 | 2/2008 | Knight et al. |
| 2008/0058521 A1 | 3/2008 | Krishnan et al. |
| 2008/0070864 A1 | 3/2008 | Martin et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0234299 A1 | 9/2008 | Buchstaller et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0030036 A1 | 1/2009 | Dalton et al. |
| 2009/0053192 A1 | 2/2009 | Millan et al. |
| 2009/0088452 A1 | 4/2009 | Coleman et al. |
| 2009/0099210 A1 | 4/2009 | Aquila et al. |
| 2009/0099214 A1 | 4/2009 | Fairhurst et al. |
| 2009/0105233 A1 | 4/2009 | Chua et al. |
| 2009/0118261 A1 | 5/2009 | Aquila et al. |
| 2009/0118283 A1 | 5/2009 | Defert et al. |
| 2009/0124638 A1 | 5/2009 | Shokat et al. |
| 2009/0124641 A1 | 5/2009 | Coleman et al. |
| 2009/0124654 A1 | 5/2009 | Mjalli et al. |
| 2009/0130097 A1 | 5/2009 | Liu et al. |
| 2009/0137581 A1 | 5/2009 | Chen et al. |
| 2009/0149484 A1 | 6/2009 | Aquila et al. |
| 2009/0163481 A1 | 6/2009 | Murphy et al. |
| 2009/0163525 A1 | 6/2009 | Aquila et al. |
| 2009/0163545 A1 | 6/2009 | Goldfarb |
| 2009/0163709 A1 | 6/2009 | Blagg |
| 2009/0170834 A1 | 7/2009 | Venkat et al. |
| 2009/0170849 A1 | 7/2009 | Aquila et al. |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0214465 A1 | 8/2009 | Becklin et al. |
| 2009/0221488 A1 | 9/2009 | Wood et al. |
| 2009/0232768 A1 | 9/2009 | Birkus et al. |
| 2009/0233907 A1 | 9/2009 | Austin et al. |
| 2009/0233947 A1 | 9/2009 | Bayliss et al. |
| 2009/0247513 A1 | 10/2009 | Burli et al. |
| 2009/0247567 A1 | 10/2009 | Do et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0280153 A1 | 11/2009 | Hunter et al. |
| 2009/0291442 A1 | 11/2009 | Hegde et al. |
| 2009/0298856 A1 | 12/2009 | Brown et al. |
| 2009/0306069 A1 | 12/2009 | Rueckle et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0099871 A1 | 4/2010 | Miller et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0189685 A1 | 7/2010 | Byrd et al. |
| 2010/0190749 A1 | 7/2010 | Ren et al. |
| 2010/0226943 A1 | 9/2010 | Brennan et al. |
| 2010/0249030 A1 | 9/2010 | Basso-Porcaro |
| 2010/0280010 A1 | 11/2010 | Gudmundsson et al. |
| 2010/0292188 A1 | 11/2010 | Denonne et al. |
| 2010/0310503 A1 | 12/2010 | Li et al. |
| 2010/0323973 A1 | 12/2010 | Leamon et al. |
| 2011/0014186 A1 | 1/2011 | Ehrhardt et al. |
| 2011/0046165 A1 | 2/2011 | Ren et al. |
| 2011/0059953 A1 | 3/2011 | Fersht et al. |
| 2011/0071148 A1 | 3/2011 | Ding et al. |
| 2011/0123486 A1 | 5/2011 | Robbins et al. |
| 2011/0124641 A1 | 5/2011 | Ren et al. |
| 2011/0144134 A1 | 6/2011 | Shokat et al. |
| 2011/0152242 A1 | 6/2011 | Bayliss et al. |
| 2011/0172228 A1 | 7/2011 | Ren et al. |
| 2011/0217300 A1 | 9/2011 | Liu et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2011/0313156 A1 | 12/2011 | Engelhardt et al. |
| 2012/0041683 A1 | 2/2012 | Vaske et al. |
| 2012/0059000 A1 | 3/2012 | Ren et al. |
| 2012/0065154 A1 | 3/2012 | Tanaka et al. |
| 2012/0065205 A1 | 3/2012 | Mercer et al. |
| 2012/0094997 A1 | 4/2012 | England et al. |
| 2012/0122838 A1 | 5/2012 | Ren et al. |

(56) References Cited

U.S. PATENT DOCUMENTS

| | | |
|---|---|---|
| 2012/0149701 A1 | 6/2012 | Ren et al. |
| 2012/0157306 A1 | 6/2012 | Frankenpohl et al. |
| 2012/0184568 A1 | 7/2012 | Ren et al. |
| 2012/0202784 A1 | 8/2012 | Aronov et al. |
| 2012/0220575 A1 | 8/2012 | Chang et al. |
| 2012/0225866 A1 | 9/2012 | Oshima et al. |
| 2012/0245136 A1 | 9/2012 | Hadida-Ruah et al. |
| 2012/0245166 A1 | 9/2012 | Grimaldi et al. |
| 2012/0245169 A1 | 9/2012 | Ren et al. |
| 2012/0270863 A1 | 10/2012 | Williams et al. |
| 2012/0289493 A1 | 11/2012 | Corkey et al. |
| 2012/0329776 A1 | 12/2012 | Ren et al. |
| 2013/0005802 A1 | 1/2013 | Chen et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2013/0116277 A1 | 5/2013 | Dalton et al. |
| 2013/0190308 A1 | 7/2013 | Jain et al. |
| 2013/0267521 A1 | 10/2013 | Castro et al. |
| 2013/0267542 A1 | 10/2013 | Chern et al. |
| 2013/0289033 A1 | 10/2013 | Griffioen et al. |
| 2013/0344061 A1 | 12/2013 | Palombella et al. |
| 2013/0345216 A1 | 12/2013 | Ren et al. |
| 2014/0045825 A1 | 2/2014 | Leahy |
| 2014/0088099 A1 | 3/2014 | Ren et al. |
| 2014/0100214 A1 | 4/2014 | Castro et al. |
| 2014/0120060 A1 | 5/2014 | Palombella et al. |
| 2014/0120083 A1 | 5/2014 | Stern et al. |
| 2014/0155387 A1 | 6/2014 | No et al. |
| 2014/0194417 A1 | 7/2014 | Greenwood et al. |
| 2014/0227321 A1 | 8/2014 | Iadonato et al. |
| 2014/0249145 A1 | 9/2014 | Marugan et al. |
| 2015/0225410 A1 | 8/2015 | Castro et al. |
| 2015/0290207 A1 | 10/2015 | Kutok et al. |
| 2016/0122365 A1 | 5/2016 | Castro et al. |

FOREIGN PATENT DOCUMENTS

| | | |
|---|---|---|
| CN | 101602768 A | 12/2009 |
| DE | 2139107 A1 | 2/1973 |
| DE | 19940859 | 3/2001 |
| DE | 102010013716 | 10/2011 |
| EP | 773023 A1 | 5/1997 |
| EP | 1020445 B1 | 8/2008 |
| EP | 2070932 | 6/2009 |
| GB | 812366 A | 4/1959 |
| GB | 937725 A | 9/1963 |
| GB | 2373186 | 9/2002 |
| JP | 61-109797 A | 5/1986 |
| JP | H05239036 | 9/1993 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2001250689 | 9/2001 |
| JP | 2002131859 A | 5/2002 |
| JP | 2003073357 A | 3/2003 |
| JP | 2004161716 A | 6/2004 |
| JP | 2005035933 | 2/2005 |
| JP | 2006265107 | 10/2006 |
| JP | 2012184225 | 9/2012 |
| JP | 5569437 | 10/2012 |
| WO | WO 1983/001446 A1 | 4/1983 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/040706 A1 | 12/1996 |
| WO | WO 1997/010221 | 3/1997 |
| WO | WO 1997/028133 A1 | 8/1997 |
| WO | WO 1997/028161 A1 | 8/1997 |
| WO | WO 1997/036901 | 10/1997 |
| WO | WO 1998/002162 | 1/1998 |
| WO | WO 1998/041525 A1 | 9/1998 |
| WO | WO 1998/052611 A1 | 11/1998 |
| WO | WO 1998/057952 A1 | 12/1998 |
| WO | WO 1999/024416 | 5/1999 |
| WO | WO 2000/017202 A1 | 3/2000 |
| WO | WO 2001/002369 A2 | 1/2001 |
| WO | WO 2001/016114 A2 | 3/2001 |
| WO | WO 2001/019829 A2 | 3/2001 |
| WO | WO 2001/025238 A2 | 4/2001 |
| WO | WO 2001/031063 A1 | 5/2001 |
| WO | WO 2001/038584 A2 | 5/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/019829 A3 | 9/2001 |
| WO | WO 2001/025238 A3 | 10/2001 |
| WO | WO 2001/038584 A3 | 10/2001 |
| WO | WO 2001/081346 A2 | 11/2001 |
| WO | WO 2001/098278 | 12/2001 |
| WO | WO 2002/006192 A1 | 1/2002 |
| WO | WO 2001/081346 A3 | 3/2002 |
| WO | WO 2002/024655 A1 | 3/2002 |
| WO | WO 2001/002369 A3 | 4/2002 |
| WO | WO 2002/030944 A2 | 4/2002 |
| WO | WO 2002/050091 | 6/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/083884 | 10/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/016275 A1 | 2/2003 |
| WO | WO 2003/020279 | 3/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/045385 | 6/2003 |
| WO | WO 2003/059884 A1 | 7/2003 |
| WO | WO 2003/076418 | 9/2003 |
| WO | WO 2003/020880 A3 | 10/2003 |
| WO | WO 2003/082341 A1 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 2003/000187 A3 | 8/2004 |
| WO | WO 2004/069145 | 8/2004 |
| WO | WO 2004/087053 A2 | 10/2004 |
| WO | WO 2004/092123 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |

(56) References Cited

FOREIGN PATENT DOCUMENTS

| | | |
|---|---|---|
| WO | WO 2005/044181 A2 | 5/2005 |
| WO | WO 2005/047289 A1 | 5/2005 |
| WO | WO 2005/061460 A1 | 7/2005 |
| WO | WO 2005/061707 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/121522 | 11/2006 |
| WO | WO 2006/068760 A3 | 12/2006 |
| WO | WO 2006/089106 A3 | 12/2006 |
| WO | WO 2006/135479 | 12/2006 |
| WO | WO 2007/002293 A2 | 1/2007 |
| WO | WO 2007/006547 A1 | 1/2007 |
| WO | WO 2007/008541 | 1/2007 |
| WO | WO 2007/015877 | 2/2007 |
| WO | WO 2007/020046 A1 | 2/2007 |
| WO | WO 2007/002293 A3 | 3/2007 |
| WO | WO 2007/025090 A2 | 3/2007 |
| WO | WO 2006/050501 A3 | 5/2007 |
| WO | WO 2007/056155 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/076055 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2008/013840 | 1/2008 |
| WO | WO 2008/013987 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/054252 | 5/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2008/094909 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/120098 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2008/153701 | 12/2008 |
| WO | WO 2009/000412 A1 | 12/2008 |
| WO | WO 2009/002808 | 12/2008 |
| WO | WO 2009/004621 A1 | 1/2009 |
| WO | WO 2009/010925 A2 | 1/2009 |
| WO | WO 2009/018811 | 2/2009 |
| WO | WO 2009/021163 | 2/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/065919 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/097233 | 8/2009 |
| WO | WO 2009/100406 A2 | 8/2009 |
| WO | WO 2009/114826 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/118207 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/046780 | 4/2010 |
| WO | WO 2010/019210 A3 | 5/2010 |
| WO | WO 2010/051391 | 5/2010 |
| WO | WO 2010/056758 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/096680 | 8/2010 |
| WO | WO 2010/127208 | 11/2010 |
| WO | WO 2010/133836 A1 | 11/2010 |
| WO | WO 2011/003065 | 1/2011 |
| WO | WO 2011/008302 A1 | 1/2011 |
| WO | WO 2011/020849 | 2/2011 |
| WO | WO 2011/025774 A1 | 3/2011 |
| WO | WO 2011/048111 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/146882 A1 | 11/2011 |
| WO | WO 2011/150201 | 12/2011 |
| WO | WO 2012/009097 A1 | 1/2012 |
| WO | WO 2012/032334 A1 | 3/2012 |

(56) References Cited

FOREIGN PATENT DOCUMENTS

| | | |
|---|---|---|
| WO | WO 2012/037204 | 3/2012 |
| WO | WO 2012/040634 | 3/2012 |
| WO | WO 2012/052753 | 4/2012 |
| WO | WO 2012/061696 A1 | 5/2012 |
| WO | WO 2012/064973 A2 | 5/2012 |
| WO | WO 2012/065019 A2 | 5/2012 |
| WO | WO 2012/065057 A2 | 5/2012 |
| WO | WO 2012/165606 | 6/2012 |
| WO | WO 2012/097000 A1 | 7/2012 |
| WO | WO 2012/177997 | 12/2012 |
| WO | WO 2013/012915 | 1/2013 |
| WO | WO 2013/012918 A1 | 1/2013 |
| WO | WO 2013/032591 | 3/2013 |
| WO | WO 2013/038381 | 3/2013 |
| WO | WO 2013/065725 | 5/2013 |
| WO | WO 2013/136076 | 9/2013 |
| WO | WO 2013/154878 A1 | 10/2013 |
| WO | WO 2013/188432 | 12/2013 |
| WO | WO 2013/190555 | 12/2013 |
| WO | WO 2014/034750 | 3/2014 |
| WO | WO 2014/158528 | 10/2014 |
| WO | WO 2015/010641 | 1/2015 |
| WO | WO 2015/048318 | 4/2015 |
| WO | WO 2015/051241 | 4/2015 |
| WO | WO 2015/051244 | 4/2015 |
| WO | WO 2015/091685 | 6/2015 |
| WO | WO 2015/143012 | 9/2015 |
| WO | WO 2016/054491 | 4/2016 |

OTHER PUBLICATIONS

Abdel-Rahman, T., "Reactivity of 3-amino-3H-quinazolin-4-one derivatives towards some electrophilic and nucleophilic reagents and using of the products in the building of some interesting heterocycles as anticancer agent," Journal of Heterocyclic Chemistry (2006), 43(3), 527-534.

Abdel-Rahman, T., "Reactivity of 3-amino-3H-quinazolin-4-one derivatives towards some electrophilic and nucleophilic reagents and using of the products in the building of some interesting heterocycles as anticancer agent," Bollettino Chimico Farmaceutico (2005), 144(3), 124-138.

Afantitis et al., "A combined LS-SVM & MLR QSAR workflow for predicting the inhibition of CXCR3 receptor by quinazolinone analogs," Molecular Diversity (2010), 14(2), 225-235.

Afify, A.A. et al., "Synthesis and reactions of substituted benzoxazinones bearing a bulky group at position-2," Indian Journal of Chemistry, Section B: Organic Chemistry Including Medicinal Chemistry (1988), 27B(10), 920-25.

Afify, A.A. et al., Synthesis and reactions of substituted benzoxazinones bearing a bulky group at position-2. Part I, Revue Roumaine de Chimie (1990), 35(4), 567-75.

Ahmad, S. et al., "Monoamine oxidase inhibitory activity of 4(3H)-quinazolinones of dopamine," Indian Journal of Pharmaceutical Sciences (1979), 41(3), 126-7.

Avila, M.A. et al., "New therapies for hepatocellular carcinoma," Oncogene (2006), 25(27), 3866-3884.

Barili, P.L. et al., "A facile one pot synthesis of 2,9-disubstituted 8-azapurin-6-ones (3,5-disubstituted 7-hydroxy-3H-1,2,3-triazolo[4,5-d]pyrimidines)," Journal of Heterocyclic Chemistry (1985), 22(6), 1607-9.

Basso et al., "SCH 1473759, a novel Aurora inhibitor, demonstrates enhanced anti-tumor activity in combination with taxanes and KSP inhibitors", Cancer Chemotherapy and Pharmacology (2011), 68(4), 923-933.

Beer, T. et al., "Southwest oncology group phase II study of ispinesib in androgen-independent prostate cancer previously treated with taxanes," Clinical Genitourinary Cancer (2008), 6(2), 103-109.

Birk et al., "Cell cycle-dependent cytotoxicity and mitotic spindle checkpoint dependency of investigational and approved antimitotic agents", International Journal of Cancer (2012), 130(4), 798-807.

Blagden, S.P. et al., "A phase I trial of ispinesib, a kinesin spindle protein inhibitor, with docetaxel in patients with advanced solid tumours," British Journal of Cancer (2008), 98(5), 894-899.

Bol'But, A.V. et al., "Condensed pyrimidine systems. 5.6-methyl-functionalized in pyrazolo[3,4-d]pyrimidin-4(5H)-ones," Zhurnal Organichnoi to Farmatsevtichnoi Khimii (2006), 4(3), 57-61.

Brunton, S. et al., "Potent Inhibitors of the Hedgehog Signaling Pathway," Journal of Medicinal Chemistry (2008), 51(5), 1108-1110.

Burris et al., "A phase I study of ispinesib, a kinesin spindle protein inhibitor, administered weekly for three consecutive weeks of a 28-day cycle in patients with solid tumors", Investigational New Drugs (2011), 29(3), 467-472.

Chau et al., "The association between EGFR variant III, HPV, p16, c-MET, EGFR gene copy number and response to EGFR inhibitors in patients with recurrent or metastatic squamous cell carcinoma of the head and neck", Head & Neck Oncology (2011), 3(11), 1-11.

Davis et al., "Increased therapeutic potential of an experimental anti-mitotic inhibitor SB715992 by genistein in PC-3 human prostate cancer cell line," BMC Cancer (2006), 6, 22.

Debnath, A. et al., "Structure-Based Identification of Small Molecule Antiviral Compounds Targeted to the gp41 Core Structure of the Human Immunodeficiency Virus Type 1," Journal of Medicinal Chemistry (1999), 42(17), 3203-3209.

El-Bassiouny et al., "Synthesis and some reactions of 2-[a-benzoylamino-b-2-furylvinyl]-6,8-dibromobenzoxazin-4(3H)-one and 3-aminoquinazolin-4(3H)-one derivatives," Asian Journal of Chemistry (1990), 2(1), 67-72.

El-Farargy et al., "Study on the reactivity of 2-[benzamido-(a-naphthylidene)]-4H-3,1-benzoxazin-4 one towards different carbon and nitrogen nucleophiles," Egyptian Journal of Chemistry (1993), vol. Date 1992, 35(5), 603-9.

El-Farargy, A.F., "Study on the stability and behavior of 2-[benzamido(naphthylidene)methyl]-4(3H)-quinazolinone," Egyptian Journal of Pharmaceutical Sciences (1991), 32(3-4), 565-74.

Elkafrawy, et al., "Steric and polar factors involving heteroring opening of 2-(a-benzoylamino-p-methoxystyiyl)-6,8-dibromo-3,1-benzoxazin-4(H)-one," Indian Journal of Chemistry, Section B: Organic Chemistry Including Medicinal Chemistry (1992), 31B(1), 19-23.

El-Khamry et al., "Synthesis and reactions of 2-(a-benzoylamino-p-chlorostyryl)-3,1(4H)-benzoxazin-4-one with some nucleophilic reagents: synthesis of quinazolinone, tetrazole and benzimidazole derivatives," Egyptian Journal of Chemistry (1990), vol. Date 1988, 31(2), 261-9.

El-Nagdy, S. et al., "Behavior of benzoxazinone derivatives bearing a bulky group at position 2 toward some nitrogen and carbon nucleophiles. Part 2," Revue Roumaine de Chimie (1990), 35(1), 55-62.

El-Nagdy, S. et al., "Behavior of benzoxazinone derivatives bearing a bulky group at position-2 towards some nitrogen and carbon nucleophiles," Indian Journal of Chemistry, Section B: Organic Chemistry Including Medicinal Chemistry (1989), 28B(2), 126-30.

El-Nagdy, S. et al., "Synthesis and some reactions of 2-(a-benzoylaminostyryl)-3,1(4H)-benzoxazin-4-one and 3-amino-2-(a-benzoylaminostyrylquinazolin-4(3H)-one," Revue Roumaine de Chimie (1988), 33(8), 827-32.

El-Nagdy, S. et al., "Synthesis and some reactions of 2-(a-benzoylaminostyryl)-3,1(4H)-benzoxazin-4-one and 3-amino-2-(a-benzoylaminostyryl)quinazolin-4(3H)-one," Egyptian Journal of Chemistry (1990), vol. Date 1988, 31(5), 599-606.

El-Nagdy, S., "Synthesis and some reactions of 2-[a-(benzoylamino)styryl]-6,8-dibromo-3,1-benzoxazin-4(H)-one, quinazolin-4(3H)-one, and chloroquinazoline derivatives with some nucleophilic reagents," Asian Journal of Chemistry (1990), 2(4), 368-78.

El-Sharief et al., "Oxidation of 3-aminoquinazolinones with lead tetraacetate. A novel synthesis of naphtho-fused azirino-pyrazolo- and 1,4,5-oxadiazepinoquinazolinones," Journal of Chemical Research, Synopses (2002), (5), 205-208.

Essawy et al., "Behavior of 2-(a-phenylimido-b-p-nitrophenyl) vinyl-(4H)-3,1-benzoxazin-4-one towards some nucleophiles," Journal of Pure and Applied Sciences (1990), 9(2), 29-35 (abstract only).

(56) References Cited

OTHER PUBLICATIONS

Gao, H. et al., "A Dramatic Substituent Effect in Silver(I)-Catalyzed Regioselective Cyclization of ortho-Aikynylaryl Aldehyde Oxime Derivatives," Advanced Synthesis & Catalysis (2009), 351(1-2), 85-88.
Garg, P. et al., "Synthesis and anti-implantation activity of 2-[2-[2-aryl-4(3H)-oxoquinazolin-3-yl]ethyl]-5-benzylidenecyclohexanone thiosemicarbazones," Biological Memoirs (1988), 14(2), 180-6.
Ghosh, T., "Quinazolines. I," Journal of the Indian Chemical Society (1937), 14, 411-13.
Guirguis, D., "The behaviour of some nucleophiles towards 2-[a-(benzoylamino)-b-(2-thienyl)vinyl]benzoxazin-4(3H)-one," Indian Journal of Chemistry, Section B: Organic Chemistry Including Medicinal Chemistry (2000), 39B(4), 264-269.
Hassanein et al., "Synthesis of 2-substituted-10H-[1,2,4]triazino[6,1-b]quinazoline-10-ones and 8,13,14,16-tetrahydronaphtho [2',3':3,4][1,2,5]triazepino[7,1-b]quinazoline-8,13,16-triones with biological interest," Al-Azhar Bulletin of Science (1997), 8(2), 417-434.
Heiser et al., "Subtype and pathway specific responses to anticancer compounds in breast cancer", Proceedings of the National Academy of Sciences of the United States of America (2012), 109(8), 2724-2729.
Huang, W. et al., "Synthesis and evaluation of quinazolin-4-ones as hypoxia-inducible factor-1 inhibitors," Bioorganic & Medicinal Chemistry Letters (2011), 21(18), 5239-5243.
Jackson, J. et al., "Targeted anti-mitotic therapies: can we improve on tubulin agents?" Nature Reviews Cancer (2007), 7(2), 107-117.
Jankowski, F. et al., "Efficient microwave-assisted two-step procedure for the synthesis of 1,3-disubstituted-imidazo[1,5-a]quinazolin-5(4H)-ones," Tetrahedron (2010), 66(1), 128-133.
Jiang, C. et al., "De novo design, synthesis and biological evaluation of 1,4-dihydroquinolin-4-ones and 1,2,3,4-tetrahydroquinazolin-4-ones as potent kinesin spindle protein (KSP) inhibitors", Bioorganic & Medicinal Chemistry (2011), 19(18), 5612-5627.
Jiang, C. et al., "Docking studies on kinesin spindle protein inhibitors: an important cooperative 'minor binding pocket' which increases the binding affinity significantly," Journal of Molecular Modeling (2007), 13(9), 987-992.
Johnson, M. et al., "Discovery and optimization of a series of quinazolinone-derived antagonists of CXCR3," Bioorganic & Medicinal Chemistry Letters (2007), 17(12), 3339-3343.
Karanov et al., "Cytokinin and anticytokinin activity of some 4-substituted 1H-pyrazoles and 8-aza analogs of adenine," Plant Growth Regulation (1993), 13(1), 7-11.
Kathman, S. et al., "A Bayesian population PK-PD model for ispinesib/docetaxel combination-induced myelosuppression," Cancer Chemotherapy and Pharmacology (2009), 63(3), 469-476.
Kathman, S. et al., "A bayesian population PK-PD model of ispinesib-induced myelosuppression," Clinical Pharmacology & Therapeutics (New York, NY, United States) (2007), 81(1), 88-94.
Kirmani et al., "Studies on the reactivity of 2-methyl-3-phenyl-4(3H)-quinazolinone," Indian Journal of Chemistry, Section B: Organic Chemistry Including Medicinal Chemistry (1979), 17B(5), 445-9.
Knox, J. et al., "A phase II and pharmacokinetic study of SB-715992, in patients with metastatic hepatocellular carcinoma: a study of the National Cancer Institute of Canada Clinical Trials Group (NCIC CTG IND.168)," Investigational New Drugs (2008), 26(3), 265-272.
Lad, L. et al., "Mechanism of Inhibition of Human KSP by Ispinesib," Biochemistry (2008), 47(11), 3576-3585.
Lee, C. et al., "A phase II study of ispinesib (SB-715992) in patients with metastatic or recurrent malignant melanoma: a National Cancer Institute of Canada Clinical Trials Group trial," Investigational New Drugs (2008), 26(3), 249-255.
Lee, R. et al., "A University of Chicago consortium phase II trial of SB-715992 in advanced renal cell cancer," Clinical Genitourinary Cancer (2008), 6(1), 21-24.
Liu F. et al., "Discovery of tetrahydro-b-calbolines as inhibitors of the mitotic kinesin KSP," Bioorganic & Medicinal Chemistry (2010), 18(12), 4167-4177.
Liu F. et al., "Pharmacophore identification of KSP inhibitors," Bioorganic & Medicinal Chemistry Letters (2007), 17(3), 722-726.
Liu, D. et al., "Impurity identification in process chemistry by mass spectrometry", Characterization of Impurities and Degradants Using Mass Spectrometry, First Edition, John Wiley & Sons, Inc., Hoboken, NJ, (2011), pp. 251-277.
Mahmoud et al., "Heteroannulated quinazoline and quinazolinone derivatives from (Z)-2[1-benzamido-2-(3,4,5-trimethoxyphenyl)vinyl]-3,1-benzoxazin-4(3H)-one," Synthetic Communications (2010), 40(10), 1516-1529.
Mahmoud et al., "Synthesis of new thiadiazoles, 1,2,4-triazolo[3,4-b]-1,3,4-thiadiazoles, and 1,2,4-triazolo[2,3-c]quinazoline derivatives from 4H-3,1-benzoxazin-4-one derivative," Phosphorus, Sulfur and Silicon and the Related Elements (2007), 182(6), 1275-1289.
Mahmoud et al., "Synthesis of novel quinazolinone and fused quinazolinones", European Journal of Chemistry (2011), 2(3), 404-409.
Marone et al., "Targeting phosphoinositide 3-kinase—Moving towards therapy," Biochimica et Biophysica Acta 1784 (2008) 159-185.
Mealy, et al., "Drugs under development for the treatment of head and neck cancer," Drugs of the Future (2006), 31(7), 627-639.
Morsy, J.M., "Use of 2-(substituted vinyl)-4(3H)-quinazolinone and -4H-3,1-benzoxazinone in synthesis of heterocycles," Bulgarian Chemical Communications (2007), 39(2), 146-151.
Mossetti et al., "Imides: forgotten players in the Ugi reaction. One-pot multicomponent synthesis of quinazolinones", Chemical Communications, (2011), 47(24), 6966-6968.
Natsugari, H. et al., "Novel, Potent, and Orally Active Substance P Antagonists: Synthesis and Antagonist Activity of N-Benzylcarboxamide Derivatives of Pyrido[3,4-b]pyridine," Journal of Medicinal Chemistry (1995), 38(16), 3106-20.
Pandey, V.K. et al., "Quinazolylthiazoles as CNS acting agents," Acta Pharmaceutica (Zagreb) (1996), 46(1), 51-9.
Pandey, V.K. et al., "Synthesis and antiviral activity of quinazolinyl sydnones," Indian Journal of Heterocyclic Chemistry (2006), 15(4), 399-400.
Pandey, V.K. et al., "Synthesis of 1-(2'-aryl-4'-oxo(3H)quinazolyl)-3- aryl-5-phenyl-formazans as potential anti-viral agents," Indian Drugs (1999), 36(1), 37-40.
Pandey, V.K., "Antiparkinsonism and CNS activities of (±)-2-aryl/alkyl-3-{b-(3',4'-dihydroxyphenyl)ethyl}quinazolin-4(3H)-ones," Biological Memoirs (1985), 11(2), 213-15.
Pandey, V.K., "Possible antiparkinsonian compounds. Part XI. Synthesis of 2-aryl/alkyl-3-[b-(3':4'-dihydroxyphenypethyl]-quinazoline(3H)-4-one and 2-aryl/alkyl-3-[(7'-(phenothiazinyl)-ethyl]-quinazoline(3H)-4-one," Acta Ciencia Indica (1978), 4(3), 230-5.
Parrish, C. et al., "Novel ATP-Competitive Kinesin Spindle Protein Inhibitors," Journal of Medicinal Chemistry (2007), 50(20), 4939-4952.
Pattan, S. et al., "Synthesis and microbiological evaluation of N'-3-(4-(4-chlorophenyl)thiazol-2-yl)quinazolin-4(3H)-ones," Indian Journal of Heterocyclic Chemistry (2005), 15(1), 79-80.
Pattan, S. et al., "Synthesis of N-3(4-(4-chlorophenyl thiazole-2-yl)-(2-(amino)methyl)-quinazoline-4(3H)-one and their derivatives for antitubercular activity," Indian Journal of Chemistry, Section B: Organic Chemistry Including Medicinal Chemistry (2006), 45B(7), 1778-1781.
Pinkerton, A. et al., "Synthesis and SAR of thiophene containing kinesin spindle protein (KSP) inhibitors," Bioorganic & Medicinal Chemistry Letters (2007), 17(13), 3562-3569.
Poupert, J.H., "Drug Design: Basic Principles and Applications", 2 Encyclopedia of Pharmaceutical Technology, 1362-1369, (James Swarbrick ed., 3rd ed., 2007).
Purcell, J. et al., "Activity of the kinesin spindle protein inhibitor ispinesib (SB-715992) in models of breast cancer," Clinical Cancer Research (2010), 16(2), 566-576.

(56) References Cited

OTHER PUBLICATIONS

Rodriguez et al., "Synthesis and characterization of tritylthioethanamine derivatives with potent KSP inhibitory activity", Bioorganic & Medicinal Chemistry (2011), 19(18), 5446-5453.
Sakowicz, R. et al., "Antitumor Activity of a Kinesin Inhibitor," Cancer Research (2004), 64(9), 3276-3280.
Saleh, R.M. et al., "Synthesis and reactions of 2-[1-benzamido-2-(o-chlorophenyl)vinyl]-4H-3,1-benzoxazin-4-one," Revue Roumaine de Chimie (1994), 39(5), 567-76.
Saleh, R.M. et al., "Synthesis and some reactions of 2-(a-benzamido-p-chlorostyryl)-3,1-benzoxazin-4-one," Pakistan Journal of Scientific and Industrial Research (1991), 34(11), 417-21.
Sheth, P. et al., "Novel Benzimidazole Inhibitors Bind to a Unique Site in the Kinesin Spindle Protein Motor Domain," Biochemistry (2010), 49(38), 8350-8358.
Sheth, P. et al., "Thermodynamics of Nucleotide and Inhibitor Binding to Wild-Type and Ispinesib-Resistant Forms of Human Kinesin Spindle Protein," Biochemistry (2009), 48(46), 11045-11055.
Singh, B. et al., "4-Quinazolones. II. Synthesis of some imidazo[1,5-a]quinazolin-5(4H)ones," Journal of the Indian Chemical Society (1969), 46(1), 21-5.
Singh, R. et al., "Synthesis and pharmacological screening of some 2-aryl-3-(phenyl-aryl-hydrazonyl)quinazolin-(3H)4-ones," Indian Drugs (1990), 28(2), 70-4.
Soliman et al., "Synthesis and reactions of substituted benzoxazinones bearing a bulky group at position 2," Revue Roumaine de Chimie (1992), 37(10), 1153-8.
Soliman et al., "Synthesis and reactions of substituted benzoxazinones bearing a bulky group at position 2," Delta Journal of Science (1990), 14(1), 166-80.
Sorbera, L.A. et al., "Ispinesib mesilate," Drugs of the Future (2006), 31(9), 778-787.
Storelli, S. et al., "Synthesis and structure-activity relationship of 3-phenyl-3H-quinazolin-4-one derivatives as CXCR3 chemokine receptor antagonists," Bioorganic & Medicinal Chemistry Letters (2005), 15(11), 2910-2913.
Storelli, S. et al., "Synthesis and structure-activity relationships of 3H-quinazolin-4-ones and 3H-pyrido[2,3-d]pyrimidin-4-ones as CXCR3 receptor antagonists," Archiv der Pharmazie (Weinheim, Germany) (2007), 340(6), 281-291.
Tang, P. et al., "Phase II study of ispinesib in recurrent or metastatic squamous cell carcinoma of the head and neck," Investigational New Drugs (2008), 26(3), 257-264.
Theoclitou et al., "Discovery of(+)-N-(3-Aminopropyl)-N-[1-(5-benzyl-3-methyl-4-oxo-[1,2]thiazolo [5,4-d]pyrimidin-6-yl)-2-methylpropyl]-4-methylbenzamide (AZD4877), a Kinesin Spindle Protein Inhibitor and Potential Anticancer Agent," Journal of Medicinal Chemistry (2011), 54(19), 6734-6750.
Tiwari, A. et al., "Synthesis and biological properties of 4-(3H)-quinazolone derivatives," European Journal of Medicinal Chemistry (2007), 42(9), 1234-1238.
Tiwari, S. et al., "Possible antifertility compounds—Part III: Synthesis of 2-hippuryl-3-arylquinazolinones," Journal of the Chemical Society of Pakistan (1981), 3(4), 215-17.
Tiwari, S. et al., "Synthesis and central nervous systems activity of 2-aryl-3(3',4'-dihydroxyphenylethyl)-6,8-substituted 4(3H)-quinazolinones," Indian Journal of Pharmaceutical Sciences (1978), 40(2), 40-3.
Tiwari, S. et al., "Synthesis of possible antiparkinsonian compounds. X. Synthesis of 2,6,8-trisubstituted benzoxazinones and their corresponding 3-hydroxyquinazolinones," Journal of the Indian Chemical Society (1975), 52(8), 736-7.
Valensin S., et al., "KIF11 inhibition for glioblastoma treatment: reason to hope or a struggle with the brain?" BMC Cancer (2009), 9.
Voultsiadou et al., "Recent advances of kinesin motor inhibitors and their clinical progress", Reviews on Recent Clinical Trials (2011), 6(3), 271-277.
Wang, F. et al., "Triphenylbutanamines: Kinesin Spindle Protein Inhibitors with in Vivo Antitumor Activity," Journal of Medicinal Chemistry (2012), 55 (4), 1511-1525.
Watkins, W. et al., "Quinazolinone fungal efflux pump inhibitors. Part 2: In vitro structure-activity relationships of (N-methylpiperazinyl)-containing derivatives," Bioorganic & Medicinal Chemistry Letters (2004), 14(20), 5133-5137.
White, M., "Targeting mitotic fragility in cancer," Future Oncology (2009), 5(5), 613-615.
Zhang, B. et al., "Crystal structure of HsEg5 in complex with clinical candidate CK0238273 provides insight into inhibitory mechanism, potency, and specificity," Biochemical and Biophysical Research Communications (2008), 72(4), 565-570.
Zhang, B. et al., "Development of a high-throughput robotic fluorescence-based assay for HsEg5 inhibitor screening," Analytical Biochemistry (2005), 345(2), 326-335.
Aksoy et al., "The p110d isoform of the kinase PI(3)K controls the subcellular compartmentalization of TLR4 signaling and protects from endotoxic shock", Nature Immunology, 2012, vol. 13(11), pp. 1045-1054.
Ali et al., "Leukocyte Extravasation: An Immunoregulatory Role for-L-Fucosidase?", J Immunol 2008, vol. 181, pp. 2407-2413.
Balla et al. (Eds.), Phosphoinositides I: Enzymes of Synthesis and Degradation, Chapter 5: PI3Ks—Drug Targets in Inflammation and Cancer Series: Subcellular Biochemistry, vol. 58, 2012, XVI, 356 p.
Burger et al, "CXCR4: a key receptor in the crosstalk between tumor cells and their microenvironment", Blood, Mar. 1, 2006;107(5), pp. 1761-1767.
Burger et al., "The microenvironment in chronic lymphocytic leukemia (CLL) and other B cell malignancies: insight into disease biology and new targeted therapies", Semin Cancer Biol., Feb. 2014; vol. 24:pp. 71-81.
Curran et al., "PD-1 and CTLA-4 combination blockade expands infiltrating T cells and reduces regulatory T and myeloid cells within B16 melanoma tumors," PNAS, Mar. 2, 2010, vol. 107(9), pp. 4275-4280.
De Palma and Lewis, "Macrophage Regulation of Tumor Responses to Anticancer Therapies", Cancer Cell, vol. 23, Issue 3, Mar. 18, 2013, pp. 277-286.
Denardo et al., "Leukocyte Complexity Predicts Breast Cancer Survival and Functionally Regulates Response to Chemotherapy", Cancer Discovery, Jun. 2011, vol. 1, pp. 54-67.
Duraiswamy et al., "Dual Blockade of PD-1 and CTLA-4 Combined with Tumor Vaccine Effectively Restores T-Cell Rejection Function in Tumors," Cancer Research, Jun. 5, 2013;73(12):3591-603.
Feig et al., "Targeting CXCL12 from FAP-expressing carcinoma associated fibroblasts synergizes with anti-PD-L1 immunotherapy in pancreatic cancer," PNAS, Dec. 10, 2013, vol. 110, No. 50, pp. 20212-20217.
Ferrandi et al., "Phosphoinositide 3-Kinase Inhibition Plays a Crucial Role in Early Steps of Inflammation by Blocking Neutrophil Recruitment", J Pharmacol Exp Ther, Sep. 2007, vol. 322, pp. 923-930.
Fruman, D., "Phosphoinositide 3-kinase and its targets in B-cell and T-cell signaling", Current Opinion in Immunology, vol. 16, Issue 3, Jun. 2004, pp. 314-320.
Ghia et al., "Chronic lymphocytic leukemia B cells are endowed with the capacity to attract CD4+, CD40L+ T cells by producing CCL22", Eur J Immunol., May 2002; vol. 32(5): pp. 1403-1413.
Hardamon et al., "Inhibition of myeloid cell PI3K is a potential therapeutic approach to treat pancreatic cancer", Cancer Research, Apr. 15, 2012; vol. 72, Issue 8, Supplement 1, Abstract 5228.
Herman et al., "Molecular pathways: targeting phosphoinositide 3-kinase p110-delta in chronic lymphocytic leukemia", Clin Cancer Res., Aug. 1, 2012; vol. 18(15): pp. 4013-4018.
Hirsch et al., "Phosphoinositide 3-kinases as a common platform for multi-hormone signaling", J Endocrinol, 2007, vol. 194 (2), pp. 243-256.
Kaneda et al., "PI3-kinase gamma controls the macrophage M1-M2 switch, thereby, promoting tumor immunosuppression and progression", AACR; Cancer Res 2014, vol. 74 (19 Suppl), Abstract 3650.

(56) References Cited

OTHER PUBLICATIONS

Lewis and Pollard, "Distinct Role of Macrophages in Different Tumor Microenvironments", Cancer Res 2006, vol. 66 (2), pp. 605-612.
Monjazeb et al., "Immunoediting and antigen loss: overcoming the Achilles heel of immunotherapy with antigen non-specific therapies", Front. Oncol., 2013, vol. 3, Article 197, pp. 1-10.
Mraz et al., "miR-34a, miR-29c and miR-17-5p are downregulated in CLL patients with TP53 abnormalities", Leukemia (2009), vol. 23(6), pp. 1159-1163.
Ni et al., "Functional Characterization of an Isoform-Selective Inhibitor of PI3K-p110b as a Potential Anticancer Agent", Cancer Discovery, May 2012, vol. 2, pp. 425-433.
Okkenhaug, K., "Signaling by the Phosphoinositide 3-Kinase Family in Immune Cells", Annu. Rev. Immunol., 2013, vol. 31, pp. 675-704.
Ries, et al., "Targeting Tumor-Associated Macrophages with Anti-CSF-1R Antibody Reveals a Strategy for Cancer Therapy", Cancer Cell, vol. 25, Issue 6, Jun. 16, 2014, pp. 846-859.
Rommel et al., Taking PI3Kδ and PI3Kγ One Step Ahead: Dual Active PI3Kδ/γ Inhibitors for the Treatment of Immune-Mediated Inflammatory Diseases, Phosphoinositide 3-Kinase in Health and Disease, 2011, vol. 1, pp. 279-299.
Roy et al., "DDB2 Suppresses Epithelial-to-Mesenchymal Transition in Colon Cancer", Cancer Res Jun. 15, 2013, 73(12), pp. 3771-3782.
Schmid et al., "PI3 Kinase gamma control of Arginase-1 expression promotes tumor immunosuppression", Cancer Research, Apr. 15, 2012, vol. 72, Issue 8, Supplement 1, Abstract 411.
Schmid et al., "ReceptorTyrosineKinasesandTLR/IL1Rs Unexpectedly Activate Myeloid Cell PI3Kg, A Single Convergent Point Promoting Tumor Inflammation and Progression", Cancer Cell, vol. 19, Issue 6, Jun. 14, 2011, pp. 715-727.
Topalian et al., "Safety, Activity, and Immune Correlates of Anti-PD-1 Antibody in Cancer", N Engl J Med 2012, 366(26), pp. 2443-2454.
Wolchok et al., "Antitumor response and new lesions in advanced melanoma patients on ipilimumab treatment", Wolchok et al., J. Clin. Oncology, 2008 ASCO (Post-Meeting Edition), vol. 26, No. 15S (May 20 Suppl), Abstract 3020.
Wolchok et al., "Nivolumab plus Ipilimumab in Advanced Melanoma", NEJM, 2013, vol. 369, pp. 122-133.
Wurth et al., "CXCL12 modulation of CXCR4 and CXCR7 activity in human glioblastoma stem-like cells and regulation of the tumor microenvironment," Frontiers in Cellular Neuroscience, May 2014, vol. 8, Article 144, pp. 1-19.
Brachman et al., "PI3K and mTOR inhibitors—a new generation of targeted anticancer agents", Current Opinion in Cell Biology (2009), vol. 21, pp. 194-198.
Dagia et al., "A preferential p110α/γ PI3K inhibitor attenuates experimental inflammation by suppressing the production of proinflammatory mediators in a NF-κB-dependent manner", American Journal of Physiology—Cell Physiology (2010), vol. 298, pp. 929-941.
Dushianthan et al., "Acute respiratory distress syndrome and acute lung injury", Post Graduate Medical Journal (2011), vol. 87, pp. 612-622.
Engelman, J. "Targeting PI3K signalling in cancer: opportunities, challenges and limitations", Nature Reviews: Cancer. vol. 9 (2009), pp. 550-562.
Ghigo et al., "PI3K Inhibition in Inflammation. Toward tailored therapies for specific diseases," BioEssays 32 (2010), pp. 185-196.
Hirsch, E. et al., "Taming the PI3K team to hold inflammation and cancer at bay", Pharmacology & Therapeutics (2008), vol. 118, pp. 192-205.
Kolliputi, N. et al., "IL-6 cytoprotection in hyperoxic acute lung injury occurs via PI3K/Akt-mediated Bax phosphorylation", American Journal of Physiology, Lung Cellular and Molecular Physiology (2009), vol. 297, pp. L6-L16.
Kong, D. et al., "Phosphatidylinositol 3-kinase inhibitors: promising drug candidates for cancer therapy", Cancer Science (2008), vol. 9, pp. 1734-1740.
Liu, Q. et al. "mTOR mediated anti-cancer drug discovery", Drug Discovery Today: Therapeutic Strategies, (2009), vol. 6, pp. 47-55.
Shuttleworth et al., "Progress in the Preclinical Discovery and Clinical Development of Class I and Dual Class I/IV Phosphoinositide 3-Kinase (PI3K) Inhibitors", Current Medicinal Chemistry (2011), vol. 18, pp. 2686-2714.
Evans, "Principles of Radiopharmacology", Colombett, L.G editor, CRC Press, 1979, pp. 11-13 and 24.
Banham-Hall et al., "The therapeutic potential for PI3K inhibitors in autoimmune and rheumatic diseases", Open Rheumatol. J. 2012, 6, 245-258.
Bell et al., "SAR studies around a series of triazolopyridines as potent and selective PI3Kc inhibitors", Bioorg. Med. Chem. Lett. 2012, 22, 5257-5263.
Bergamini et al., "A selective inhibitor reveals PI3Kγ dependence of TH17 cell differentiation", Nat. Chem. Biol. 2012, 8, 576-582.
Bruce et al., "Development of isoform selective PI3K-kinase inhibitors as pharmacological tools for elucidating the PI3K pathway", Bioorg. Med. Chem. Lett. 2012, 22, 5445-5450.
Cantley, L.C., "The phosphoinositide 3-kinase pathway", Science, 2002, 296, 1655-1657.
Collier et al., "Discovery of highly isoform selective thiazolopiperidine inhibitors of phosphoinositide 3-kinase γ", J. Med. Chem. 2015, 58, 5684-5688.
Collier et al., "Structural basis for isoform selectivity in a class of benzothiazole inhibitors of phosphoinositide 3-kinase γ", J. Med Chem. 2015, 58, 517-521.
DeHenau et al., "Checkpoint Blockade Therapy is Improved by Altering the Immune-Suppressive Microenvironment with IPI-549, a Potent and Selective Inhibitor of PI3K-γ, in Preclinical Models," AACR Annual Meeeting 2016, Apr. 17, 2016, New Orleans, Poster 554.
Gunderson et al., "Bruton tryrosine kinase-dependent immune cell cross-talk drives pancreas cancer", Cancer Discovery 2016, 6, 270-285.
Hawkins et al., PI3K signalling in inflammation Biochim. Biophys. Acta, Mol. Cell Biol. Lipids 2015, 1851, 882-897.
Joshi et al., "A macrophage-dominant PI3K isoform controls hypoxia-induced HIF 1alpha nad HIF2alpha stability and tumor growth, angiogenesis, and metastasis", Mol. Cancer. Res. 2014, 12, 1520-1531.
Kutok et al., "The Potent and Selective Phosphoinositide-3-Kinase (PI3K)-γ Inhibitor, IPI-549, Inhibits Tumor Growth in Murine Syngeneic Solid Tumor Models through Alterations in the Immune Suppressive Microenvironment", CRI-CIMT-EATI-AACR—The Inaugural International Cancer Immunotherapy Conference, Sep. 18, 2015, New York, NY, Poster.
Leahy et al., "Discovery of a novel series of potent and orally bioavailable phosphoinositide 3-kinase γ inhibitiors", J. Med. Chem. 2012, 55, 5467-5482.
NCT02637531: A dose-escalation study to evaluate the safety, tolerability, pharmacokinetics, and pharmacodynamics of IPI-549. www.clinicaltrials.gov, May 19, 2016.
Oka et al., "Discovery of N-{5-[3-(3-hydroxypiperdin-1-yl)-1,2,4-oxadiazol-5-yl]-4-methyl-1,3-thiazol-2-yl}acetamide (TASP0415914) as an orally potent phosphosititide 3-kinase γ inhibitor for the treatment of inflammatory diseases", Bioorg. Med. Chem. 2013, 21, 7578-7583.
Reif et al., "Cutting Edge: Differential Roles for Phosphoinositide 3-Kinases, p110γ and p110δ, in Lymphocyte Chemotaxis and Homing," J. Immunol. 173:2236-2240 (2004).
Rivera et al., "Intratumoral myeloid cells regulate repsoniveness and resistance to antiangiogenic therapy", Cell Rep. 2015, 11, 577-591.
Sunose et al., "Discovery of 5-(2-amino-[1,2,4]triazolo[1,5-a]pyridin-7-yl)-N-(tert-butyl)pyridine-3-sulfonamide (CZC24758), as a potent, orally bioavailable and selective inhibitor of PI3K for the treatment of inflammatory disease", Bioorg. Med. Chem. Lett. 2012, 22, 4613-4618.

(56) References Cited

OTHER PUBLICATIONS

Thorpe et al., "PI3K in cancer: divergent rols of isoforms, modes of activation and therapeutic targeting", Nat. Rev. Cancer 2015, 15, 7-24.
Tolcher et al., "A Phase 1/1b First-In-Human Study of IPI-549, a PI3K-g Inhibitor, as Monotherapy and in Combination with an Anti-PD1 Antibody in Subjects with Advanced Solid Tumors", ASCO Annual Meeting Jun. 3-7, 2016, Chicago, IL, Poster.
Vanhaesebroeck et al., "Molecules in medicine mini-review: isoforms of PI3K in biology and disease", J. Mol. Med. 2016, 94, 5-11.
Winkler et al., "PI3K-d and PI3K-g Inhibition by IPI-145 Abrogates Immune Responses and Suppresses Activity in Autoimmune and Inflammatory Disease Models," Chem. Biol. 2013, 20, 1364-1374.
Brunk et al., "Anti-PD-L1 therapy yielded durable responses in early NSCLC trials, Oncology Practice Digital Network", Feb. 2014, pp. 1-3.
Tomasini et al., "Ipilimumab: its potential in non-small cell lung cancer", Ther Ad Med Oncol, 2012, Issue 4, No. 2, pp. 43-50.
Evans et al., "Discovery of a Selective Phosphoinositide-3-Kinase {PI3K}-γ Inhibitor (IP1-549) as an Immuno-Oncology Clinical Candidate," ACS Med. Chem. Lett., 2016, 7, 862-867.
Golub, T.R., et al., "Molecular classification of Cancer: Class Discover and Class Predication by Expression Monitoring," Science, 286:531-537, 1999.
Pomel et al, "Furan-2-ylmethylene Thiazolidinediones as Novel, Potent, and Selective Inhibitors of Phosphoinositide 3-Kinase γ," J. Med. Chem. 49:3857-3871, 2006.
Braga et al., "Crystal polymorphism and multiple crystal forms," Struct. Bond. 132:25-50 (2009).
Zell et al., "Investigation of polymorphism in aspartame and neotame using solid-state NMR spectroscopy," Tetrahedron, 56:6603-6616 (2000).
Pirrung, "Handbook of Synthetic Organic Chemistry," $2^{nd}$ Ed., 2017, p. 178.
Bernstein, "Polymorphism in Molecular Crystals," Oxford, 2002, p. 46.
Guillory, "Generation of Polymorphs, Hydrates, Solvates, and Amorphous Solids". Chapter 5 in Polymorphism in Pharmaceutical Solids, Ed. By Harry G. Brittain, Dekker: New York, 1999, pp. 183-226.
Brittain, "Effects of Pharmaceutical Processing on Drug Polymorphs and Solvates", Chapter 8 in Polymorphism is Pharmaceutical Solids, Ed. By Harry G. Brittain, Dekker: New York, 1999, pp. 331-360.
Sapey et al., "Abnormal Neutrophil Migration is a Feature of Early COPO, Present Across Disease Phenotypes and Causally Related to Increased PhospholNOSitide-3-Kinase Signalling", American Journal of Respiratoly and Critical Care Medicine, 2013, vol. 187, Supp., A3492.
U.S. Appl. No. 16/312,896, filed Dec. 21, 2018, Combination Therapies.
U.S. Appl. No. 16/308,377, filed Dec. 7, 2018, Heterocyclic Compounds and Uses Thereof.
U.S. Appl. No. 15/347,489, filed Nov. 9, 2016, 2017-0281614, Certain Chemical Entitites, Compositions and Methods.
U.S. Appl. No. 15/599,378, filed May 18, 2017, 2018-0098983, Certain Chemical Entitites, Compositions and Methods.
U.S. Appl. No. 15/621,815, filed Jun. 13, 2017, 2017-0369511, Heterocyclic Compounds and Uses Thereof.
U.S. Appl. No. 15/672,964, filed Aug. 9, 2017, 2018-0055852, Heterocyclic Compounds and Uses Thereof.
U.S. Appl. No. 15/794,816, filed Oct. 26, 2017, 2018-0044346, Heterocyclic Compounds and Uses Thereof.
U.S. Appl. No. 16/172,539, filed Oct. 26, 2018, Certain Chemical Entitites, Compositions and Methods.
U.S. Appl. No. 16/197,195, filed Nov. 20, 2018, Solid Forms of Isoquinolinones, and Process of Making, Composition Comprising, and Methods of Using the Same.
Pitt et al., "Resistance Mechanisms to Immune-Checkpoint Blockade in Cancer: Tumor-Intrinsic and -Extrinsic Factors", Immunity, 2016, 44, 1255-1269.
Kushner et al., "Pharmacological uses and perspectives of heavy water and deuterated compounds", Can. J. Physiol. Pharmacol. 77: 79-88 ( 1999).
Tung, "The Development of Deuterium-Containing Drugs", 2010.
Anderson et al., "The Use of Esters of N-Hydroxysuccinimide in Peptide Synthesis," Journal of the American Chemical Society, 1964, 86:1839-1842.
El-Faham et al., "Peptide Coupling Reagents, More than a Letter Soup," Chem. Rev. 2011, 111:6557-6602.
Abdel-Mohsen, "Synthesis, Reactions and Antimicrobial Activity of 2-Amino-4-(8-quinolinol-5-yl)-1-(p-tolyl)-pyrrole-3-carbonitrile," Bull. Korean Chem. Soc. 26(5):719-728 (2005).
Abe et al., "T cell receptor-mediated recognition of self-ligand induces signaling in immature thymocytes before negative selection," J. Exp. Med. 176(2):459-468 (1992).
Abrahamian et al., "Immunological and Clinical Profile of Adult Patients with Selective Immunoglobulin Subclass deficiency: response to intravenous immunoglobulin therapy," Clin. Exp. Immunol. 159(3):344-350 (2010).
Abraham, T., "Thermally induced intramolecular cycloaddition reaction of N-phenyl-2-phenylethynlbenzamide potential cure reaction for thermosetting polymers," J. Polym. Sci. Polym. Chem. Ed. 20(7):1953-1957 (1982).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," J.C.S. Perkin I 1390-1395 (1975).
Anderson et al., "Paradoxical inhibition of T-cell function in response to CTLA-4 blockade; heterogeneity within the human T-cell population." Nat. Med. 6(2):211-214 (2000).
Andrews et al., "Effects of the 11β-hydroxysteroid dehydrogenase inhibitor carbenoxolone on insulin sensitive in men with type 2 diabetes," J. Clin. Endocrinol. Metab. 88(1):285-291 (2003).
Arcaro et al., "Wortmannin is a potent phosphatidylinositol 3-kinase inhibitor: the role of phosphatidylinositol 3,4,5-triphosphate in neutrophil responses," Biochem. J., 296(Pt 2):297-301 (1993).
Arnold et al., "Pyrrolo[2,3-d]pyrimidines containing an extended 5-substituent as potent and selective inhibitors of Ick I," Bioorg. Med. Chem. Lett. 10(19):2167-2170 (2000).
Augustine et al., "Interleukin 2- and polyomavirus middle T antigen-induced modification of phosphatidylinositol 3-kinase activity in activated T lymphocytes," Mol. Cell. Biol. 11(9):4431-4440 (1991).
Baggiolini et al., "Inhibition of the phagocytosis-induced respiratory burst by the fungal metabolite wortmannin and some analogues," Exp. Cell. Res. 169(2): 408-418 (1987).
Ballell et al. "New Thiopyrazolo[3,4-d] pyrimidine derivatives as anti-mycobacterial agents," Bioorg. Med. Chem. Lett. 17(6):1736-1740 (2007).
Banker et al., Modern Pharmaceutics, pp. 451, 596, $3^{rd}$ ed, Marcel Dekker, New York (1996).
Bansal et al., "The Molecular Biology of Endometrial Cancers and the Implications for Pathogenesis, Classification, and Targeted Therapies," Cancer Control 16(1):8-13 (2009).
Barber et al., "PI3Kgamma inhibition blocks glomerulonephritis and extends lifespan in a mouse model of systemic lupus," Nat. Med. 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxysteroid dehydrogenase Type 1," J. Med. Chem. 45(18):3813-3815 (2002).
Barnes et al., "Efficacy and Safety of Inhaled Corticosteroids in Asthma—Report of a Workshop Held in Eze, France Oct. 1992," Am. Rev. Respir. Dis. 148:S1-S26 (1993).
Bartholomeusz et al., "Targeting the PI3K Signaling Pathway in Cancer Therapy," Expert Opin. Ther. Targets 16(1):121-130 (2012).
Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retrieved from the Internet Nov. 29, 2011.

(56) References Cited

OTHER PUBLICATIONS

Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).
Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation." *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GSI1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," (2009). *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.(Tokyo)* 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," J. Clin. Oncol. 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Dijksman et al., "271.1: 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).

(56) References Cited

OTHER PUBLICATIONS

Ding et al., "A concise and traceless linker strategy toward combinatorial libraries of 2,6,9-substituted purines," *J. Org. Chem.* 66(24):8273-8276 (2001).

Ding et al., "Resin-capture and release strategy toward combinatorial libraries of 2,6,9-substituted purines," *J. Comb. Chem.* 4(2):183-186 (2002).

Donati, G., "Emerging therapies for neovascular age-related macular degeneration: state of the art," *Ophthalmologica* 221(6):366-377 (2007).

European Examination Report for EP Application No. 07873406.8 dated Sep. 14, 2011.

European Search Report for EP Application No. 05857011.0 dated Feb. 4, 2011.

European Search Report for EP Application No. 09700784.3 dated Oct. 28, 2011.

European Search Report and Search Opinion for EP Application No. 09700424.6 dated Oct. 26, 2011.

European Search Report for EP Application No. 07873406.8 dated Mar. 1, 2010.

European Search Report for EP Application No. 07754845.1 dated Sep. 20, 2011.

Examination Report for GB Application No. GB 0819947.3 dated Oct. 27, 2010.

Extended European Search Report for EP Application No. 09816603.6 dated Mar. 19, 2012.

Extended European Search Report from European Application No. 09700784.3 dated Oct. 28, 2011.

Fajans et al., "Maturity onset diabetes of the young (MODY)," *Diabet. Med.* 13(9 Suppl.6):S90-S95 (1996).

Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).

Feldman et al., "Active-Site Inhibitors of mTOR Target Rapamycin-Resistant Outputs of mTORC1 and mTORC2," *PLoS Biol.* 7(2):371-383 (2009).

Fingl et al., "Chapter 1—General Principles," The Pharmacological Basis of Therapeutics, 5th edition, Goodman and Gilman editors, MacMillan Publishings Co., Inc., New York, pp. 1-46, (1975).

Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).

Forrest et al., "Carbonyl Reductase," *Chem. Biol. Interact.* 129(1-2): 21-40 (2000).

Forrest et al., "Induction of a human carbonyl reductase gene located on chromosome 21," *Biochem. Biophys. Acta.* 1048(2-3):149-155 (1990).

Franzen, "The Suzuki, the Heck, and the Stille reaction—three versatile methods for the introduction of new C—C bonds on solid support," *Can. J. Chem.* 78:957-962 (2000).

Funder et al., "Mineralocorticoid action: target tissue specificity is enzyme, not receptor, mediated," *Science* 242:583-585 (1998).

Fung-Leung, W. P., "Phosphoinositide 3-kinase delta (PI3Kδ) in leukocyte signaling and function," *Cell Signal* 23:603-608 (2011).

Furukawa, T., "Molecular Targeting Therapy for Pancreatic Cancer: Current Knowledge and Perspectives from Bench to Bedside," *J. Gastroenterol.* 43(12):905-911 (2008).

Garber et al., "Diversity of gene expression in adenocarcinoma of the lung," *Proc. Natl. Acad. Sci. U.S.A.* 98(24):13784-13789 (2001).

Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," *Bioorg. Med. Chem. Lett.* 18(9):2924-2929 (2008).

Gonzalez et al., "Protection against daunorubicin cytotoxicity by expression of a cloned human carbonyl reductase cDNA in K562 leukemia cells," *Cancer Res.* 55(20):4646-4650.

Graber et al., "The protein tyrosine kinase inhibitor herbimycin A, but not genistein, specifically inhibits signal transduction by the T cell antigen receptor," *Int. Immunol.* 4(1):1201-1210 (1992).

Graupera et al., "Angiogenesis selectively requires the p110α isoform of PI3K to control endothelial cell migration," *Nature* 453(7195):662-666 (2008).

Gunther et al., "Acute pathological effects on rats of orally administered wortmannin-containing preparations and purified wortmannin from Fusarium oxysponun," *Food Chem. Toxicol.* 27(3):173-179 (1989).

Gunther et al., "Immunosuppressive effects of dietary wortmannin on rats and mice," *Immunopharmacol. Inununotoxicol.* 11(4):559-570 (1989).

Haase et al., "Detection of viral nucleic acids by in situ hybridization," *Methods in Virology* 7:189-226 (1984).

Haluska et al., "The RTK/RAS/BRAF/PI3K Pathways in Melanoma: Biology, Small Molecule Inhibitors, and Potential Applications," *Semin. Oncol.* 34(6):546-554 (2007).

Hanefeld et al., "One-pot synthesis of tetrasubstituted pyrazoles proof of regiochemistiy," *J. Chem. Soc. Perkin* 1 1545-1552 (1996).

Harada et al., "Novel role of phosphatidylinositol 3-kinase in CD28-mediated costimulation," *J. Biol. Chem.* 276(12):9003-9008 (2001).

Harding et al., "CD28-mediated signalling co-stimulates murine T cells and prevents induction of anergy in T-cell clones," *Nature* 356(6370):607-609 (1992).

Hasselblom et al., "High immunohistochemical expression of p-AKT predicts inferior survival in patients with diffuse large B-cell lymphoma treated with immunochemotherapy," *Brit. J. Haematol.* 149:560-568 (2010).

Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).

Hellwinkel et al., "Heterocyclensynthesen mit MF/A1203-basensystemen; 2-arylbenzofumne and 2,3-diarylisochinolin-1(2H)-one," *Synthesis* 1995( 9):1135-1141 (1995).

Herishanu et al., "The lymph node microenvironment promotes B-cell receptor signaling, NF-κB activation, and tumor proliferation in chronic lymphocytic leukemia," *Blood* 117(2):563-574 (2011).

Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).

Herman et al., "The role of phosphatidylinositol 3-kinase-δ in the immunomodulatory effects of lenalidomide in chronic lymphocytic leukemia," *Blood* 117(16):4323-4327 (2011).

Herrera et al., "The dual PI3K/mTOR inhibitor BEZ235 is effective in lung cancer cell lines," *Anticancer Res.* 31:849-854 (2011).

Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).

Hirsch et al., "CALming Down T Cell Acute Leukemia," *Cancer Cell* 21:449-450 (2012).

Hirsch et al., "Central Role for G Protein-Coupled Phosphoinositide 3-Kinase γ in Inflammation," *Science* 287:1049-1053 (2000).

Hoellenriegel and Burger, "Phosphoinositide 3'-kinase delta: turning off BCR signaling in Chronic Lymphocytic Leukemia," *Oncotarget* 2(10):737-738 (2011).

Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).

Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).

Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).

Ikeda et al., "PI3K/p110δ is a novel therapeutic target in multiple myeloma," *Blood* 116(9):1460-1468 (2010).

(56) References Cited

OTHER PUBLICATIONS

International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-Y-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin* 18:857-862 (1978).
Kundu et al., "Palladium-catalysed heteroannualation with terminal alkynes; a highly regio-and stereoselective synthesis of (Z)-3-aryl(alykl)idene isoindolin-l-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).

(56) References Cited

OTHER PUBLICATIONS

Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition As a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," *Curr. Med. Chem.* 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," *Blood (ASH Annual Meeting Abstracts)*, 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase" *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV-synthesis of methyl, 3-formyl & other 3-substituted N-arylisoquinolones." *Indian J. Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more " *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).

Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteroid dehydrogenases with retained oxidoreductase activities," *Protein Expr. Purif.* 26(3):349-356 (2002).
Norman, "Selective PI3K-delta Inhibitors, A Review of the Patent Literature," Expert Opinion on Therapeutic Patents, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3):163-166 (1989).
Petrie et al., "Novel biotinylated adenylate analogue derived from pymzolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pm-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).
Prasad et al., "Src-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7[1,3-dihydroxy-2-propoxy)methyl]pyrrolo[2,3-d]pyrimidines," *J. Med. Chem.* 33(7):1984-1992 (1990).

(56) References Cited

OTHER PUBLICATIONS

Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2( Suppl. 1):S5-S19 (1992).
Rizzatti et al., "Gene expression profiling of mantle cell lymphoma cells reveals aberrant expression of genes from the PI3K-AKT, WNT and TGFβ signaling pathways,", *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Romero et al., "Cloning and expression of the bovine 11b-hydroxysteroid dehydrogenase type-2," *J. Steroid Biochem. Mol. Biol.* 72(5):231-237 (2000).
Rommel et al., "PI3Kδ and PI3Kγ: partners in crime in inflammation in rheumatoid arthritis and beyond?" *Nat. Rev. Immunol.* 7:191-201 (2007).
Roti et al., "Recent developments in the use of biologics in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, A PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 ( Pt 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).

Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecatboxylic Acids into N-Amino Pyrazolopyridinones," *Journal of Heterocyclic Chemistry* 39(6): 1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).

(56) References Cited

OTHER PUBLICATIONS

Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood* (*ASH Annual Meeting Abstracts*) 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines-potent inhibitors of the tyrosine kinase c-Src," Bioorg. Med. Chem. Lett. 11(6):849-852 (2001).
Wiesinger et al., "Antiinflammatory activity of the new mould metabolite 11-desacetoxy-wortmannin and of some of its derivatives," *Experientia* 30(2):135-136 (1974).
Wolff, Burger's Medicinal Chemistry, $5^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late Gi phase of the cell cycle," *Cancer Res.* 52(23):6676-6681 (1992).
Zhao and Vogt, "Class I PI3K in oncogenic cellular transformation," *Oncogene* 27(41):5486-5496 (2008).
U.S. Appl. No. 13/552,460, filed Jul. 18, 2012, U.S. Pat. No. 8,969,363, Heterocyclic Compounds and Uses Thereof.
U.S. Appl. No. 13/552,473, filed Jul. 18, 2012, U.S. Pat. No. 9,056,877, Heterocyclic Compounds and Uses Thereof.
U.S. Appl. No. 13/552,516, filed Jul. 18, 2012, U.S. Pat. No. 8,785,470, Heterocyclic Compounds and Uses Thereof.
U.S. Appl. No. 13/841,265, filed Mar. 15, 2013, U.S. Pat. No. 8,940,742, Heterocyclic Compounds and Uses Thereof.
U.S. Appl. No. 13/839,912, filed Mar. 15, 2013, 2014-0120060, Treatment of Rheumatoid Arthritis and Asthma Using PI3 Kinase Inhibitors.
U.S. Appl. No. 14/209,842, filed Mar. 13, 2014, U.S. Pat. No. 9,481,667, Salts and Solid Forms of Isoquinolinones and Composition Comprising and Methods of Using the Same.
U.S. Appl. No. 14/840,822, filed Mar. 15, 2013, 2014-0120083, Treatment of Cancers Using PI3 Kinase Isoform Modulators.
U.S. Appl. No. 12/811,695, filed Nov. 11, 2010, U.S. Pat. No. 8,703,777, Substituted Bicyclic Compounds and Methods of Use Thereof.
U.S. Appl. No. 12/503,776, filed Jul. 15, 2009, U.S. Pat. No. 8,193,182, Substituted Isoquinolin-1(2H)-Ones, and Methods of Use Thereof.
U.S. Appl. No. 13/403,394, filed Feb. 23, 2012, U.S. Pat. No. 8,785,456, Certain Chemical Entities, Compositions and Methods.
U.S. Appl. No. 13/350,444, filed Jan. 13, 2012, U.S. Pat. No. 8,569,323, Substituted Isoquinolin-1(2H)-One Compounds, Compositions, and Methods Thereof.
U.S. Appl. No. 13/121,157, filed Aug. 2, 2011, U.S. Pat. No. 8,703,778, Heterocyclic Kinase Inhibitors.
U.S. Appl. No. 13/289,540, filed Nov. 4, 2011, U.S. Pat. No. 8,785,454, Heterocyclic Compounds and Uses Thereof.
U.S. Appl. No. 13/293,828, filed Nov. 10, 2011, U.S. Pat. No. 8,901,133, Heterocyclic Compounds and Uses Thereof.
U.S. Appl. No. 13/112,611, filed May 20, 2011, U.S. Pat. No. 8,604,032, Chemical Compounds, Compositions and Methods for Kinase Modulation.
U.S. Appl. No. 13/347,423, filed Jan. 10, 2012, U.S. Pat. No. 8,809,349, Processes for Preparing Isoquinolinones and Solid Forms of Isoquinolinones.
U.S. Appl. No. 13/837,195, filed Mar. 15, 2013, U.S. Pat. No. 8,828,998, Treatment of Lupus, Fibrotic Conditions, and Inflammatory Myopathies and Other Disorders Using PI3 Kinase Inhibitors.
U.S. Appl. No. 14/222,488, filed Mar. 21, 2014, 2014-0206684, Certain Chemical Entities, Compositions and Methods.
U.S. Appl. No. 14/085,660, filed Nov. 20, 2013, U.S. Pat. No. 9,181,221, Chemical Compounds, Compositions and Methods for Kinase Modulation.
U.S. Appl. No. 14/099,831, filed Dec. 6, 2013, U.S. Pat. No. 9,115,141, Heterocyclic Compounds and Uses Thereof.
U.S. Appl. No. 14/776,604, filed Sep. 14, 2015, 2016-0024051, Salts and Solid Forms of Isoquinolinones and Composition Comprising and Methods of Using the Same.
U.S. Appl. No. 13/971,793, filed Aug. 20, 2013, U.S. Pat. No. 9,206,182, Certain Chemical Entities, Compositions and Methods.
U.S. Appl. No. 15/026,947, filed Apr. 1, 2016, U.S. Pat. No. 9,751,888, Heterocyclic Compounds and Uses Thereof.
U.S. Appl. No. 14/506,429, filed Oct. 3, 2014, U.S. Pat. No. 9,359,365, Heterocyclic Compounds and Uses Thereof.
U.S. Appl. No. 14/222,500, filed Mar. 21, 2014, U.S. Pat. No. 9,296,742, Heterocyclic Kinase Inhibitors.
U.S. Appl. No. 14/292,475, filed May 30, 2014, 2014-0377258, Treatment of Cancers Using PI3 Kinase Isoform Modulators.
U.S. Appl. No. 15/030,701, filed Apr. 20, 2016, 2016-0244452, Heterocyclic Compounds and Uses Thereof.
U.S. Appl. No. 14/297,526, filed Jun. 5, 2014, U.S. Pat. No. 9,546,180, Heterocyclic Compounds and Uses Thereof.
U.S. Appl. No. 14/296,953, filed Jun. 5, 2014, U.S. Pat. No. 9,216,982, Certain Chemical Entities, Compositions and Methods.
U.S. Appl. No. 14/302,340, filed Jun. 11, 2014, U.S. Pat. No. 9,315,505, Heterocyclic Compounds and Uses Thereof.
U.S. Appl. No. 14/327,499, filed Jul. 9, 2014, U.S. Pat. No. 9,290,497, Processes for Preparing Isoquinolinones and Solid Forms of Isoquinolinones.
U.S. Appl. No. 14/439,965, filed Apr. 30, 2015, 2015-0283142, Treatment of Cancers Using PI3 Kinase Isoform Modulators.
U.S. Appl. No. 14/448,998, filed Jul. 31, 2014, U.S. Pat. No. 9,527,847, Treatment of Lupus, Fibrotic Conditions, and Inflammatory Myopathies and Other Disorders Using PI3 Kinase Inhibitors.
U.S. Appl. No. 14/512,262, filed Oct. 10, 2014, U.S. Pat. No. 9,388,183, Heterocyclic Compounds and Uses Thereof.
U.S. Appl. No. 14/573,961, filed Dec. 17, 2014, U.S. Pat. No. 9,255,108, Heterocyclic Compounds and Uses Thereof.

(56) References Cited

OTHER PUBLICATIONS

U.S. Appl. No. 15/059,962, filed Mar. 3, 2016, U.S. Pat. No. 9,822,131, Certain Chemical Entities, Compositions and Methods.
U.S. Appl. No. 14/661,656, filed Mar. 18, 2015, U.S. Pat. No. 9,775,844, Heterocyclic Compounds and Uses Thereof.
U.S. Appl. No. 14/592,628, filed Jan. 8, 2015, U.S. Pat. No. 9,718,815, Heterocyclic Compounds and Uses Thereof.
U.S. Appl. No. 14/687,714, filed Apr. 15, 2015, 2015-0320754, Combination Therapies.
U.S. Appl. No. 14/687,768, filed Apr. 15, 2015, 2015-0320755, Combination Therapies.
U.S. Appl. No. 14/695,699, filed Apr. 24, 2015, U.S. Pat. No. 9,828,377, Heterocyclic Compounds and Uses Thereof.
U.S. Appl. No. 14/710,336, filed May 12, 2015, U.S. Pat. No. 9,605,003, Heterocyclic Compounds and Uses Thereof.
U.S. Appl. No. 15/051,529, filed Feb. 23, 2016, U.S. Pat. No. Re. 46,621, Processes for Preparing Isoquinolinones and Solid Forms of Isoquinolinones.
U.S. Appl. No. 14/874,328, filed Oct. 2, 2015, U.S. Pat. No. 9,708,348, Heterocyclic Compounds and Uses Thereof.
U.S. Appl. No. 15/264,417, filed Sep. 13, 2016, U.S. Pat. No. 10,160,761, Solid Forms of Isoquinolinones, and Process of Making, Composition Comprising, and Methods of Using the Same.
U.S. Appl. No. 14/869,637, filed Sep. 29, 2015, U.S. Pat. No. 9,738,644, Chemical Compounds, Compositions and Methods for Kinase Modulation.
U.S. Appl. No. 14/876,589, filed Oct. 6, 2015, 2016-0022692, Treatment of Rheumatoid Arthritis and Asthma Using PI3 Kinase Inhibitors.
U.S. Appl. No. 14/884,612, filed Oct. 15, 2015, U.S. Pat. No. 9,522,146, Certain Chemical Entities, Compositions and Methods.
U.S. Appl. No. 14/894,854, filed Nov. 30, 2015, 2016-0113932, Treatment of Cancers Using PI3 Kinase Isoform Modulators.
U.S. Appl. No. 14/938,647, filed Nov. 11, 2015, U.S. Pat. No. 9,655,892, Certain Chemical Entities, Compositions and Methods.
U.S. Appl. No. 14/971,954, filed Dec. 16, 2015, 2016-0207940, Heterocyclic Compounds and Uses Thereof.
U.S. Appl. No. 15/016,117, filed Feb. 4, 2016, U.S. Pat. No. 9,840,505, Processes for Preparing Isoquinolinones and Solid Forms of Isoquinolinones.
U.S. Appl. No. 15/050,029, filed Feb. 22, 2016, U.S. Pat. No. 9,790,228, Heterocyclic Kinase Inhibitors.
U.S. Appl. No. 16/312,896, filed Dec. 21, 2018, 2019-0216816, Combination Therapies.
U.S. Appl. No. 16/308,377, filed Dec. 7, 2018, 2019-0135833, Heterocyclic Compounds and Uses Thereof.
U.S. Appl. No. 15/179,570, filed Jun. 10, 2016, Heterocyclic Compounds and Uses Thereof.
U.S. Appl. No. 15/333,803, filed Oct. 25, 2016, 2017-0137407, Heterocyclic Compounds and Uses Thereof.
U.S. Appl. No. 15/347,489, filed Nov. 9, 2016, 2017-0281614, Certain Chemical Entities, Compositions and Methods.
U.S. Appl. No. 15/599,378, filed May 18, 2017, 2018-0098983, Certain Chemical Entities, Compositions and Methods.
U.S. Appl. No. 15/621,815, filed Jun. 13, 2017, U.S. Pat. No. 10,253,047, Heterocyclic Compounds and Uses Thereof.
U.S. Appl. No. 15/621,764, filed Jun. 13, 2017, Chemical Compounds, Compositions and Methods for Kinase Modulation.
U.S. Appl. No. 15/621,964, filed Aug. 9, 2017, 2018-0055852, Heterocyclic Compounds and Uses Thereof.
U.S. Appl. No. 15/675,185, filed Aug. 11, 2017, Heterocyclic Compounds and Uses Thereof.
U.S. Appl. No. 15/794,816, filed Oct. 26, 2017, U.S. Pat. No. 10,329,299, Heterocyclic Compounds and Uses Thereof.
U.S. Appl. No. 15/799,612, filed Oct. 31, 2017, 2018-0273535, Processes for Preparing Isoquinolinones and Solid Forms of Isoquinolinones.
U.S. Appl. No. 15/789,868, filed Oct. 20, 2017, 2018-0258103, Certain Chemical Entities, Compositions and Methods.
U.S. Appl. No. 16/172,539, filed Oct. 26, 2018, 2019-0290636, Certain Chemical Entities, Compositions and Methods.
U.S. Appl. No. 16/197,195, filed Nov. 20, 2018, 2019-0185477, Solid Forms of Isoquinolinones, and Process of Making, Composition Comprising, and Methods of Using the Same.
U.S. Appl. No. 16/290,545, filed Mar. 1, 2019, Heterocyclic Compounds and Uses Thereof.
U.S. Appl. No. 16/417,420, filed May 20, 2019, Heterocyclic Compounds and Uses Thereof.
U.S. Appl. No. 16/556,048, filed Aug. 29, 2019, Certain Chemical Entities, Compositions and Methods.

* cited by examiner

US 10,759,806 B2

ISOTOPOLOGUES OF ISOQUINOLINONE AND QUINAZOLINONE COMPOUNDS AND USES THEREOF AS PI3K KINASE INHIBITORS

This application is a national phase entry pursuant to 35 U.S.C. § 371 of International Application No. PCT/US2017/022705, filed Mar. 16, 2017, which claims priority to U.S. Provisional Application No. 62/309,769, filed Mar. 17, 2016, the entirety of each of which is incorporated herein by reference.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K-δ is expressed primarily in hematopoietic cells including leukocytes such as T-cells, dendritic cells, neutrophils, mast cells, B-cells, and macrophages. PI3K-δ is integrally involved in mammalian immune system functions such as T-cell function, B-cell activation, mast cell activation, dendritic cell function, and neutrophil activity. Due to its integral role in immune system function, PI3K-δ is also involved in a number of diseases related to undesirable immune response such as allergic reactions, inflammatory diseases, inflammation mediated angiogenesis, rheumatoid arthritis, and auto-immune diseases such as lupus, asthma, emphysema and other respiratory diseases. Other class I PI3K involved in immune system function includes PI3K-γ, which plays a role in leukocyte signaling and has been implicated in inflammation, rheumatoid arthritis, and autoimmune diseases such as lupus. For example, PI3K-γ and PI3K-δ are highly expressed in leukocytes and have been associated with adaptive and innate immunity; thus, these PI3K isoforms can be important mediators in inflammatory disorders and hematologic malignancies.

The gamma (γ) isoform of class I PI3K consists of a catalytic subunit p110γ, which is associated with a p101 regulatory subunit. PI3K-γ is regulated by G protein-coupled receptors (GPCRs) via association with the β/γ subunits of heterotrimeric G proteins. PI3K-γ is expressed primarily in hematopoietic cells and cardiomyocytes and is involved in inflammation and mast cell function. Inhibitors of PI3K-γ are useful for treating a variety of inflammatory diseases, allergies, and cardiovascular diseases, among others.

Unlike PI3K-δ, the beta (β) isoform of class I PI3K appears to be ubiquitously expressed. PI3K-β has been implicated primarily in various types of cancer including PTEN-negative cancer (Edgar et al. *Cancer Research* (2010) 70(3):1164-1172), and HER2-overexpressing cancer such as breast cancer and ovarian cancer.

Certain isoquinolinone or quinazolinone compounds that are capable of selectively inhibiting one or more isoform(s) of class I PI3K have been described in International Application Publication Nos. WO 2015/051244 and WO 2015/143012, the entireties of which are incorporated herein by reference. A need still exists for developing isotopologues of the isoquinolinone or quinazolinone compounds that are more metabolically stable, more therapeutically effective, or can be prepared by more efficient and scalable processes.

SUMMARY

Provided herein are isotopologues of certain isoquinolinone or quinazolinone compounds that are capable of selectively inhibiting one or more isoform(s) of class I PI3K without substantially affecting the activity of the remaining isoforms of the same class. For example, in some embodiments, non-limiting examples of inhibitors capable of selectively inhibiting PI3K-δ and/or PI3K-γ, but without substantially affecting the activity of PI3K-α and/or PI3K-β are provided. In one embodiment, the inhibitors provided herein can be effective in ameliorating disease conditions associated with PI3K-δ and/or PI3K-γ activity. In one embodiment, the compounds are capable of selectively inhibiting PI3K-γ over PI3K-δ.

In one embodiment, provided herein is a compound of Formula (AB'):

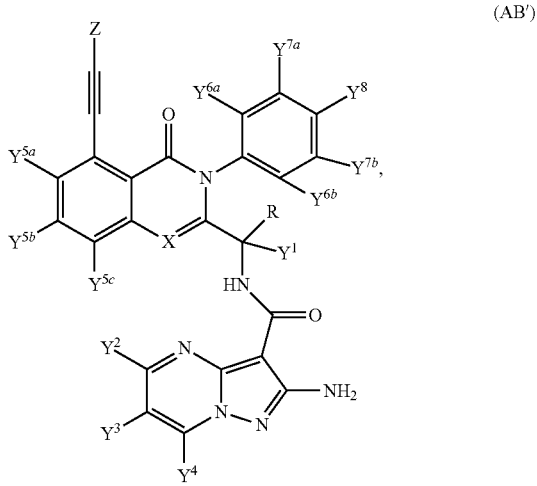

(AB')

or a pharmaceutically acceptable form thereof, wherein R, X, $Y^1$, $Y^2$, $Y^3$, $Y^4$, $Y^{5a}$, $Y^{5b}$, $Y^{5c}$, $Y^{6a}$, $Y^{6b}$, $Y^{7a}$, $Y^{7b}$, $Y^8$, and Z are defined herein.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DETAILED DESCRIPTION

Definitions

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, an "isotopologue" is an isotopically enriched compound.

The term "isotopic enrichment" refers to the percentage of incorporation of an amount of a specific isotope at a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

The term "isotopic enrichment factor" refers to the ratio between the isotopic composition and the natural isotopic composition of a specified isotope.

With regard to the compounds provided herein, when a particular atomic position is designated as deuterium or "D," it is understood that the abundance of deuterium at that position is substantially greater than the natural abundance of deuterium, which is about 0.0156%. A position designated as deuterium typically has a minimum isotopic enrichment factor of, in certain embodiments, at least about 1000 (about 15% deuterium incorporation), at least about 2000 (about 30% deuterium incorporation), at least about 3000 (about 45% deuterium incorporation), at least about 3500 (about 52.5% deuterium incorporation), at least about 4000 (about 60% deuterium incorporation), at least about 4500 (about 67.5% deuterium incorporation), at least about 5000 (about 75% deuterium incorporation), at least about 5500 (about 82.5% deuterium incorporation), at least about 6000 (about 90% deuterium incorporation), at least about 6333.3 (about 95% deuterium incorporation), at least about 6466.7 (about 97% deuterium incorporation), at least about 6600 (about 99% deuterium incorporation), or at least about 6633.3 (about 99.5% deuterium incorporation) at each designated deuterium atom.

The isotopic enrichment and isotopic enrichment factor of the compounds provided herein can be determined using conventional analytical methods known to one of ordinary skill in the art, including mass spectrometry and nuclear magnetic resonance spectroscopy.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis*, 3rd ed., Cambridge University Press, Cambridge, 1987.

As used herein, and unless otherwise specified, the term "alkyl" refers to a straight or branched hydrocarbon chain radical consisting solely of carbon and hydrogen atoms, containing no unsaturation, having, in some embodiments, from one to ten carbon atoms (e.g., $C_1$-$C_{10}$ alkyl). Linear or straight alkyl refers to an alkyl with no branching, e.g., methyl, ethyl, n-propyl. Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, 4 carbon atoms, etc., up to and including 10 carbon atoms, although the present definition also covers the occurrence of the term "alkyl" where no numerical range is designated. In some embodiments, an alkyl is a $C_1$-$C_6$ alkyl group. In some embodiments, alkyl groups have 1 to 10, 1 to 6, 1 to 4, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, and unless otherwise specified, the term "alkenyl" refers to a straight or branched hydrocarbon chain radical group consisting solely of carbon and hydrogen atoms, containing at least one double bond, and in some embodiments, having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, 4 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)—$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, and unless otherwise specified, the term "alkynyl" refers to a straight or branched hydrocarbon chain radical group consisting solely of carbon and hydrogen atoms, containing at least one triple bond, having, in some embodiments, from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, 4 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)—$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, and unless otherwise specified, the term "cycloalkyl," or alternatively, "carbocyclyl," refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl, and the like. Unless stated otherwise in the specification, a cycloalkyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "cycloalkyl" or "carbocyclyl" also includes ring systems wherein the cycloalkyl or carbocyclyl ring, as defined above, is fused with one or more aryl or heteroaryl groups wherein the point of attachment to the parent molecular structure is on the cycloalkyl or carbocyclyl ring.

As used herein, and unless otherwise specified, the term "heterocyclyl", "heterocycloalkyl" or 'heterocarbocyclyl' each refer to any 3- to 18-membered non-aromatic radical monocyclic or polycyclic moiety comprising at least one ring heteroatom selected from nitrogen, oxygen, phosphorous, and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or more rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heterocyclyl radicals whose names end in "-yl" by removal of one hydrogen atom from the atom with the free valence are named by adding "-idene" to the name of the corresponding univalent radical, e.g., a piperidyl group with two points of attachment is a piperidylidene.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3- to 10-membered non-aromatic ring system having ring carbon atoms and 1 to 4 ring heteroatoms, wherein each heteroatom is independently selected from nitrogen, oxygen, phosphorous, and sulfur ("3- to 10-membered heterocyclyl"). In some embodiments, a heterocyclyl group is a 5- to 8-membered non-aromatic ring system having ring carbon atoms and 1 to 4 ring heteroatoms, wherein each heteroatom is independently selected from nitrogen, oxygen, phosphorous, and sulfur ("5- to 8-membered heterocyclyl"). In some embodiments, a heterocyclyl group is a 5- to 6-membered non-aromatic ring system having ring carbon atoms and 1 to 4 ring heteroatoms, wherein each heteroatom is independently selected from nitrogen, oxygen, phosphorous, and sulfur ("5- to 6-membered heterocyclyl"). In some embodiments, the 5- to 6-membered heterocyclyl has 1 to 3 ring heteroatoms independently selected from nitrogen, oxygen, phosphorous, and sulfur. In some embodiments, the 5- to 6-membered heterocyclyl has 1 to 2 ring heteroatoms independently selected from nitrogen, oxygen, phosphorous, and sulfur. In some embodiments, the 5- to 6-membered heterocyclyl has 1 ring heteroatom selected from nitrogen, oxygen, phosphorous, and sulfur.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydro-pyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

As used herein, and unless otherwise specified, the term "aryl" refers to a radical with six to fourteen ring atoms (e.g., $C_6$-$C_{14}$ or $C_6$-$C_{10}$ aryl) which has at least one carbocyclic ring having a conjugated pi electron system which is aromatic (e.g., having 6, 10, or 14 π electrons shared in a cyclic array) (e.g., phenyl, fluorenyl, and naphthyl). In one embodiment, bivalent radicals formed from substituted benzene derivatives and having the free valences at ring atoms are named as substituted phenylene radicals. In other embodiments, bivalent radicals derived from univalent monocyclic or polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "aryl" also includes ring systems wherein the aryl ring, as defined above, is fused with one or more cycloalkyl or heterocyclyl groups wherein the point of attachment to the parent molecular structure is on the aryl ring.

As used herein, and unless otherwise specified, the term "heteroaryl", or alternatively, "heteroaromatic", refers to a radical of a 5- to 18-membered monocyclic or polycyclic (e.g., bicyclic or tricyclic) aromatic ring system (e.g., having 6, 10 or 14 π electrons shared in a cyclic array) having ring carbon atoms and 1 to 6 ring heteroatoms provided in the aromatic ring system, wherein each heteroatom is independently selected from nitrogen, oxygen, phosphorous, and sulfur ("5- to 18-membered heteroaryl"). Heteroaryl polycyclic ring systems can include one or more heteroatoms in one or more rings. Whenever it appears herein, a numerical range such as "5 to 18" refers to each integer in the given range; e.g., "5 to 18 ring atoms" means that the heteroaryl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either the ring bearing a heteroatom (e.g., 2-indolyl) or the ring that does not contain a heteroatom (e.g., 5-indolyl). In some embodiments, a heteroaryl group is a 5 to 10 membered aromatic ring system having ring carbon atoms and 1 to 4 ring heteroatoms provided in the aromatic ring system, wherein each heteroatom is independently selected from nitrogen, oxygen, phosphorous, and sulfur ("5- to 10-membered heteroaryl"). In some embodiments, a heteroaryl group is a 5- to 8-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 8-membered heteroaryl"). In some embodiments, a heteroaryl group is a 5- to 6-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 6-membered heteroaryl"). In some embodiments, the 5- to 6-membered heteroaryl has 1 to 3 ring heteroatoms independently selected from nitrogen, oxygen, phosphorous, and sulfur. In some embodiments, the 5- to 6-membered heteroaryl has 1 to 2 ring heteroatoms independently selected from nitrogen, oxygen, phosphorous, and sulfur. In some embodiments, the 5- to 6-membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocyclocta[d]pyrimidinyl, 5,6,7,8,9,10-hexahydrocyclooctа[d]pyridazinyl, 5,6,7,8,9,10-hexahydrocyclooctа[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl).

Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

As used herein, and unless otherwise specified, the term "halo", "halide", or, alternatively, "halogen" means fluoro, chloro, bromo, or iodo.

As used herein, and unless otherwise specified, the term "pharmaceutically acceptable form" of a compound provided herein includes, but is not limited to, pharmaceutically acceptable salts, hydrates, solvates, isomers, prodrugs, and isotopically labeled derivatives of compounds provided herein.

As used herein, and unless otherwise specified, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, naphthalene-m,n-bissulfonates, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, naphthalene-m,n-bissulfonic acids and the like.

Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

As used herein, and unless otherwise specified, the term "solvate" refers to compounds that further include a stoichiometric or non-stoichiometric amount of solvent bound by non-covalent intermolecular forces. The solvate can be of a compound provided herein or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

As used herein, and unless otherwise specified, the term "prodrug" refers to compounds that are transformed in vivo to yield a compound provided herein or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a compound provided herein or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound provided herein or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from naturally occurring L-amino acids, P(O)(OH)$_2$, —P(O)(O($C_1$-$C_6$)alkyl)$_2$, and glycosyl (the radical resulting from the removal of a hydroxyl group of the hemiacetal form of a carbohydrate).

If a compound provided herein or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

As used herein, and unless otherwise specified, the term "isomers" refers to different compounds that have the same molecular formula. "Atropisomers" are stereoisomers from hindered rotation about single bonds and can be resolved or isolated by methods known to those skilled in the art.

As used herein, and unless otherwise specified, the term "stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

As used herein, and unless otherwise specified, the term "enantiomers" are a pair of stereoisomers that are nonsuperimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry can be specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)—. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer.

$$ee=(90-10)/100=80\%.$$

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40%, about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers). such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture contains identical chemical entities except for their stereochemical orientations, namely (S)- or (R)-isomers. For example, if a compound provided herein has —CH(R)— unit, and R is not hydrogen, then the —CH(R)— is in an (S)- or (R)-stereochemical orientation for each of the identical chemical entities (i.e., (S)- or (R)-stereoisomers). In some embodiments, the mixture of identical chemical entities (i.e., mixture of stereoisomers) is a racemic mixture of (S)- and (R)-isomers. In another embodiment, the mixture of the identical chemical entities (i.e., mixture of stereoisomers)

contains predominately (S)-isomer or predominately (R)-isomer. For example, in some embodiments, the (S)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (S)-isomer in the mixture of identical chemical entities (i.e., mixture of stereoisomers) is present at an (S)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the (R)-isomer in the mixture of identical chemical entities (i.e., mixture of stereoisomers) is present at about 55%, about 60%, about 65%, about 70%, about 75%, about 80%, about 85%, about 90%, about 95%, about 96%, about 9'7%, about 98%, about 99%, or about 99.5% by weight, or more, relative to the total weight of the mixture of (S)- and (R)-isomers. In some embodiments, the (R)-isomers in the mixture of identical chemical entities (i.e., mixture of stereoisomers) is present at an (R)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N Y, 1962); and *Tables of Resolving Agents and Optical Resolutions* p. 268 (E. L. Eliel, Ed., Univ. of Notre Dame Press, Notre Dame, Ind. 1972).

As used herein, and unless otherwise specified, the term "tautomer" refers to a type of isomer that includes two or more interconvertable compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent.

Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

As used herein, and unless otherwise specified, the term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as provided herein is contemplated. Supplementary active ingredients can also be incorporated into the pharmaceutical compositions.

As used herein, and unless otherwise specified, the term "subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, and unless otherwise specified, the term "treatment" or "treating" refers to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, and unless otherwise specified, the term "prevention" or "preventing" refers to an approach for obtaining beneficial or desired results including, but not limited, to prophylactic benefit. For prophylactic benefit, the pharmaceutical compositions can be administered to a patient at risk of developing a particular disease, or to a patient reporting one or more of the physiological symptoms of a disease, even though a diagnosis of this disease may not have been made.

As used herein, and unless otherwise specified, the term "selective inhibition" or "selectively inhibit" as applied to a biologically active agent refers to the agent's ability to selectively reduce the target signaling activity as compared to off-target signaling activity, via direct or indirect interaction with the target. For example, a compound that selectively inhibits one isoform of PI3K over another isoform of PI3K has an activity of at least greater than about 1× against a first isoform relative to the compound's activity against the second isoform (e.g., at least about 2×, 3×, 5×, 10×, 20×, 50×, 100×, 200×, 500×, or 1000×). In certain embodiments, these terms refer to (1) a compound of described herein that selectively inhibits the gamma isoform over the alpha, beta, or delta isoform; or (2) a compound described herein that selectively inhibits the delta isoform over the alpha or beta isoform. By way of non-limiting example, the ratio of selectivity can be greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, which in turn can be measured by, e.g., in vitro or in vivo assays such as those described in Examples described herein. In one embodiment, the selectivity of a first PI3K isoform over a second PI3K isoform is measured by the ratio of the $IC_{50}$ value against the second PI3K isoform to the $IC_{50}$ value against the first PI3K gamma isoform. For example, a delta/gamma selectivity ratio of a compound can be measured by the ratio of the compound's inhibitory activity against the delta isoform in terms of $IC_{50}$ or the like to the compound's inhibitory activity against the gamma isoform in terms of $IC_{50}$ or the like. If the delta/gamma selectivity ratio is larger than 1, the compound selectively inhibits the gamma isoform over the delta isoform. In certain embodiments, the PI3K gamma isoform $IC_{50}$ activity of a compound of provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM. In certain embodiments, the PI3K delta isoform $IC_{50}$ activity of a compound provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM.

As used herein, and unless otherwise indicated, the term "about" or "approximately" refers to an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Compounds

Provided herein are isotopologues of certain isoquinolinone or quinazolinone compounds. In some embodiment, the compounds are capable of selectively inhibiting one or more isoform(s) of class I PI3K without substantially affecting the activity of the remaining isoforms of the same class. For example, in some embodiments, non-limiting examples of inhibitors capable of selectively inhibiting PI3K-δ and/or PI3K-γ, but without substantially affecting the activity of PI3K-α and/or PI3K-β are provided. In one embodiment, the inhibitors provided herein can be effective in ameliorating disease conditions associated with PI3K-δ and/or PI3K-γ activity. In one embodiment, the compounds are capable of selectively inhibiting PI3K-γ over PI3K-δ.

Isotopic enrichment (e.g., deuteration) of pharmaceuticals to improve pharmacokinetics ("PK"), pharmacodynamics ("PD"), and toxicity profiles, has been demonstrated previously with some classes of drugs. (See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999)).

Without being limited by a particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In certain embodiments, the deuterium enrichment is performed on the site of C—H bond cleavage during metabolism.

Furthermore, racemization of many compounds involves the breaking of a C—H bond at the chiral center and may be retarded by selective incorporation of deuterium. Therefore, in certain embodiments, provided herein are compounds of Formula (AB') or (AB), in which racemization of the chiral center is retarded by selective incorporation of deuterium. In certain embodiments, provided herein is selective incorporation of deuterium at the $Y^1$ position of Formula (AB') or (AB).

In certain embodiments, provided herein is a compound of Formula (AB'):

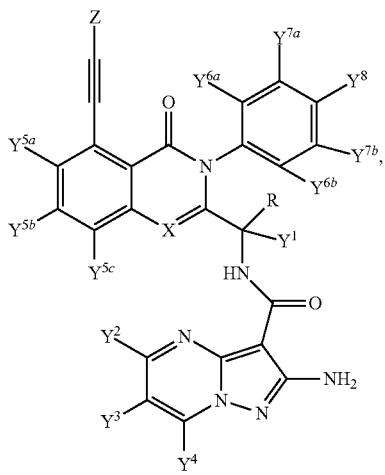

(AB')

or a pharmaceutically acceptable form thereof, wherein

R is $C_1$-$C_3$ alkyl optionally substituted with one or more deuterium or halogen;

X is $CY^{5d}$ or N;

$Y^1$ is hydrogen or deuterium;

$Y^2$, $Y^3$, and $Y^4$ are each independently hydrogen or deuterium;

$Y^{5a}$, $Y^{5b}$, $Y^{5c}$, and $Y^{5d}$ are each independently hydrogen or deuterium;

$Y^{6a}$, $Y^{6b}$, $Y^{7a}$, $Y^{7b}$, and $Y^8$ are each independently hydrogen, deuterium, halogen, or $C_1$-$C_3$ alkyl, wherein each instance of the $C_1$-$C_3$ alkyl is independently optionally substituted with one or more deuterium or halogen;

Z is a 5- to 10-membered heteroaryl optionally substituted with one or more deuterium, halogen, or $C_1$-$C_3$ alkyl, wherein each instance of the $C_1$-$C_3$ alkyl is independently optionally substituted with one or more deuterium or halogen; and at least one of R, $Y^1$, $Y^2$, $Y^3$, $Y^4$, $Y^{5a}$, $Y^{5b}$, $Y^{5c}$, $Y^{5d}$, $Y^{6a}$, $Y^{6b}$, $Y^{7a}$, $Y^{7b}$, $Y^8$, and Z is or comprises a deuterium;

provided that, when $Y^{6a}$, $Y^{6b}$, $Y^{7a}$, $Y^{7b}$, and $Y^8$ are all deuterium, at least one of R, $Y^1$, $Y^2$, $Y^3$, $Y^4$, $Y^{5a}$, $Y^{5b}$, $Y^{5c}$, $Y^{5d}$, and Z is or comprises a deuterium.

In certain embodiments, provided herein is a compound of Formula (AB):

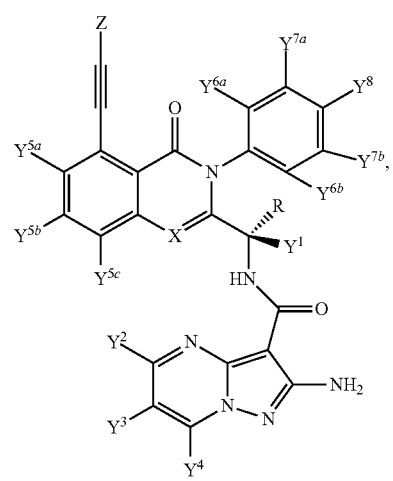

(AB)

or a pharmaceutically acceptable form thereof, wherein

R is $C_1$-$C_3$ alkyl optionally substituted with one or more deuterium or halogen;

X is $CY^{5d}$ or N;

$Y^1$ is hydrogen or deuterium;

$Y^2$, $Y^3$, and $Y^4$ are each independently hydrogen or deuterium;

$Y^{5a}$, $Y^{5b}$, $Y^{5c}$, and $Y^{5d}$ are each independently hydrogen or deuterium;

$Y^{6a}$, $Y^{6b}$, $Y^{7a}$, $Y^{7b}$, and $Y^8$ are each independently hydrogen, deuterium, halogen, or $C_1$-$C_3$ alkyl, wherein each instance of the $C_1$-$C_3$ alkyl is independently optionally substituted with one or more deuterium or halogen;

Z is a 5- to 10-membered heteroaryl optionally substituted with one or more deuterium, halogen, or $C_1$-$C_3$ alkyl, wherein each instance of the $C_1$-$C_3$ alkyl is independently optionally substituted with one or more deuterium or halogen; and at least one of R, $Y^1$, $Y^2$, $Y^3$, $Y^4$, $Y^{5a}$, $Y^{5b}$, $Y^{5c}$, $Y^{5d}$, $Y^{6a}$, $Y^{6b}$, $Y^{7a}$, $Y^{7b}$, $Y^8$, and Z is or comprises a deuterium;

provided that, when $Y^{6a}$, $Y^{6b}$, $Y^{7a}$, $Y^{7b}$, and $Y^8$ are all deuterium, at least one of R, $Y^1$, $Y^2$, $Y^3$, $Y^4$, $Y^{5a}$, $Y^{5b}$, $Y^{5c}$, $Y^{5d}$, and Z is or comprises a deuterium.

In one embodiment, the compound of Formula (AB') is a compound of Formula (A'):

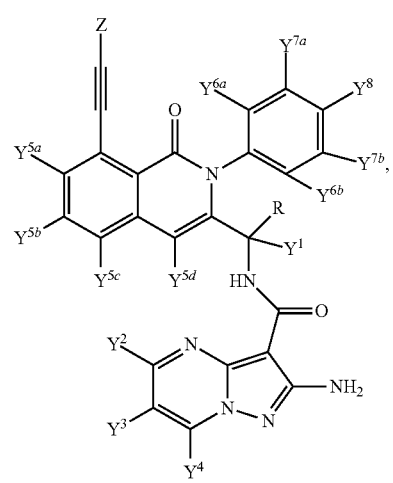

(A')

or a pharmaceutically acceptable form thereof.

In one embodiment, the compound of Formula (AB) is a compound of Formula (A):

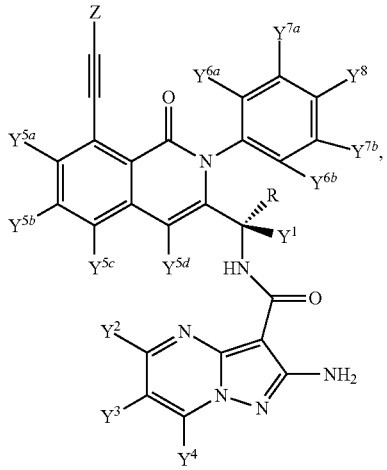

(A)

or a pharmaceutically acceptable form thereof.

In one embodiment, $Y^{5d}$ is deuterium. In another embodiment, $Y^{5d}$ is hydrogen.

In one embodiment, the compound of Formula (AB') is a compound of Formula (B'):

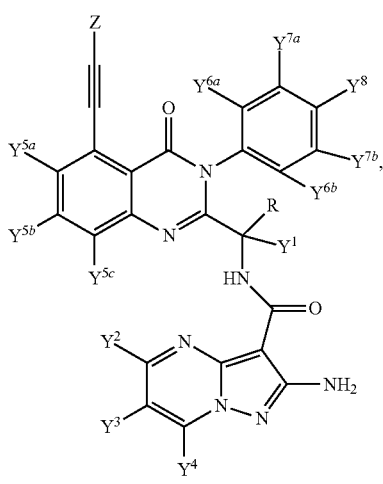

(B')

or a pharmaceutically acceptable form thereof.

In one embodiment, the compound of Formula (AB) is a compound of Formula (B):

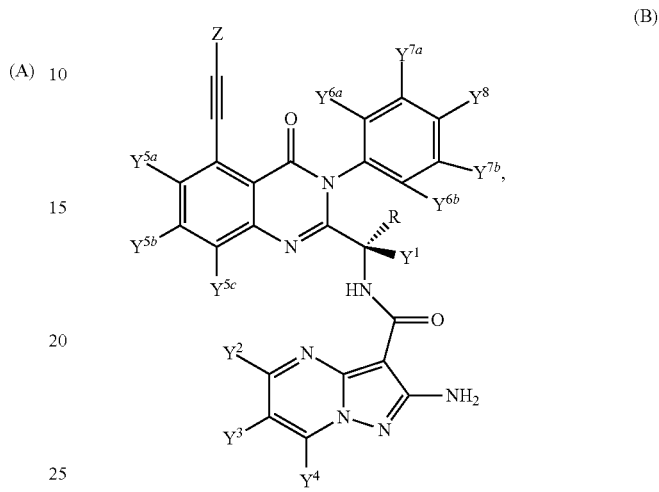

(B)

or a pharmaceutically acceptable form thereof.

In one embodiment, $Y^{5a}$ is deuterium. In another embodiment, $Y^{5a}$ is hydrogen.

In one embodiment, $Y^{5b}$ is deuterium. In another embodiment, $Y^{5b}$ is hydrogen.

In one embodiment, $Y^{5c}$ is deuterium. In another embodiment, $Y^{5c}$ is hydrogen.

In one embodiment, $Y^{5a}$, $Y^{5b}$, and $Y^{5c}$ are all hydrogen.

In one embodiment, one of $Y^{5a}$, $Y^{5b}$, and $Y^{5c}$ is deuterium, and the other two of $Y^{5a}$, $Y^{5b}$, and $Y^{5c}$ are hydrogen. In one embodiment, $Y^{5a}$ is deuterium, and $Y^{5b}$ and $Y^{5c}$ are hydrogen. In one embodiment, $Y^{5b}$ is deuterium, and $Y^{5a}$ and $Y^{5c}$ are hydrogen. In one embodiment, $Y^{5c}$ is deuterium, and $Y^{5a}$ and $Y^{5b}$ are hydrogen.

In one embodiment, two of $Y^{5a}$, $Y^{5b}$, and $Y^{5c}$ are deuterium, and the other of $Y^{5a}$, $Y^{5b}$, and $Y^{5c}$ is hydrogen. In one embodiment, $Y^{5a}$ and $Y^{5b}$ are deuterium, and $Y^{5c}$ is hydrogen. In one embodiment, $Y^{5a}$ and $Y^{5c}$ are deuterium, and $Y^{5b}$ is hydrogen. In one embodiment, $Y^{5b}$ and $Y^{5c}$ are deuterium, and $Y^{5a}$ is hydrogen.

In one embodiment, $Y^{5a}$, $Y^{5b}$, and $Y^{5c}$ are all deuterium.

In one embodiment, the

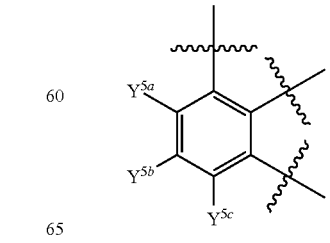

moiety is

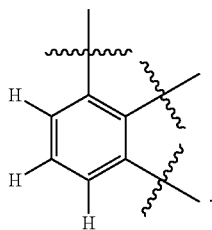 [SMILES: *c1cccc(*)c1*]

In one embodiment, the

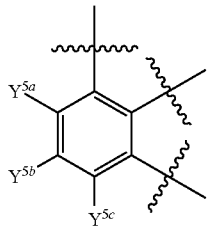

moiety is

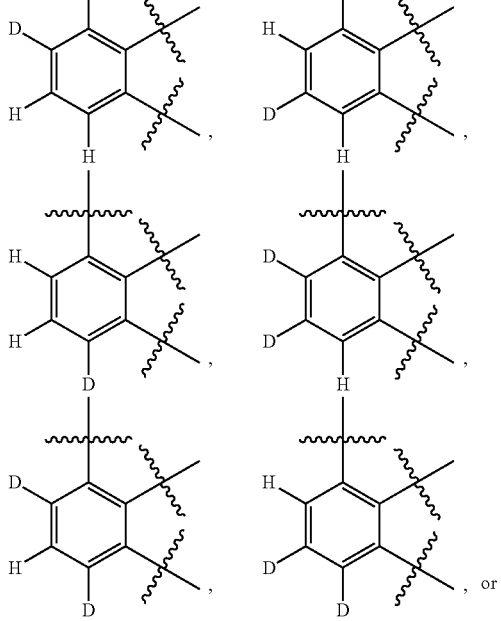

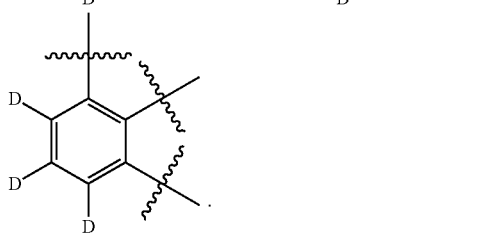

In one embodiment, $Y^{6a}$, $Y^{6b}$, $Y^{7a}$, $Y^{7b}$, and $Y^8$ are each independently hydrogen or deuterium.

In one embodiment, $Y^{6a}$ and $Y^{6b}$ are both hydrogen. In one embodiment, at least one of $Y^{6a}$ and $Y^{6b}$ is deuterium. In one embodiment, one of $Y^{6a}$ and $Y^{6b}$ is deuterium, and the other is hydrogen. In one embodiment, $Y^{6a}$ and $Y^{6b}$ are both deuterium.

In one embodiment, $Y^{7a}$ and $Y^{7b}$ are both hydrogen. In one embodiment, at least one of $Y^{7a}$ and $Y^{7b}$ is deuterium. In one embodiment, one of $Y^{7a}$ and $Y^{7b}$ is deuterium, and the other is hydrogen. In one embodiment, $Y^{7a}$ and $Y^{7b}$ are both deuterium.

In one embodiment, $Y^8$ is deuterium. In another embodiment, $Y^8$ is hydrogen.

In one embodiment, $Y^{6a}$, $Y^{6b}$, $Y^{7a}$, $Y^{7b}$, and $Y^8$ are all hydrogen. In one embodiment, one of $Y^{6a}$, $Y^{6b}$, $Y^{7a}$, $Y^{7b}$, and $Y^8$ is deuterium, and the other four of $Y^{6a}$, $Y^{6b}$, $Y^{7a}$, $Y^{7b}$, and $Y^8$ are hydrogen. In one embodiment, two of $Y^{6a}$, $Y^{6b}$, $Y^{7a}$, $Y^{7b}$, and $Y^8$ are deuterium, and the other three of $Y^{6a}$, $Y^{6b}$, $Y^{7a}$, $Y^{7b}$, and $Y^8$ are hydrogen. In one embodiment, three of $Y^{6a}$, $Y^{6b}$, $Y^{7a}$, $Y^{7b}$, and $Y^8$ are deuterium, and the other two of $Y^{6a}$, $Y^{6b}$, $Y^{7a}$, $Y^{7b}$, and $Y^8$ are hydrogen. In one embodiment, four of $Y^{6a}$, $Y^{6b}$, $Y^{7a}$, $Y^{7b}$, and $Y^8$ are deuterium, and the other one of $Y^{6a}$, $Y^{6b}$, $Y^{7a}$, $Y^{7b}$, and $Y^8$ is hydrogen. In one embodiment, $Y^{6a}$, $Y^{6b}$, $Y^{7a}$, $Y^{7b}$, and $Y^8$ are all deuterium.

In one embodiment, the

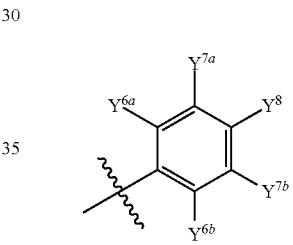

moiety is

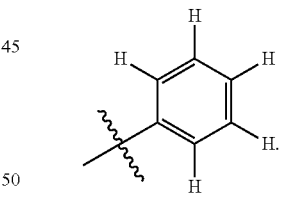

In one embodiment, the

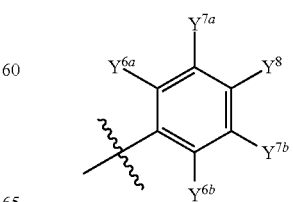

moiety is

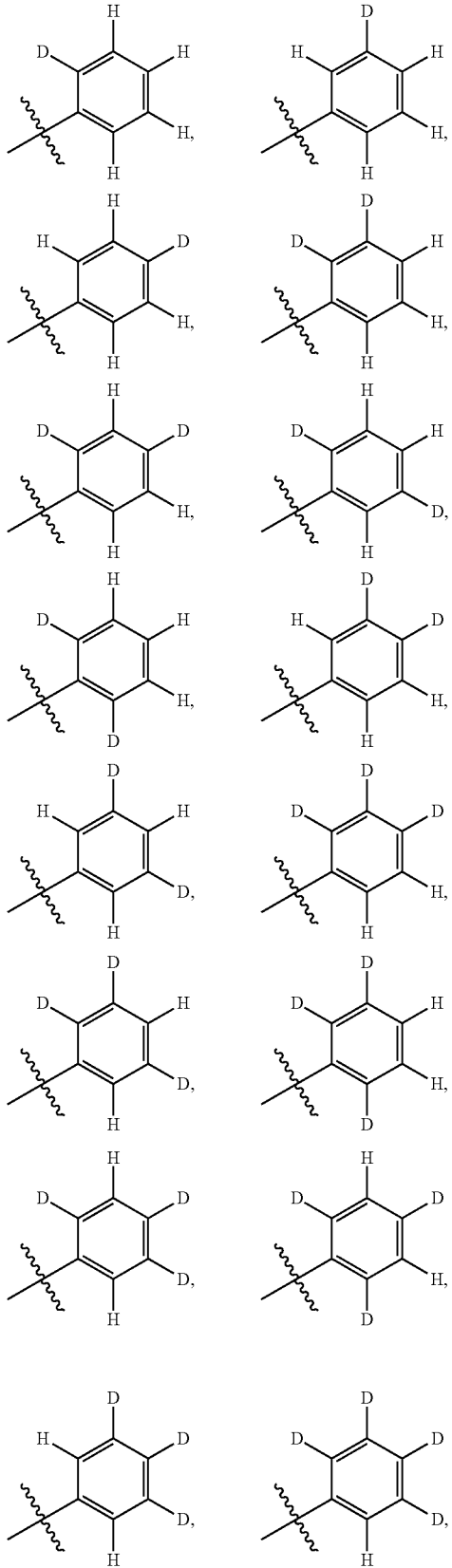

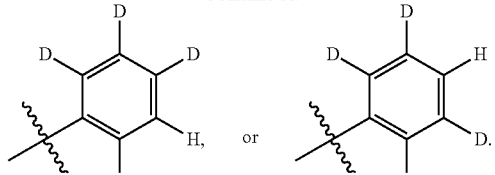

In one embodiment, the

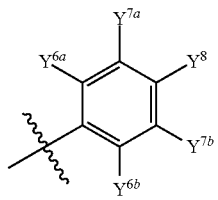

moiety is

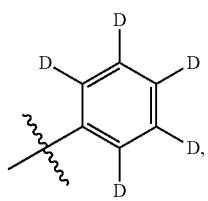

provided that at least one of R, $Y^1$, $Y^2$, $Y^3$, $Y^4$, $Y^{5a}$, $Y^{5b}$, $Y^{5c}$, $Y^{5d}$, and Z is or comprises a deuterium.

In one embodiment, one or more of $Y^{6a}$, $Y^{6b}$, $Y^{7a}$, $Y^{7b}$, and $Y^8$ are halogen. In one embodiment, one of $Y^{6a}$, $Y^{6b}$, $Y^{7a}$, $Y^{7b}$, and $Y^8$ is halogen. In one embodiment, two of $Y^{6a}$, $Y^{6b}$, $Y^{7a}$, $Y^{7b}$, and $Y^8$ are halogen. In one embodiment, three of $Y^{6a}$, $Y^{6b}$, $Y^{7a}$, $Y^{7b}$, and $Y^8$ are halogen. In one embodiment, four of $Y^{6a}$, $Y^{6b}$, $Y^{7a}$, $Y^{7b}$, and $Y^8$ are halogen. In one embodiment, $Y^{6a}$, $Y^{6b}$, $Y^{7a}$, $Y^{7b}$, and $Y^8$ are all halogen. Each instance of the halogen is independently F, Cl, Br, or I. In one embodiment, the halogen is F. In one embodiment, the halogen is Cl. In one embodiment, the halogen is Br. In one embodiment, the halogen is I.

In one embodiment, one or more of $Y^{6a}$, $Y^{6b}$, $Y^{7a}$, $Y^{7b}$, and $Y^8$ are $C_1$-$C_3$ alkyl, wherein the $C_1$-$C_3$ alkyl is optionally substituted with one or more deuterium or halogen. In one embodiment, one of $Y^{6a}$, $Y^{6b}$, $Y^{7a}$, $Y^{7b}$, and $Y^8$ is $C_1$-$C_3$ alkyl, wherein the $C_1$-$C_3$ alkyl is optionally substituted with one or more deuterium or halogen. In one embodiment, two of $Y^{6a}$, $Y^{6b}$, $Y^{7a}$, $Y^{7b}$, and $Y^8$ are $C_1$-$C_3$ alkyl, wherein each instance of the $C_1$-$C_3$ alkyl is independently optionally substituted with one or more deuterium or halogen. In one embodiment, three of $Y^{6a}$, $Y^{6b}$, $Y^{7a}$, $Y^{7b}$, and $Y^8$ are $C_1$-$C_3$ alkyl, wherein each instance of the $C_1$-$C_3$ alkyl is independently optionally substituted with one or more deuterium or halogen. In one embodiment, four of $Y^{6a}$, $Y^{6b}$, $Y^{7a}$, $Y^{7b}$, and $Y^8$ are $C_1$-$C_3$ alkyl, wherein each instance of the $C_1$-$C_3$ alkyl is independently optionally substituted with one or more deuterium or halogen. In one embodiment, $Y^{6a}$, $Y^{6b}$, $Y^{7a}$, $Y^{7b}$, and $Y^8$ are all $C_1$-$C_3$ alkyl, wherein each instance of the $C_1$-$C_3$ alkyl is independently optionally substituted with one or more deuterium or halogen. Each instance of the $C_1$-$C_3$ alkyl is independent of the other, and can be the same or different. In one embodiment, the $C_1$-$C_3$ alkyl is —$CH_3$. In one embodiment, the $C_1$-$C_3$ alkyl is —$CD_3$. In one embodiment, the $C_1$-$C_3$ alkyl is —$CF_3$.

In one embodiment, Z is a 6-membered heteroaryl. In one embodiment, Z is a pyridinyl or pyrimidinyl.

In one embodiment, Z is a 5-membered heteroaryl. In one embodiment, Z is a thiazolyl, pyrazolyl, or imidazolyl. In one embodiment, Z is a pyrazolyl. In one embodiment, Z is a 3-pyrazolyl. In one embodiment, Z is a 4-pyrazolyl. In one embodiment, Z is a 5-pyrazolyl.

In one embodiment, Z is substituted with one or more deuterium, halogen, or $C_1$-$C_3$ alkyl, wherein each instance of the $C_1$-$C_3$ alkyl is independently optionally substituted with one or more deuterium or halogen.

In one embodiment, Z is substituted with one or more $C_1$-$C_3$ alkyl, wherein each instance of the $C_1$-$C_3$ alkyl is independently optionally substituted with one or more deuterium or halogen.

In one embodiment, Z is substituted with one or two $C_1$-$C_3$ alkyl, wherein each instance of the $C_1$-$C_3$ alkyl is independently optionally substituted with one or more deuterium or halogen.

In one embodiment, Z is substituted with one or two methyl, wherein each instance of the methyl is independently optionally substituted with one or more deuterium or halogen. In one embodiment, Z is substituted with one or two —$CH_3$. In one embodiment, Z is substituted with one or two —$CD_3$. In one embodiment, Z is substituted with one or two —$CF_3$.

In one embodiment, Z is

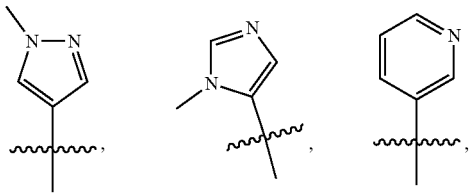

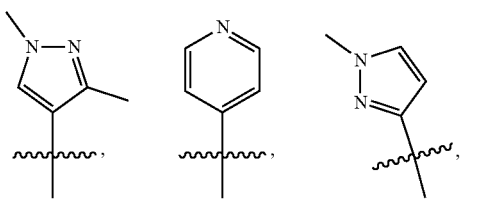

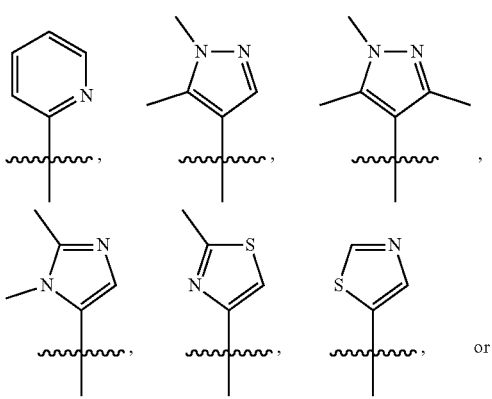

or

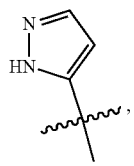

wherein each unspecified position is independently hydrogen or deuterium.

In one embodiment, the compound is a compound of Formula (A-I), (A-II), or (A-III):

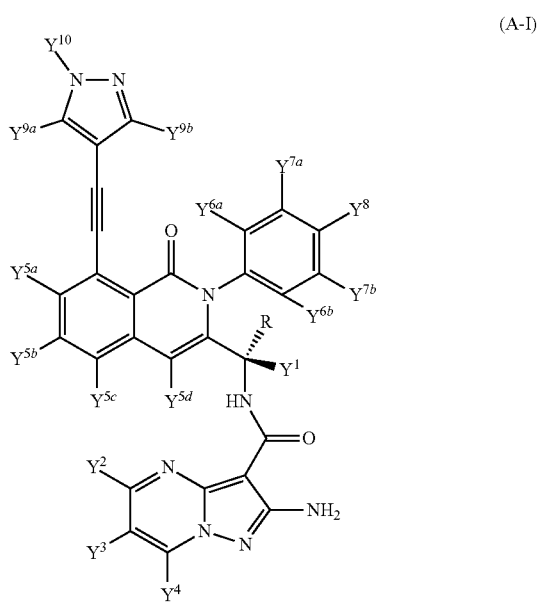

(A-I)

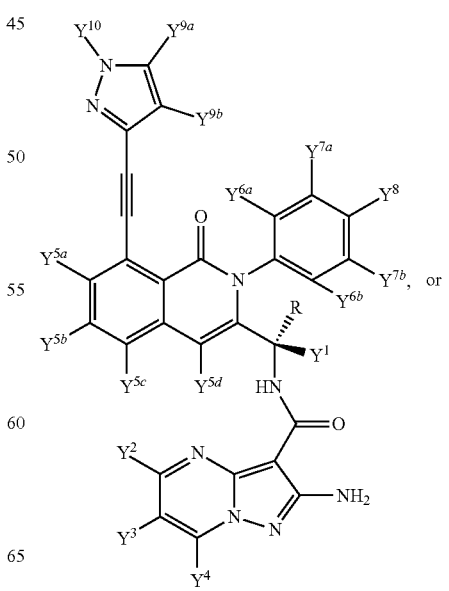

(A-II), or (A-III)

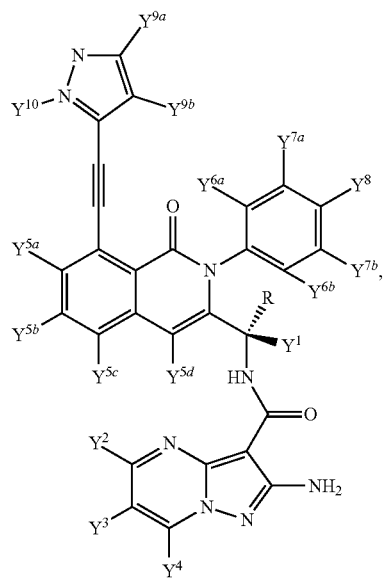

or a pharmaceutically acceptable form thereof, wherein
$Y^{9a}$ and $Y^{9b}$ are each independently hydrogen, deuterium, or $C_1$-$C_3$ alkyl, wherein each instance of the $C_1$-$C_3$ alkyl is independently optionally substituted with one or more deuterium or halogen; and $Y^{10}$ is hydrogen or $C_1$-$C_3$ alkyl, wherein the $C_1$-$C_3$ alkyl itself is optionally substituted with one or more deuterium or halogen.

In one embodiment, the compound is a compound of Formula (B-I), (B-II), or (B-III):

(B-I)

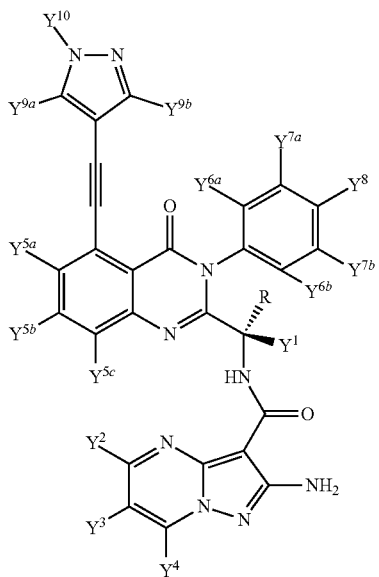

(B-II)

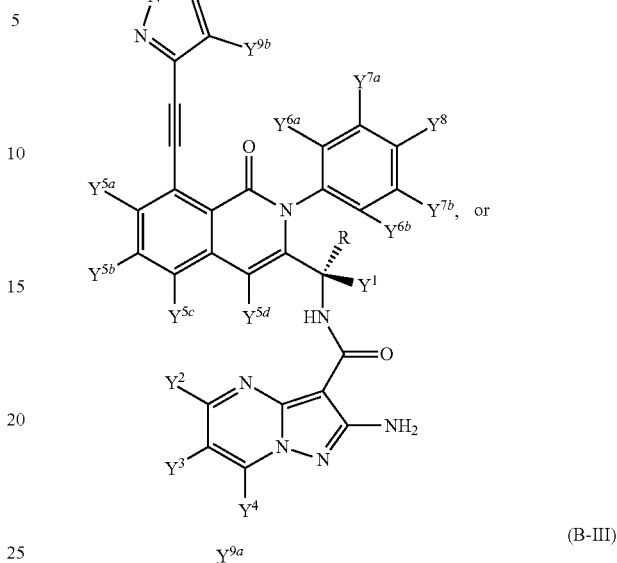

or (B-III)

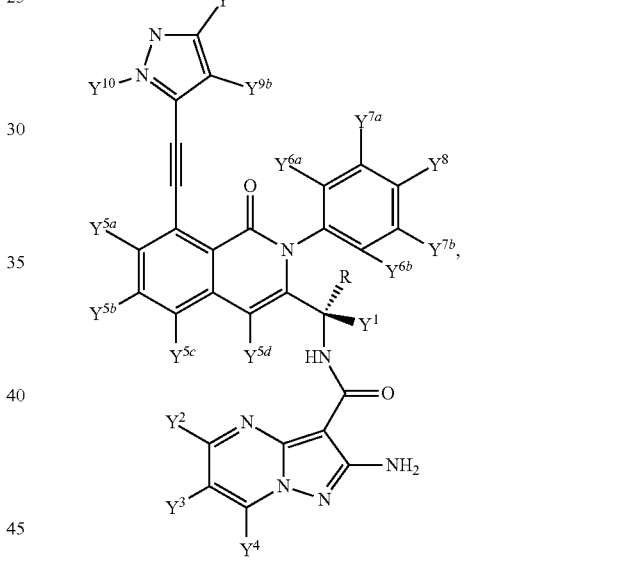

or a pharmaceutically acceptable form thereof, wherein
$Y^{9a}$ and $Y^{9b}$ are each independently hydrogen, deuterium, or $C_1$-$C_3$ alkyl, wherein each instance of the $C_1$-$C_3$ alkyl is independently optionally substituted with one or more deuterium or halogen; and
$Y^{10}$ is hydrogen or $C_1$-$C_3$ alkyl, wherein the $C_1$-$C_3$ alkyl itself is optionally substituted with one or more deuterium or halogen.

In one embodiment, $Y^{9a}$ and $Y^{9b}$ are each independently hydrogen or deuterium. In one embodiment, $Y^{9a}$ and $Y^{9b}$ are both hydrogen. In one embodiment, $Y^{9a}$ is deuterium, and $Y^{9b}$ is hydrogen. In one embodiment, $Y^{9a}$ is hydrogen, and $Y^{9b}$ is deuterium. In one embodiment, $Y^{9a}$ and $Y^{9b}$ are both deuterium.

In one embodiment, one of $Y^{9a}$ and $Y^{9b}$ is hydrogen or deuterium, and the other is $C_1$-$C_3$ alkyl, wherein the $C_1$-$C_3$ alkyl itself is optionally substituted with one or more deuterium or halogen. In one embodiment, $Y^{9a}$ and $Y^{9b}$ are both $C_1$-$C_3$ alkyl, wherein each instance of the $C_1$-$C_3$ alkyl is independently optionally substituted with one or more deuterium or halogen. In one embodiment, the $C_1$-$C_3$ alkyl is —$CH_3$. In one embodiment, the $C_1$-$C_3$ alkyl is —$CD_3$. In one embodiment, the $C_1$-$C_3$ alkyl is —$CF_3$.

In one embodiment, $Y^{10}$ is hydrogen.

In one embodiment, $Y^{10}$ is $C_1$-$C_3$ alkyl, wherein the $C_1$-$C_3$ alkyl itself is optionally substituted with one or more deuterium or halogen. In one embodiment, the $C_1$-$C_3$ alkyl is —$CH_3$. In one embodiment, the $C_1$-$C_3$ alkyl is —$CD_3$. In one embodiment, the $C_1$-$C_3$ alkyl is —$CF_3$.

In one embodiment, R is $C_1$-$C_3$ alkyl optionally substituted with one or more deuterium. In one embodiment, R is methyl or ethyl optionally substituted with one or more deuterium.

In one embodiment, R is methyl optionally substituted with one or more deuterium. In one embodiment, R is —$CH_3$. In one embodiment, R is —$CH_2D$. In one embodiment, R is —$CHD_2$. In one embodiment, R is —$CD_3$.

In one embodiment, R is ethyl optionally substituted with one or more deuterium. In one embodiment, R is —$CH_2$—$CH_3$. In one embodiment, R is —$CH_2$—$CH_2D$. In one embodiment, R is —$CH_2$—$CHD_2$. In one embodiment, R is —$CH_2$-$CD_3$. In one embodiment, R is —CHD-$CH_3$. In one embodiment, R is —CHD-$CH_2D$. In one embodiment, R is —CHD-$CHD_2$. In one embodiment, R is —CHD-$CD_3$. In one embodiment, R is —$CD_2$-$CH_3$. In one embodiment, R is —$CD_2$-$CH_2D$. In one embodiment, R is —$CD_2$-$CHD_2$. In one embodiment, R is —$CD_2$-$CD_3$.

In one embodiment, R is $C_1$-$C_3$ alkyl optionally substituted with one or more halogen. In one embodiment, R is methyl or ethyl optionally substituted with one or more halogen. In one embodiment, R is methyl optionally substituted with one or more halogen. In one embodiment, R is —$CF_3$.

In one embodiment, $Y^1$ is deuterium. In one embodiment, $Y^1$ is hydrogen.

In one embodiment, $Y^2$ is deuterium. In one embodiment, $Y^2$ is hydrogen.

In one embodiment, $Y^3$ is deuterium. In one embodiment, $Y^3$ is hydrogen.

In one embodiment, $Y^4$ is deuterium. In one embodiment, $Y^4$ is hydrogen.

In one embodiment, $Y^2$, $Y^3$, and $Y^4$ are all hydrogen.

In one embodiment, one of $Y^2$, $Y^3$, and $Y^4$ is deuterium, and the other two of $Y^2$, $Y^3$, and $Y^4$ are hydrogen. In one embodiment, $Y^2$ is deuterium, and $Y^3$ and $Y^4$ are hydrogen. In one embodiment, $Y^3$ is deuterium, and $Y^2$ and $Y^4$ are hydrogen. In one embodiment, $Y^4$ is deuterium, and $Y^2$ and $Y^3$ are hydrogen.

In one embodiment, two of $Y^2$, $Y^3$, and $Y^4$ are deuterium, and the other of $Y^2$, $Y^3$, and $Y^4$ is hydrogen. In one embodiment, $Y^2$ and $Y^3$ are deuterium, and $Y^4$ is hydrogen. In one embodiment, $Y^2$ and $Y^4$ are deuterium, and $Y^3$ is hydrogen. In one embodiment, $Y^3$ and $Y^4$ are deuterium, and $Y^2$ is hydrogen.

In one embodiment, $Y^2$, $Y^3$, and $Y^4$ are all deuterium.

In one embodiment, the

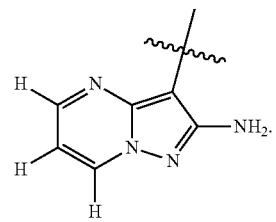 [SMILES: *c1c(N)nn2cccnc12]

moiety is

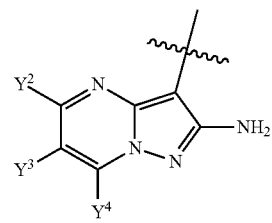

In one embodiment, the

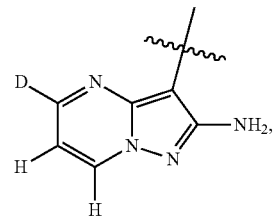

moiety is

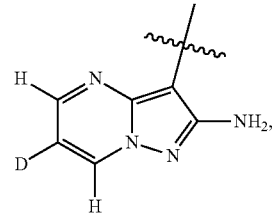

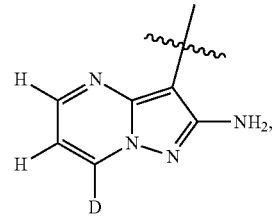

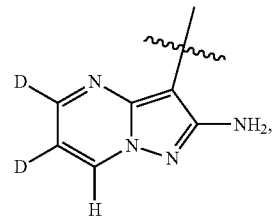

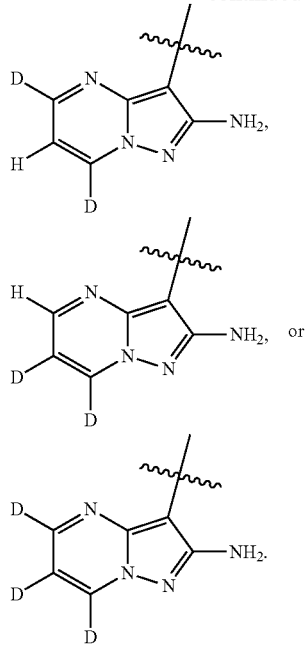

In one embodiment, the compound is a compound of Formula (A-I-a):

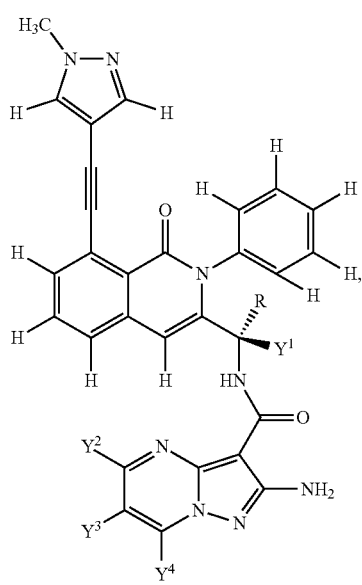

(A-I-a)

or a pharmaceutically acceptable form thereof.

In one embodiment, the compound is a compound of Formula (A-I-a) selected from any one of the compounds in Table 1.

TABLE 1

| Exemplary compounds of Formula (A-I-a) | | | | | |
|---|---|---|---|---|---|
| Compound | $Y^1$ | $Y^2$ | $Y^3$ | $Y^4$ | R |
| 101 | D | H | H | H | —CH$_3$ |
| 102 | H | D | H | H | —CH$_3$ |
| 103 | H | H | D | H | —CH$_3$ |
| 104 | H | H | H | D | —CH$_3$ |
| 105 | D | D | H | H | —CH$_3$ |
| 106 | D | H | D | H | —CH$_3$ |
| 107 | D | H | H | D | —CH$_3$ |
| 108 | H | D | D | H | —CH$_3$ |
| 109 | H | D | H | D | —CH$_3$ |
| 110 | H | H | D | D | —CH$_3$ |
| 111 | D | D | D | H | —CH$_3$ |
| 112 | D | D | H | D | —CH$_3$ |
| 113 | D | H | D | D | —CH$_3$ |
| 114 | H | D | D | D | —CH$_3$ |
| 115 | D | D | D | D | —CH$_3$ |
| 116 | H | H | H | H | —CD$_3$ |
| 117 | D | H | H | H | —CD$_3$ |
| 118 | H | D | H | H | —CD$_3$ |
| 119 | H | H | D | H | —CD$_3$ |
| 120 | H | H | H | D | —CD$_3$ |
| 121 | D | D | H | H | —CD$_3$ |
| 122 | D | H | D | H | —CD$_3$ |
| 123 | D | H | H | D | —CD$_3$ |
| 124 | H | D | D | H | —CD$_3$ |
| 125 | H | D | H | D | —CD$_3$ |
| 126 | H | H | D | D | —CD$_3$ |
| 127 | D | D | D | H | —CD$_3$ |
| 128 | D | D | H | D | —CD$_3$ |
| 129 | D | H | D | D | —CD$_3$ |
| 130 | H | D | D | D | —CD$_3$ |
| 131 | D | D | D | D | —CD$_3$ | or a pharmaceutically acceptable form thereof.

In one embodiment, the compound is a compound of the following Formula:

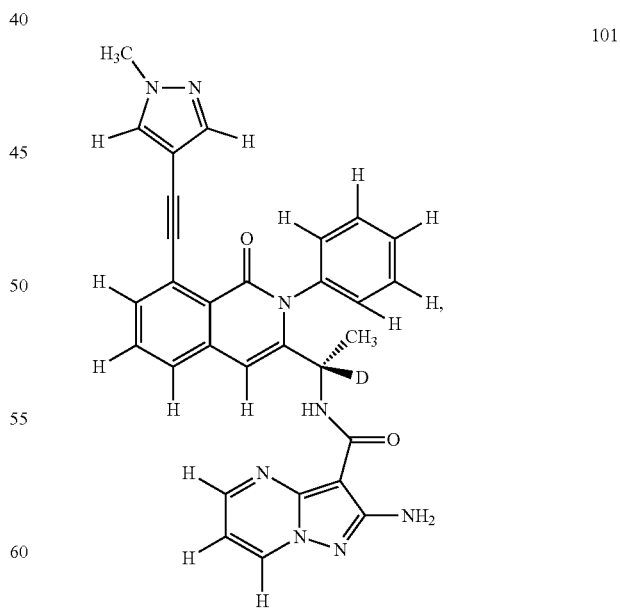

101 or a pharmaceutically acceptable form thereof.

In one embodiment, the compound is a compound of Formula (A-I-b):

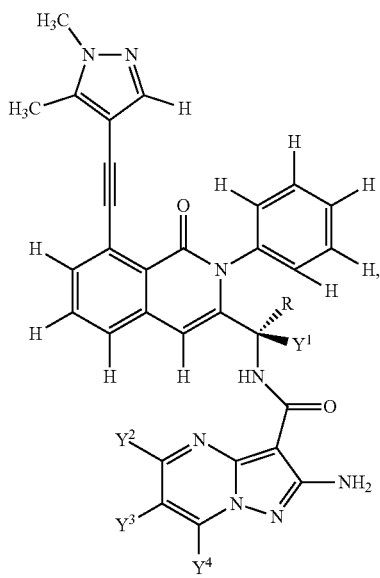

(A-I-b)

or a pharmaceutically acceptable form thereof.

In one embodiment, the compound is a compound of Formula (A-I-b) selected from any one of the compounds in Table 2.

TABLE 2

Exemplary compounds of Formula (A-I-b)

| Compound | $Y^1$ | $Y^2$ | $Y^3$ | $Y^4$ | R |
|---|---|---|---|---|---|
| 201 | D | H | H | H | —$CH_3$ |
| 202 | H | D | H | H | —$CH_3$ |
| 203 | H | H | D | H | —$CH_3$ |
| 204 | H | H | H | D | —$CH_3$ |
| 205 | D | D | H | H | —$CH_3$ |
| 206 | D | H | D | H | —$CH_3$ |
| 207 | D | H | H | D | —$CH_3$ |
| 208 | H | D | D | H | —$CH_3$ |
| 209 | H | D | H | D | —$CH_3$ |
| 210 | H | H | D | D | —$CH_3$ |
| 211 | D | D | D | H | —$CH_3$ |
| 212 | D | D | H | D | —$CH_3$ |
| 213 | D | H | D | D | —$CH_3$ |
| 214 | H | D | D | D | —$CH_3$ |
| 215 | D | D | D | D | —$CH_3$ |
| 216 | H | H | H | H | —$CD_3$ |
| 217 | D | H | H | H | —$CD_3$ |
| 218 | H | D | H | H | —$CD_3$ |
| 219 | H | H | D | H | —$CD_3$ |
| 220 | H | H | H | D | —$CD_3$ |
| 221 | D | D | H | H | —$CD_3$ |
| 222 | D | H | D | H | —$CD_3$ |
| 223 | D | H | H | D | —$CD_3$ |
| 224 | H | D | D | H | —$CD_3$ |
| 225 | H | D | H | D | —$CD_3$ |
| 226 | H | H | D | D | —$CD_3$ |
| 227 | D | D | D | H | —$CD_3$ |
| 228 | D | D | H | D | —$CD_3$ |
| 229 | D | H | D | D | —$CD_3$ |
| 230 | H | D | D | D | —$CD_3$ |
| 231 | D | D | D | D | —$CD_3$ | or a pharmaceutically acceptable form thereof.

In one embodiment, the compound is a compound of the following Formula:

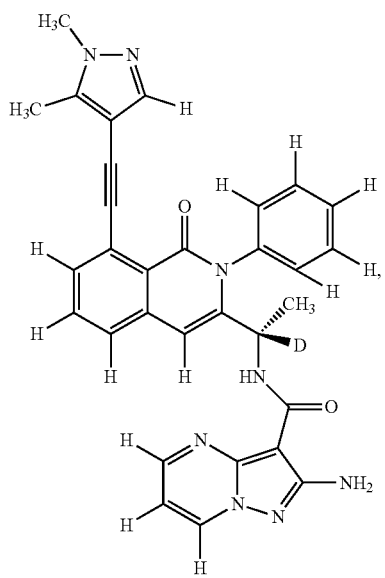

201 or a pharmaceutically acceptable form thereof.

In one embodiment, the compound is a compound of Formula (A-II-a):

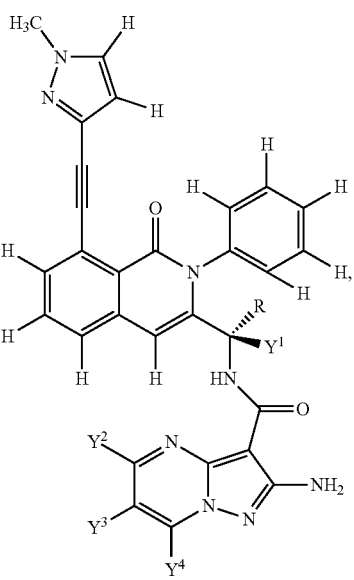

(A-II-a)

or a pharmaceutically acceptable form thereof.

In one embodiment, the compound is a compound of Formula (A-II-a) selected from any one of the compounds in Table 3.

TABLE 3

Exemplary compounds of Formula (A-II-a)

| Compound | $Y^1$ | $Y^2$ | $Y^3$ | $Y^4$ | R |
|---|---|---|---|---|---|
| 301 | D | H | H | H | —$CH_3$ |
| 302 | H | D | H | H | —$CH_3$ |
| 303 | H | H | D | H | —$CH_3$ |

TABLE 3-continued

Exemplary compounds of Formula (A-II-a)

| Compound | Y¹ | Y² | Y³ | Y⁴ | R |
|---|---|---|---|---|---|
| 304 | H | H | H | D | —CH₃ |
| 305 | D | D | H | H | —CH₃ |
| 306 | D | H | D | H | —CH₃ |
| 307 | D | H | H | D | —CH₃ |
| 308 | H | D | D | H | —CH₃ |
| 309 | H | D | H | D | —CH₃ |
| 310 | H | H | D | D | —CH₃ |
| 311 | D | D | D | H | —CH₃ |
| 312 | D | D | H | D | —CH₃ |
| 313 | D | H | D | D | —CH₃ |
| 314 | H | D | D | D | —CH₃ |
| 315 | D | D | D | D | —CH₃ |
| 316 | H | H | H | H | —CD₃ |
| 317 | D | H | H | H | —CD₃ |
| 318 | H | D | H | H | —CD₃ |
| 319 | H | H | D | H | —CD₃ |
| 320 | H | H | H | D | —CD₃ |
| 321 | D | D | H | H | —CD₃ |
| 322 | D | H | D | H | —CD₃ |
| 323 | D | H | H | D | —CD₃ |
| 324 | H | D | D | H | —CD₃ |
| 325 | H | D | H | D | —CD₃ |
| 326 | H | H | D | D | —CD₃ |
| 327 | D | D | D | H | —CD₃ |
| 328 | D | D | H | D | —CD₃ |
| 329 | D | H | D | D | —CD₃ |
| 330 | H | D | D | D | —CD₃ |
| 331 | D | D | D | D | —CD₃ | or a pharmaceutically acceptable form thereof.

In one embodiment, the compound is a compound of the following Formula:

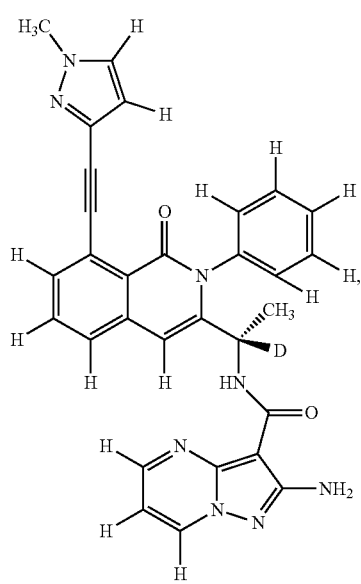

301 or a pharmaceutically acceptable form thereof.

In one embodiment, the compound is a compound of Formula (B-I-a):

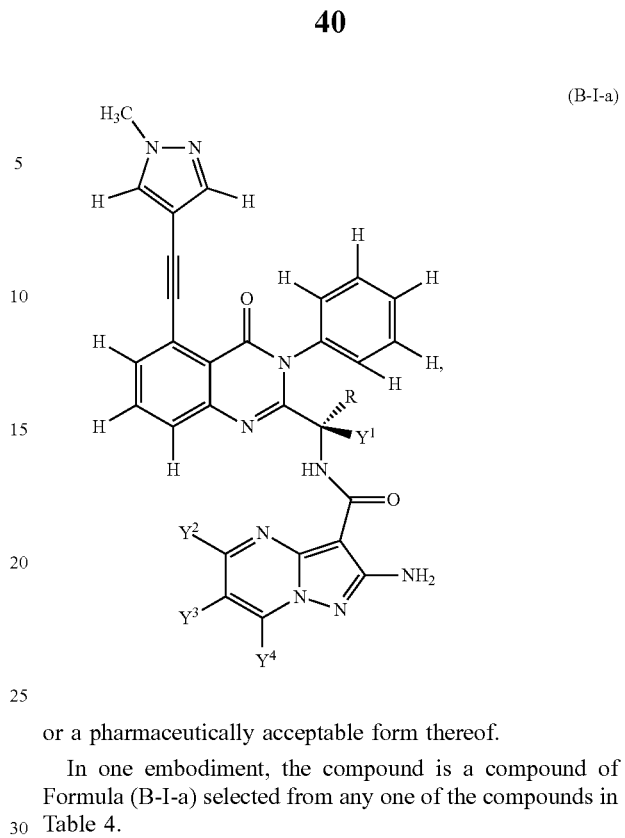

(B-I-a)

or a pharmaceutically acceptable form thereof.

In one embodiment, the compound is a compound of Formula (B-I-a) selected from any one of the compounds in Table 4.

TABLE 4

Exemplary compounds of Formula (B-I-a)

| Compound | Y¹ | Y² | Y³ | Y⁴ | R |
|---|---|---|---|---|---|
| 401 | D | H | H | H | —CH₃ |
| 402 | H | D | H | H | —CH₃ |
| 403 | H | H | D | H | —CH₃ |
| 404 | H | H | H | D | —CH₃ |
| 405 | D | D | H | H | —CH₃ |
| 406 | D | H | D | H | —CH₃ |
| 407 | D | H | H | D | —CH₃ |
| 408 | H | D | D | H | —CH₃ |
| 409 | H | D | H | D | —CH₃ |
| 410 | H | H | D | D | —CH₃ |
| 411 | D | D | D | H | —CH₃ |
| 412 | D | D | H | D | —CH₃ |
| 413 | D | H | D | D | —CH₃ |
| 414 | H | D | D | D | —CH₃ |
| 415 | D | D | D | D | —CH₃ |
| 416 | H | H | H | H | —CD₃ |
| 417 | D | H | H | H | —CD₃ |
| 418 | H | D | H | H | —CD₃ |
| 419 | H | H | D | H | —CD₃ |
| 420 | H | H | H | D | —CD₃ |
| 421 | D | D | H | H | —CD₃ |
| 422 | D | H | D | H | —CD₃ |
| 423 | D | H | H | D | —CD₃ |
| 424 | H | D | D | H | —CD₃ |
| 425 | H | D | H | D | —CD₃ |
| 426 | H | H | D | D | —CD₃ |
| 427 | D | D | D | H | —CD₃ |
| 428 | D | D | H | D | —CD₃ |
| 429 | D | H | D | D | —CD₃ |
| 430 | H | D | D | D | —CD₃ |
| 431 | D | D | D | D | —CD₃ | or a pharmaceutically acceptable form thereof.

In one embodiment, the compound is a compound of the following Formula:

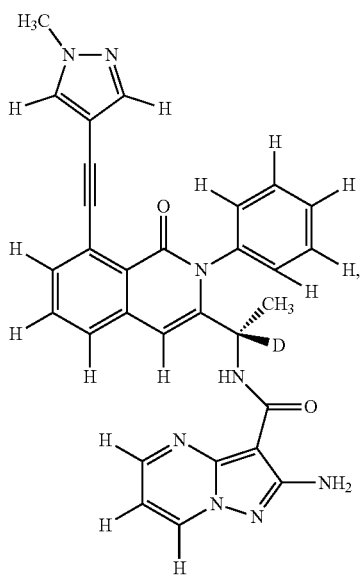

or a pharmaceutically acceptable form thereof.

In one embodiment, the compound is a compound of Formula (B-I-b):

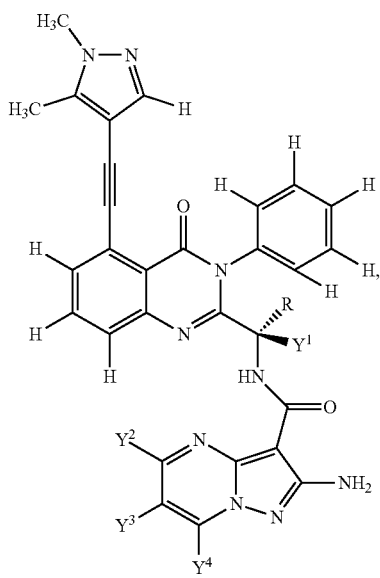

(B-I-b)

or a pharmaceutically acceptable form thereof.

In one embodiment, the compound is a compound of Formula (B-I-b) selected from any one of the compounds in Table 5.

TABLE 5

Exemplary compounds of Formula (B-I-b)

| Compound | $Y^1$ | $Y^2$ | $Y^3$ | $Y^4$ | R |
|---|---|---|---|---|---|
| 501 | D | H | H | H | —CH$_3$ |
| 502 | H | D | H | H | —CH$_3$ |
| 503 | H | H | D | H | —CH$_3$ |

TABLE 5-continued

Exemplary compounds of Formula (B-I-b)

| Compound | $Y^1$ | $Y^2$ | $Y^3$ | $Y^4$ | R |
|---|---|---|---|---|---|
| 504 | H | H | H | D | —CH$_3$ |
| 505 | D | D | H | H | —CH$_3$ |
| 506 | D | H | D | H | —CH$_3$ |
| 507 | D | H | H | D | —CH$_3$ |
| 508 | H | D | D | H | —CH$_3$ |
| 509 | H | D | H | D | —CH$_3$ |
| 510 | H | H | D | D | —CH$_3$ |
| 511 | D | D | D | H | —CH$_3$ |
| 512 | D | D | H | D | —CH$_3$ |
| 513 | D | H | D | D | —CH$_3$ |
| 514 | H | D | D | D | —CH$_3$ |
| 515 | D | D | D | D | —CH$_3$ |
| 516 | H | H | H | H | —CD$_3$ |
| 517 | D | H | H | H | —CD$_3$ |
| 518 | H | D | H | H | —CD$_3$ |
| 519 | H | H | D | H | —CD$_3$ |
| 520 | H | H | H | D | —CD$_3$ |
| 521 | D | D | H | H | —CD$_3$ |
| 522 | D | H | D | H | —CD$_3$ |
| 523 | D | H | H | D | —CD$_3$ |
| 524 | H | D | D | H | —CD$_3$ |
| 525 | H | D | H | D | —CD$_3$ |
| 526 | H | H | D | D | —CD$_3$ |
| 527 | D | D | D | H | —CD$_3$ |
| 528 | D | D | H | D | —CD$_3$ |
| 529 | D | H | D | D | —CD$_3$ |
| 530 | H | D | D | D | —CD$_3$ |
| 531 | D | D | D | D | —CD$_3$ | or a pharmaceutically acceptable form thereof.

In one embodiment, the compound is a compound of the following Formula:

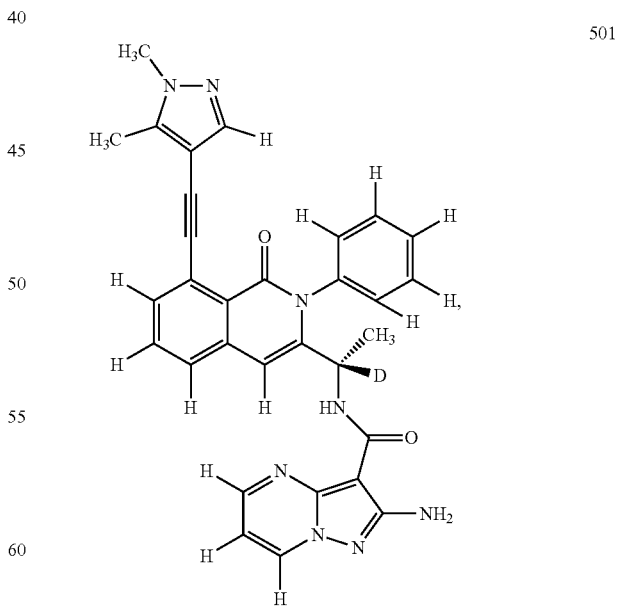

or a pharmaceutically acceptable form thereof.

In one embodiment, the compound is a compound of Formula (B-II-a):

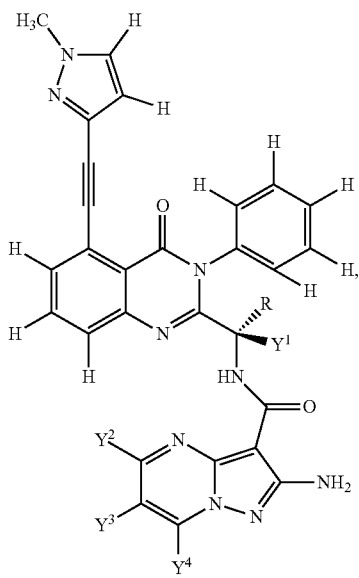

(B-II-a)

or a pharmaceutically acceptable form thereof.

In one embodiment, the compound is a compound of Formula (B-II-a) selected from any one of the compounds in Table 6.

TABLE 6

Exemplary compounds of Formula (B-II-a)

| Compound | Y¹ | Y² | Y³ | Y⁴ | R |
|---|---|---|---|---|---|
| 601 | D | H | H | H | —CH₃ |
| 602 | H | D | H | H | —CH₃ |
| 603 | H | H | D | H | —CH₃ |
| 604 | H | H | H | D | —CH₃ |
| 605 | D | D | H | H | —CH₃ |
| 606 | D | H | D | H | —CH₃ |
| 607 | D | H | H | D | —CH₃ |
| 608 | H | D | D | H | —CH₃ |
| 609 | H | D | H | D | —CH₃ |
| 610 | H | H | D | D | —CH₃ |
| 611 | D | D | D | H | —CH₃ |
| 612 | D | D | H | D | —CH₃ |
| 613 | D | H | D | D | —CH₃ |
| 614 | H | D | D | D | —CH₃ |
| 615 | D | D | D | D | —CH₃ |
| 616 | H | H | H | H | —CD₃ |
| 617 | D | H | H | H | —CD₃ |
| 618 | H | D | H | H | —CD₃ |
| 619 | H | H | D | H | —CD₃ |
| 620 | H | H | H | D | —CD₃ |
| 621 | D | D | H | H | —CD₃ |
| 622 | D | H | D | H | —CD₃ |
| 623 | D | H | H | D | —CD₃ |
| 624 | H | D | D | H | —CD₃ |
| 625 | H | D | H | D | —CD₃ |
| 626 | H | H | D | D | —CD₃ |
| 627 | D | D | D | H | —CD₃ |
| 628 | D | D | H | D | —CD₃ |
| 629 | D | H | D | D | —CD₃ |
| 630 | H | D | D | D | —CD₃ |
| 631 | D | D | D | D | —CD₃ | or a pharmaceutically acceptable form thereof.

In one embodiment, the compound is a compound of the following Formula:

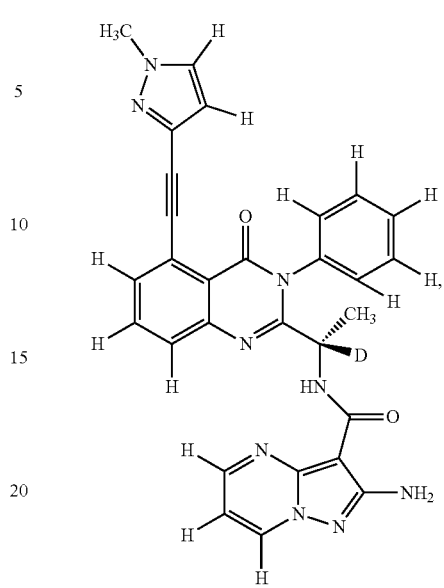

601 or a pharmaceutically acceptable form thereof.

In one embodiment, the compound is a compound of Formula (A-I-c):

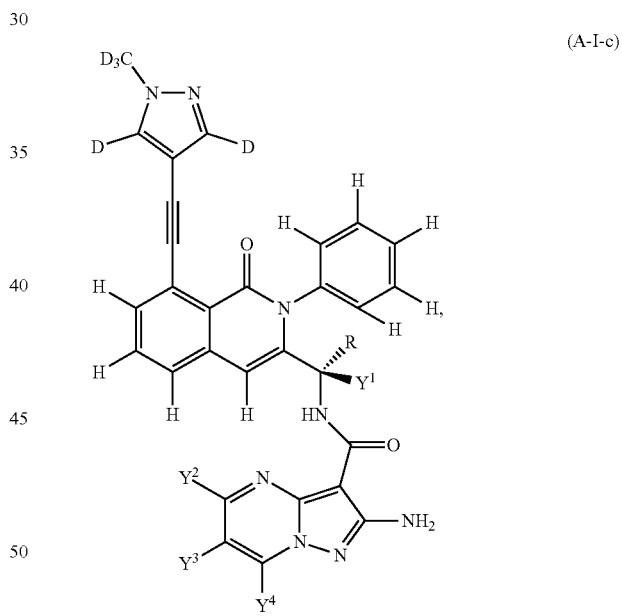

(A-I-c)

or a pharmaceutically acceptable form thereof.

In one embodiment, the compound is a compound of Formula (A-I-c) selected from any one of the compounds in Table 7.

TABLE 7

Exemplary compounds of Formula (A-I-c)

| Compound | Y¹ | Y² | Y³ | Y⁴ | R |
|---|---|---|---|---|---|
| 701 | H | H | H | H | —CH₃ |
| 702 | D | H | H | H | —CH₃ |
| 703 | H | D | H | H | —CH₃ |

TABLE 7-continued

Exemplary compounds of Formula (A-I-c)

| Compound | $Y^1$ | $Y^2$ | $Y^3$ | $Y^4$ | R |
|---|---|---|---|---|---|
| 704 | H | H | D | H | —$CH_3$ |
| 705 | H | H | H | D | —$CH_3$ |
| 706 | D | D | H | H | —$CH_3$ |
| 707 | D | H | D | H | —$CH_3$ |
| 708 | D | H | H | D | —$CH_3$ |
| 709 | H | D | D | H | —$CH_3$ |
| 710 | H | D | H | D | —$CH_3$ |
| 711 | H | H | D | D | —$CH_3$ |
| 712 | D | D | D | H | —$CH_3$ |
| 713 | D | D | H | D | —$CH_3$ |
| 714 | D | H | D | D | —$CH_3$ |
| 715 | H | D | D | D | —$CH_3$ |
| 716 | D | D | D | D | —$CH_3$ |
| 717 | H | H | H | H | —$CD_3$ |
| 718 | D | H | H | H | —$CD_3$ |
| 719 | H | D | H | H | —$CD_3$ |
| 720 | H | H | D | H | —$CD_3$ |
| 721 | H | H | H | D | —$CD_3$ |
| 722 | D | D | H | H | —$CD_3$ |
| 723 | D | H | D | H | —$CD_3$ |
| 724 | D | H | H | D | —$CD_3$ |
| 725 | H | D | D | H | —$CD_3$ |
| 726 | H | D | H | D | —$CD_3$ |
| 727 | H | H | D | D | —$CD_3$ |
| 728 | D | D | D | H | —$CD_3$ |
| 729 | D | D | H | D | —$CD_3$ |
| 730 | D | H | D | D | —$CD_3$ |
| 731 | H | D | D | D | —$CD_3$ |
| 732 | D | D | D | D | —$CD_3$ | or a pharmaceutically acceptable form thereof.

In one embodiment, the compound is a compound of Formula (A-I-d):

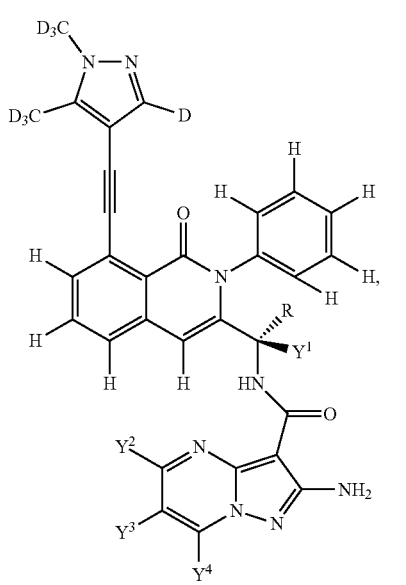

(A-I-d)

or a pharmaceutically acceptable form thereof.

In one embodiment, the compound is a compound of Formula (A-I-d) selected from any one of the compounds in Table 8.

TABLE 8

Exemplary compounds of Formula (A-I-d)

| Compound | $Y^1$ | $Y^2$ | $Y^3$ | $Y^4$ | R |
|---|---|---|---|---|---|
| 801 | H | H | H | H | —$CH_3$ |
| 802 | D | H | H | H | —$CH_3$ |
| 803 | H | D | H | H | —$CH_3$ |
| 804 | H | H | D | H | —$CH_3$ |
| 805 | H | H | H | D | —$CH_3$ |
| 806 | D | D | H | H | —$CH_3$ |
| 807 | D | H | D | H | —$CH_3$ |
| 808 | D | H | H | D | —$CH_3$ |
| 809 | H | D | D | H | —$CH_3$ |
| 810 | H | D | H | D | —$CH_3$ |
| 811 | H | H | D | D | —$CH_3$ |
| 812 | D | D | D | H | —$CH_3$ |
| 813 | D | D | H | D | —$CH_3$ |
| 814 | D | H | D | D | —$CH_3$ |
| 815 | H | D | D | D | —$CH_3$ |
| 816 | D | D | D | D | —$CH_3$ |
| 817 | H | H | H | H | —$CD_3$ |
| 818 | D | H | H | H | —$CD_3$ |
| 819 | H | D | H | H | —$CD_3$ |
| 820 | H | H | D | H | —$CD_3$ |
| 821 | H | H | H | D | —$CD_3$ |
| 822 | D | D | H | H | —$CD_3$ |
| 823 | D | H | D | H | —$CD_3$ |
| 824 | D | H | H | D | —$CD_3$ |
| 825 | H | D | D | H | —$CD_3$ |
| 826 | H | D | H | D | —$CD_3$ |
| 827 | H | H | D | D | —$CD_3$ |
| 828 | D | D | D | H | —$CD_3$ |
| 829 | D | D | H | D | —$CD_3$ |
| 830 | D | H | D | D | —$CD_3$ |
| 831 | H | D | D | D | —$CD_3$ |
| 832 | D | D | D | D | —$CD_3$ | or a pharmaceutically acceptable form thereof.

In one embodiment, the compound is a compound of Formula (A-II-b):

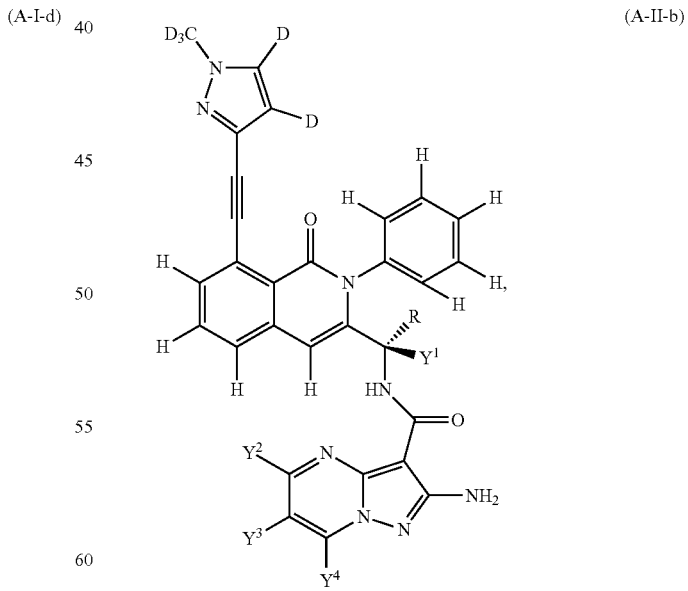

(A-II-b)

or a pharmaceutically acceptable form thereof.

In one embodiment, the compound is a compound of Formula (A-II-b) selected from any one of the compounds in Table 9.

TABLE 9

Exemplary compounds of Formula (A-II-b)

| Compound | Y$^1$ | Y$^2$ | Y$^3$ | Y$^4$ | R |
|---|---|---|---|---|---|
| 901 | H | H | H | H | —CH$_3$ |
| 902 | D | H | H | H | —CH$_3$ |
| 903 | H | D | H | H | —CH$_3$ |
| 904 | H | H | D | H | —CH$_3$ |
| 905 | H | H | H | D | —CH$_3$ |
| 906 | D | D | H | H | —CH$_3$ |
| 907 | D | H | D | H | —CH$_3$ |
| 908 | D | H | H | D | —CH$_3$ |
| 909 | H | D | D | H | —CH$_3$ |
| 910 | H | D | H | D | —CH$_3$ |
| 911 | H | H | D | D | —CH$_3$ |
| 912 | D | D | D | H | —CH$_3$ |
| 913 | D | D | H | D | —CH$_3$ |
| 914 | D | H | D | D | —CH$_3$ |
| 915 | H | D | D | D | —CH$_3$ |
| 916 | D | D | D | D | —CH$_3$ |
| 917 | H | H | H | H | —CD$_3$ |
| 918 | D | H | H | H | —CD$_3$ |
| 919 | H | D | H | H | —CD$_3$ |
| 920 | H | H | D | H | —CD$_3$ |
| 921 | H | H | H | D | —CD$_3$ |
| 922 | D | D | H | H | —CD$_3$ |
| 923 | D | H | D | H | —CD$_3$ |
| 924 | D | H | H | D | —CD$_3$ |
| 925 | H | D | D | H | —CD$_3$ |
| 926 | H | D | H | D | —CD$_3$ |
| 927 | H | H | D | D | —CD$_3$ |
| 928 | D | D | D | H | —CD$_3$ |
| 929 | D | D | H | D | —CD$_3$ |
| 930 | D | H | D | D | —CD$_3$ |
| 931 | H | D | D | D | —CD$_3$ |
| 932 | D | D | D | D | —CD$_3$ |

TABLE 10

Exemplary compounds of Formula (B-I-c)

| Compound | Y$^1$ | Y$^2$ | Y$^3$ | Y$^4$ | R |
|---|---|---|---|---|---|
| 1001 | H | H | H | H | —CH$_3$ |
| 1002 | D | H | H | H | —CH$_3$ |
| 1003 | H | D | H | H | —CH$_3$ |
| 1004 | H | H | D | H | —CH$_3$ |
| 1005 | H | H | H | D | —CH$_3$ |
| 1006 | D | D | H | H | —CH$_3$ |
| 1007 | D | H | D | H | —CH$_3$ |
| 1008 | D | H | H | D | —CH$_3$ |
| 1009 | H | D | D | H | —CH$_3$ |
| 1010 | H | D | H | D | —CH$_3$ |
| 1011 | H | H | D | D | —CH$_3$ |
| 1012 | D | D | D | H | —CH$_3$ |
| 1013 | D | D | H | D | —CH$_3$ |
| 1014 | D | H | D | D | —CH$_3$ |
| 1015 | H | D | D | D | —CH$_3$ |
| 1016 | D | D | D | D | —CH$_3$ |
| 1017 | H | H | H | H | —CD$_3$ |
| 1018 | D | H | H | H | —CD$_3$ |
| 1019 | H | D | H | H | —CD$_3$ |
| 1020 | H | H | D | H | —CD$_3$ |
| 1021 | H | H | H | D | —CD$_3$ |
| 1022 | D | D | H | H | —CD$_3$ |
| 1023 | D | H | D | H | —CD$_3$ |
| 1024 | D | H | H | D | —CD$_3$ |
| 1025 | H | D | D | H | —CD$_3$ |
| 1026 | H | D | H | D | —CD$_3$ |
| 1027 | H | H | D | D | —CD$_3$ |
| 1028 | D | D | D | H | —CD$_3$ |
| 1029 | D | D | H | D | —CD$_3$ |
| 1030 | D | H | D | D | —CD$_3$ |
| 1031 | H | D | D | D | —CD$_3$ |
| 1032 | D | D | D | D | —CD$_3$ | or a pharmaceutically acceptable form thereof.

In one embodiment, the compound is a compound of Formula (B-I-c):

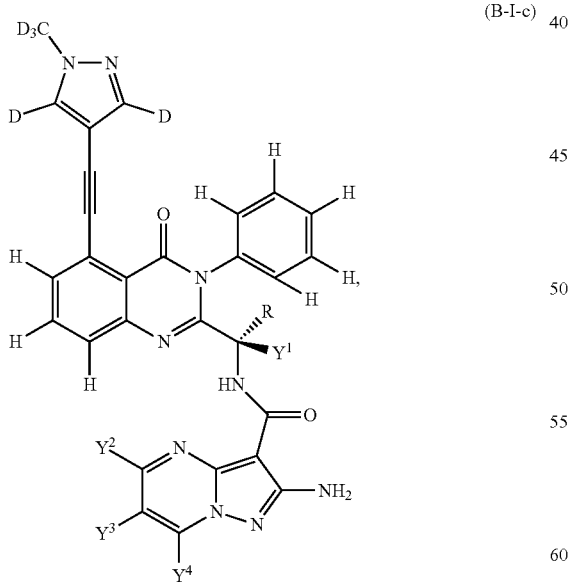

(B-I-c)

or a pharmaceutically acceptable form thereof.

In one embodiment, the compound is a compound of Formula (B-I-c) selected from any one of the compounds in Table 10.

or a pharmaceutically acceptable form thereof.

In one embodiment, the compound is a compound of Formula (B-I-d):

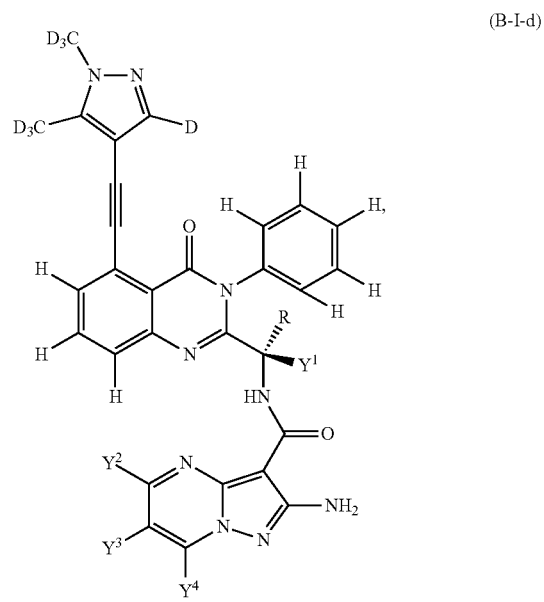

(B-I-d)

or a pharmaceutically acceptable form thereof.

In one embodiment, the compound is a compound of Formula (B-I-d) selected from any one of the compounds in Table 11.

TABLE 11

Exemplary compounds of Formula (B-I-d)

| Compound | $Y^1$ | $Y^2$ | $Y^3$ | $Y^4$ | R |
|---|---|---|---|---|---|
| 1101 | H | H | H | H | —$CH_3$ |
| 1102 | D | H | H | H | —$CH_3$ |
| 1103 | H | D | H | H | —$CH_3$ |
| 1104 | H | H | D | H | —$CH_3$ |
| 1105 | H | H | H | D | —$CH_3$ |
| 1106 | D | D | H | H | —$CH_3$ |
| 1107 | D | H | D | H | —$CH_3$ |
| 1108 | D | H | H | D | —$CH_3$ |
| 1109 | H | D | D | H | —$CH_3$ |
| 1110 | H | D | H | D | —$CH_3$ |
| 1111 | H | H | D | D | —$CH_3$ |
| 1112 | D | D | D | H | —$CH_3$ |
| 1113 | D | D | H | D | —$CH_3$ |
| 1114 | D | H | D | D | —$CH_3$ |
| 1115 | H | D | D | D | —$CH_3$ |
| 1116 | D | D | D | D | —$CH_3$ |
| 1117 | H | H | H | H | —$CD_3$ |
| 1118 | D | H | H | H | —$CD_3$ |
| 1119 | H | D | H | H | —$CD_3$ |
| 1120 | H | H | D | H | —$CD_3$ |
| 1121 | H | H | H | D | —$CD_3$ |
| 1122 | D | D | H | H | —$CD_3$ |
| 1123 | D | H | D | H | —$CD_3$ |
| 1124 | D | H | H | D | —$CD_3$ |
| 1125 | H | D | D | H | —$CD_3$ |
| 1126 | H | D | H | D | —$CD_3$ |
| 1127 | H | H | D | D | —$CD_3$ |
| 1128 | D | D | D | H | —$CD_3$ |
| 1129 | D | D | H | D | —$CD_3$ |
| 1130 | D | H | D | D | —$CD_3$ |
| 1131 | H | D | D | D | —$CD_3$ |
| 1132 | D | D | D | D | —$CD_3$ | or a pharmaceutically acceptable form thereof.

In one embodiment, the compound is a compound of Formula (B-II-b):

TABLE 12

Exemplary compounds of Formula (B-II-b)

| Compound | $Y^1$ | $Y^2$ | $Y^3$ | $Y^4$ | R |
|---|---|---|---|---|---|
| 1201 | H | H | H | H | —$CH_3$ |
| 1202 | D | H | H | H | —$CH_3$ |
| 1203 | H | D | H | H | —$CH_3$ |
| 1204 | H | H | D | H | —$CH_3$ |
| 1205 | H | H | H | D | —$CH_3$ |
| 1206 | D | D | H | H | —$CH_3$ |
| 1207 | D | H | D | H | —$CH_3$ |
| 1208 | D | H | H | D | —$CH_3$ |
| 1209 | H | D | D | H | —$CH_3$ |
| 1210 | H | D | H | D | —$CH_3$ |
| 1211 | H | H | D | D | —$CH_3$ |
| 1212 | D | D | D | H | —$CH_3$ |
| 1213 | D | D | H | D | —$CH_3$ |
| 1214 | D | H | D | D | —$CH_3$ |
| 1215 | H | D | D | D | —$CH_3$ |
| 1216 | D | D | D | D | —$CH_3$ |
| 1217 | H | H | H | H | —$CD_3$ |
| 1218 | D | H | H | H | —$CD_3$ |
| 1219 | H | D | H | H | —$CD_3$ |
| 1220 | H | H | D | H | —$CD_3$ |
| 1221 | H | H | H | D | —$CD_3$ |
| 1222 | D | D | H | H | —$CD_3$ |
| 1223 | D | H | D | H | —$CD_3$ |
| 1224 | D | H | H | D | —$CD_3$ |
| 1225 | H | D | D | H | —$CD_3$ |
| 1226 | H | D | H | D | —$CD_3$ |
| 1227 | H | H | D | D | —$CD_3$ |
| 1228 | D | D | D | H | —$CD_3$ |
| 1229 | D | D | H | D | —$CD_3$ |
| 1230 | D | H | D | D | —$CD_3$ |
| 1231 | H | D | D | D | —$CD_3$ |
| 1232 | D | D | D | D | —$CD_3$ | or a pharmaceutically acceptable form thereof.

In one embodiment, the compound is a compound of Formula (A-I-e):

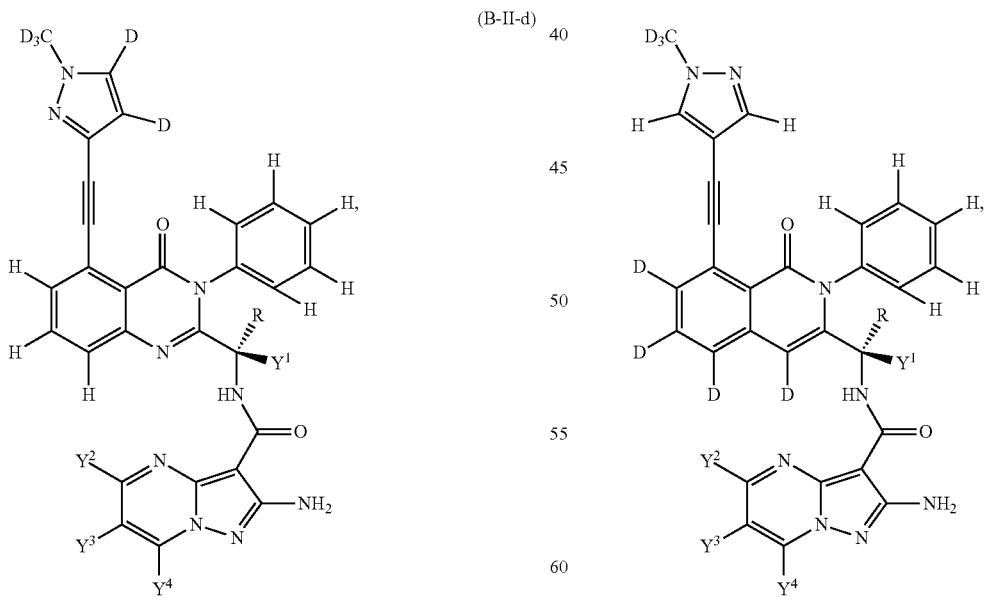

(B-II-d)

(A-I-e)

or a pharmaceutically acceptable form thereof.

In one embodiment, the compound is a compound of Formula (B-II-b) selected from any one of the compounds in Table 12.

or a pharmaceutically acceptable form thereof.

In one embodiment, the compound is a compound of Formula (A-I-e) selected from any one of the compounds in Table 13.

TABLE 13

Exemplary compounds of Formula (A-I-e)

| Compound | Y¹ | Y² | Y³ | Y⁴ | R |
|---|---|---|---|---|---|
| 1301 | H | H | H | H | —CH$_3$ |
| 1302 | D | H | H | H | —CH$_3$ |
| 1303 | H | D | H | H | —CH$_3$ |
| 1304 | H | H | D | H | —CH$_3$ |
| 1305 | H | H | H | D | —CH$_3$ |
| 1306 | D | D | H | H | —CH$_3$ |
| 1307 | D | H | D | H | —CH$_3$ |
| 1308 | D | H | H | D | —CH$_3$ |
| 1309 | H | D | D | H | —CH$_3$ |
| 1310 | H | D | H | D | —CH$_3$ |
| 1311 | H | H | D | D | —CH$_3$ |
| 1312 | D | D | D | H | —CH$_3$ |
| 1313 | D | D | H | D | —CH$_3$ |
| 1314 | D | H | D | D | —CH$_3$ |
| 1315 | H | D | D | D | —CH$_3$ |
| 1316 | D | D | D | D | —CH$_3$ |
| 1317 | H | H | H | H | —CD$_3$ |
| 1318 | D | H | H | H | —CD$_3$ |
| 1319 | H | D | H | H | —CD$_3$ |
| 1320 | H | H | D | H | —CD$_3$ |
| 1321 | H | H | H | D | —CD$_3$ |
| 1322 | D | D | H | H | —CD$_3$ |
| 1323 | D | H | D | H | —CD$_3$ |
| 1324 | D | H | H | D | —CD$_3$ |
| 1325 | H | D | D | H | —CD$_3$ |
| 1326 | H | D | H | D | —CD$_3$ |
| 1327 | H | H | D | D | —CD$_3$ |
| 1328 | D | D | D | H | —CD$_3$ |
| 1329 | D | D | H | D | —CD$_3$ |
| 1330 | D | H | D | D | —CD$_3$ |
| 1331 | H | D | D | D | —CD$_3$ |
| 1332 | D | D | D | D | —CD$_3$ |

TABLE 14

Exemplary compounds of Formula (A-I-f)

| Compound | Y¹ | Y² | Y³ | Y⁴ | R |
|---|---|---|---|---|---|
| 1401 | H | H | H | H | —CH$_3$ |
| 1402 | D | H | H | H | —CH$_3$ |
| 1403 | H | D | H | H | —CH$_3$ |
| 1404 | H | H | D | H | —CH$_3$ |
| 1405 | H | H | H | D | —CH$_3$ |
| 1406 | D | D | H | H | —CH$_3$ |
| 1407 | D | H | D | H | —CH$_3$ |
| 1408 | D | H | H | D | —CH$_3$ |
| 1409 | H | D | D | H | —CH$_3$ |
| 1410 | H | D | H | D | —CH$_3$ |
| 1411 | H | H | D | D | —CH$_3$ |
| 1412 | D | D | D | H | —CH$_3$ |
| 1413 | D | D | H | D | —CH$_3$ |
| 1414 | D | H | D | D | —CH$_3$ |
| 1415 | H | D | D | D | —CH$_3$ |
| 1416 | D | D | D | D | —CH$_3$ |
| 1417 | H | H | H | H | —CD$_3$ |
| 1418 | D | H | H | H | —CD$_3$ |
| 1419 | H | D | H | H | —CD$_3$ |
| 1420 | H | H | D | H | —CD$_3$ |
| 1421 | H | H | H | D | —CD$_3$ |
| 1422 | D | D | H | H | —CD$_3$ |
| 1423 | D | H | D | H | —CD$_3$ |
| 1424 | D | H | H | D | —CD$_3$ |
| 1425 | H | D | D | H | —CD$_3$ |
| 1426 | H | D | H | D | —CD$_3$ |
| 1427 | H | H | D | D | —CD$_3$ |
| 1428 | D | D | D | H | —CD$_3$ |
| 1429 | D | D | H | D | —CD$_3$ |
| 1430 | D | H | D | D | —CD$_3$ |
| 1431 | H | D | D | D | —CD$_3$ |
| 1432 | D | D | D | D | —CD$_3$ | or a pharmaceutically acceptable form thereof.

In one embodiment, the compound is a compound of Formula (A-I-f):

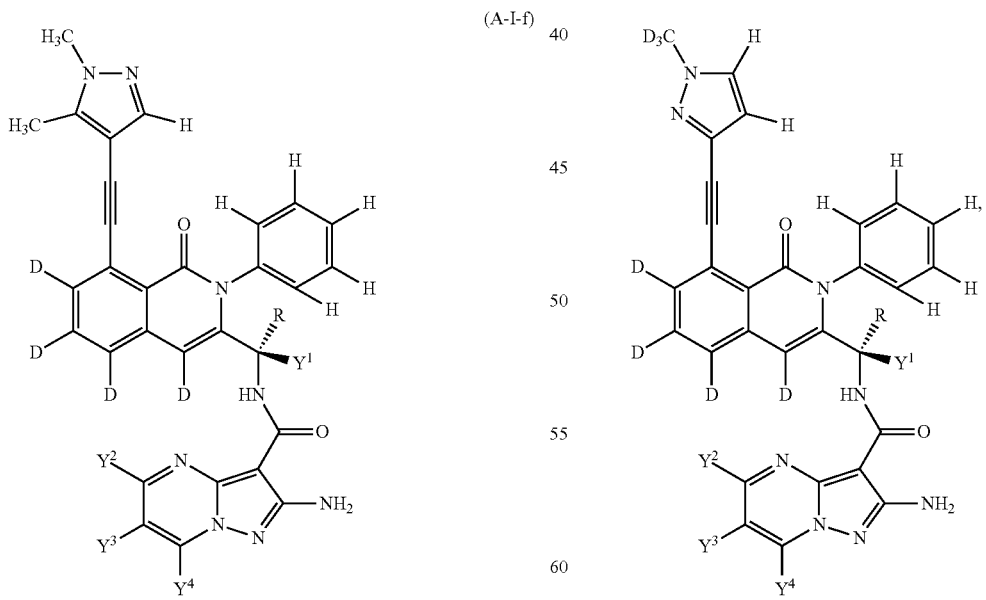

(A-I-f)

or a pharmaceutically acceptable form thereof.

In one embodiment, the compound is a compound of Formula (A-I-f) selected from any one of the compounds in Table 14.

or a pharmaceutically acceptable form thereof.

In one embodiment, the compound is a compound of Formula (A-II-c):

(A-II-c)

or a pharmaceutically acceptable form thereof.

In one embodiment, the compound is a compound of Formula (A-II-c) selected from any one of the compounds in Table 15.

TABLE 15

Exemplary compounds of Formula (A-II-c)

| Compound | Y¹ | Y² | Y³ | Y⁴ | R |
|---|---|---|---|---|---|
| 1501 | H | H | H | H | —CH₃ |
| 1502 | D | H | H | H | —CH₃ |
| 1503 | H | D | H | H | —CH₃ |
| 1504 | H | H | D | H | —CH₃ |
| 1505 | H | H | H | D | —CH₃ |
| 1506 | D | D | H | H | —CH₃ |
| 1507 | D | H | D | H | —CH₃ |
| 1508 | D | H | H | D | —CH₃ |
| 1509 | H | D | D | H | —CH₃ |
| 1510 | H | D | H | D | —CH₃ |
| 1511 | H | H | D | D | —CH₃ |
| 1512 | D | D | D | H | —CH₃ |
| 1513 | D | D | H | D | —CH₃ |
| 1514 | D | H | D | D | —CH₃ |
| 1515 | H | D | D | D | —CH₃ |
| 1516 | D | D | D | D | —CH₃ |
| 1517 | H | H | H | H | —CD₃ |
| 1518 | D | H | H | H | —CD₃ |
| 1519 | H | D | H | H | —CD₃ |
| 1520 | H | H | D | H | —CD₃ |
| 1521 | H | H | H | D | —CD₃ |
| 1522 | D | D | H | H | —CD₃ |
| 1523 | D | H | D | H | —CD₃ |
| 1524 | D | H | H | D | —CD₃ |
| 1525 | H | D | D | H | —CD₃ |
| 1526 | H | D | H | D | —CD₃ |
| 1527 | H | H | D | D | —CD₃ |
| 1528 | D | D | D | H | —CD₃ |
| 1529 | D | D | H | D | —CD₃ |
| 1530 | D | H | D | D | —CD₃ |
| 1531 | H | D | D | D | —CD₃ |
| 1532 | D | D | D | D | —CD₃ | or a pharmaceutically acceptable form thereof.

In one embodiment, the compound is a compound of Formula (B-I-e):

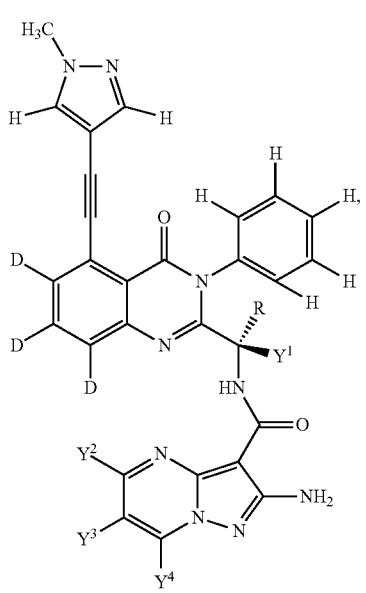

(B-I-e)

or a pharmaceutically acceptable form thereof.

In one embodiment, the compound is a compound of Formula (B-I-e) selected from any one of the compounds in Table 16.

TABLE 16

Exemplary compounds of Formula (B-I-e)

| Compound | Y¹ | Y² | Y³ | Y⁴ | R |
|---|---|---|---|---|---|
| 1601 | H | H | H | H | —CH₃ |
| 1602 | D | H | H | H | —CH₃ |
| 1603 | H | D | H | H | —CH₃ |
| 1604 | H | H | D | H | —CH₃ |
| 1605 | H | H | H | D | —CH₃ |
| 1606 | D | D | H | H | —CH₃ |
| 1607 | D | H | D | H | —CH₃ |
| 1608 | D | H | H | D | —CH₃ |
| 1609 | H | D | D | H | —CH₃ |
| 1610 | H | D | H | D | —CH₃ |
| 1611 | H | H | D | D | —CH₃ |
| 1612 | D | D | D | H | —CH₃ |
| 1613 | D | D | H | D | —CH₃ |
| 1614 | D | H | D | D | —CH₃ |
| 1615 | H | D | D | D | —CH₃ |
| 1616 | D | D | D | D | —CH₃ |
| 1617 | H | H | H | H | —CD₃ |
| 1618 | D | H | H | H | —CD₃ |
| 1619 | H | D | H | H | —CD₃ |
| 1620 | H | H | D | H | —CD₃ |
| 1621 | H | H | H | D | —CD₃ |
| 1622 | D | D | H | H | —CD₃ |
| 1623 | D | H | D | H | —CD₃ |
| 1624 | D | H | H | D | —CD₃ |
| 1625 | H | D | D | H | —CD₃ |
| 1626 | H | D | H | D | —CD₃ |
| 1627 | H | H | D | D | —CD₃ |
| 1628 | D | D | D | H | —CD₃ |
| 1629 | D | D | H | D | —CD₃ |
| 1630 | D | H | D | D | —CD₃ |
| 1631 | H | D | D | D | —CD₃ |
| 1632 | D | D | D | D | —CD₃ | or a pharmaceutically acceptable form thereof.

In one embodiment, the compound is a compound of Formula (B-I-f):

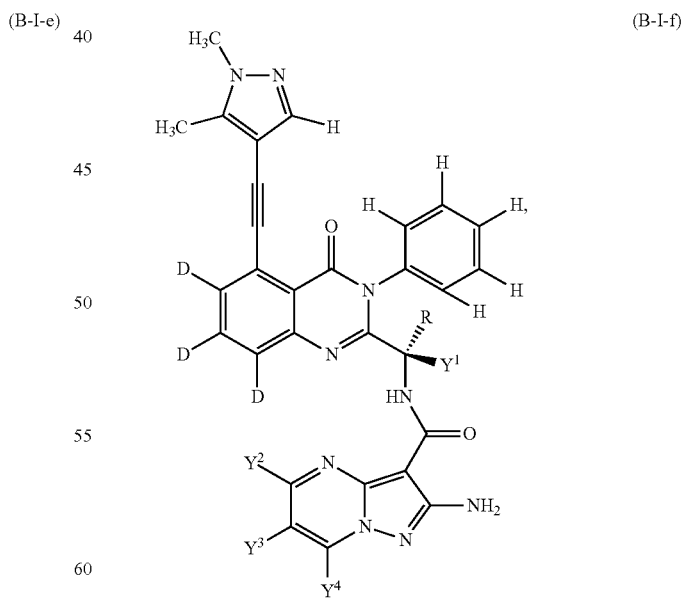

(B-I-f)

or a pharmaceutically acceptable form thereof.

In one embodiment, the compound is a compound of Formula (B-I-f) selected from any one of the compounds in Table 17.

TABLE 17

Exemplary compounds of Formula (B-I-f)

| Compound | Y¹ | Y² | Y³ | Y⁴ | R |
|---|---|---|---|---|---|
| 1701 | H | H | H | H | —CH₃ |
| 1702 | D | H | H | H | —CH₃ |
| 1703 | H | D | H | H | —CH₃ |
| 1704 | H | H | D | H | —CH₃ |
| 1705 | H | H | H | D | —CH₃ |
| 1706 | D | D | H | H | —CH₃ |
| 1707 | D | H | D | H | —CH₃ |
| 1708 | D | H | H | D | —CH₃ |
| 1709 | H | D | D | H | —CH₃ |
| 1710 | H | D | H | D | —CH₃ |
| 1711 | H | H | D | D | —CH₃ |
| 1712 | D | D | D | H | —CH₃ |
| 1713 | D | D | H | D | —CH₃ |
| 1714 | D | H | D | D | —CH₃ |
| 1715 | H | D | D | D | —CH₃ |
| 1716 | D | D | D | D | —CH₃ |
| 1717 | H | H | H | H | —CD₃ |
| 1718 | D | H | H | H | —CD₃ |
| 1719 | H | D | H | H | —CD₃ |
| 1720 | H | H | D | H | —CD₃ |
| 1721 | H | H | H | D | —CD₃ |
| 1722 | D | D | H | H | —CD₃ |
| 1723 | D | H | D | H | —CD₃ |
| 1724 | D | H | H | D | —CD₃ |
| 1725 | H | D | D | H | —CD₃ |
| 1726 | H | D | H | D | —CD₃ |
| 1727 | H | H | D | D | —CD₃ |
| 1728 | D | D | D | H | —CD₃ |
| 1729 | D | D | H | D | —CD₃ |
| 1730 | D | H | D | D | —CD₃ |
| 1731 | H | D | D | D | —CD₃ |
| 1732 | D | D | D | D | —CD₃ | or a pharmaceutically acceptable form thereof.

In one embodiment, the compound is a compound of Formula (B-II-c):

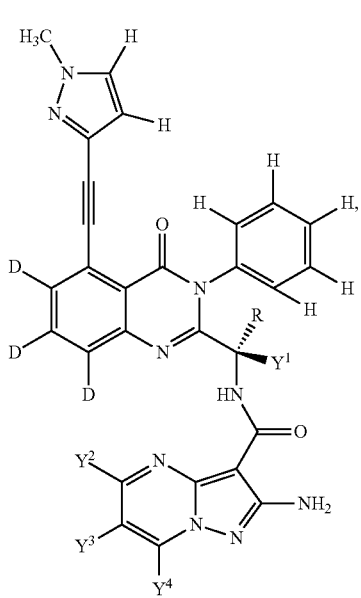

(B-II-c)

or a pharmaceutically acceptable form thereof.

In one embodiment, the compound is a compound of Formula (B-II-c) selected from any one of the compounds in Table 18.

TABLE 18

Exemplary compounds of Formula (B-II-c)

| Compound | Y¹ | Y² | Y³ | Y⁴ | R |
|---|---|---|---|---|---|
| 1801 | H | H | H | H | —CH₃ |
| 1802 | D | H | H | H | —CH₃ |
| 1803 | H | D | H | H | —CH₃ |
| 1804 | H | H | D | H | —CH₃ |
| 1805 | H | H | H | D | —CH₃ |
| 1806 | D | D | H | H | —CH₃ |
| 1807 | D | H | D | H | —CH₃ |
| 1808 | D | H | H | D | —CH₃ |
| 1809 | H | D | D | H | —CH₃ |
| 1810 | H | D | H | D | —CH₃ |
| 1811 | H | H | D | D | —CH₃ |
| 1812 | D | D | D | H | —CH₃ |
| 1813 | D | D | H | D | —CH₃ |
| 1814 | D | H | D | D | —CH₃ |
| 1815 | H | D | D | D | —CH₃ |
| 1816 | D | D | D | D | —CH₃ |
| 1817 | H | H | H | H | —CD₃ |
| 1818 | D | H | H | H | —CD₃ |
| 1819 | H | D | H | H | —CD₃ |
| 1820 | H | H | D | H | —CD₃ |
| 1821 | H | H | H | D | —CD₃ |
| 1822 | D | D | H | H | —CD₃ |
| 1823 | D | H | D | H | —CD₃ |
| 1824 | D | H | H | D | —CD₃ |
| 1825 | H | D | D | H | —CD₃ |
| 1826 | H | D | H | D | —CD₃ |
| 1827 | H | H | D | D | —CD₃ |
| 1828 | D | D | D | H | —CD₃ |
| 1829 | D | D | H | D | —CD₃ |
| 1830 | D | H | D | D | —CD₃ |
| 1831 | H | D | D | D | —CD₃ |
| 1832 | D | D | D | D | —CD₃ | or a pharmaceutically acceptable form thereof.

In one embodiment, the compound is a compound of Formula (A-I-g):

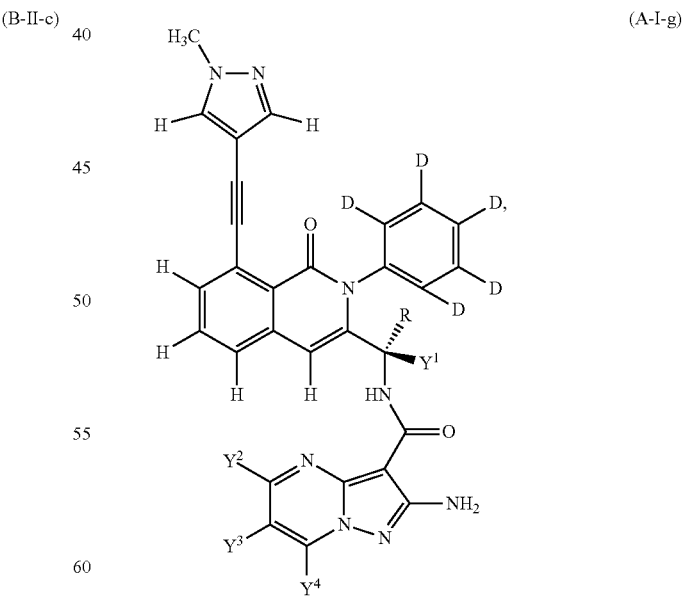

(A-I-g)

or a pharmaceutically acceptable form thereof.

In one embodiment, the compound is a compound of Formula (A-I-g) selected from any one of the compounds in Table 19.

TABLE 19

Exemplary compounds of Formula (A-I-g)

| Compound | $Y^1$ | $Y^2$ | $Y^3$ | $Y^4$ | R |
|---|---|---|---|---|---|
| 1901 | D | H | H | H | —CH₃ |
| 1902 | H | D | H | H | —CH₃ |
| 1903 | H | H | D | H | —CH₃ |
| 1904 | H | H | H | D | —CH₃ |
| 1905 | D | D | H | H | —CH₃ |
| 1906 | D | H | D | H | —CH₃ |
| 1907 | D | H | H | D | —CH₃ |
| 1908 | H | D | D | H | —CH₃ |
| 1909 | H | D | H | D | —CH₃ |
| 1910 | H | H | D | D | —CH₃ |
| 1911 | D | D | D | H | —CH₃ |
| 1912 | D | D | H | D | —CH₃ |
| 1913 | D | H | D | D | —CH₃ |
| 1914 | H | D | D | D | —CH₃ |
| 1915 | D | D | D | D | —CH₃ |
| 1916 | H | H | H | H | —CD₃ |
| 1917 | D | H | H | H | —CD₃ |
| 1918 | H | D | H | H | —CD₃ |
| 1919 | H | H | D | H | —CD₃ |
| 1920 | H | H | H | D | —CD₃ |
| 1921 | D | D | H | H | —CD₃ |
| 1922 | D | H | D | H | —CD₃ |
| 1923 | D | H | H | D | —CD₃ |
| 1924 | H | D | D | H | —CD₃ |
| 1925 | H | D | H | D | —CD₃ |
| 1926 | H | H | D | D | —CD₃ |
| 1927 | D | D | D | H | —CD₃ |
| 1928 | D | D | H | D | —CD₃ |
| 1929 | D | H | D | D | —CD₃ |
| 1930 | H | D | D | D | —CD₃ |
| 1931 | D | D | D | D | —CD₃ |

TABLE 20

Exemplary compounds of Formula (A-I-h)

| Compound | $Y^1$ | $Y^2$ | $Y^3$ | $Y^4$ | R |
|---|---|---|---|---|---|
| 2001 | D | H | H | H | —CH₃ |
| 2002 | H | D | H | H | —CH₃ |
| 2003 | H | H | D | H | —CH₃ |
| 2004 | H | H | H | D | —CH₃ |
| 2005 | D | D | H | H | —CH₃ |
| 2006 | D | H | D | H | —CH₃ |
| 2007 | D | H | H | D | —CH₃ |
| 2008 | H | D | D | H | —CH₃ |
| 2009 | H | D | H | D | —CH₃ |
| 2010 | H | H | D | D | —CH₃ |
| 2011 | D | D | D | H | —CH₃ |
| 2012 | D | D | H | D | —CH₃ |
| 2013 | D | H | D | D | —CH₃ |
| 2014 | H | D | D | D | —CH₃ |
| 2015 | D | D | D | D | —CH₃ |
| 2016 | H | H | H | H | —CD₃ |
| 2017 | D | H | H | H | —CD₃ |
| 2018 | H | D | H | H | —CD₃ |
| 2019 | H | H | D | H | —CD₃ |
| 2020 | H | H | H | D | —CD₃ |
| 2021 | D | D | H | H | —CD₃ |
| 2022 | D | H | D | H | —CD₃ |
| 2023 | D | H | H | D | —CD₃ |
| 2024 | H | D | D | H | —CD₃ |
| 2025 | H | D | H | D | —CD₃ |
| 2026 | H | H | D | D | —CD₃ |
| 2027 | D | D | D | H | —CD₃ |
| 2028 | D | D | H | D | —CD₃ |
| 2029 | D | H | D | D | —CD₃ |
| 2030 | H | D | D | D | —CD₃ |
| 2031 | D | D | D | D | —CD₃ | or a pharmaceutically acceptable form thereof.

In one embodiment, the compound is a compound of Formula (A-I-h):

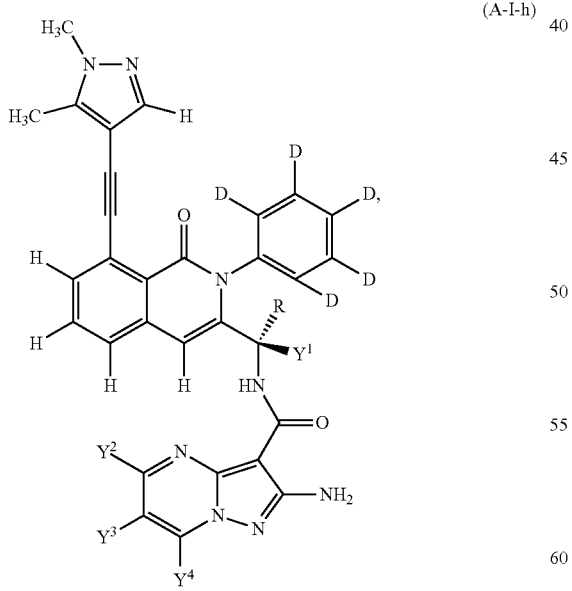

(A-I-h)

or a pharmaceutically acceptable form thereof.

In one embodiment, the compound is a compound of Formula (A-I-h) selected from any one of the compounds in Table 20.

or a pharmaceutically acceptable form thereof.

In one embodiment, the compound is a compound of Formula (A-II-d):

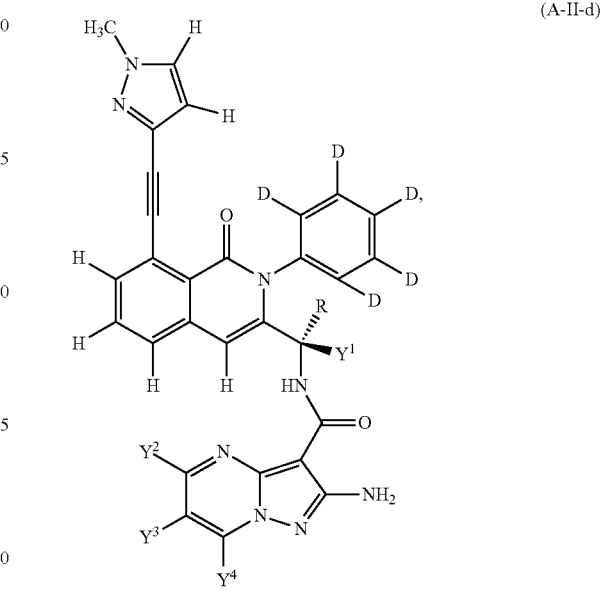

(A-II-d)

or a pharmaceutically acceptable form thereof.

In one embodiment, the compound is a compound of Formula (A-II-d) selected from any one of the compounds in Table 21.

TABLE 21

Exemplary compounds of Formula (A-II-d)

| Compound | $Y^1$ | $Y^2$ | $Y^3$ | $Y^4$ | R |
|---|---|---|---|---|---|
| 2101 | D | H | H | H | —$CH_3$ |
| 2102 | H | D | H | H | —$CH_3$ |
| 2103 | H | H | D | H | —$CH_3$ |
| 2104 | H | H | H | D | —$CH_3$ |
| 2105 | D | D | H | H | —$CH_3$ |
| 2106 | D | H | D | H | —$CH_3$ |
| 2107 | D | H | H | D | —$CH_3$ |
| 2108 | H | D | D | H | —$CH_3$ |
| 2109 | H | D | H | D | —$CH_3$ |
| 2110 | H | H | D | D | —$CH_3$ |
| 2111 | D | D | D | H | —$CH_3$ |
| 2112 | D | D | H | D | —$CH_3$ |
| 2113 | D | H | D | D | —$CH_3$ |
| 2114 | H | D | D | D | —$CH_3$ |
| 2115 | D | D | D | D | —$CH_3$ |
| 2116 | H | H | H | H | —$CD_3$ |
| 2117 | D | H | H | H | —$CD_3$ |
| 2118 | H | D | H | H | —$CD_3$ |
| 2119 | H | H | D | H | —$CD_3$ |
| 2120 | H | H | H | D | —$CD_3$ |
| 2121 | D | D | H | H | —$CD_3$ |
| 2122 | D | H | D | H | —$CD_3$ |
| 2123 | D | H | H | D | —$CD_3$ |
| 2124 | H | D | D | H | —$CD_3$ |
| 2125 | H | D | H | D | —$CD_3$ |
| 2126 | H | H | D | D | —$CD_3$ |
| 2127 | D | D | D | H | —$CD_3$ |
| 2128 | D | D | H | D | —$CD_3$ |
| 2129 | D | H | D | D | —$CD_3$ |
| 2130 | H | D | D | D | —$CD_3$ |
| 2131 | D | D | D | D | —$CD_3$ | or a pharmaceutically acceptable form thereof.

In one embodiment, the compound is a compound of Formula (B-I-g):

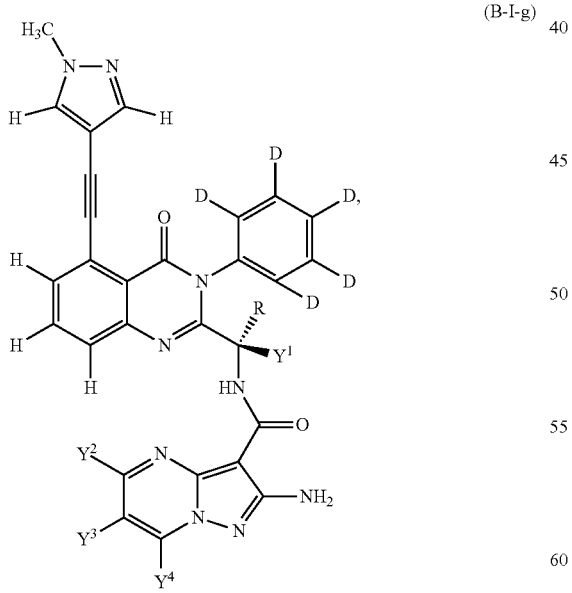

(B-I-g)

or a pharmaceutically acceptable form thereof.

In one embodiment, the compound is a compound of Formula (B-I-g) selected from any one of the compounds in Table 22.

TABLE 22

Exemplary compounds of Formula (B-I-g)

| Compound | $Y^1$ | $Y^2$ | $Y^3$ | $Y^4$ | R |
|---|---|---|---|---|---|
| 2201 | D | H | H | H | —$CH_3$ |
| 2202 | H | D | H | H | —$CH_3$ |
| 2203 | H | H | D | H | —$CH_3$ |
| 2204 | H | H | H | D | —$CH_3$ |
| 2205 | D | D | H | H | —$CH_3$ |
| 2206 | D | H | D | H | —$CH_3$ |
| 2207 | D | H | H | D | —$CH_3$ |
| 2208 | H | D | D | H | —$CH_3$ |
| 2209 | H | D | H | D | —$CH_3$ |
| 2210 | H | H | D | D | —$CH_3$ |
| 2211 | D | D | D | H | —$CH_3$ |
| 2212 | D | D | H | D | —$CH_3$ |
| 2213 | D | H | D | D | —$CH_3$ |
| 2214 | H | D | D | D | —$CH_3$ |
| 2215 | D | D | D | D | —$CH_3$ |
| 2216 | H | H | H | H | —$CD_3$ |
| 2217 | D | H | H | H | —$CD_3$ |
| 2218 | H | D | H | H | —$CD_3$ |
| 2219 | H | H | D | H | —$CD_3$ |
| 2220 | H | H | H | D | —$CD_3$ |
| 2221 | D | D | H | H | —$CD_3$ |
| 2222 | D | H | D | H | —$CD_3$ |
| 2223 | D | H | H | D | —$CD_3$ |
| 2224 | H | D | D | H | —$CD_3$ |
| 2225 | H | D | H | D | —$CD_3$ |
| 2226 | H | H | D | D | —$CD_3$ |
| 2227 | D | D | D | H | —$CD_3$ |
| 2228 | D | D | H | D | —$CD_3$ |
| 2229 | D | H | D | D | —$CD_3$ |
| 2230 | H | D | D | D | —$CD_3$ |
| 2231 | D | D | D | D | —$CD_3$ | or a pharmaceutically acceptable form thereof.

In one embodiment, the compound is a compound of Formula (B-I-h):

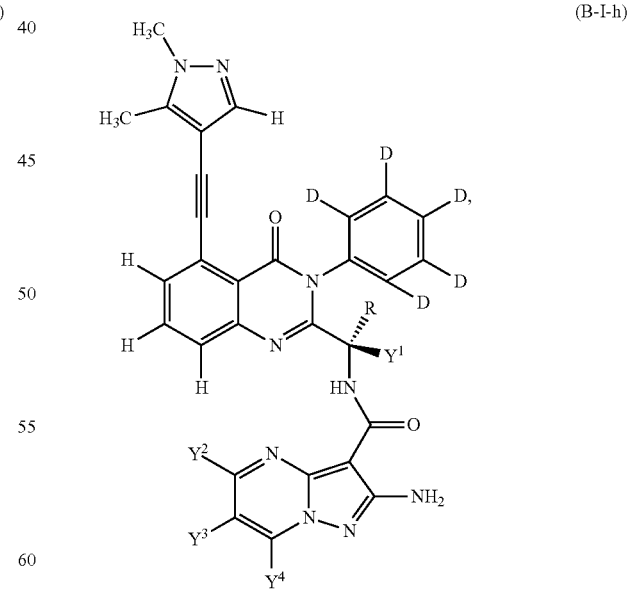

(B-I-h)

or a pharmaceutically acceptable form thereof.

In one embodiment, the compound is a compound of Formula (B-I-h) selected from any one of the compounds in Table 23.

TABLE 23

Exemplary compounds of Formula (B-I-h)

| Compound | $Y^1$ | $Y^2$ | $Y^3$ | $Y^4$ | R |
|---|---|---|---|---|---|
| 2301 | D | H | H | H | —$CH_3$ |
| 2302 | H | D | H | H | —$CH_3$ |
| 2303 | H | H | D | H | —$CH_3$ |
| 2304 | H | H | H | D | —$CH_3$ |
| 2305 | D | D | H | H | —$CH_3$ |
| 2306 | D | H | D | H | —$CH_3$ |
| 2307 | D | H | H | D | —$CH_3$ |
| 2308 | H | D | D | H | —$CH_3$ |
| 2309 | H | D | H | D | —$CH_3$ |
| 2310 | H | H | D | D | —$CH_3$ |
| 2311 | D | D | D | H | —$CH_3$ |
| 2312 | D | D | H | D | —$CH_3$ |
| 2313 | D | H | D | D | —$CH_3$ |
| 2314 | H | D | D | D | —$CH_3$ |
| 2315 | D | D | D | D | —$CH_3$ |
| 2316 | H | H | H | H | —$CD_3$ |
| 2317 | D | H | H | H | —$CD_3$ |
| 2318 | H | D | H | H | —$CD_3$ |
| 2319 | H | H | D | H | —$CD_3$ |
| 2320 | H | H | H | D | —$CD_3$ |
| 2321 | D | D | H | H | —$CD_3$ |
| 2322 | D | H | D | H | —$CD_3$ |
| 2323 | D | H | H | D | —$CD_3$ |
| 2324 | H | D | D | H | —$CD_3$ |
| 2325 | H | D | H | D | —$CD_3$ |
| 2326 | H | H | D | D | —$CD_3$ |
| 2327 | D | D | D | H | —$CD_3$ |
| 2328 | D | D | H | D | —$CD_3$ |
| 2329 | D | H | D | D | —$CD_3$ |
| 2330 | H | D | D | D | —$CD_3$ |
| 2331 | D | D | D | D | —$CD_3$ | or a pharmaceutically acceptable form thereof.

In one embodiment, the compound is a compound of Formula (B-II-d):

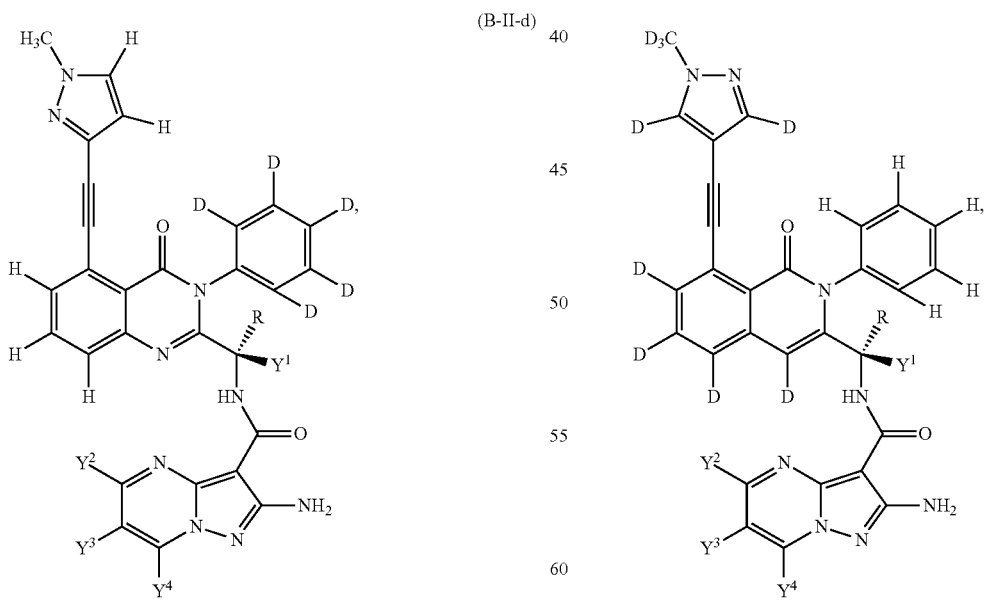

or a pharmaceutically acceptable form thereof.

In one embodiment, the compound is a compound of Formula (B-II-d) selected from any one of the compounds in Table 24.

TABLE 24

Exemplary compounds of Formula (B-II-d)

| Compound | $Y^1$ | $Y^2$ | $Y^3$ | $Y^4$ | R |
|---|---|---|---|---|---|
| 2401 | D | H | H | H | —$CH_3$ |
| 2402 | H | D | H | H | —$CH_3$ |
| 2403 | H | H | D | H | —$CH_3$ |
| 2404 | H | H | H | D | —$CH_3$ |
| 2405 | D | D | H | H | —$CH_3$ |
| 2406 | D | H | D | H | —$CH_3$ |
| 2407 | D | H | H | D | —$CH_3$ |
| 2408 | H | D | D | H | —$CH_3$ |
| 2409 | H | D | H | D | —$CH_3$ |
| 2410 | H | H | D | D | —$CH_3$ |
| 2411 | D | D | D | H | —$CH_3$ |
| 2412 | D | D | H | D | —$CH_3$ |
| 2413 | D | H | D | D | —$CH_3$ |
| 2414 | H | D | D | D | —$CH_3$ |
| 2415 | D | D | D | D | —$CH_3$ |
| 2416 | H | H | H | H | —$CD_3$ |
| 2417 | D | H | H | H | —$CD_3$ |
| 2418 | H | D | H | H | —$CD_3$ |
| 2419 | H | H | D | H | —$CD_3$ |
| 2420 | H | H | H | D | —$CD_3$ |
| 2421 | D | D | H | H | —$CD_3$ |
| 2422 | D | H | D | H | —$CD_3$ |
| 2423 | D | H | H | D | —$CD_3$ |
| 2424 | H | D | D | H | —$CD_3$ |
| 2425 | H | D | H | D | —$CD_3$ |
| 2426 | H | H | D | D | —$CD_3$ |
| 2427 | D | D | D | H | —$CD_3$ |
| 2428 | D | D | H | D | —$CD_3$ |
| 2429 | D | H | D | D | —$CD_3$ |
| 2430 | H | D | D | D | —$CD_3$ |
| 2431 | D | D | D | D | —$CD_3$ | or a pharmaceutically acceptable form thereof.

In one embodiment, the compound is a compound of Formula (A-I-i):

or a pharmaceutically acceptable form thereof.

In one embodiment, the compound is a compound of Formula (A-I-i) selected from any one of the compounds in Table 25.

TABLE 25

Exemplary compounds of Formula (A-I-i)

| Compound | Y¹ | Y² | Y³ | Y⁴ | R |
|---|---|---|---|---|---|
| 2501 | H | H | H | H | —CH₃ |
| 2502 | D | H | H | H | —CH₃ |
| 2503 | H | D | H | H | —CH₃ |
| 2504 | H | H | D | H | —CH₃ |
| 2505 | H | H | H | D | —CH₃ |
| 2506 | D | D | H | H | —CH₃ |
| 2507 | D | H | D | H | —CH₃ |
| 2508 | D | H | H | D | —CH₃ |
| 2509 | H | D | D | H | —CH₃ |
| 2510 | H | D | H | D | —CH₃ |
| 2511 | H | H | D | D | —CH₃ |
| 2512 | D | D | D | H | —CH₃ |
| 2513 | D | D | H | D | —CH₃ |
| 2514 | D | H | D | D | —CH₃ |
| 2515 | H | D | D | D | —CH₃ |
| 2516 | D | D | D | D | —CH₃ |
| 2517 | H | H | H | H | —CD₃ |
| 2518 | D | H | H | H | —CD₃ |
| 2519 | H | D | H | H | —CD₃ |
| 2520 | H | H | D | H | —CD₃ |
| 2521 | H | H | H | D | —CD₃ |
| 2522 | D | D | H | H | —CD₃ |
| 2523 | D | H | D | H | —CD₃ |
| 2524 | D | H | H | D | —CD₃ |
| 2525 | H | D | D | H | —CD₃ |
| 2526 | H | D | H | D | —CD₃ |
| 2527 | H | H | D | D | —CD₃ |
| 2528 | D | D | D | H | —CD₃ |
| 2529 | D | D | H | D | —CD₃ |
| 2530 | D | H | D | D | —CD₃ |
| 2531 | H | D | D | D | —CD₃ |
| 2532 | D | D | D | D | —CD₃ |

TABLE 26

Exemplary compounds of Formula (A-I-j)

| Compound | Y¹ | Y² | Y³ | Y⁴ | R |
|---|---|---|---|---|---|
| 2601 | H | H | H | H | —CH₃ |
| 2602 | D | H | H | H | —CH₃ |
| 2603 | H | D | H | H | —CH₃ |
| 2604 | H | H | D | H | —CH₃ |
| 2605 | H | H | H | D | —CH₃ |
| 2606 | D | D | H | H | —CH₃ |
| 2607 | D | H | D | H | —CH₃ |
| 2608 | D | H | H | D | —CH₃ |
| 2609 | H | D | D | H | —CH₃ |
| 2610 | H | D | H | D | —CH₃ |
| 2611 | H | H | D | D | —CH₃ |
| 2612 | D | D | D | H | —CH₃ |
| 2613 | D | D | H | D | —CH₃ |
| 2614 | D | H | D | D | —CH₃ |
| 2615 | H | D | D | D | —CH₃ |
| 2616 | D | D | D | D | —CH₃ |
| 2617 | H | H | H | H | —CD₃ |
| 2618 | D | H | H | H | —CD₃ |
| 2619 | H | D | H | H | —CD₃ |
| 2620 | H | H | D | H | —CD₃ |
| 2621 | H | H | H | D | —CD₃ |
| 2622 | D | D | H | H | —CD₃ |
| 2623 | D | H | D | H | —CD₃ |
| 2624 | D | H | H | D | —CD₃ |
| 2625 | H | D | D | H | —CD₃ |
| 2626 | H | D | H | D | —CD₃ |
| 2627 | H | H | D | D | —CD₃ |
| 2628 | D | D | D | H | —CD₃ |
| 2629 | D | D | H | D | —CD₃ |
| 2630 | D | H | D | D | —CD₃ |
| 2631 | H | D | D | D | —CD₃ |
| 2632 | D | D | D | D | —CD₃ | or a pharmaceutically acceptable form thereof.

In one embodiment, the compound is a compound of Formula (A-I-j):

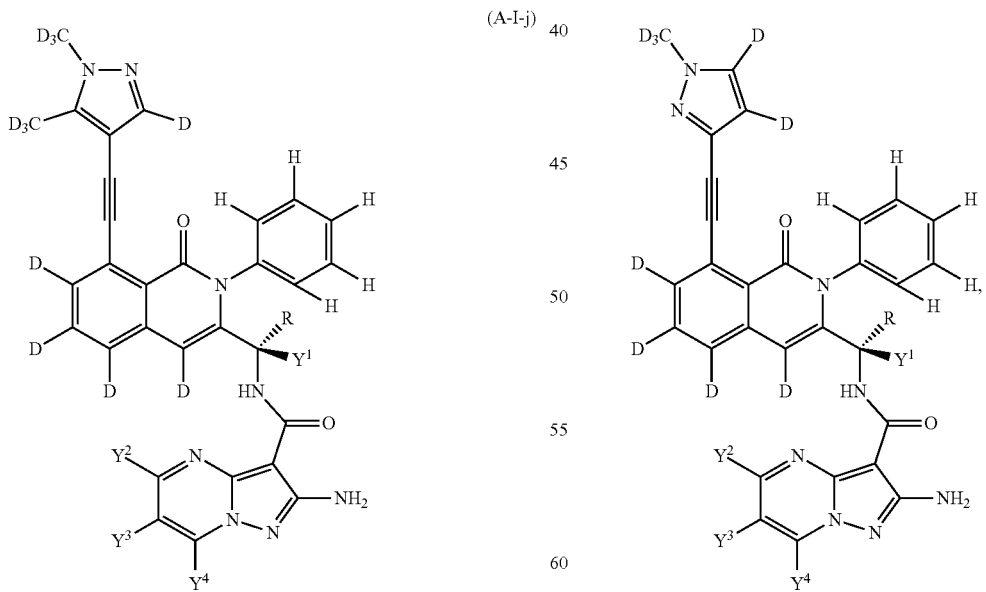

(A-I-j)

or a pharmaceutically acceptable form thereof.

In one embodiment, the compound is a compound of Formula (A-I-j) selected from any one of the compounds in Table 26.

or a pharmaceutically acceptable form thereof.

In one embodiment, the compound is a compound of Formula (A-II-e):

(A-II-e)

or a pharmaceutically acceptable form thereof.

In one embodiment, the compound is a compound of Formula (A-II-e) selected from any one of the compounds in Table 27.

TABLE 27

Exemplary compounds of Formula (A-II-e)

| Compound | $Y^1$ | $Y^2$ | $Y^3$ | $Y^4$ | R |
|---|---|---|---|---|---|
| 2701 | H | H | H | H | —CH$_3$ |
| 2702 | D | H | H | H | —CH$_3$ |
| 2703 | H | D | H | H | —CH$_3$ |
| 2704 | H | H | D | H | —CH$_3$ |
| 2705 | H | H | H | D | —CH$_3$ |
| 2706 | D | D | H | H | —CH$_3$ |
| 2707 | D | H | D | H | —CH$_3$ |
| 2708 | D | H | H | D | —CH$_3$ |
| 2709 | H | D | D | H | —CH$_3$ |
| 2710 | H | D | H | D | —CH$_3$ |
| 2711 | H | H | D | D | —CH$_3$ |
| 2712 | D | D | D | H | —CH$_3$ |
| 2713 | D | D | H | D | —CH$_3$ |
| 2714 | D | H | D | D | —CH$_3$ |
| 2715 | H | D | D | D | —CH$_3$ |
| 2716 | D | D | D | D | —CH$_3$ |
| 2717 | H | H | H | H | —CD$_3$ |
| 2718 | D | H | H | H | —CD$_3$ |
| 2719 | H | D | H | H | —CD$_3$ |
| 2720 | H | H | D | H | —CD$_3$ |
| 2721 | H | H | H | D | —CD$_3$ |
| 2722 | D | D | H | H | —CD$_3$ |
| 2723 | D | H | D | H | —CD$_3$ |
| 2724 | D | H | H | D | —CD$_3$ |
| 2725 | H | D | D | H | —CD$_3$ |
| 2726 | H | D | H | D | —CD$_3$ |
| 2727 | H | H | D | D | —CD$_3$ |
| 2728 | D | D | D | H | —CD$_3$ |
| 2729 | D | D | H | D | —CD$_3$ |
| 2730 | D | H | D | D | —CD$_3$ |
| 2731 | H | D | D | D | —CD$_3$ |
| 2732 | D | D | D | D | —CD$_3$ |

TABLE 28

Exemplary compounds of Formula (B-I-i)

| Compound | $Y^1$ | $Y^2$ | $Y^3$ | $Y^4$ | R |
|---|---|---|---|---|---|
| 2801 | H | H | H | H | —CH$_3$ |
| 2802 | D | H | H | H | —CH$_3$ |
| 2803 | H | D | H | H | —CH$_3$ |
| 2804 | H | H | D | H | —CH$_3$ |
| 2805 | H | H | H | D | —CH$_3$ |
| 2806 | D | D | H | H | —CH$_3$ |
| 2807 | D | H | D | H | —CH$_3$ |
| 2808 | D | H | H | D | —CH$_3$ |
| 2809 | H | D | D | H | —CH$_3$ |
| 2810 | H | D | H | D | —CH$_3$ |
| 2811 | H | H | D | D | —CH$_3$ |
| 2812 | D | D | D | H | —CH$_3$ |
| 2813 | D | D | H | D | —CH$_3$ |
| 2814 | D | H | D | D | —CH$_3$ |
| 2815 | H | D | D | D | —CH$_3$ |
| 2816 | D | D | D | D | —CH$_3$ |
| 2817 | H | H | H | H | —CD$_3$ |
| 2818 | D | H | H | H | —CD$_3$ |
| 2819 | H | D | H | H | —CD$_3$ |
| 2820 | H | H | D | H | —CD$_3$ |
| 2821 | H | H | H | D | —CD$_3$ |
| 2822 | D | D | H | H | —CD$_3$ |
| 2823 | D | H | D | H | —CD$_3$ |
| 2824 | D | H | H | D | —CD$_3$ |
| 2825 | H | D | D | H | —CD$_3$ |
| 2826 | H | D | H | D | —CD$_3$ |
| 2827 | H | H | D | D | —CD$_3$ |
| 2828 | D | D | D | H | —CD$_3$ |
| 2829 | D | D | H | D | —CD$_3$ |
| 2830 | D | H | D | D | —CD$_3$ |
| 2831 | H | D | D | D | —CD$_3$ |
| 2832 | D | D | D | D | —CD$_3$ | or a pharmaceutically acceptable form thereof.

In one embodiment, the compound is a compound of Formula (B-I-i):

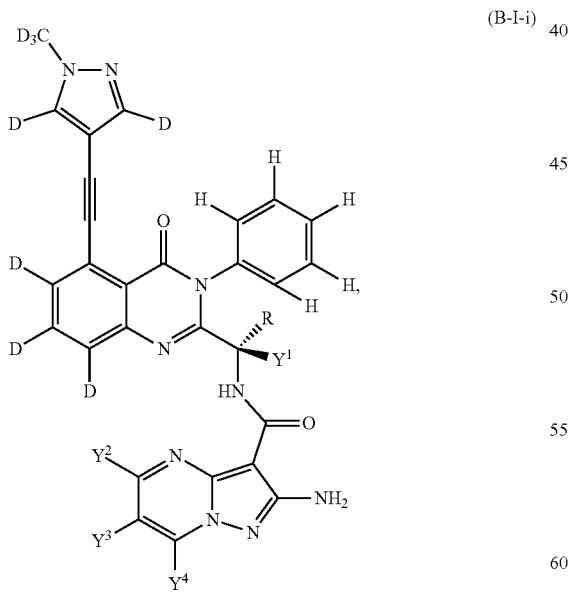

(B-I-i)

or a pharmaceutically acceptable form thereof.

In one embodiment, the compound is a compound of Formula (B-I-i) selected from any one of the compounds in Table 28.

or a pharmaceutically acceptable form thereof.

In one embodiment, the compound is a compound of Formula (B-I-j):

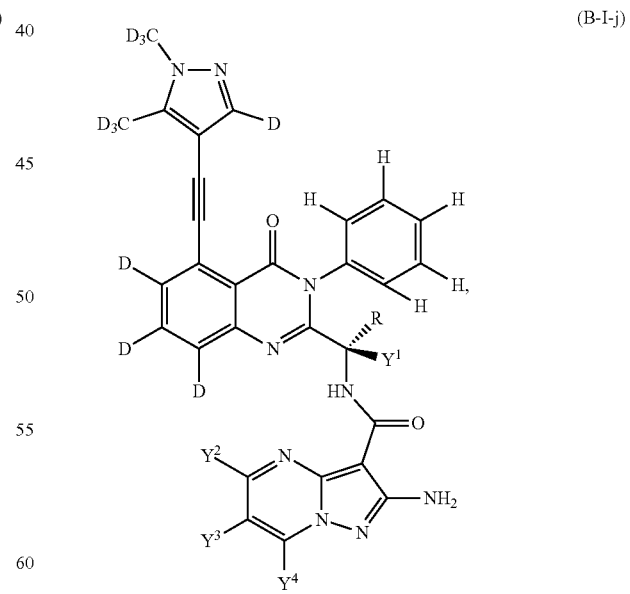

(B-I-j)

or a pharmaceutically acceptable form thereof.

In one embodiment, the compound is a compound of Formula (B-I-j) selected from any one of the compounds in Table 29.

TABLE 29

Exemplary compounds of Formula (B-I-j)

| Compound | Y¹ | Y² | Y³ | Y⁴ | R |
|---|---|---|---|---|---|
| 2901 | H | H | H | H | —CH₃ |
| 2902 | D | H | H | H | —CH₃ |
| 2903 | H | D | H | H | —CH₃ |
| 2904 | H | H | D | H | —CH₃ |
| 2905 | H | H | H | D | —CH₃ |
| 2906 | D | D | H | H | —CH₃ |
| 2907 | D | H | D | H | —CH₃ |
| 2908 | D | H | H | D | —CH₃ |
| 2909 | H | D | D | H | —CH₃ |
| 2910 | H | D | H | D | —CH₃ |
| 2911 | H | H | D | D | —CH₃ |
| 2912 | D | D | D | H | —CH₃ |
| 2913 | D | D | H | D | —CH₃ |
| 2914 | D | H | D | D | —CH₃ |
| 2915 | H | D | D | D | —CH₃ |
| 2916 | D | D | D | D | —CH₃ |
| 2917 | H | H | H | H | —CD₃ |
| 2918 | D | H | H | H | —CD₃ |
| 2919 | H | D | H | H | —CD₃ |
| 2920 | H | H | D | H | —CD₃ |
| 2921 | H | H | H | D | —CD₃ |
| 2922 | D | D | H | H | —CD₃ |
| 2923 | D | H | D | H | —CD₃ |
| 2924 | D | H | H | D | —CD₃ |
| 2925 | H | D | D | H | —CD₃ |
| 2926 | H | D | H | D | —CD₃ |
| 2927 | H | H | D | D | —CD₃ |
| 2928 | D | D | D | H | —CD₃ |
| 2929 | D | D | H | D | —CD₃ |
| 2930 | D | H | D | D | —CD₃ |
| 2931 | H | D | D | D | —CD₃ |
| 2932 | D | D | D | D | —CD₃ | or a pharmaceutically acceptable form thereof.

In one embodiment, the compound is a compound of Formula (B-II-e):

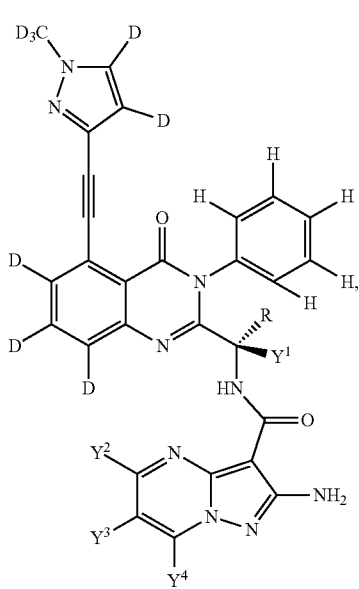

(B-II-e)

or a pharmaceutically acceptable form thereof.

In one embodiment, the compound is a compound of Formula (B-II-e) selected from any one of the compounds in Table 30.

TABLE 30

Exemplary compounds of Formula (B-II-e)

| Compound | Y¹ | Y² | Y³ | Y⁴ | R |
|---|---|---|---|---|---|
| 3001 | H | H | H | H | —CH₃ |
| 3002 | D | H | H | H | —CH₃ |
| 3003 | H | D | H | H | —CH₃ |
| 3004 | H | H | D | H | —CH₃ |
| 3005 | H | H | H | D | —CH₃ |
| 3006 | D | D | H | H | —CH₃ |
| 3007 | D | H | D | H | —CH₃ |
| 3008 | D | H | H | D | —CH₃ |
| 3009 | H | D | D | H | —CH₃ |
| 3010 | H | D | H | D | —CH₃ |
| 3011 | H | H | D | D | —CH₃ |
| 3012 | D | D | D | H | —CH₃ |
| 3013 | D | D | H | D | —CH₃ |
| 3014 | D | H | D | D | —CH₃ |
| 3015 | H | D | D | D | —CH₃ |
| 3016 | D | D | D | D | —CH₃ |
| 3017 | H | H | H | H | —CD₃ |
| 3018 | D | H | H | H | —CD₃ |
| 3019 | H | D | H | H | —CD₃ |
| 3020 | H | H | D | H | —CD₃ |
| 3021 | H | H | H | D | —CD₃ |
| 3022 | D | D | H | H | —CD₃ |
| 3023 | D | H | D | H | —CD₃ |
| 3024 | D | H | H | D | —CD₃ |
| 3025 | H | D | D | H | —CD₃ |
| 3026 | H | D | H | D | —CD₃ |
| 3027 | H | H | D | D | —CD₃ |
| 3028 | D | D | D | H | —CD₃ |
| 3029 | D | D | H | D | —CD₃ |
| 3030 | D | H | D | D | —CD₃ |
| 3031 | H | D | D | D | —CD₃ |
| 3032 | D | D | D | D | —CD₃ | or a pharmaceutically acceptable form thereof.

In one embodiment, the compound is a compound of Formula (A-I-k):

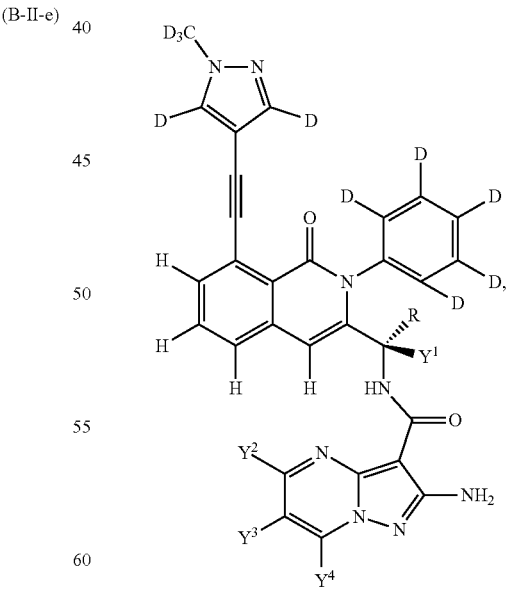

(A-I-k)

or a pharmaceutically acceptable form thereof.

In one embodiment, the compound is a compound of Formula (A-I-k) selected from any one of the compounds in Table 31.

TABLE 31

Exemplary compounds of Formula (A-I-k)

| Compound | $Y^1$ | $Y^2$ | $Y^3$ | $Y^4$ | R |
|---|---|---|---|---|---|
| 3101 | H | H | H | H | —CH$_3$ |
| 3102 | D | H | H | H | —CH$_3$ |
| 3103 | H | D | H | H | —CH$_3$ |
| 3104 | H | H | D | H | —CH$_3$ |
| 3105 | H | H | H | D | —CH$_3$ |
| 3106 | D | D | H | H | —CH$_3$ |
| 3107 | D | H | D | H | —CH$_3$ |
| 3108 | D | H | H | D | —CH$_3$ |
| 3109 | H | D | D | H | —CH$_3$ |
| 3110 | H | D | H | D | —CH$_3$ |
| 3111 | H | H | D | D | —CH$_3$ |
| 3112 | D | D | D | H | —CH$_3$ |
| 3113 | D | D | H | D | —CH$_3$ |
| 3114 | D | H | D | D | —CH$_3$ |
| 3115 | H | D | D | D | —CH$_3$ |
| 3116 | D | D | D | D | —CH$_3$ |
| 3117 | H | H | H | H | —CD$_3$ |
| 3118 | D | H | H | H | —CD$_3$ |
| 3119 | H | D | H | H | —CD$_3$ |
| 3120 | H | H | D | H | —CD$_3$ |
| 3121 | H | H | H | D | —CD$_3$ |
| 3122 | D | D | H | H | —CD$_3$ |
| 3123 | D | H | D | H | —CD$_3$ |
| 3124 | D | H | H | D | —CD$_3$ |
| 3125 | H | D | D | H | —CD$_3$ |
| 3126 | H | D | H | D | —CD$_3$ |
| 3127 | H | H | D | D | —CD$_3$ |
| 3128 | D | D | D | H | —CD$_3$ |
| 3129 | D | D | H | D | —CD$_3$ |
| 3130 | D | H | D | D | —CD$_3$ |
| 3131 | H | D | D | D | —CD$_3$ |
| 3132 | D | D | D | D | —CD$_3$ |

TABLE 32

Exemplary compounds of Formula (A-I-l)

| Compound | $Y^1$ | $Y^2$ | $Y^3$ | $Y^4$ | R |
|---|---|---|---|---|---|
| 3201 | H | H | H | H | —CH$_3$ |
| 3202 | D | H | H | H | —CH$_3$ |
| 3203 | H | D | H | H | —CH$_3$ |
| 3204 | H | H | D | H | —CH$_3$ |
| 3205 | H | H | H | D | —CH$_3$ |
| 3206 | D | D | H | H | —CH$_3$ |
| 3207 | D | H | D | H | —CH$_3$ |
| 3208 | D | H | H | D | —CH$_3$ |
| 3209 | H | D | D | H | —CH$_3$ |
| 3210 | H | D | H | D | —CH$_3$ |
| 3211 | H | H | D | D | —CH$_3$ |
| 3212 | D | D | D | H | —CH$_3$ |
| 3213 | D | D | H | D | —CH$_3$ |
| 3214 | D | H | D | D | —CH$_3$ |
| 3215 | H | D | D | D | —CH$_3$ |
| 3216 | D | D | D | D | —CH$_3$ |
| 3217 | H | H | H | H | —CD$_3$ |
| 3218 | D | H | H | H | —CD$_3$ |
| 3219 | H | D | H | H | —CD$_3$ |
| 3220 | H | H | D | H | —CD$_3$ |
| 3221 | H | H | H | D | —CD$_3$ |
| 3222 | D | D | H | H | —CD$_3$ |
| 3223 | D | H | D | H | —CD$_3$ |
| 3224 | D | H | H | D | —CD$_3$ |
| 3225 | H | D | D | H | —CD$_3$ |
| 3226 | H | D | H | D | —CD$_3$ |
| 3227 | H | H | D | D | —CD$_3$ |
| 3228 | D | D | D | H | —CD$_3$ |
| 3229 | D | D | H | D | —CD$_3$ |
| 3230 | D | H | D | D | —CD$_3$ |
| 3231 | H | D | D | D | —CD$_3$ |
| 3232 | D | D | D | D | —CD$_3$ | or a pharmaceutically acceptable form thereof.

In one embodiment, the compound is a compound of Formula (A-I-l):

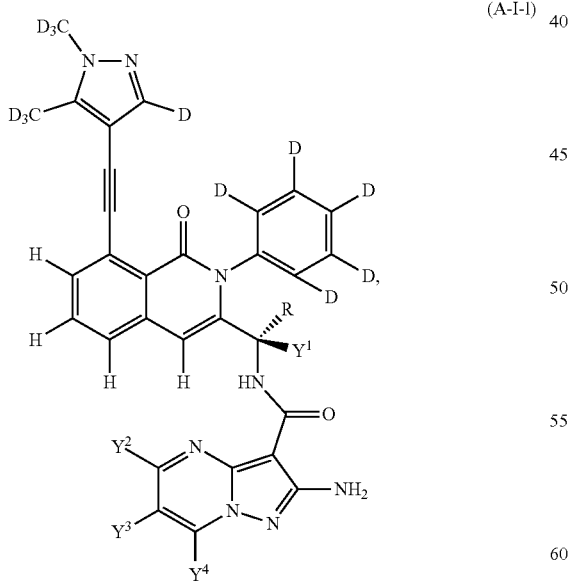

(A-I-l)

or a pharmaceutically acceptable form thereof.

In one embodiment, the compound is a compound of Formula (A-I-l) selected from any one of the compounds in Table 32.

or a pharmaceutically acceptable form thereof.

In one embodiment, the compound is a compound of Formula (A-II-f):

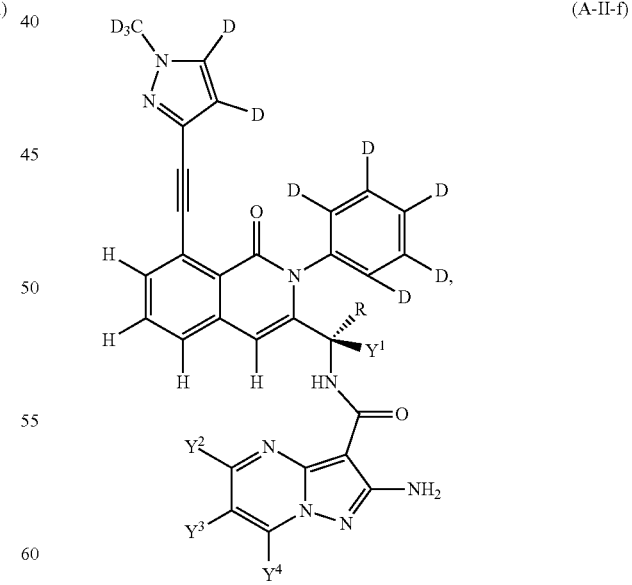

(A-II-f)

or a pharmaceutically acceptable form thereof.

In one embodiment, the compound is a compound of Formula (A-II-f) selected from any one of the compounds in Table 33.

TABLE 33

Exemplary compounds of Formula (A-II-f)

| Compound | Y$^1$ | Y$^2$ | Y$^3$ | Y$^4$ | R |
|---|---|---|---|---|---|
| 3301 | H | H | H | H | —CH$_3$ |
| 3302 | D | H | H | H | —CH$_3$ |
| 3303 | H | D | H | H | —CH$_3$ |
| 3304 | H | H | D | H | —CH$_3$ |
| 3305 | H | H | H | D | —CH$_3$ |
| 3306 | D | D | H | H | —CH$_3$ |
| 3307 | D | H | D | H | —CH$_3$ |
| 3308 | D | H | H | D | —CH$_3$ |
| 3309 | H | D | D | H | —CH$_3$ |
| 3310 | H | D | H | D | —CH$_3$ |
| 3311 | H | H | D | D | —CH$_3$ |
| 3312 | D | D | D | H | —CH$_3$ |
| 3313 | D | D | H | D | —CH$_3$ |
| 3314 | D | H | D | D | —CH$_3$ |
| 3315 | H | D | D | D | —CH$_3$ |
| 3316 | D | D | D | D | —CH$_3$ |
| 3317 | H | H | H | H | —CD$_3$ |
| 3318 | D | H | H | H | —CD$_3$ |
| 3319 | H | D | H | H | —CD$_3$ |
| 3320 | H | H | D | H | —CD$_3$ |
| 3321 | H | H | H | D | —CD$_3$ |
| 3322 | D | D | H | H | —CD$_3$ |
| 3323 | D | H | D | H | —CD$_3$ |
| 3324 | D | H | H | D | —CD$_3$ |
| 3325 | H | D | D | H | —CD$_3$ |
| 3326 | H | D | H | D | —CD$_3$ |
| 3327 | H | H | D | D | —CD$_3$ |
| 3328 | D | D | D | H | —CD$_3$ |
| 3329 | D | D | H | D | —CD$_3$ |
| 3330 | D | H | D | D | —CD$_3$ |
| 3331 | H | D | D | D | —CD$_3$ |
| 3332 | D | D | D | D | —CD$_3$ |

TABLE 34

Exemplary compounds of Formula (B-I-k)

| Compound | Y$^1$ | Y$^2$ | Y$^3$ | Y$^4$ | R |
|---|---|---|---|---|---|
| 3401 | H | H | H | H | —CH$_3$ |
| 3402 | D | H | H | H | —CH$_3$ |
| 3403 | H | D | H | H | —CH$_3$ |
| 3404 | H | H | D | H | —CH$_3$ |
| 3405 | H | H | H | D | —CH$_3$ |
| 3406 | D | D | H | H | —CH$_3$ |
| 3407 | D | H | D | H | —CH$_3$ |
| 3408 | D | H | H | D | —CH$_3$ |
| 3409 | H | D | D | H | —CH$_3$ |
| 3410 | H | D | H | D | —CH$_3$ |
| 3411 | H | H | D | D | —CH$_3$ |
| 3412 | D | D | D | H | —CH$_3$ |
| 3413 | D | D | H | D | —CH$_3$ |
| 3414 | D | H | D | D | —CH$_3$ |
| 3415 | H | D | D | D | —CH$_3$ |
| 3416 | D | D | D | D | —CH$_3$ |
| 3417 | H | H | H | H | —CD$_3$ |
| 3418 | D | H | H | H | —CD$_3$ |
| 3419 | H | D | H | H | —CD$_3$ |
| 3420 | H | H | D | H | —CD$_3$ |
| 3421 | H | H | H | D | —CD$_3$ |
| 3422 | D | D | H | H | —CD$_3$ |
| 3423 | D | H | D | H | —CD$_3$ |
| 3424 | D | H | H | D | —CD$_3$ |
| 3425 | H | D | D | H | —CD$_3$ |
| 3426 | H | D | H | D | —CD$_3$ |
| 3427 | H | H | D | D | —CD$_3$ |
| 3428 | D | D | D | H | —CD$_3$ |
| 3429 | D | D | H | D | —CD$_3$ |
| 3430 | D | H | D | D | —CD$_3$ |
| 3431 | H | D | D | D | —CD$_3$ |
| 3432 | D | D | D | D | —CD$_3$ | or a pharmaceutically acceptable form thereof.

In one embodiment, the compound is a compound of Formula (B-I-k):

or a pharmaceutically acceptable form thereof.

In one embodiment, the compound is a compound of Formula (B-I-l):

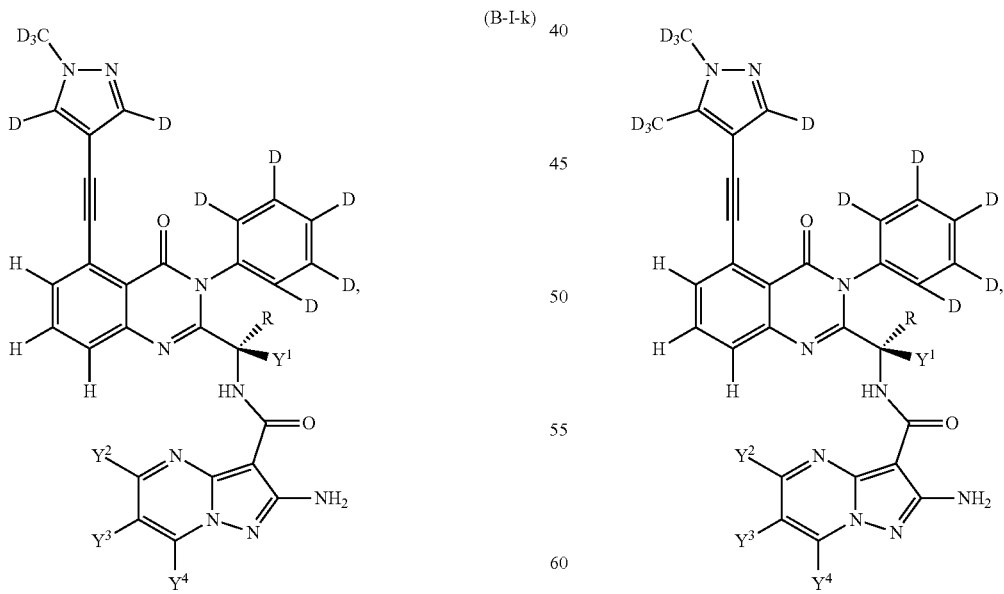

(B-I-k)

(B-I-l)

or a pharmaceutically acceptable form thereof.

In one embodiment, the compound is a compound of Formula (B-I-k) selected from any one of the compounds in Table 34.

or a pharmaceutically acceptable form thereof.

In one embodiment, the compound is a compound of Formula (B-I-l) selected from any one of the compounds in Table 35.

TABLE 35

Exemplary compounds of Formula (B-I-l)

| Compound | Y¹ | Y² | Y³ | Y⁴ | R |
|---|---|---|---|---|---|
| 3501 | H | H | H | H | —CH₃ |
| 3502 | D | H | H | H | —CH₃ |
| 3503 | H | D | H | H | —CH₃ |
| 3504 | H | H | D | H | —CH₃ |
| 3505 | H | H | H | D | —CH₃ |
| 3506 | D | D | H | H | —CH₃ |
| 3507 | D | H | D | H | —CH₃ |
| 3508 | D | H | H | D | —CH₃ |
| 3509 | H | D | D | H | —CH₃ |
| 3510 | H | D | H | D | —CH₃ |
| 3511 | H | H | D | D | —CH₃ |
| 3512 | D | D | D | H | —CH₃ |
| 3513 | D | D | H | D | —CH₃ |
| 3514 | D | H | D | D | —CH₃ |
| 3515 | H | D | D | D | —CH₃ |
| 3516 | D | D | D | D | —CH₃ |
| 3517 | H | H | H | H | —CD₃ |
| 3518 | D | H | H | H | —CD₃ |
| 3519 | H | D | H | H | —CD₃ |
| 3520 | H | H | D | H | —CD₃ |
| 3521 | H | H | H | D | —CD₃ |
| 3522 | D | D | H | H | —CD₃ |
| 3523 | D | H | D | H | —CD₃ |
| 3524 | D | H | H | D | —CD₃ |
| 3525 | H | D | D | H | —CD₃ |
| 3526 | H | D | H | D | —CD₃ |
| 3527 | H | H | D | D | —CD₃ |
| 3528 | D | D | D | H | —CD₃ |
| 3529 | D | D | H | D | —CD₃ |
| 3530 | D | H | D | D | —CD₃ |
| 3531 | H | D | D | D | —CD₃ |
| 3532 | D | D | D | D | —CD₃ | or a pharmaceutically acceptable form thereof.

In one embodiment, the compound is a compound of Formula (B-II-f):

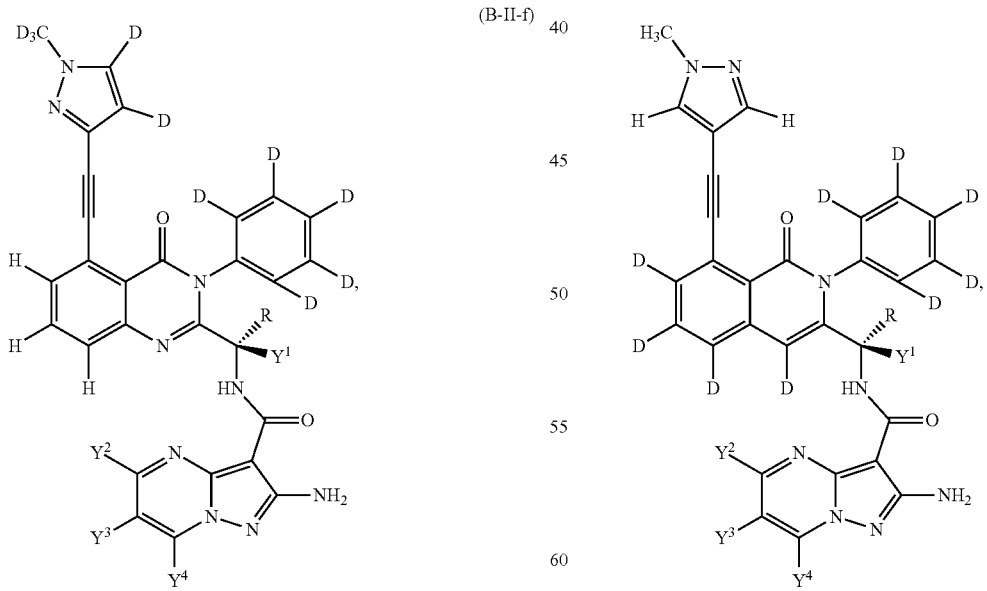

(B-II-f)

or a pharmaceutically acceptable form thereof.

In one embodiment, the compound is a compound of Formula (B-II-f) selected from any one of the compounds in Table 36.

TABLE 36

Exemplary compounds of Formula (B-II-f)

| Compound | Y¹ | Y² | Y³ | Y⁴ | R |
|---|---|---|---|---|---|
| 3601 | H | H | H | H | —CH₃ |
| 3602 | D | H | H | H | —CH₃ |
| 3603 | H | D | H | H | —CH₃ |
| 3604 | H | H | D | H | —CH₃ |
| 3605 | H | H | H | D | —CH₃ |
| 3606 | D | D | H | H | —CH₃ |
| 3607 | D | H | D | H | —CH₃ |
| 3608 | D | H | H | D | —CH₃ |
| 3609 | H | D | D | H | —CH₃ |
| 3610 | H | D | H | D | —CH₃ |
| 3611 | H | H | D | D | —CH₃ |
| 3612 | D | D | D | H | —CH₃ |
| 3613 | D | D | H | D | —CH₃ |
| 3614 | D | H | D | D | —CH₃ |
| 3615 | H | D | D | D | —CH₃ |
| 3616 | D | D | D | D | —CH₃ |
| 3617 | H | H | H | H | —CD₃ |
| 3618 | D | H | H | H | —CD₃ |
| 3619 | H | D | H | H | —CD₃ |
| 3620 | H | H | D | H | —CD₃ |
| 3621 | H | H | H | D | —CD₃ |
| 3622 | D | D | H | H | —CD₃ |
| 3623 | D | H | D | H | —CD₃ |
| 3624 | D | H | H | D | —CD₃ |
| 3625 | H | D | D | H | —CD₃ |
| 3626 | H | D | H | D | —CD₃ |
| 3627 | H | H | D | D | —CD₃ |
| 3628 | D | D | D | H | —CD₃ |
| 3629 | D | D | H | D | —CD₃ |
| 3630 | D | H | D | D | —CD₃ |
| 3631 | H | D | D | D | —CD₃ |
| 3632 | D | D | D | D | —CD₃ | or a pharmaceutically acceptable form thereof.

In one embodiment, the compound is a compound of Formula (A-I-m):

(A-I-m)

or a pharmaceutically acceptable form thereof.

In one embodiment, the compound is a compound of Formula (A-I-m) selected from any one of the compounds in Table 37.

TABLE 37

Exemplary compounds of Formula (A-I-m)

| Compound | Y¹ | Y² | Y³ | Y⁴ | R |
|---|---|---|---|---|---|
| 3701 | H | H | H | H | —CH₃ |
| 3702 | D | H | H | H | —CH₃ |
| 3703 | H | D | H | H | —CH₃ |
| 3704 | H | H | D | H | —CH₃ |
| 3705 | H | H | H | D | —CH₃ |
| 3706 | D | D | H | H | —CH₃ |
| 3707 | D | H | D | H | —CH₃ |
| 3708 | D | H | H | D | —CH₃ |
| 3709 | H | D | D | H | —CH₃ |
| 3710 | H | D | H | D | —CH₃ |
| 3711 | H | H | D | D | —CH₃ |
| 3712 | D | D | D | H | —CH₃ |
| 3713 | D | D | H | D | —CH₃ |
| 3714 | D | H | D | D | —CH₃ |
| 3715 | H | D | D | D | —CH₃ |
| 3716 | D | D | D | D | —CH₃ |
| 3717 | H | H | H | H | —CD₃ |
| 3718 | D | H | H | H | —CD₃ |
| 3719 | H | D | H | H | —CD₃ |
| 3720 | H | H | D | H | —CD₃ |
| 3721 | H | H | H | D | —CD₃ |
| 3722 | D | D | H | H | —CD₃ |
| 3723 | D | H | D | H | —CD₃ |
| 3724 | D | H | H | D | —CD₃ |
| 3725 | H | D | D | H | —CD₃ |
| 3726 | H | D | H | D | —CD₃ |
| 3727 | H | H | D | D | —CD₃ |
| 3728 | D | D | D | H | —CD₃ |
| 3729 | D | D | H | D | —CD₃ |
| 3730 | D | H | D | D | —CD₃ |
| 3731 | H | D | D | D | —CD₃ |
| 3732 | D | D | D | D | —CD₃ | or a pharmaceutically acceptable form thereof.

In one embodiment, the compound is a compound of Formula (A-I-n):

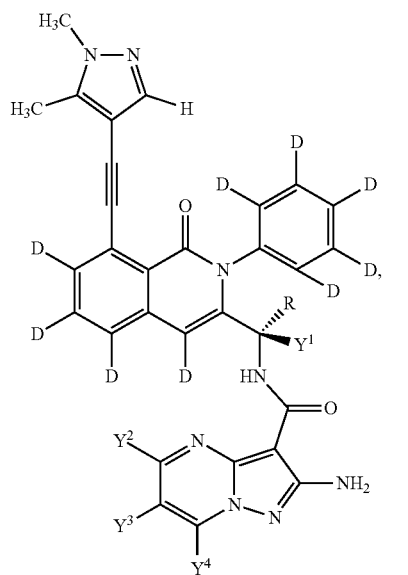

(A-I-n)

or a pharmaceutically acceptable form thereof.

In one embodiment, the compound is a compound of Formula (A-I-n) selected from any one of the compounds in Table 38.

TABLE 38

Exemplary compounds of Formula (A-I-n)

| Compound | Y¹ | Y² | Y³ | Y⁴ | R |
|---|---|---|---|---|---|
| 3801 | H | H | H | H | —CH₃ |
| 3802 | D | H | H | H | —CH₃ |
| 3803 | H | D | H | H | —CH₃ |
| 3804 | H | H | D | H | —CH₃ |
| 3805 | H | H | H | D | —CH₃ |
| 3806 | D | D | H | H | —CH₃ |
| 3807 | D | H | D | H | —CH₃ |
| 3808 | D | H | H | D | —CH₃ |
| 3809 | H | D | D | H | —CH₃ |
| 3810 | H | D | H | D | —CH₃ |
| 3811 | H | H | D | D | —CH₃ |
| 3812 | D | D | D | H | —CH₃ |
| 3813 | D | D | H | D | —CH₃ |
| 3814 | D | H | D | D | —CH₃ |
| 3815 | H | D | D | D | —CH₃ |
| 3816 | D | D | D | D | —CH₃ |
| 3817 | H | H | H | H | —CD₃ |
| 3818 | D | H | H | H | —CD₃ |
| 3819 | H | D | H | H | —CD₃ |
| 3820 | H | H | D | H | —CD₃ |
| 3821 | H | H | H | D | —CD₃ |
| 3822 | D | D | H | H | —CD₃ |
| 3823 | D | H | D | H | —CD₃ |
| 3824 | D | H | H | D | —CD₃ |
| 3825 | H | D | D | H | —CD₃ |
| 3826 | H | D | H | D | —CD₃ |
| 3827 | H | H | D | D | —CD₃ |
| 3828 | D | D | D | H | —CD₃ |
| 3829 | D | D | H | D | —CD₃ |
| 3830 | D | H | D | D | —CD₃ |
| 3831 | H | D | D | D | —CD₃ |
| 3832 | D | D | D | D | —CD₃ | or a pharmaceutically acceptable form thereof.

In one embodiment, the compound is a compound of Formula (A-II-g):

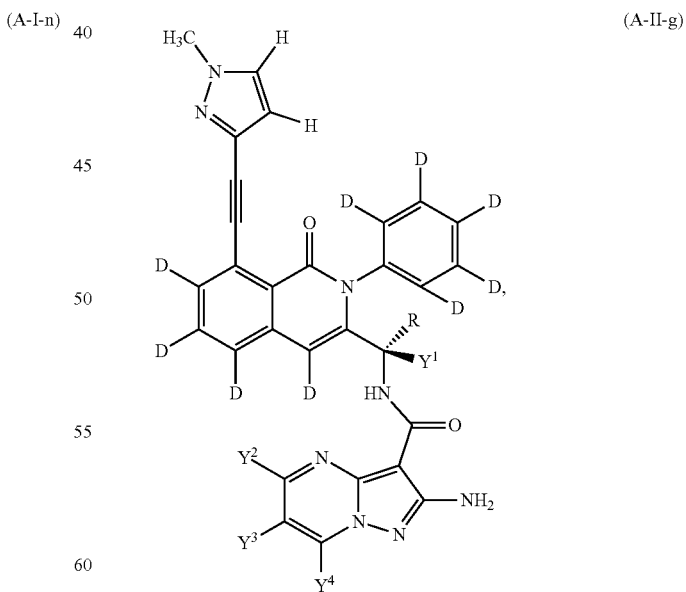

(A-II-g)

or a pharmaceutically acceptable form thereof.

In one embodiment, the compound is a compound of Formula (A-II-g) selected from any one of the compounds in Table 39.

TABLE 39

Exemplary compounds of Formula (A-II-g)

| Compound | Y¹ | Y² | Y³ | Y⁴ | R |
|---|---|---|---|---|---|
| 3901 | H | H | H | H | —CH₃ |
| 3902 | D | H | H | H | —CH₃ |
| 3903 | H | D | H | H | —CH₃ |
| 3904 | H | H | D | H | —CH₃ |
| 3905 | H | H | H | D | —CH₃ |
| 3906 | D | D | H | H | —CH₃ |
| 3907 | D | H | D | H | —CH₃ |
| 3908 | D | H | H | D | —CH₃ |
| 3909 | H | D | D | H | —CH₃ |
| 3910 | H | D | H | D | —CH₃ |
| 3911 | H | H | D | D | —CH₃ |
| 3912 | D | D | D | H | —CH₃ |
| 3913 | D | D | H | D | —CH₃ |
| 3914 | D | H | D | D | —CH₃ |
| 3915 | H | D | D | D | —CH₃ |
| 3916 | D | D | D | D | —CH₃ |
| 3917 | H | H | H | H | —CD₃ |
| 3918 | D | H | H | H | —CD₃ |
| 3919 | H | D | H | H | —CD₃ |
| 3920 | H | H | D | H | —CD₃ |
| 3921 | H | H | H | D | —CD₃ |
| 3922 | D | D | H | H | —CD₃ |
| 3923 | D | H | D | H | —CD₃ |
| 3924 | D | H | H | D | —CD₃ |
| 3925 | H | D | D | H | —CD₃ |
| 3926 | H | D | H | D | —CD₃ |
| 3927 | H | H | D | D | —CD₃ |
| 3928 | D | D | D | H | —CD₃ |
| 3929 | D | D | H | D | —CD₃ |
| 3930 | D | H | D | D | —CD₃ |
| 3931 | H | D | D | D | —CD₃ |
| 3932 | D | D | D | D | —CD₃ |

TABLE 40

Exemplary compounds of Formula (B-I-m)

| Compound | Y¹ | Y² | Y³ | Y⁴ | R |
|---|---|---|---|---|---|
| 4001 | H | H | H | H | —CH₃ |
| 4002 | D | H | H | H | —CH₃ |
| 4003 | H | D | H | H | —CH₃ |
| 4004 | H | H | D | H | —CH₃ |
| 4005 | H | H | H | D | —CH₃ |
| 4006 | D | D | H | H | —CH₃ |
| 4007 | D | H | D | H | —CH₃ |
| 4008 | D | H | H | D | —CH₃ |
| 4009 | H | D | D | H | —CH₃ |
| 4010 | H | D | H | D | —CH₃ |
| 4011 | H | H | D | D | —CH₃ |
| 4012 | D | D | D | H | —CH₃ |
| 4013 | D | D | H | D | —CH₃ |
| 4014 | D | H | D | D | —CH₃ |
| 4015 | H | D | D | D | —CH₃ |
| 4016 | D | D | D | D | —CH₃ |
| 4017 | H | H | H | H | —CD₃ |
| 4018 | D | H | H | H | —CD₃ |
| 4019 | H | D | H | H | —CD₃ |
| 4020 | H | H | D | H | —CD₃ |
| 4021 | H | H | H | D | —CD₃ |
| 4022 | D | D | H | H | —CD₃ |
| 4023 | D | H | D | H | —CD₃ |
| 4024 | D | H | H | D | —CD₃ |
| 4025 | H | D | D | H | —CD₃ |
| 4026 | H | D | H | D | —CD₃ |
| 4027 | H | H | D | D | —CD₃ |
| 4028 | D | D | D | H | —CD₃ |
| 4029 | D | D | H | D | —CD₃ |
| 4030 | D | H | D | D | —CD₃ |
| 4031 | H | D | D | D | —CD₃ |
| 4032 | D | D | D | D | —CD₃ | or a pharmaceutically acceptable form thereof.

In one embodiment, the compound is a compound of Formula (B-I-m):

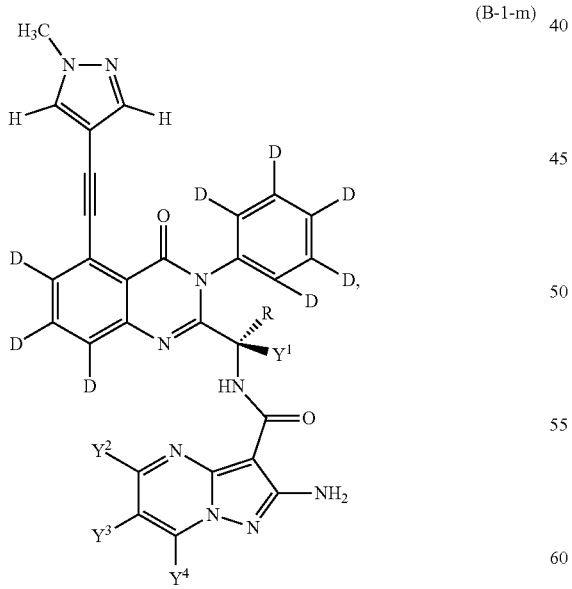

(B-I-m)

or a pharmaceutically acceptable form thereof.

In one embodiment, the compound is a compound of Formula (B-I-m) selected from any one of the compounds in Table 40.

or a pharmaceutically acceptable form thereof.

In one embodiment, the compound is a compound of Formula (B-I-n):

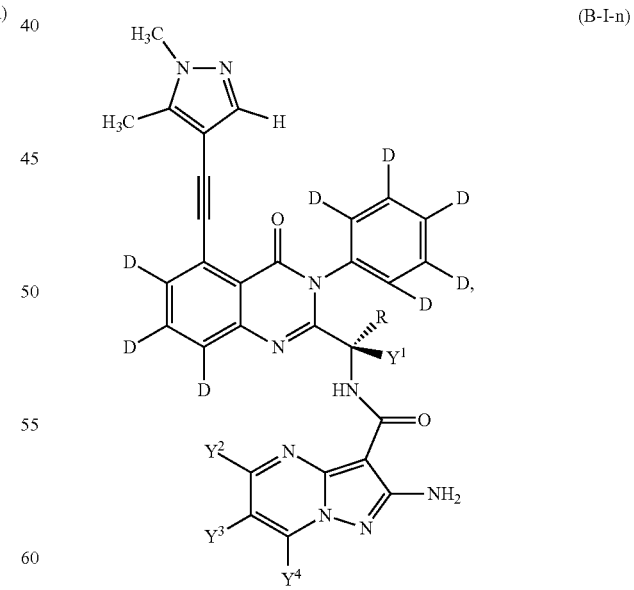

(B-I-n)

or a pharmaceutically acceptable form thereof.

In one embodiment, the compound is a compound of Formula (B-I-n) selected from any one of the compounds in Table 41.

TABLE 41

Exemplary compounds of Formula (B-I-n)

| Compound | Y¹ | Y² | Y³ | Y⁴ | R |
|---|---|---|---|---|---|
| 4101 | H | H | H | H | —CH₃ |
| 4102 | D | H | H | H | —CH₃ |
| 4103 | H | D | H | H | —CH₃ |
| 4104 | H | H | D | H | —CH₃ |
| 4105 | H | H | H | D | —CH₃ |
| 4106 | D | D | H | H | —CH₃ |
| 4107 | D | H | D | H | —CH₃ |
| 4108 | D | H | H | D | —CH₃ |
| 4109 | H | D | D | H | —CH₃ |
| 4110 | H | D | H | D | —CH₃ |
| 4111 | H | H | D | D | —CH₃ |
| 4112 | D | D | D | H | —CH₃ |
| 4113 | D | D | H | D | —CH₃ |
| 4114 | D | H | D | D | —CH₃ |
| 4115 | H | D | D | D | —CH₃ |
| 4116 | D | D | D | D | —CH₃ |
| 4117 | H | H | H | H | —CD₃ |
| 4118 | D | H | H | H | —CD₃ |
| 4119 | H | D | H | H | —CD₃ |
| 4120 | H | H | D | H | —CD₃ |
| 4121 | H | H | H | D | —CD₃ |
| 4122 | D | D | H | H | —CD₃ |
| 4123 | D | H | D | H | —CD₃ |
| 4124 | D | H | H | D | —CD₃ |
| 4125 | H | D | D | H | —CD₃ |
| 4126 | H | D | H | D | —CD₃ |
| 4127 | H | H | D | D | —CD₃ |
| 4128 | D | D | D | H | —CD₃ |
| 4129 | D | D | H | D | —CD₃ |
| 4130 | D | H | D | D | —CD₃ |
| 4131 | H | D | D | D | —CD₃ |
| 4132 | D | D | D | D | —CD₃ |

TABLE 42

Exemplary compounds of Formula (B-II-g)

| Compound | Y¹ | Y² | Y³ | Y⁴ | R |
|---|---|---|---|---|---|
| 4201 | H | H | H | H | —CH₃ |
| 4202 | D | H | H | H | —CH₃ |
| 4203 | H | D | H | H | —CH₃ |
| 4204 | H | H | D | H | —CH₃ |
| 4205 | H | H | H | D | —CH₃ |
| 4206 | D | D | H | H | —CH₃ |
| 4207 | D | H | D | H | —CH₃ |
| 4208 | D | H | H | D | —CH₃ |
| 4209 | H | D | D | H | —CH₃ |
| 4210 | H | D | H | D | —CH₃ |
| 4211 | H | H | D | D | —CH₃ |
| 4212 | D | D | D | H | —CH₃ |
| 4213 | D | D | H | D | —CH₃ |
| 4214 | D | H | D | D | —CH₃ |
| 4215 | H | D | D | D | —CH₃ |
| 4216 | D | D | D | D | —CH₃ |
| 4217 | H | H | H | H | —CD₃ |
| 4218 | D | H | H | H | —CD₃ |
| 4219 | H | D | H | H | —CD₃ |
| 4220 | H | H | D | H | —CD₃ |
| 4221 | H | H | H | D | —CD₃ |
| 4222 | D | D | H | H | —CD₃ |
| 4223 | D | H | D | H | —CD₃ |
| 4224 | D | H | H | D | —CD₃ |
| 4225 | H | D | D | H | —CD₃ |
| 4226 | H | D | H | D | —CD₃ |
| 4227 | H | H | D | D | —CD₃ |
| 4228 | D | D | D | H | —CD₃ |
| 4229 | D | D | H | D | —CD₃ |
| 4230 | D | H | D | D | —CD₃ |
| 4231 | H | D | D | D | —CD₃ |
| 4232 | D | D | D | D | —CD₃ | or a pharmaceutically acceptable form thereof.

In one embodiment, the compound is a compound of Formula (B-II-g):

or a pharmaceutically acceptable form thereof.

In one embodiment, the compound is a compound of Formula (A-I-o):

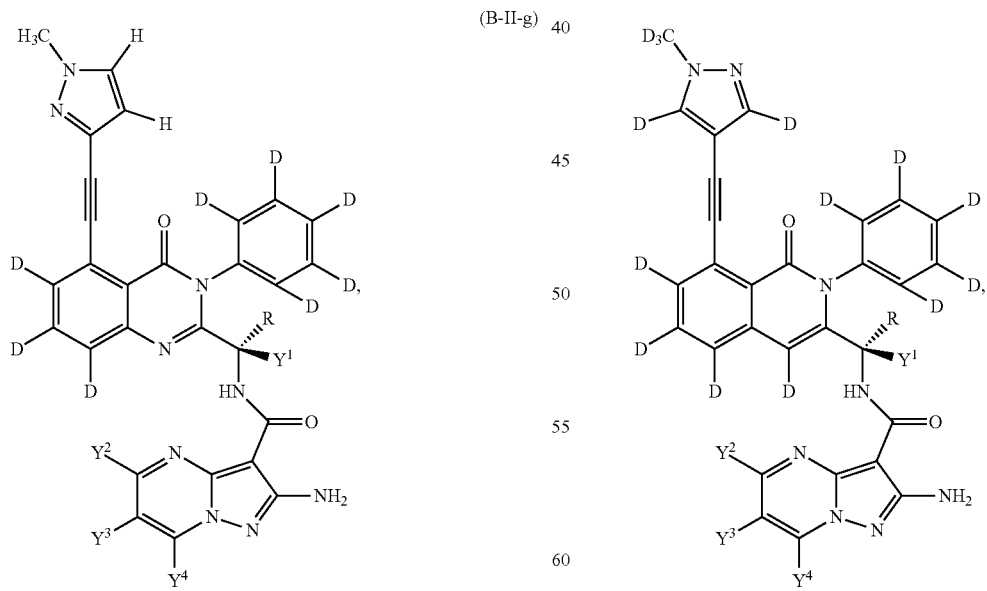

(B-II-g)

(A-I-o)

or a pharmaceutically acceptable form thereof.

In one embodiment, the compound is a compound of Formula (B-II-g) selected from any one of the compounds in Table 42.

or a pharmaceutically acceptable form thereof.

In one embodiment, the compound is a compound of Formula (A-I-o) selected from any one of the compounds in Table 43.

TABLE 43
Exemplary compounds of Formula (A-I-o)

| Compound | Y¹ | Y² | Y³ | Y⁴ | R |
|---|---|---|---|---|---|
| 4301 | H | H | H | H | —CH₃ |
| 4302 | D | H | H | H | —CH₃ |
| 4303 | H | D | H | H | —CH₃ |
| 4304 | H | H | D | H | —CH₃ |
| 4305 | H | H | H | D | —CH₃ |
| 4306 | D | D | H | H | —CH₃ |
| 4307 | D | H | D | H | —CH₃ |
| 4308 | D | H | H | D | —CH₃ |
| 4309 | H | D | D | H | —CH₃ |
| 4310 | H | D | H | D | —CH₃ |
| 4311 | H | H | D | D | —CH₃ |
| 4312 | D | D | D | H | —CH₃ |
| 4313 | D | D | H | D | —CH₃ |
| 4314 | D | H | D | D | —CH₃ |
| 4315 | H | D | D | D | —CH₃ |
| 4316 | D | D | D | D | —CH₃ |
| 4317 | H | H | H | H | —CD₃ |
| 4318 | D | H | H | H | —CD₃ |
| 4319 | H | D | H | H | —CD₃ |
| 4320 | H | H | D | H | —CD₃ |
| 4321 | H | H | H | D | —CD₃ |
| 4322 | D | D | H | H | —CD₃ |
| 4323 | D | H | D | H | —CD₃ |
| 4324 | D | H | H | D | —CD₃ |
| 4325 | H | D | D | H | —CD₃ |
| 4326 | H | D | H | D | —CD₃ |
| 4327 | H | H | D | D | —CD₃ |
| 4328 | D | D | D | H | —CD₃ |
| 4329 | D | D | H | D | —CD₃ |
| 4330 | D | H | D | D | —CD₃ |
| 4331 | H | D | D | D | —CD₃ |
| 4332 | D | D | D | D | —CD₃ | or a pharmaceutically acceptable form thereof.

In one embodiment, the compound is a compound of Formula (A-I-p):

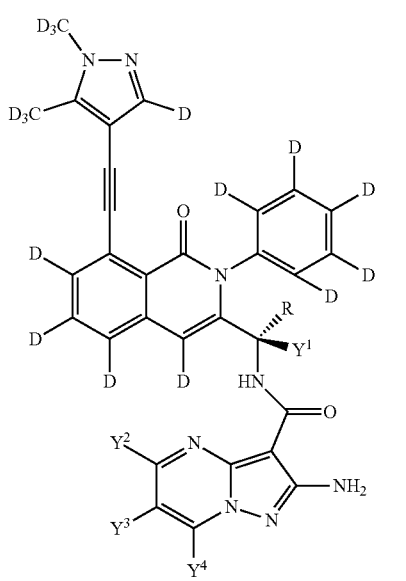

(A-I-p)

or a pharmaceutically acceptable form thereof.

In one embodiment, the compound is a compound of Formula (A-I-p) selected from any one of the compounds in Table 44.

TABLE 44
Exemplary compounds of Formula (A-I-p)

| Compound | Y¹ | Y² | Y³ | Y⁴ | R |
|---|---|---|---|---|---|
| 4401 | H | H | H | H | —CH₃ |
| 4402 | D | H | H | H | —CH₃ |
| 4403 | H | D | H | H | —CH₃ |
| 4404 | H | H | D | H | —CH₃ |
| 4405 | H | H | H | D | —CH₃ |
| 4406 | D | D | H | H | —CH₃ |
| 4407 | D | H | D | H | —CH₃ |
| 4408 | D | H | H | D | —CH₃ |
| 4409 | H | D | D | H | —CH₃ |
| 4410 | H | D | H | D | —CH₃ |
| 4411 | H | H | D | D | —CH₃ |
| 4412 | D | D | D | H | —CH₃ |
| 4413 | D | D | H | D | —CH₃ |
| 4414 | D | H | D | D | —CH₃ |
| 4415 | H | D | D | D | —CH₃ |
| 4416 | D | D | D | D | —CH₃ |
| 4417 | H | H | H | H | —CD₃ |
| 4418 | D | H | H | H | —CD₃ |
| 4419 | H | D | H | H | —CD₃ |
| 4420 | H | H | D | H | —CD₃ |
| 4421 | H | H | H | D | —CD₃ |
| 4422 | D | D | H | H | —CD₃ |
| 4423 | D | H | D | H | —CD₃ |
| 4424 | D | H | H | D | —CD₃ |
| 4425 | H | D | D | H | —CD₃ |
| 4426 | H | D | H | D | —CD₃ |
| 4427 | H | H | D | D | —CD₃ |
| 4428 | D | D | D | H | —CD₃ |
| 4429 | D | D | H | D | —CD₃ |
| 4430 | D | H | D | D | —CD₃ |
| 4431 | H | D | D | D | —CD₃ |
| 4432 | D | D | D | D | —CD₃ | or a pharmaceutically acceptable form thereof.

In one embodiment, the compound is a compound of Formula (A-II-h):

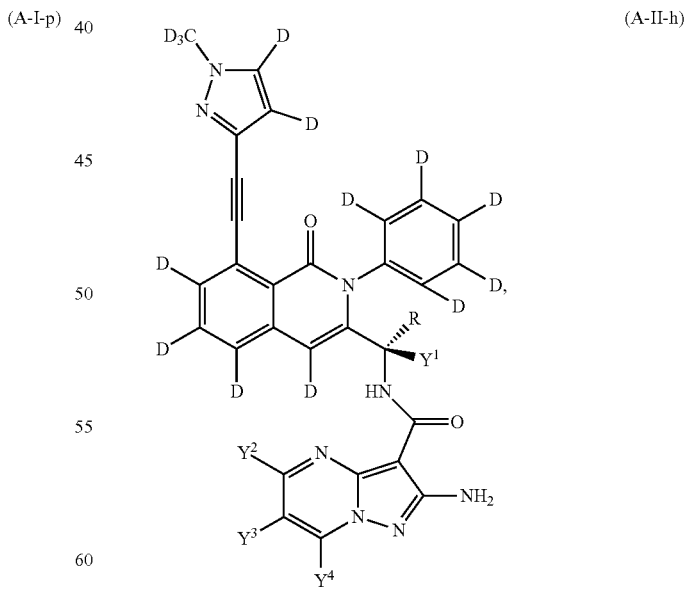

(A-II-h)

or a pharmaceutically acceptable form thereof.

In one embodiment, the compound is a compound of Formula (A-II-h) selected from any one of the compounds in Table 45.

TABLE 45

Exemplary compounds of Formula (A-II-h)

| Compound | Y¹ | Y² | Y³ | Y⁴ | R |
|---|---|---|---|---|---|
| 4501 | H | H | H | H | —CH₃ |
| 4502 | D | H | H | H | —CH₃ |
| 4503 | H | D | H | H | —CH₃ |
| 4504 | H | H | D | H | —CH₃ |
| 4505 | H | H | H | D | —CH₃ |
| 4506 | D | D | H | H | —CH₃ |
| 4507 | D | H | D | H | —CH₃ |
| 4508 | D | H | H | D | —CH₃ |
| 4509 | H | D | D | H | —CH₃ |
| 4510 | H | D | H | D | —CH₃ |
| 4511 | H | H | D | D | —CH₃ |
| 4512 | D | D | D | H | —CH₃ |
| 4513 | D | D | H | D | —CH₃ |
| 4514 | D | H | D | D | —CH₃ |
| 4515 | H | D | D | D | —CH₃ |
| 4516 | D | D | D | D | —CH₃ |
| 4517 | H | H | H | H | —CD₃ |
| 4518 | D | H | H | H | —CD₃ |
| 4519 | H | D | H | H | —CD₃ |
| 4520 | H | H | D | H | —CD₃ |
| 4521 | H | H | H | D | —CD₃ |
| 4522 | D | D | H | H | —CD₃ |
| 4523 | D | H | D | H | —CD₃ |
| 4524 | D | H | H | D | —CD₃ |
| 4525 | H | D | D | H | —CD₃ |
| 4526 | H | D | H | D | —CD₃ |
| 4527 | H | H | D | D | —CD₃ |
| 4528 | D | D | D | H | —CD₃ |
| 4529 | D | D | H | D | —CD₃ |
| 4530 | D | H | D | D | —CD₃ |
| 4531 | H | D | D | D | —CD₃ |
| 4532 | D | D | D | D | —CD₃ |

TABLE 46

Exemplary compounds of Formula (B-I-o)

| Compound | Y¹ | Y² | Y³ | Y⁴ | R |
|---|---|---|---|---|---|
| 4601 | H | H | H | H | —CH₃ |
| 4602 | D | H | H | H | —CH₃ |
| 4603 | H | D | H | H | —CH₃ |
| 4604 | H | H | D | H | —CH₃ |
| 4605 | H | H | H | D | —CH₃ |
| 4606 | D | D | H | H | —CH₃ |
| 4607 | D | H | D | H | —CH₃ |
| 4608 | D | H | H | D | —CH₃ |
| 4609 | H | D | D | H | —CH₃ |
| 4610 | H | D | H | D | —CH₃ |
| 4611 | H | H | D | D | —CH₃ |
| 4612 | D | D | D | H | —CH₃ |
| 4613 | D | D | H | D | —CH₃ |
| 4614 | D | H | D | D | —CH₃ |
| 4615 | H | D | D | D | —CH₃ |
| 4616 | D | D | D | D | —CH₃ |
| 4617 | H | H | H | H | —CD₃ |
| 4618 | D | H | H | H | —CD₃ |
| 4619 | H | D | H | H | —CD₃ |
| 4620 | H | H | D | H | —CD₃ |
| 4621 | H | H | H | D | —CD₃ |
| 4622 | D | D | H | H | —CD₃ |
| 4623 | D | H | D | H | —CD₃ |
| 4624 | D | H | H | D | —CD₃ |
| 4625 | H | D | D | H | —CD₃ |
| 4626 | H | D | H | D | —CD₃ |
| 4627 | H | H | D | D | —CD₃ |
| 4628 | D | D | D | H | —CD₃ |
| 4629 | D | D | H | D | —CD₃ |
| 4630 | D | H | D | D | —CD₃ |
| 4631 | H | D | D | D | —CD₃ |
| 4632 | D | D | D | D | —CD₃ | or a pharmaceutically acceptable form thereof.

In one embodiment, the compound is a compound of Formula (B-I-o):

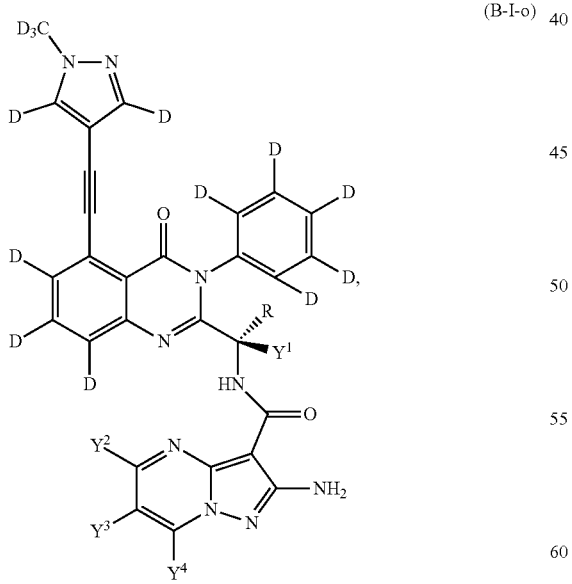

(B-I-o)

or a pharmaceutically acceptable form thereof.

In one embodiment, the compound is a compound of Formula (B-I-o) selected from any one of the compounds in Table 46.

or a pharmaceutically acceptable form thereof.

In one embodiment, the compound is a compound of Formula (B-I-p):

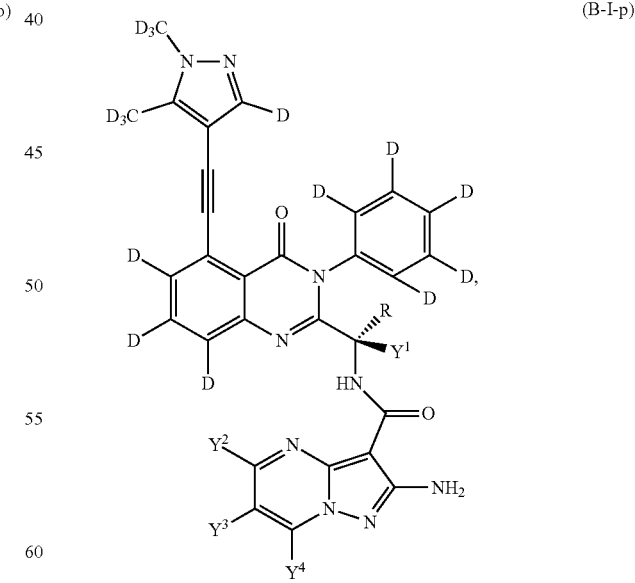

(B-I-p)

or a pharmaceutically acceptable form thereof.

In one embodiment, the compound is a compound of Formula (B-I-p) selected from any one of the compounds in Table 47.

TABLE 47

Exemplary compounds of Formula (B-I-p)

| Compound | Y¹ | Y² | Y³ | Y⁴ | R |
|---|---|---|---|---|---|
| 4701 | H | H | H | H | —CH₃ |
| 4702 | D | H | H | H | —CH₃ |
| 4703 | H | D | H | H | —CH₃ |
| 4704 | H | H | D | H | —CH₃ |
| 4705 | H | H | H | D | —CH₃ |
| 4706 | D | D | H | H | —CH₃ |
| 4707 | D | H | D | H | —CH₃ |
| 4708 | D | H | H | D | —CH₃ |
| 4709 | H | D | D | H | —CH₃ |
| 4710 | H | D | H | D | —CH₃ |
| 4711 | H | H | D | D | —CH₃ |
| 4712 | D | D | D | H | —CH₃ |
| 4713 | D | D | H | D | —CH₃ |
| 4714 | D | H | D | D | —CH₃ |
| 4715 | H | D | D | D | —CH₃ |
| 4716 | D | D | D | D | —CH₃ |
| 4717 | H | H | H | H | —CD₃ |
| 4718 | D | H | H | H | —CD₃ |
| 4719 | H | D | H | H | —CD₃ |
| 4720 | H | H | D | H | —CD₃ |
| 4721 | H | H | H | D | —CD₃ |
| 4722 | D | D | H | H | —CD₃ |
| 4723 | D | H | D | H | —CD₃ |
| 4724 | D | H | H | D | —CD₃ |
| 4725 | H | D | D | H | —CD₃ |
| 4726 | H | D | H | D | —CD₃ |
| 4727 | H | H | D | D | —CD₃ |
| 4728 | D | D | D | H | —CD₃ |
| 4729 | D | D | H | D | —CD₃ |
| 4730 | D | H | D | D | —CD₃ |
| 4731 | H | D | D | D | —CD₃ |
| 4732 | D | D | D | D | —CD₃ | or a pharmaceutically acceptable form thereof.

In one embodiment, the compound is a compound of Formula (B-II-h):

TABLE 48

Exemplary compounds of Formula (B-II-h)

| Compound | Y¹ | Y² | Y³ | Y⁴ | R |
|---|---|---|---|---|---|
| 4801 | H | H | H | H | —CH₃ |
| 4802 | D | H | H | H | —CH₃ |
| 4803 | H | D | H | H | —CH₃ |
| 4804 | H | H | D | H | —CH₃ |
| 4805 | H | H | H | D | —CH₃ |
| 4806 | D | D | H | H | —CH₃ |
| 4807 | D | H | D | H | —CH₃ |
| 4808 | D | H | H | D | —CH₃ |
| 4809 | H | D | D | H | —CH₃ |
| 4810 | H | D | H | D | —CH₃ |
| 4811 | H | H | D | D | —CH₃ |
| 4812 | D | D | D | H | —CH₃ |
| 4813 | D | D | H | D | —CH₃ |
| 4814 | D | H | D | D | —CH₃ |
| 4815 | H | D | D | D | —CH₃ |
| 4816 | D | D | D | D | —CH₃ |
| 4817 | H | H | H | H | —CD₃ |
| 4818 | D | H | H | H | —CD₃ |
| 4819 | H | D | H | H | —CD₃ |
| 4820 | H | H | D | H | —CD₃ |
| 4821 | H | H | H | D | —CD₃ |
| 4822 | D | D | H | H | —CD₃ |
| 4823 | D | H | D | H | —CD₃ |
| 4824 | D | H | H | D | —CD₃ |
| 4825 | H | D | D | H | —CD₃ |
| 4826 | H | D | H | D | —CD₃ |
| 4827 | H | H | D | D | —CD₃ |
| 4828 | D | D | D | H | —CD₃ |
| 4829 | D | D | H | D | —CD₃ |
| 4830 | D | H | D | D | —CD₃ |
| 4831 | H | D | D | D | —CD₃ |
| 4832 | D | D | D | D | —CD₃ | or a pharmaceutically acceptable form thereof.

In one embodiment, the compound is a compound of Formula (A-I-q):

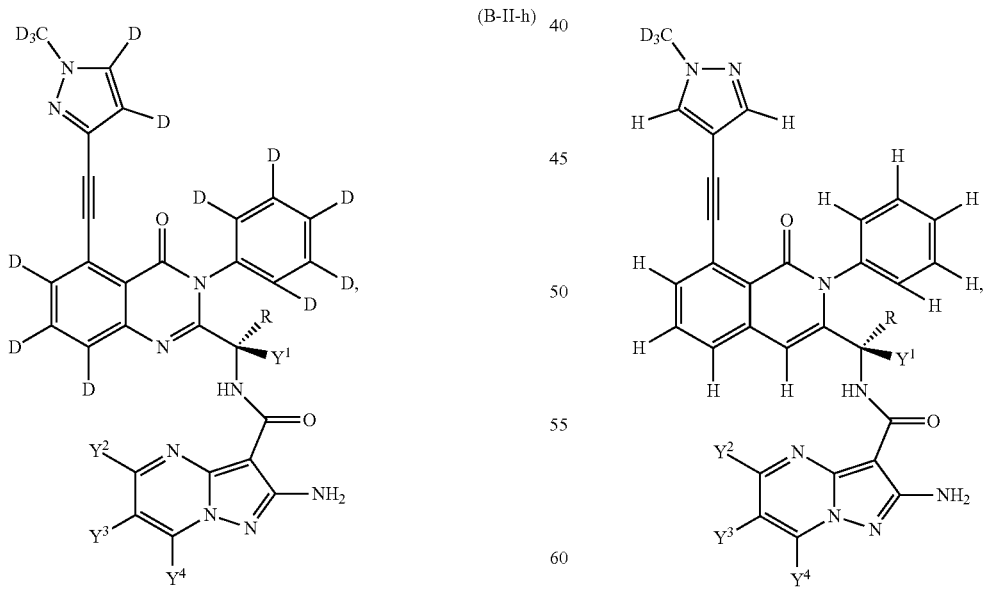

or a pharmaceutically acceptable form thereof.

In one embodiment, the compound is a compound of Formula (B-II-h) selected from any one of the compounds in Table 48.

or a pharmaceutically acceptable form thereof.

In one embodiment, the compound is a compound of Formula (A-I-q) selected from any one of the compounds in Table 49.

TABLE 49

Exemplary compounds of Formula (A—I-q)

| Compound | Y$^1$ | Y$^2$ | Y$^3$ | Y$^4$ | R |
|---|---|---|---|---|---|
| 4901 | H | H | H | H | —CH$_3$ |
| 4902 | D | H | H | H | —CH$_3$ |
| 4903 | H | D | H | H | —CH$_3$ |
| 4904 | H | H | D | H | —CH$_3$ |
| 4905 | H | H | H | D | —CH$_3$ |
| 4906 | D | D | H | H | —CH$_3$ |
| 4907 | D | H | D | H | —CH$_3$ |
| 4908 | D | H | H | D | —CH$_3$ |
| 4909 | H | D | D | H | —CH$_3$ |
| 4910 | H | D | H | D | —CH$_3$ |
| 4911 | H | H | D | D | —CH$_3$ |
| 4912 | D | D | D | H | —CH$_3$ |
| 4913 | D | D | H | D | —CH$_3$ |
| 4914 | D | H | D | D | —CH$_3$ |
| 4915 | H | D | D | D | —CH$_3$ |
| 4916 | D | D | D | D | —CH$_3$ |
| 4917 | H | H | H | H | —CD$_3$ |
| 4918 | D | H | H | H | —CD$_3$ |
| 4919 | H | D | H | H | —CD$_3$ |
| 4920 | H | H | D | H | —CD$_3$ |
| 4921 | H | H | H | D | —CD$_3$ |
| 4922 | D | D | H | H | —CD$_3$ |
| 4923 | D | H | D | H | —CD$_3$ |
| 4924 | D | H | H | D | —CD$_3$ |
| 4925 | H | D | D | H | —CD$_3$ |
| 4926 | H | D | H | D | —CD$_3$ |
| 4927 | H | H | D | D | —CD$_3$ |
| 4928 | D | D | D | H | —CD$_3$ |
| 4929 | D | D | H | D | —CD$_3$ |
| 4930 | D | H | D | D | —CD$_3$ |
| 4931 | H | D | D | D | —CD$_3$ |
| 4932 | D | D | D | D | —CD$_3$ |

TABLE 50

Exemplary compounds of Formula (A—I-r)

| Compound | Y$^1$ | Y$^2$ | Y$^3$ | Y$^4$ | R |
|---|---|---|---|---|---|
| 5001 | H | H | H | H | —CH$_3$ |
| 5002 | D | H | H | H | —CH$_3$ |
| 5003 | H | D | H | H | —CH$_3$ |
| 5004 | H | H | D | H | —CH$_3$ |
| 5005 | H | H | H | D | —CH$_3$ |
| 5006 | D | D | H | H | —CH$_3$ |
| 5007 | D | H | D | H | —CH$_3$ |
| 5008 | D | H | H | D | —CH$_3$ |
| 5009 | H | D | D | H | —CH$_3$ |
| 5010 | H | D | H | D | —CH$_3$ |
| 5011 | H | H | D | D | —CH$_3$ |
| 5012 | D | D | D | H | —CH$_3$ |
| 5013 | D | D | H | D | —CH$_3$ |
| 5014 | D | H | D | D | —CH$_3$ |
| 5015 | H | D | D | D | —CH$_3$ |
| 5016 | D | D | D | D | —CH$_3$ |
| 5017 | H | H | H | H | —CD$_3$ |
| 5018 | D | H | H | H | —CD$_3$ |
| 5019 | H | D | H | H | —CD$_3$ |
| 5020 | H | H | D | H | —CD$_3$ |
| 5021 | H | H | H | D | —CD$_3$ |
| 5022 | D | D | H | H | —CD$_3$ |
| 5023 | D | H | D | H | —CD$_3$ |
| 5024 | D | H | H | D | —CD$_3$ |
| 5025 | H | D | D | H | —CD$_3$ |
| 5026 | H | D | H | D | —CD$_3$ |
| 5027 | H | H | D | D | —CD$_3$ |
| 5028 | D | D | D | H | —CD$_3$ |
| 5029 | D | D | H | D | —CD$_3$ |
| 5030 | D | H | D | D | —CD$_3$ |
| 5031 | H | D | D | D | —CD$_3$ |
| 5032 | D | D | D | D | —CD$_3$ | or a pharmaceutically acceptable form thereof.

In one embodiment, the compound is a compound of Formula (A-I-r):

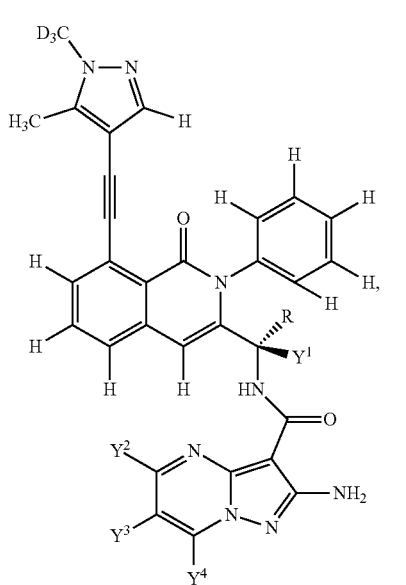

(A-I-r)

or a pharmaceutically acceptable form thereof.

In one embodiment, the compound is a compound of Formula (A-I-r) selected from any one of the compounds in Table 50.

or a pharmaceutically acceptable form thereof.

In one embodiment, the compound is a compound of Formula (A-II-i):

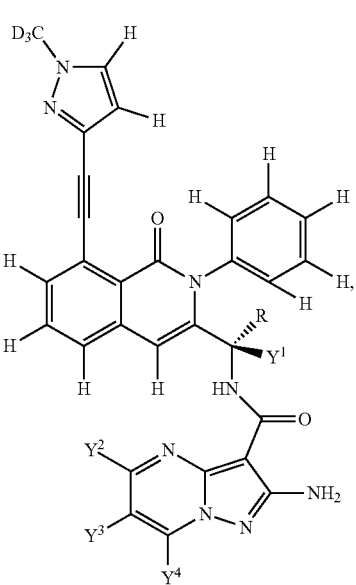

(A-II-i)

or a pharmaceutically acceptable form thereof.

In one embodiment, the compound is a compound of Formula (A-II-i) selected from any one of the compounds in Table 51.

TABLE 51

Exemplary compounds of Formula (A—II-i)

| Compound | Y¹ | Y² | Y³ | Y⁴ | R |
|---|---|---|---|---|---|
| 5101 | H | H | H | H | —CH₃ |
| 5102 | D | H | H | H | —CH₃ |
| 5103 | H | D | H | H | —CH₃ |
| 5104 | H | H | D | H | —CH₃ |
| 5105 | H | H | H | D | —CH₃ |
| 5106 | D | D | H | H | —CH₃ |
| 5107 | D | H | D | H | —CH₃ |
| 5108 | D | H | H | D | —CH₃ |
| 5109 | H | D | D | H | —CH₃ |
| 5110 | H | D | H | D | —CH₃ |
| 5111 | H | H | D | D | —CH₃ |
| 5112 | D | D | D | H | —CH₃ |
| 5113 | D | D | H | D | —CH₃ |
| 5114 | D | H | D | D | —CH₃ |
| 5115 | H | D | D | D | —CH₃ |
| 5116 | D | D | D | D | —CH₃ |
| 5117 | H | H | H | H | —CD₃ |
| 5118 | D | H | H | H | —CD₃ |
| 5119 | H | D | H | H | —CD₃ |
| 5120 | H | H | D | H | —CD₃ |
| 5121 | H | H | H | D | —CD₃ |
| 5122 | D | D | H | H | —CD₃ |
| 5123 | D | H | D | H | —CD₃ |
| 5124 | D | H | H | D | —CD₃ |
| 5125 | H | D | D | H | —CD₃ |
| 5126 | H | D | H | D | —CD₃ |
| 5127 | H | H | D | D | —CD₃ |
| 5128 | D | D | D | H | —CD₃ |
| 5129 | D | D | H | D | —CD₃ |
| 5130 | D | H | D | D | —CD₃ |
| 5131 | H | D | D | D | —CD₃ |
| 5132 | D | D | D | D | —CD₃ | or a pharmaceutically acceptable form thereof.

In one embodiment, the compound is a compound of Formula (B-I-q):

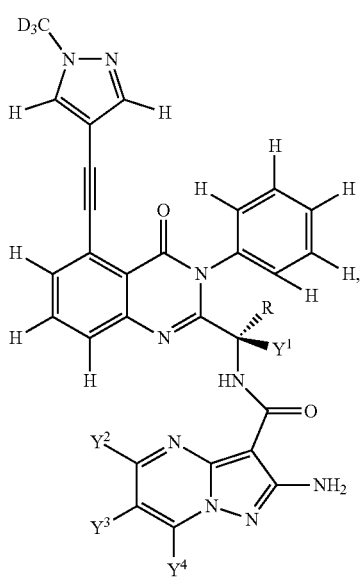

(B-I-q)

or a pharmaceutically acceptable form thereof.

In one embodiment, the compound is a compound of Formula (B-I-q) selected from any one of the compounds in Table 52.

TABLE 52

Exemplary compounds of Formula (B—I-q)

| Compound | Y¹ | Y² | Y³ | Y⁴ | R |
|---|---|---|---|---|---|
| 5201 | H | H | H | H | —CH₃ |
| 5202 | D | H | H | H | —CH₃ |
| 5203 | H | D | H | H | —CH₃ |
| 5204 | H | H | D | H | —CH₃ |
| 5205 | H | H | H | D | —CH₃ |
| 5206 | D | D | H | H | —CH₃ |
| 5207 | D | H | D | H | —CH₃ |
| 5208 | D | H | H | D | —CH₃ |
| 5209 | H | D | D | H | —CH₃ |
| 5210 | H | D | H | D | —CH₃ |
| 5211 | H | H | D | D | —CH₃ |
| 5212 | D | D | D | H | —CH₃ |
| 5213 | D | D | H | D | —CH₃ |
| 5214 | D | H | D | D | —CH₃ |
| 5215 | H | D | D | D | —CH₃ |
| 5216 | D | D | D | D | —CH₃ |
| 5217 | H | H | H | H | —CD₃ |
| 5218 | D | H | H | H | —CD₃ |
| 5219 | H | D | H | H | —CD₃ |
| 5220 | H | H | D | H | —CD₃ |
| 5221 | H | H | H | D | —CD₃ |
| 5222 | D | D | H | H | —CD₃ |
| 5223 | D | H | D | H | —CD₃ |
| 5224 | D | H | H | D | —CD₃ |
| 5225 | H | D | D | H | —CD₃ |
| 5226 | H | D | H | D | —CD₃ |
| 5227 | H | H | D | D | —CD₃ |
| 5228 | D | D | D | H | —CD₃ |
| 5229 | D | D | H | D | —CD₃ |
| 5230 | D | H | D | D | —CD₃ |
| 5231 | H | D | D | D | —CD₃ |
| 5232 | D | D | D | D | —CD₃ | or a pharmaceutically acceptable form thereof.

In one embodiment, the compound is a compound of Formula (B-I-r):

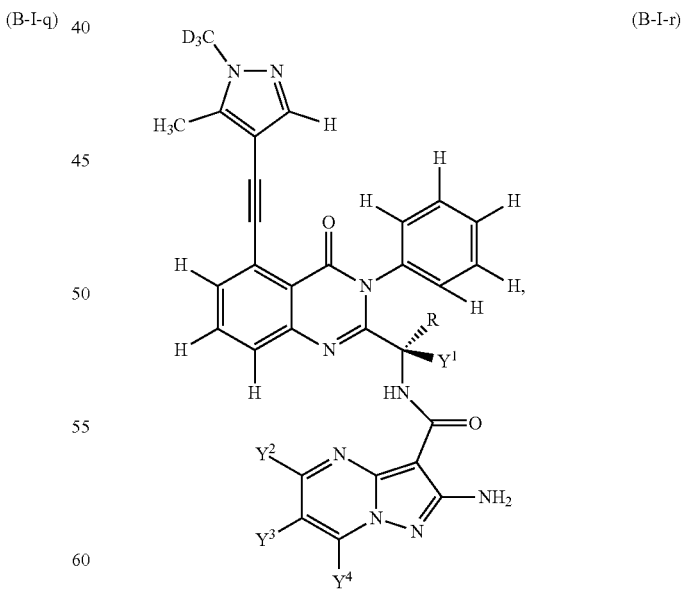

(B-I-r)

or a pharmaceutically acceptable form thereof.

In one embodiment, the compound is a compound of Formula (B-I-r) selected from any one of the compounds in Table 53.

TABLE 53

Exemplary compounds of Formula (B—I-r)

| Compound | $Y^1$ | $Y^2$ | $Y^3$ | $Y^4$ | R |
|---|---|---|---|---|---|
| 5301 | H | H | H | H | —$CH_3$ |
| 5302 | D | H | H | H | —$CH_3$ |
| 5303 | H | D | H | H | —$CH_3$ |
| 5304 | H | H | D | H | —$CH_3$ |
| 5305 | H | H | H | D | —$CH_3$ |
| 5306 | D | D | H | H | —$CH_3$ |
| 5307 | D | H | D | H | —$CH_3$ |
| 5308 | D | H | H | D | —$CH_3$ |
| 5309 | H | D | D | H | —$CH_3$ |
| 5310 | H | D | H | D | —$CH_3$ |
| 5311 | H | H | D | D | —$CH_3$ |
| 5312 | D | D | D | H | —$CH_3$ |
| 5313 | D | D | H | D | —$CH_3$ |
| 5314 | D | H | D | D | —$CH_3$ |
| 5315 | H | D | D | D | —$CH_3$ |
| 5316 | D | D | D | D | —$CH_3$ |
| 5317 | H | H | H | H | —$CD_3$ |
| 5318 | D | H | H | H | —$CD_3$ |
| 5319 | H | D | H | H | —$CD_3$ |
| 5320 | H | H | D | H | —$CD_3$ |
| 5321 | H | H | H | D | —$CD_3$ |
| 5322 | D | D | H | H | —$CD_3$ |
| 5323 | D | H | D | H | —$CD_3$ |
| 5324 | D | H | H | D | —$CD_3$ |
| 5325 | H | D | D | H | —$CD_3$ |
| 5326 | H | D | H | D | —$CD_3$ |
| 5327 | H | H | D | D | —$CD_3$ |
| 5328 | D | D | D | H | —$CD_3$ |
| 5329 | D | D | H | D | —$CD_3$ |
| 5330 | D | H | D | D | —$CD_3$ |
| 5331 | H | D | D | D | —$CD_3$ |
| 5332 | D | D | D | D | —$CD_3$ |

TABLE 54

Exemplary compounds of Formula (B—II-i)

| Compound | $Y^1$ | $Y^2$ | $Y^3$ | $Y^4$ | R |
|---|---|---|---|---|---|
| 5401 | H | H | H | H | —$CH_3$ |
| 5402 | D | H | H | H | —$CH_3$ |
| 5403 | H | D | H | H | —$CH_3$ |
| 5404 | H | H | D | H | —$CH_3$ |
| 5405 | H | H | H | D | —$CH_3$ |
| 5406 | D | D | H | H | —$CH_3$ |
| 5407 | D | H | D | H | —$CH_3$ |
| 5408 | D | H | H | D | —$CH_3$ |
| 5409 | H | D | D | H | —$CH_3$ |
| 5410 | H | D | H | D | —$CH_3$ |
| 5411 | H | H | D | D | —$CH_3$ |
| 5412 | D | D | D | H | —$CH_3$ |
| 5413 | D | D | H | D | —$CH_3$ |
| 5414 | D | H | D | D | —$CH_3$ |
| 5415 | H | D | D | D | —$CH_3$ |
| 5416 | D | D | D | D | —$CH_3$ |
| 5417 | H | H | H | H | —$CD_3$ |
| 5418 | D | H | H | H | —$CD_3$ |
| 5419 | H | D | H | H | —$CD_3$ |
| 5420 | H | H | D | H | —$CD_3$ |
| 5421 | H | H | H | D | —$CD_3$ |
| 5422 | D | D | H | H | —$CD_3$ |
| 5423 | D | H | D | H | —$CD_3$ |
| 5424 | D | H | H | D | —$CD_3$ |
| 5425 | H | D | D | H | —$CD_3$ |
| 5426 | H | D | H | D | —$CD_3$ |
| 5427 | H | H | D | D | —$CD_3$ |
| 5428 | D | D | D | H | —$CD_3$ |
| 5429 | D | D | H | D | —$CD_3$ |
| 5430 | D | H | D | D | —$CD_3$ |
| 5431 | H | D | D | D | —$CD_3$ |
| 5432 | D | D | D | D | —$CD_3$ | or a pharmaceutically acceptable form thereof.

In one embodiment, the compound is a compound of Formula (B-II-i):

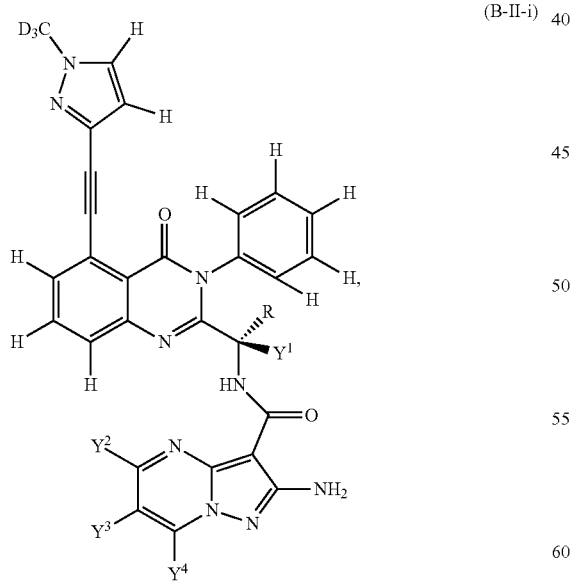

(B-II-i)

or a pharmaceutically acceptable form thereof.

In one embodiment, the compound is a compound of Formula (B-II-i) selected from any one of the compounds in Table 54.

or a pharmaceutically acceptable form thereof.

In one embodiment, the compound is a compound of Formula (A-I-s):

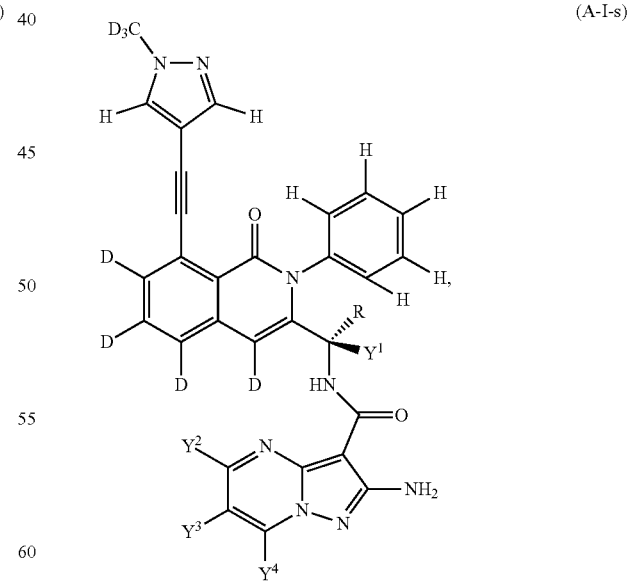

(A-I-s)

or a pharmaceutically acceptable form thereof.

In one embodiment, the compound is a compound of Formula (A-I-s) selected from any one of the compounds in Table 55.

TABLE 55

Exemplary compounds of Formula (A—I-s)

| Compound | Y¹ | Y² | Y³ | Y⁴ | R |
|---|---|---|---|---|---|
| 5501 | H | H | H | H | —CH₃ |
| 5502 | D | H | H | H | —CH₃ |
| 5503 | H | D | H | H | —CH₃ |
| 5504 | H | H | D | H | —CH₃ |
| 5505 | H | H | H | D | —CH₃ |
| 5506 | D | D | H | H | —CH₃ |
| 5507 | D | H | D | H | —CH₃ |
| 5508 | D | H | H | D | —CH₃ |
| 5509 | H | D | D | H | —CH₃ |
| 5510 | H | D | H | D | —CH₃ |
| 5511 | H | H | D | D | —CH₃ |
| 5512 | D | D | D | H | —CH₃ |
| 5513 | D | D | H | D | —CH₃ |
| 5514 | D | H | D | D | —CH₃ |
| 5515 | H | D | D | D | —CH₃ |
| 5516 | D | D | D | D | —CH₃ |
| 5517 | H | H | H | H | —CD₃ |
| 5518 | D | H | H | H | —CD₃ |
| 5519 | H | D | H | H | —CD₃ |
| 5520 | H | H | D | H | —CD₃ |
| 5521 | H | H | H | D | —CD₃ |
| 5522 | D | D | H | H | —CD₃ |
| 5523 | D | H | D | H | —CD₃ |
| 5524 | D | H | H | D | —CD₃ |
| 5525 | H | D | D | H | —CD₃ |
| 5526 | H | D | H | D | —CD₃ |
| 5527 | H | H | D | D | —CD₃ |
| 5528 | D | D | D | H | —CD₃ |
| 5529 | D | D | H | D | —CD₃ |
| 5530 | D | H | D | D | —CD₃ |
| 5531 | H | D | D | D | —CD₃ |
| 5532 | D | D | D | D | —CD₃ | or a pharmaceutically acceptable form thereof.

In one embodiment, the compound is a compound of Formula (A-I-t):

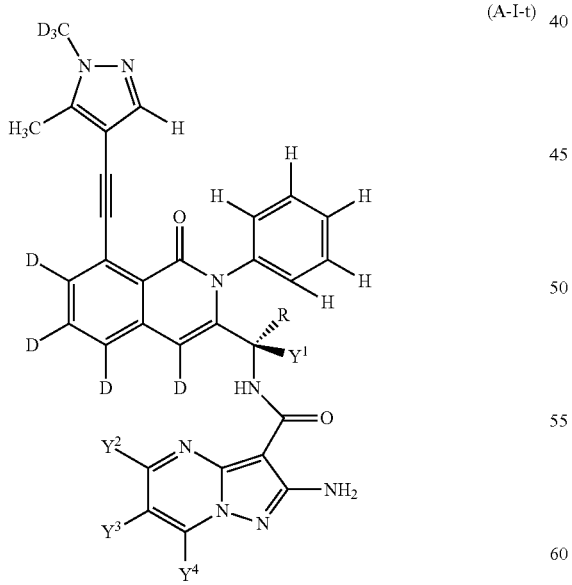

(A-I-t)

or a pharmaceutically acceptable form thereof.

In one embodiment, the compound is a compound of Formula (A-I-t) selected from any one of the compounds in Table 56.

TABLE 56

Exemplary compounds of Formula (A—I-t)

| Compound | Y¹ | Y² | Y³ | Y⁴ | R |
|---|---|---|---|---|---|
| 5601 | H | H | H | H | —CH₃ |
| 5602 | D | H | H | H | —CH₃ |
| 5603 | H | D | H | H | —CH₃ |
| 5604 | H | H | D | H | —CH₃ |
| 5605 | H | H | H | D | —CH₃ |
| 5606 | D | D | H | H | —CH₃ |
| 5607 | D | H | D | H | —CH₃ |
| 5608 | D | H | H | D | —CH₃ |
| 5609 | H | D | D | H | —CH₃ |
| 5610 | H | D | H | D | —CH₃ |
| 5611 | H | H | D | D | —CH₃ |
| 5612 | D | D | D | H | —CH₃ |
| 5613 | D | D | H | D | —CH₃ |
| 5614 | D | H | D | D | —CH₃ |
| 5615 | H | D | D | D | —CH₃ |
| 5616 | D | D | D | D | —CH₃ |
| 5617 | H | H | H | H | —CD₃ |
| 5618 | D | H | H | H | —CD₃ |
| 5619 | H | D | H | H | —CD₃ |
| 5620 | H | H | D | H | —CD₃ |
| 5621 | H | H | H | D | —CD₃ |
| 5622 | D | D | H | H | —CD₃ |
| 5623 | D | H | D | H | —CD₃ |
| 5624 | D | H | H | D | —CD₃ |
| 5625 | H | D | D | H | —CD₃ |
| 5626 | H | D | H | D | —CD₃ |
| 5627 | H | H | D | D | —CD₃ |
| 5628 | D | D | D | H | —CD₃ |
| 5629 | D | D | H | D | —CD₃ |
| 5630 | D | H | D | D | —CD₃ |
| 5631 | H | D | D | D | —CD₃ |
| 5632 | D | D | D | D | —CD₃ | or a pharmaceutically acceptable form thereof.

In one embodiment, the compound is a compound of Formula (A-II-j):

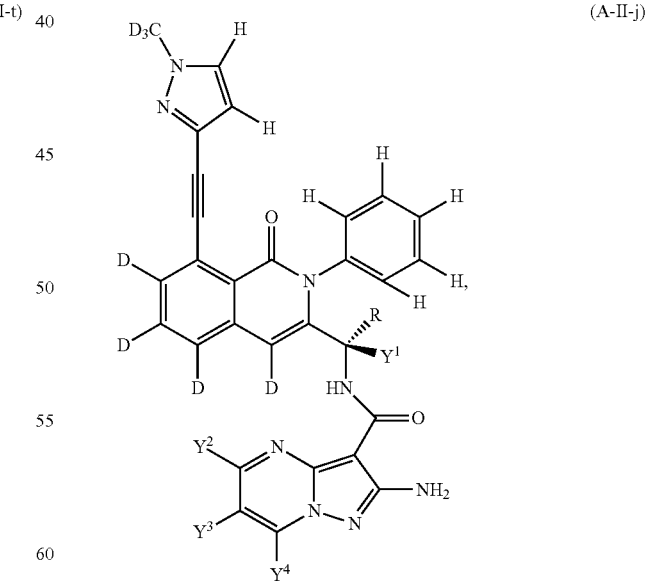

(A-II-j)

or a pharmaceutically acceptable form thereof.

In one embodiment, the compound is a compound of Formula (A-II-j) selected from any one of the compounds in Table 57.

TABLE 57

Exemplary compounds of Formula (A—II-j)

| Compound | Y¹ | Y² | Y³ | Y⁴ | R |
|---|---|---|---|---|---|
| 5701 | H | H | H | H | —CH₃ |
| 5702 | D | H | H | H | —CH₃ |
| 5703 | H | D | H | H | —CH₃ |
| 5704 | H | H | D | H | —CH₃ |
| 5705 | H | H | H | D | —CH₃ |
| 5706 | D | D | H | H | —CH₃ |
| 5707 | D | H | D | H | —CH₃ |
| 5708 | D | H | H | D | —CH₃ |
| 5709 | H | D | D | H | —CH₃ |
| 5710 | H | D | H | D | —CH₃ |
| 5711 | H | H | D | D | —CH₃ |
| 5712 | D | D | D | H | —CH₃ |
| 5713 | D | D | H | D | —CH₃ |
| 5714 | D | H | D | D | —CH₃ |
| 5715 | H | D | D | D | —CH₃ |
| 5716 | D | D | D | D | —CH₃ |
| 5717 | H | H | H | H | —CD₃ |
| 5718 | D | H | H | H | —CD₃ |
| 5719 | H | D | H | H | —CD₃ |
| 5720 | H | H | D | H | —CD₃ |
| 5721 | H | H | H | D | —CD₃ |
| 5722 | D | D | H | H | —CD₃ |
| 5723 | D | H | D | H | —CD₃ |
| 5724 | D | H | H | D | —CD₃ |
| 5725 | H | D | D | H | —CD₃ |
| 5726 | H | D | H | D | —CD₃ |
| 5727 | H | H | D | D | —CD₃ |
| 5728 | D | D | D | H | —CD₃ |
| 5729 | D | D | H | D | —CD₃ |
| 5730 | D | H | D | D | —CD₃ |
| 5731 | H | D | D | D | —CD₃ |
| 5732 | D | D | D | D | —CD₃ | or a pharmaceutically acceptable form thereof.

In one embodiment, the compound is a compound of Formula (B-I-s):

TABLE 58

Exemplary compounds of Formula (B-I-s)

| Compound | Y¹ | Y² | Y³ | Y⁴ | R |
|---|---|---|---|---|---|
| 5801 | H | H | H | H | —CH₃ |
| 5802 | D | H | H | H | —CH₃ |
| 5803 | H | D | H | H | —CH₃ |
| 5804 | H | H | D | H | —CH₃ |
| 5805 | H | H | H | D | —CH₃ |
| 5806 | D | D | H | H | —CH₃ |
| 5807 | D | H | D | H | —CH₃ |
| 5808 | D | H | H | D | —CH₃ |
| 5809 | H | D | D | H | —CH₃ |
| 5810 | H | D | H | D | —CH₃ |
| 5811 | H | H | D | D | —CH₃ |
| 5812 | D | D | D | H | —CH₃ |
| 5813 | D | D | H | D | —CH₃ |
| 5814 | D | H | D | D | —CH₃ |
| 5815 | H | D | D | D | —CH₃ |
| 5816 | D | D | D | D | —CH₃ |
| 5817 | H | H | H | H | —CD₃ |
| 5818 | D | H | H | H | —CD₃ |
| 5819 | H | D | H | H | —CD₃ |
| 5820 | H | H | D | H | —CD₃ |
| 5821 | H | H | H | D | —CD₃ |
| 5822 | D | D | H | H | —CD₃ |
| 5823 | D | H | D | H | —CD₃ |
| 5824 | D | H | H | D | —CD₃ |
| 5825 | H | D | D | H | —CD₃ |
| 5826 | H | D | H | D | —CD₃ |
| 5827 | H | H | D | D | —CD₃ |
| 5828 | D | D | D | H | —CD₃ |
| 5829 | D | D | H | D | —CD₃ |
| 5830 | D | H | D | D | —CD₃ |
| 5831 | H | D | D | D | —CD₃ |
| 5832 | D | D | D | D | —CD₃ | or a pharmaceutically acceptable form thereof.

In one embodiment, the compound is a compound of Formula (B-I-t):

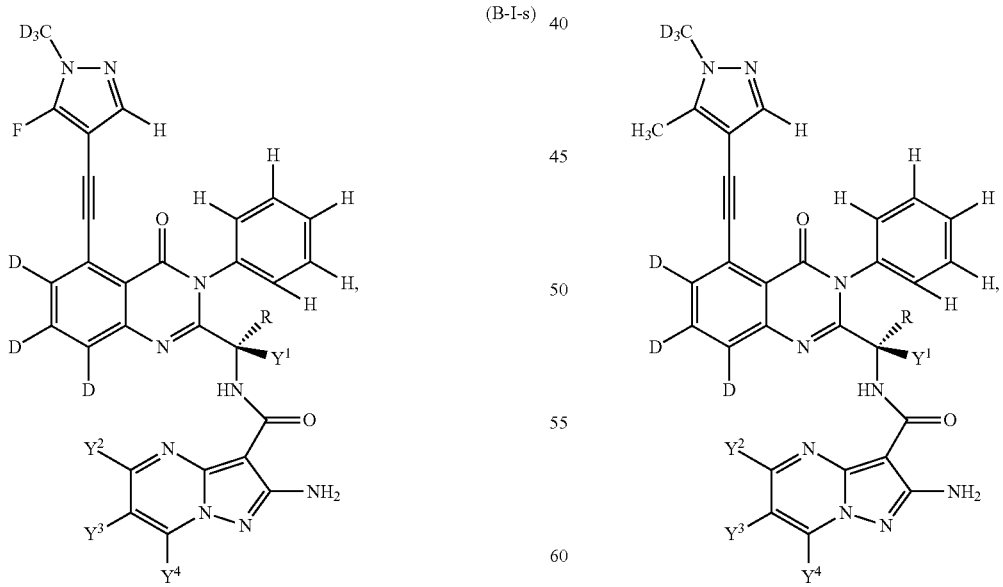

or a pharmaceutically acceptable form thereof.

In one embodiment, the compound is a compound of Formula (B-I-s) selected from any one of the compounds in Table 58.

or a pharmaceutically acceptable form thereof.

In one embodiment, the compound is a compound of Formula (B-I-t) selected from any one of the compounds in Table 59.

TABLE 59

Exemplary compounds of Formula (B-I-t)

| Compound | Y¹ | Y² | Y³ | Y⁴ | R |
|---|---|---|---|---|---|
| 5901 | H | H | H | H | —CH₃ |
| 5902 | D | H | H | H | —CH₃ |
| 5903 | H | D | H | H | —CH₃ |
| 5904 | H | H | D | H | —CH₃ |
| 5905 | H | H | H | D | —CH₃ |
| 5906 | D | D | H | H | —CH₃ |
| 5907 | D | H | D | H | —CH₃ |
| 5908 | D | H | H | D | —CH₃ |
| 5909 | H | D | D | H | —CH₃ |
| 5910 | H | D | H | D | —CH₃ |
| 5911 | H | H | D | D | —CH₃ |
| 5912 | D | D | D | H | —CH₃ |
| 5913 | D | D | H | D | —CH₃ |
| 5914 | D | H | D | D | —CH₃ |
| 5915 | H | D | D | D | —CH₃ |
| 5916 | D | D | D | D | —CH₃ |
| 5917 | H | H | H | H | —CD₃ |
| 5918 | D | H | H | H | —CD₃ |
| 5919 | H | D | H | H | —CD₃ |
| 5920 | H | H | D | H | —CD₃ |
| 5921 | H | H | H | D | —CD₃ |
| 5922 | D | D | H | H | —CD₃ |
| 5923 | D | H | D | H | —CD₃ |
| 5924 | D | H | H | D | —CD₃ |
| 5925 | H | D | D | H | —CD₃ |
| 5926 | H | D | H | D | —CD₃ |
| 5927 | H | H | D | D | —CD₃ |
| 5928 | D | D | D | H | —CD₃ |
| 5929 | D | D | H | D | —CD₃ |
| 5930 | D | H | D | D | —CD₃ |
| 5931 | H | D | D | D | —CD₃ |
| 5932 | D | D | D | D | —CD₃ | or a pharmaceutically acceptable form thereof.

In one embodiment, the compound is a compound of Formula (B-II-j):

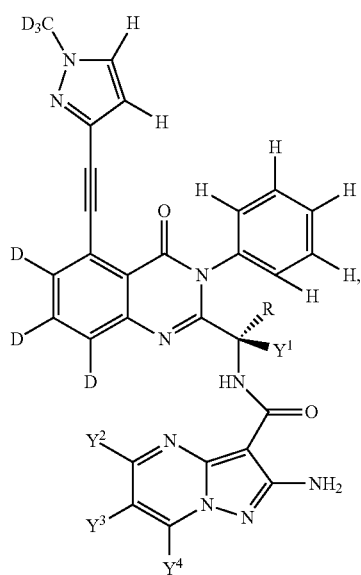

(B-II-j)

or a pharmaceutically acceptable form thereof.

In one embodiment, the compound is a compound of Formula (B-II-j) selected from any one of the compounds in Table 60.

TABLE 60

Exemplary compounds of Formula (B-II-j)

| Compound | Y¹ | Y² | Y³ | Y⁴ | R |
|---|---|---|---|---|---|
| 6001 | H | H | H | H | —CH₃ |
| 6002 | D | H | H | H | —CH₃ |
| 6003 | H | D | H | H | —CH₃ |
| 6004 | H | H | D | H | —CH₃ |
| 6005 | H | H | H | D | —CH₃ |
| 6006 | D | D | H | H | —CH₃ |
| 6007 | D | H | D | H | —CH₃ |
| 6008 | D | H | H | D | —CH₃ |
| 6009 | H | D | D | H | —CH₃ |
| 6010 | H | D | H | D | —CH₃ |
| 6011 | H | H | D | D | —CH₃ |
| 6012 | D | D | D | H | —CH₃ |
| 6013 | D | D | H | D | —CH₃ |
| 6014 | D | H | D | D | —CH₃ |
| 6015 | H | D | D | D | —CH₃ |
| 6016 | D | D | D | D | —CH₃ |
| 6017 | H | H | H | H | —CD₃ |
| 6018 | D | H | H | H | —CD₃ |
| 6019 | H | D | H | H | —CD₃ |
| 6020 | H | H | D | H | —CD₃ |
| 6021 | H | H | H | D | —CD₃ |
| 6022 | D | D | H | H | —CD₃ |
| 6023 | D | H | D | H | —CD₃ |
| 6024 | D | H | H | D | —CD₃ |
| 6025 | H | D | D | H | —CD₃ |
| 6026 | H | D | H | D | —CD₃ |
| 6027 | H | H | D | D | —CD₃ |
| 6028 | D | D | D | H | —CD₃ |
| 6029 | D | D | H | D | —CD₃ |
| 6030 | D | H | D | D | —CD₃ |
| 6031 | H | D | D | D | —CD₃ |
| 6032 | D | D | D | D | —CD₃ | or a pharmaceutically acceptable form thereof.

In one embodiment, the compound is a compound of Formula (A-I-u):

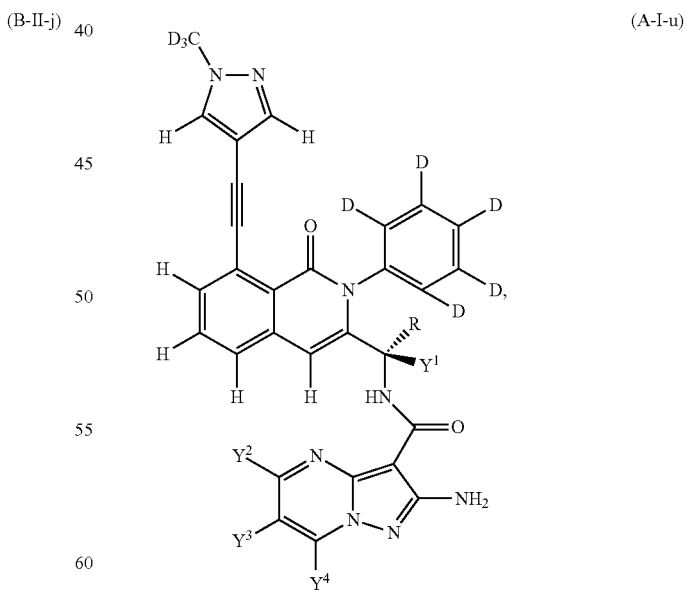

(A-I-u)

or a pharmaceutically acceptable form thereof.

In one embodiment, the compound is a compound of Formula (A-I-u) selected from any one of the compounds in Table 61.

TABLE 61

Exemplary compounds of Formula (A-I-u)

| Compound | Y¹ | Y² | Y³ | Y⁴ | R |
|---|---|---|---|---|---|
| 6101 | H | H | H | H | —CH₃ |
| 6102 | D | H | H | H | —CH₃ |
| 6103 | H | D | H | H | —CH₃ |
| 6104 | H | H | D | H | —CH₃ |
| 6105 | H | H | H | D | —CH₃ |
| 6106 | D | D | H | H | —CH₃ |
| 6107 | D | H | D | H | —CH₃ |
| 6108 | D | H | H | D | —CH₃ |
| 6109 | H | D | D | H | —CH₃ |
| 6110 | H | D | H | D | —CH₃ |
| 6111 | H | H | D | D | —CH₃ |
| 6112 | D | D | D | H | —CH₃ |
| 6113 | D | D | H | D | —CH₃ |
| 6114 | D | H | D | D | —CH₃ |
| 6115 | H | D | D | D | —CH₃ |
| 6116 | D | D | D | D | —CH₃ |
| 6117 | H | H | H | H | —CD₃ |
| 6118 | D | H | H | H | —CD₃ |
| 6119 | H | D | H | H | —CD₃ |
| 6120 | H | H | D | H | —CD₃ |
| 6121 | H | H | H | D | —CD₃ |
| 6122 | D | D | H | H | —CD₃ |
| 6123 | D | H | D | H | —CD₃ |
| 6124 | D | H | H | D | —CD₃ |
| 6125 | H | D | D | H | —CD₃ |
| 6126 | H | D | H | D | —CD₃ |
| 6127 | H | H | D | D | —CD₃ |
| 6128 | D | D | D | H | —CD₃ |
| 6129 | D | D | H | D | —CD₃ |
| 6130 | D | H | D | D | —CD₃ |
| 6131 | H | D | D | D | —CD₃ |
| 6132 | D | D | D | D | —CD₃ | or a pharmaceutically acceptable form thereof.

In one embodiment, the compound is a compound of Formula (A-I-v):

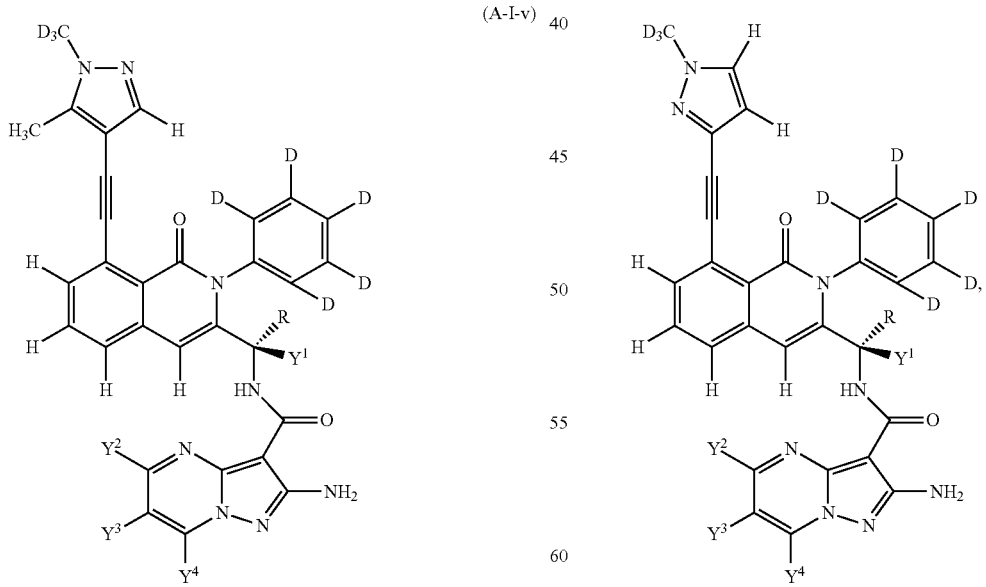

(A-I-v)

or a pharmaceutically acceptable form thereof.

In one embodiment, the compound is a compound of Formula (A-I-v) selected from any one of the compounds in Table 62.

TABLE 62

Exemplary compounds of Formula (A-I-v)

| Compound | Y¹ | Y² | Y³ | Y⁴ | R |
|---|---|---|---|---|---|
| 6201 | H | H | H | H | —CH₃ |
| 6202 | D | H | H | H | —CH₃ |
| 6203 | H | D | H | H | —CH₃ |
| 6204 | H | H | D | H | —CH₃ |
| 6205 | H | H | H | D | —CH₃ |
| 6206 | D | D | H | H | —CH₃ |
| 6207 | D | H | D | H | —CH₃ |
| 6208 | D | H | H | D | —CH₃ |
| 6209 | H | D | D | H | —CH₃ |
| 6210 | H | D | H | D | —CH₃ |
| 6211 | H | H | D | D | —CH₃ |
| 6212 | D | D | D | H | —CH₃ |
| 6213 | D | D | H | D | —CH₃ |
| 6214 | D | H | D | D | —CH₃ |
| 6215 | H | D | D | D | —CH₃ |
| 6216 | D | D | D | D | —CH₃ |
| 6217 | H | H | H | H | —CD₃ |
| 6218 | D | H | H | H | —CD₃ |
| 6219 | H | D | H | H | —CD₃ |
| 6220 | H | H | D | H | —CD₃ |
| 6221 | H | H | H | D | —CD₃ |
| 6222 | D | D | H | H | —CD₃ |
| 6223 | D | H | D | H | —CD₃ |
| 6224 | D | H | H | D | —CD₃ |
| 6225 | H | D | D | H | —CD₃ |
| 6226 | H | D | H | D | —CD₃ |
| 6227 | H | H | D | D | —CD₃ |
| 6228 | D | D | D | H | —CD₃ |
| 6229 | D | D | H | D | —CD₃ |
| 6230 | D | H | D | D | —CD₃ |
| 6231 | H | D | D | D | —CD₃ |
| 6232 | D | D | D | D | —CD₃ | or a pharmaceutically acceptable form thereof.

In one embodiment, the compound is a compound of Formula (A-II-l):

(A-II-l)

or a pharmaceutically acceptable form thereof.

In one embodiment, the compound is a compound of Formula (A-II-l) selected from any one of the compounds in Table 63.

TABLE 63

Exemplary compounds of Formula (A-II-l)

| Compound | $Y^1$ | $Y^2$ | $Y^3$ | $Y^4$ | R |
|---|---|---|---|---|---|
| 6301 | H | H | H | H | —CH$_3$ |
| 6302 | D | H | H | H | —CH$_3$ |
| 6303 | H | D | H | H | —CH$_3$ |
| 6304 | H | H | D | H | —CH$_3$ |
| 6305 | H | H | H | D | —CH$_3$ |
| 6306 | D | D | H | H | —CH$_3$ |
| 6307 | D | H | D | H | —CH$_3$ |
| 6308 | D | H | H | D | —CH$_3$ |
| 6309 | H | D | D | H | —CH$_3$ |
| 6310 | H | D | H | D | —CH$_3$ |
| 6311 | H | H | D | D | —CH$_3$ |
| 6312 | D | D | D | H | —CH$_3$ |
| 6313 | D | D | H | D | —CH$_3$ |
| 6314 | D | H | D | D | —CH$_3$ |
| 6315 | H | D | D | D | —CH$_3$ |
| 6316 | D | D | D | D | —CH$_3$ |
| 6317 | H | H | H | H | —CD$_3$ |
| 6318 | D | H | H | H | —CD$_3$ |
| 6319 | H | D | H | H | —CD$_3$ |
| 6320 | H | H | D | H | —CD$_3$ |
| 6321 | H | H | H | D | —CD$_3$ |
| 6322 | D | D | H | H | —CD$_3$ |
| 6323 | D | H | D | H | —CD$_3$ |
| 6324 | D | H | H | D | —CD$_3$ |
| 6325 | H | D | D | H | —CD$_3$ |
| 6326 | H | D | H | D | —CD$_3$ |
| 6327 | H | H | D | D | —CD$_3$ |
| 6328 | D | D | D | H | —CD$_3$ |
| 6329 | D | D | H | D | —CD$_3$ |
| 6330 | D | H | D | D | —CD$_3$ |
| 6331 | H | D | D | D | —CD$_3$ |
| 6332 | D | D | D | D | —CD$_3$ | or a pharmaceutically acceptable form thereof.

In one embodiment, the compound is a compound of Formula (B-I-u):

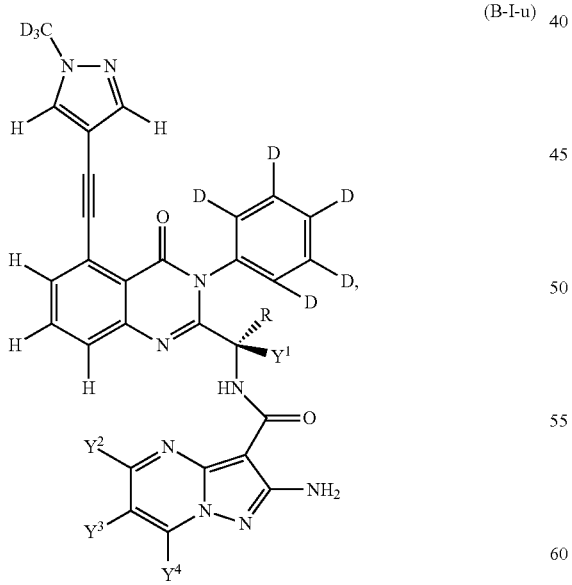

(B-I-u)

or a pharmaceutically acceptable form thereof.

In one embodiment, the compound is a compound of Formula (B-I-u) selected from any one of the compounds in Table 64.

TABLE 64

Exemplary compounds of Formula (B-I-u)

| Compound | $Y^1$ | $Y^2$ | $Y^3$ | $Y^4$ | R |
|---|---|---|---|---|---|
| 6401 | H | H | H | H | —CH$_3$ |
| 6402 | D | H | H | H | —CH$_3$ |
| 6403 | H | D | H | H | —CH$_3$ |
| 6404 | H | H | D | H | —CH$_3$ |
| 6405 | H | H | H | D | —CH$_3$ |
| 6406 | D | D | H | H | —CH$_3$ |
| 6407 | D | H | D | H | —CH$_3$ |
| 6408 | D | H | H | D | —CH$_3$ |
| 6409 | H | D | D | H | —CH$_3$ |
| 6410 | H | D | H | D | —CH$_3$ |
| 6411 | H | H | D | D | —CH$_3$ |
| 6412 | D | D | D | H | —CH$_3$ |
| 6413 | D | D | H | D | —CH$_3$ |
| 6414 | D | H | D | D | —CH$_3$ |
| 6415 | H | D | D | D | —CH$_3$ |
| 6416 | D | D | D | D | —CH$_3$ |
| 6417 | H | H | H | H | —CD$_3$ |
| 6418 | D | H | H | H | —CD$_3$ |
| 6419 | H | D | H | H | —CD$_3$ |
| 6420 | H | H | D | H | —CD$_3$ |
| 6421 | H | H | H | D | —CD$_3$ |
| 6422 | D | D | H | H | —CD$_3$ |
| 6423 | D | H | D | H | —CD$_3$ |
| 6424 | D | H | H | D | —CD$_3$ |
| 6425 | H | D | D | H | —CD$_3$ |
| 6426 | H | D | H | D | —CD$_3$ |
| 6427 | H | H | D | D | —CD$_3$ |
| 6428 | D | D | D | H | —CD$_3$ |
| 6429 | D | D | H | D | —CD$_3$ |
| 6430 | D | H | D | D | —CD$_3$ |
| 6431 | H | D | D | D | —CD$_3$ |
| 6432 | D | D | D | D | —CD$_3$ | or a pharmaceutically acceptable form thereof.

In one embodiment, the compound is a compound of Formula (B-I-v):

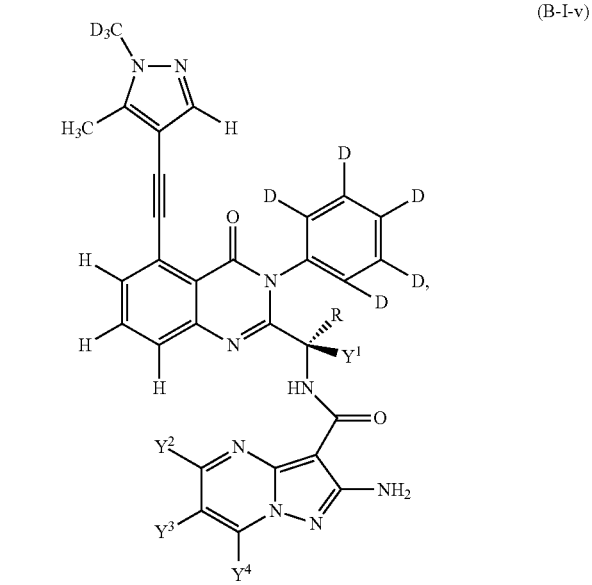

(B-I-v)

or a pharmaceutically acceptable form thereof.

In one embodiment, the compound is a compound of Formula (B-I-v) selected from any one of the compounds in Table 65.

TABLE 65

Exemplary compounds of Formula (B-I-v)

| Compound | Y¹ | Y² | Y³ | Y⁴ | R |
|---|---|---|---|---|---|
| 6501 | H | H | H | H | —CH₃ |
| 6502 | D | H | H | H | —CH₃ |
| 6503 | H | D | H | H | —CH₃ |
| 6504 | H | H | D | H | —CH₃ |
| 6505 | H | H | H | D | —CH₃ |
| 6506 | D | D | H | H | —CH₃ |
| 6507 | D | H | D | H | —CH₃ |
| 6508 | D | H | H | D | —CH₃ |
| 6509 | H | D | D | H | —CH₃ |
| 6510 | H | D | H | D | —CH₃ |
| 6511 | H | H | D | D | —CH₃ |
| 6512 | D | D | D | H | —CH₃ |
| 6513 | D | D | H | D | —CH₃ |
| 6514 | D | H | D | D | —CH₃ |
| 6515 | H | D | D | D | —CH₃ |
| 6516 | D | D | D | D | —CH₃ |
| 6517 | H | H | H | H | —CD₃ |
| 6518 | D | H | H | H | —CD₃ |
| 6519 | H | D | H | H | —CD₃ |
| 6520 | H | H | D | H | —CD₃ |
| 6521 | H | H | H | D | —CD₃ |
| 6522 | D | D | H | H | —CD₃ |
| 6523 | D | H | D | H | —CD₃ |
| 6524 | D | H | H | D | —CD₃ |
| 6525 | H | D | D | H | —CD₃ |
| 6526 | H | D | H | D | —CD₃ |
| 6527 | H | H | D | D | —CD₃ |
| 6528 | D | D | D | H | —CD₃ |
| 6529 | D | D | H | D | —CD₃ |
| 6530 | D | H | D | D | —CD₃ |
| 6531 | H | D | D | D | —CD₃ |
| 6532 | D | D | D | D | —CD₃ | or a pharmaceutically acceptable form thereof.

In one embodiment, the compound is a compound of Formula (B-II-l):

TABLE 66

Exemplary compounds of Formula (B-II-l)

| Compound | Y¹ | Y² | Y³ | Y⁴ | R |
|---|---|---|---|---|---|
| 6601 | H | H | H | H | —CH₃ |
| 6602 | D | H | H | H | —CH₃ |
| 6603 | H | D | H | H | —CH₃ |
| 6604 | H | H | D | H | —CH₃ |
| 6605 | H | H | H | D | —CH₃ |
| 6606 | D | D | H | H | —CH₃ |
| 6607 | D | H | D | H | —CH₃ |
| 6608 | D | H | H | D | —CH₃ |
| 6609 | H | D | D | H | —CH₃ |
| 6610 | H | D | H | D | —CH₃ |
| 6611 | H | H | D | D | —CH₃ |
| 6612 | D | D | D | H | —CH₃ |
| 6613 | D | D | H | D | —CH₃ |
| 6614 | D | H | D | D | —CH₃ |
| 6615 | H | D | D | D | —CH₃ |
| 6616 | D | D | D | D | —CH₃ |
| 6617 | H | H | H | H | —CD₃ |
| 6618 | D | H | H | H | —CD₃ |
| 6619 | H | D | H | H | —CD₃ |
| 6620 | H | H | D | H | —CD₃ |
| 6621 | H | H | H | D | —CD₃ |
| 6622 | D | D | H | H | —CD₃ |
| 6623 | D | H | D | H | —CD₃ |
| 6624 | D | H | H | D | —CD₃ |
| 6625 | H | D | D | H | —CD₃ |
| 6626 | H | D | H | D | —CD₃ |
| 6627 | H | H | D | D | —CD₃ |
| 6628 | D | D | D | H | —CD₃ |
| 6629 | D | D | H | D | —CD₃ |
| 6630 | D | H | D | D | —CD₃ |
| 6631 | H | D | D | D | —CD₃ |
| 6632 | D | D | D | D | —CD₃ | or a pharmaceutically acceptable form thereof.

In one embodiment, the compound is a compound of Formula (A-I-w):

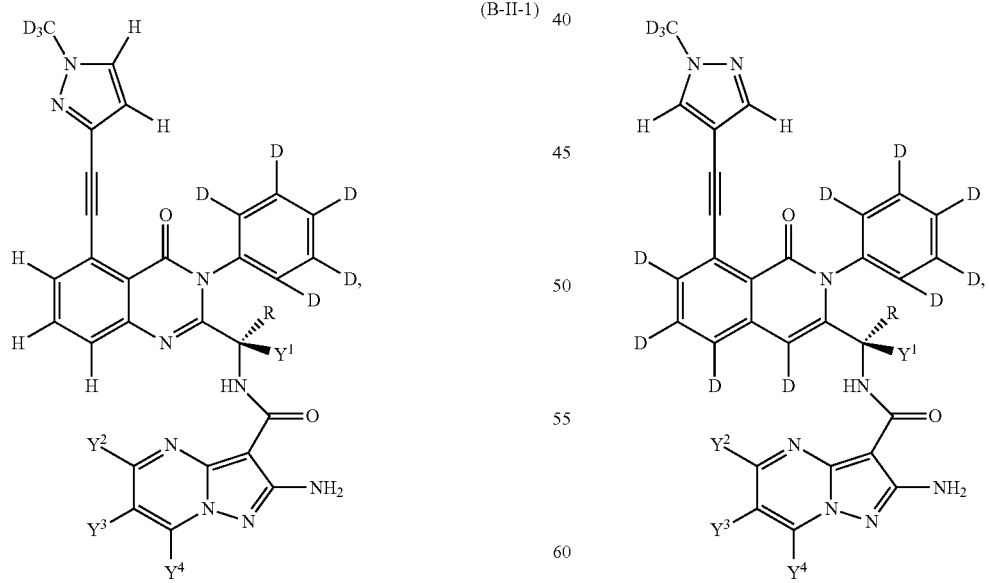

or a pharmaceutically acceptable form thereof.

In one embodiment, the compound is a compound of Formula (B-II-l) selected from any one of the compounds in Table 66.

or a pharmaceutically acceptable form thereof.

In one embodiment, the compound is a compound of Formula (A-I-w) selected from any one of the compounds in Table 67.

TABLE 67

Exemplary compounds of Formula (A-I-w)

| Compound | Y¹ | Y² | Y³ | Y⁴ | R |
|---|---|---|---|---|---|
| 6701 | H | H | H | H | —CH₃ |
| 6702 | D | H | H | H | —CH₃ |
| 6703 | H | D | H | H | —CH₃ |
| 6704 | H | H | D | H | —CH₃ |
| 6705 | H | H | H | D | —CH₃ |
| 6706 | D | D | H | H | —CH₃ |
| 6707 | D | H | D | H | —CH₃ |
| 6708 | D | H | H | D | —CH₃ |
| 6709 | H | D | D | H | —CH₃ |
| 6710 | H | D | H | D | —CH₃ |
| 6711 | H | H | D | D | —CH₃ |
| 6712 | D | D | D | H | —CH₃ |
| 6713 | D | D | H | D | —CH₃ |
| 6714 | D | H | D | D | —CH₃ |
| 6715 | H | D | D | D | —CH₃ |
| 6716 | D | D | D | D | —CH₃ |
| 6717 | H | H | H | H | —CD₃ |
| 6718 | D | H | H | H | —CD₃ |
| 6719 | H | D | H | H | —CD₃ |
| 6720 | H | H | D | H | —CD₃ |
| 6721 | H | H | H | D | —CD₃ |
| 6722 | D | D | H | H | —CD₃ |
| 6723 | D | H | D | H | —CD₃ |
| 6724 | D | H | H | D | —CD₃ |
| 6725 | H | D | D | H | —CD₃ |
| 6726 | H | D | H | D | —CD₃ |
| 6727 | H | H | D | D | —CD₃ |
| 6728 | D | D | D | H | —CD₃ |
| 6729 | D | D | H | D | —CD₃ |
| 6730 | D | H | D | D | —CD₃ |
| 6731 | H | D | D | D | —CD₃ |
| 6732 | D | D | D | D | —CD₃ | or a pharmaceutically acceptable form thereof.

In one embodiment, the compound is a compound of Formula (A-I-x):

TABLE 68

Exemplary compounds of Formula (A-I-x)

| Compound | Y¹ | Y² | Y³ | Y⁴ | R |
|---|---|---|---|---|---|
| 6801 | H | H | H | H | —CH₃ |
| 6802 | D | H | H | H | —CH₃ |
| 6803 | H | D | H | H | —CH₃ |
| 6804 | H | H | D | H | —CH₃ |
| 6805 | H | H | H | D | —CH₃ |
| 6806 | D | D | H | H | —CH₃ |
| 6807 | D | H | D | H | —CH₃ |
| 6808 | D | H | H | D | —CH₃ |
| 6809 | H | D | D | H | —CH₃ |
| 6810 | H | D | H | D | —CH₃ |
| 6811 | H | H | D | D | —CH₃ |
| 6812 | D | D | D | H | —CH₃ |
| 6813 | D | D | H | D | —CH₃ |
| 6814 | D | H | D | D | —CH₃ |
| 6815 | H | D | D | D | —CH₃ |
| 6816 | D | D | D | D | —CH₃ |
| 6817 | H | H | H | H | —CD₃ |
| 6818 | D | H | H | H | —CD₃ |
| 6819 | H | D | H | H | —CD₃ |
| 6820 | H | H | D | H | —CD₃ |
| 6821 | H | H | H | D | —CD₃ |
| 6822 | D | D | H | H | —CD₃ |
| 6823 | D | H | D | H | —CD₃ |
| 6824 | D | H | H | D | —CD₃ |
| 6825 | H | D | D | H | —CD₃ |
| 6826 | H | D | H | D | —CD₃ |
| 6827 | H | H | D | D | —CD₃ |
| 6828 | D | D | D | H | —CD₃ |
| 6829 | D | D | H | D | —CD₃ |
| 6830 | D | H | D | D | —CD₃ |
| 6831 | H | D | D | D | —CD₃ |
| 6832 | D | D | D | D | —CD₃ | or a pharmaceutically acceptable form thereof.

In one embodiment, the compound is a compound of Formula (A-II-m):

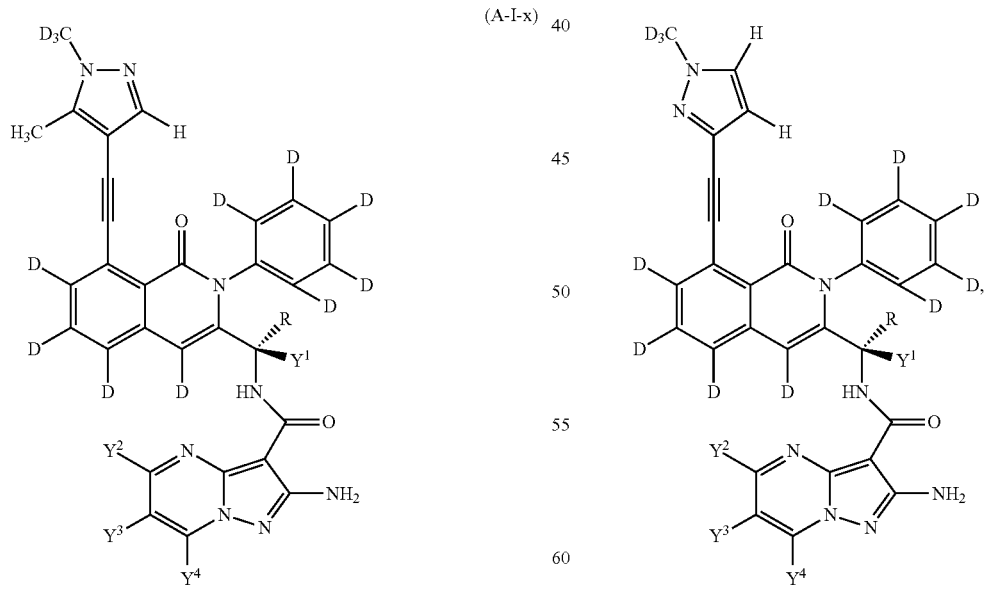

or a pharmaceutically acceptable form thereof.

In one embodiment, the compound is a compound of Formula (A-I-x) selected from any one of the compounds in Table 68.

or a pharmaceutically acceptable form thereof.

In one embodiment, the compound is a compound of Formula (A-II-m) selected from any one of the compounds in Table 69.

TABLE 69

Exemplary compounds of Formula (A-II-m)

| Compound | Y¹ | Y² | Y³ | Y⁴ | R |
|---|---|---|---|---|---|
| 6901 | H | H | H | H | —CH₃ |
| 6902 | D | H | H | H | —CH₃ |
| 6903 | H | D | H | H | —CH₃ |
| 6904 | H | H | D | H | —CH₃ |
| 6905 | H | H | H | D | —CH₃ |
| 6906 | D | D | H | H | —CH₃ |
| 6907 | D | H | D | H | —CH₃ |
| 6908 | D | H | H | D | —CH₃ |
| 6909 | H | D | D | H | —CH₃ |
| 6910 | H | D | H | D | —CH₃ |
| 6911 | H | H | D | D | —CH₃ |
| 6912 | D | D | D | H | —CH₃ |
| 6913 | D | D | H | D | —CH₃ |
| 6914 | D | H | D | D | —CH₃ |
| 6915 | H | D | D | D | —CH₃ |
| 6916 | D | D | D | D | —CH₃ |
| 6917 | H | H | H | H | —CD₃ |
| 6918 | D | H | H | H | —CD₃ |
| 6919 | H | D | H | H | —CD₃ |
| 6920 | H | H | D | H | —CD₃ |
| 6921 | H | H | H | D | —CD₃ |
| 6922 | D | D | H | H | —CD₃ |
| 6923 | D | H | D | H | —CD₃ |
| 6924 | D | H | H | D | —CD₃ |
| 6925 | H | D | D | H | —CD₃ |
| 6926 | H | D | H | D | —CD₃ |
| 6927 | H | H | D | D | —CD₃ |
| 6928 | D | D | D | H | —CD₃ |
| 6929 | D | D | H | D | —CD₃ |
| 6930 | D | H | D | D | —CD₃ |
| 6931 | H | D | D | D | —CD₃ |
| 6932 | D | D | D | D | —CD₃ | or a pharmaceutically acceptable form thereof.

In one embodiment, the compound is a compound of Formula (B-I-w):

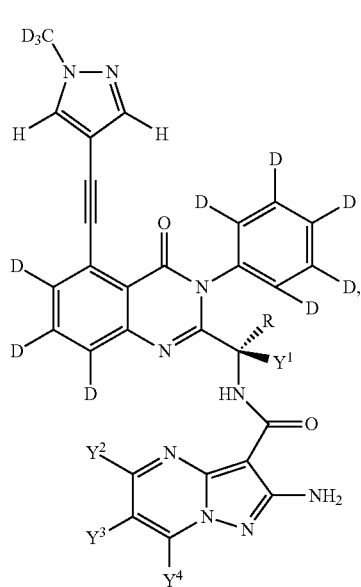

(B-I-w)

or a pharmaceutically acceptable form thereof.

In one embodiment, the compound is a compound of Formula (B-I-w) selected from any one of the compounds in Table 70.

TABLE 70

Exemplary compounds of Formula (B-I-w)

| Compound | Y¹ | Y² | Y³ | Y⁴ | R |
|---|---|---|---|---|---|
| 7001 | H | H | H | H | —CH₃ |
| 7002 | D | H | H | H | —CH₃ |
| 7003 | H | D | H | H | —CH₃ |
| 7004 | H | H | D | H | —CH₃ |
| 7005 | H | H | H | D | —CH₃ |
| 7006 | D | D | H | H | —CH₃ |
| 7007 | D | H | D | H | —CH₃ |
| 7008 | D | H | H | D | —CH₃ |
| 7009 | H | D | D | H | —CH₃ |
| 7010 | H | D | H | D | —CH₃ |
| 7011 | H | H | D | D | —CH₃ |
| 7012 | D | D | D | H | —CH₃ |
| 7013 | D | D | H | D | —CH₃ |
| 7014 | D | H | D | D | —CH₃ |
| 7015 | H | D | D | D | —CH₃ |
| 7016 | D | D | D | D | —CH₃ |
| 7017 | H | H | H | H | —CD₃ |
| 7018 | D | H | H | H | —CD₃ |
| 7019 | H | D | H | H | —CD₃ |
| 7020 | H | H | D | H | —CD₃ |
| 7021 | H | H | H | D | —CD₃ |
| 7022 | D | D | H | H | —CD₃ |
| 7023 | D | H | D | H | —CD₃ |
| 7024 | D | H | H | D | —CD₃ |
| 7025 | H | D | D | H | —CD₃ |
| 7026 | H | D | H | D | —CD₃ |
| 7027 | H | H | D | D | —CD₃ |
| 7028 | D | D | D | H | —CD₃ |
| 7029 | D | D | H | D | —CD₃ |
| 7030 | D | H | D | D | —CD₃ |
| 7031 | H | D | D | D | —CD₃ |
| 7032 | D | D | D | D | —CD₃ | or a pharmaceutically acceptable form thereof.

In one embodiment, the compound is a compound of Formula (B-I-x):

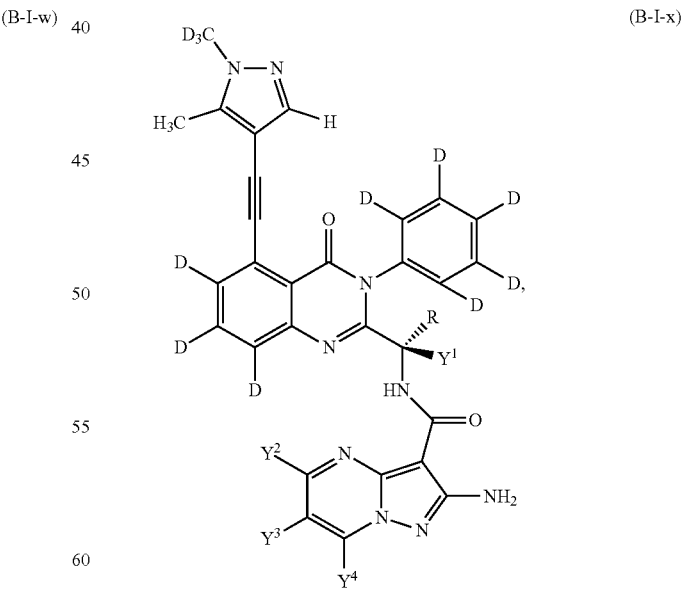

(B-I-x)

or a pharmaceutically acceptable form thereof.

In one embodiment, the compound is a compound of Formula (B-I-x) selected from any one of the compounds in Table 71.

TABLE 71

Exemplary compounds of Formula (B-I-x)

| Compound | $Y^1$ | $Y^2$ | $Y^3$ | $Y^4$ | R |
|---|---|---|---|---|---|
| 7101 | H | H | H | H | —$CH_3$ |
| 7102 | D | H | H | H | —$CH_3$ |
| 7103 | H | D | H | H | —$CH_3$ |
| 7104 | H | H | D | H | —$CH_3$ |
| 7105 | H | H | H | D | —$CH_3$ |
| 7106 | D | D | H | H | —$CH_3$ |
| 7107 | D | H | D | H | —$CH_3$ |
| 7108 | D | H | H | D | —$CH_3$ |
| 7109 | H | D | D | H | —$CH_3$ |
| 7110 | H | D | H | D | —$CH_3$ |
| 7111 | H | H | D | D | —$CH_3$ |
| 7112 | D | D | D | H | —$CH_3$ |
| 7113 | D | D | H | D | —$CH_3$ |
| 7114 | D | H | D | D | —$CH_3$ |
| 7115 | H | D | D | D | —$CH_3$ |
| 7116 | D | D | D | D | —$CH_3$ |
| 7117 | H | H | H | H | —$CD_3$ |
| 7118 | D | H | H | H | —$CD_3$ |
| 7119 | H | D | H | H | —$CD_3$ |
| 7120 | H | H | D | H | —$CD_3$ |
| 7121 | H | H | H | D | —$CD_3$ |
| 7122 | D | D | H | H | —$CD_3$ |
| 7123 | D | H | D | H | —$CD_3$ |
| 7124 | D | H | H | D | —$CD_3$ |
| 7125 | H | D | D | H | —$CD_3$ |
| 7126 | H | D | H | D | —$CD_3$ |
| 7127 | H | H | D | D | —$CD_3$ |
| 7128 | D | D | D | H | —$CD_3$ |
| 7129 | D | D | H | D | —$CD_3$ |
| 7130 | D | H | D | D | —$CD_3$ |
| 7131 | H | D | D | D | —$CD_3$ |
| 7132 | D | D | D | D | —$CD_3$ |

TABLE 72

Exemplary compounds of Formula (B-II-m)

| Compound | $Y^1$ | $Y^2$ | $Y^3$ | $Y^4$ | R |
|---|---|---|---|---|---|
| 7201 | H | H | H | H | —$CH_3$ |
| 7202 | D | H | H | H | —$CH_3$ |
| 7203 | H | D | H | H | —$CH_3$ |
| 7204 | H | H | D | H | —$CH_3$ |
| 7205 | H | H | H | D | —$CH_3$ |
| 7206 | D | D | H | H | —$CH_3$ |
| 7207 | D | H | D | H | —$CH_3$ |
| 7208 | D | H | H | D | —$CH_3$ |
| 7209 | H | D | D | H | —$CH_3$ |
| 7210 | H | D | H | D | —$CH_3$ |
| 7211 | H | H | D | D | —$CH_3$ |
| 7212 | D | D | D | H | —$CH_3$ |
| 7213 | D | D | H | D | —$CH_3$ |
| 7214 | D | H | D | D | —$CH_3$ |
| 7215 | H | D | D | D | —$CH_3$ |
| 7216 | D | D | D | D | —$CH_3$ |
| 7217 | H | H | H | H | —$CD_3$ |
| 7218 | D | H | H | H | —$CD_3$ |
| 7219 | H | D | H | H | —$CD_3$ |
| 7220 | H | H | D | H | —$CD_3$ |
| 7221 | H | H | H | D | —$CD_3$ |
| 7222 | D | D | H | H | —$CD_3$ |
| 7223 | D | H | D | H | —$CD_3$ |
| 7224 | D | H | H | D | —$CD_3$ |
| 7225 | H | D | D | H | —$CD_3$ |
| 7226 | H | D | H | D | —$CD_3$ |
| 7227 | H | H | D | D | —$CD_3$ |
| 7228 | D | D | D | H | —$CD_3$ |
| 7229 | D | D | H | D | —$CD_3$ |
| 7230 | D | H | D | D | —$CD_3$ |
| 7231 | H | D | D | D | —$CD_3$ |
| 7232 | D | D | D | D | —$CD_3$ | or a pharmaceutically acceptable form thereof.

In one embodiment, the compound is a compound of Formula (B-II-m):

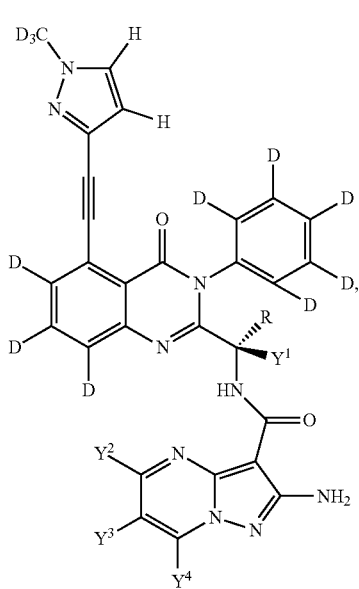

(B-II-m)

or a pharmaceutically acceptable form thereof.

In one embodiment, the compound is a compound of Formula (B-II-m) selected from any one of the compounds in Table 72.

or a pharmaceutically acceptable form thereof.

In one embodiment, the compound is a compound of Formula (A-I-y):

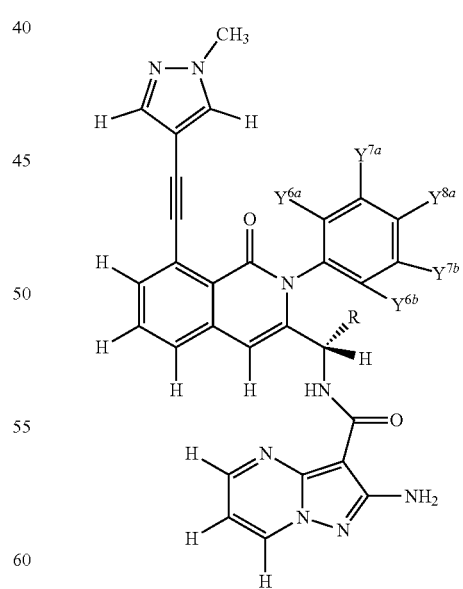

(A-I-y)

or a pharmaceutically acceptable form thereof.

In one embodiment, the compound is a compound of Formula (A-I-y) selected from any one of the compounds in Table 73.

TABLE 73

Exemplary compounds of Formula (A-I-y)

| Compound | $Y^{6a}$ | $Y^{7a}$ | $Y^8$ | $Y^{7b}$ | $Y^{6b}$ | R |
|---|---|---|---|---|---|---|
| 7301 | D | H | H | H | H | —CH$_3$ |
| 7302 | H | D | H | H | H | —CH$_3$ |
| 7303 | H | H | D | H | H | —CH$_3$ |
| 7304 | D | D | H | H | H | —CH$_3$ |
| 7305 | D | H | D | H | H | —CH$_3$ |
| 7306 | D | H | H | D | H | —CH$_3$ |
| 7307 | D | H | H | H | D | —CH$_3$ |
| 7308 | H | D | D | H | H | —CH$_3$ |
| 7309 | H | D | H | D | H | —CH$_3$ |
| 7310 | D | D | D | H | H | —CH$_3$ |
| 7311 | D | D | H | D | H | —CH$_3$ |
| 7312 | D | D | H | H | D | —CH$_3$ |
| 7313 | D | H | D | D | H | —CH$_3$ |
| 7314 | D | H | D | H | D | —CH$_3$ |
| 7315 | H | D | D | D | H | —CH$_3$ |
| 7316 | D | D | D | D | H | —CH$_3$ |
| 7317 | D | D | D | H | D | —CH$_3$ |
| 7318 | D | D | H | D | D | —CH$_3$ |
| 7319 | D | H | H | H | H | —CD$_3$ |
| 7320 | H | D | H | H | H | —CD$_3$ |
| 7321 | H | H | D | H | H | —CD$_3$ |
| 7322 | D | D | H | H | H | —CD$_3$ |
| 7323 | D | H | D | H | H | —CD$_3$ |
| 7324 | D | H | H | D | H | —CD$_3$ |
| 7325 | D | H | H | H | D | —CD$_3$ |
| 7326 | H | D | D | H | H | —CD$_3$ |
| 7327 | H | D | H | D | H | —CD$_3$ |
| 7328 | D | D | D | H | H | —CD$_3$ |
| 7329 | D | D | H | D | H | —CD$_3$ |
| 7330 | D | D | H | H | D | —CD$_3$ |
| 7331 | D | H | D | D | H | —CD$_3$ |
| 7332 | D | H | D | H | D | —CD$_3$ |
| 7333 | H | D | D | D | H | —CD$_3$ |
| 7334 | D | D | D | D | H | —CD$_3$ |
| 7335 | D | D | D | H | D | —CD$_3$ |
| 7336 | D | D | H | D | D | —CD$_3$ | or a pharmaceutically acceptable form thereof.

In one embodiment, the compound is a compound of Formula (B-I-y):

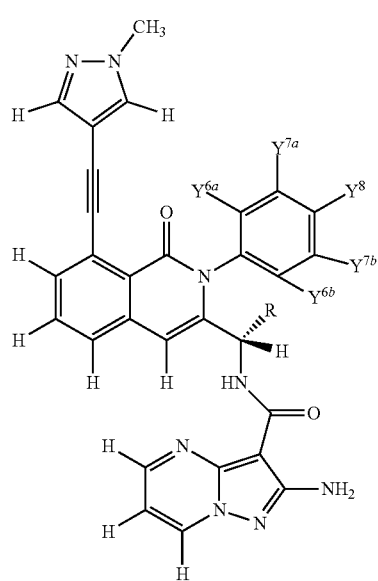

(B-I-y)

or a pharmaceutically acceptable form thereof.

In one embodiment, the compound is a compound of Formula (B-I-y) selected from any one of the compounds in Table 74.

TABLE 74

Exemplary compounds of Formula (B-I-y)

| Compound | $Y^{6a}$ | $Y^{7a}$ | $Y^8$ | $Y^{7b}$ | $Y^{6b}$ | R |
|---|---|---|---|---|---|---|
| 7401 | D | H | H | H | H | —CH$_3$ |
| 7402 | H | D | H | H | H | —CH$_3$ |
| 7403 | H | H | D | H | H | —CH$_3$ |
| 7404 | D | D | H | H | H | —CH$_3$ |
| 7405 | D | H | D | H | H | —CH$_3$ |
| 7406 | D | H | H | D | H | —CH$_3$ |
| 7407 | D | H | H | H | D | —CH$_3$ |
| 7408 | H | D | D | H | H | —CH$_3$ |
| 7409 | H | D | H | D | H | —CH$_3$ |
| 7410 | D | D | D | H | H | —CH$_3$ |
| 7411 | D | D | H | D | H | —CH$_3$ |
| 7412 | D | D | H | H | D | —CH$_3$ |
| 7413 | D | H | D | D | H | —CH$_3$ |
| 7414 | D | H | D | H | D | —CH$_3$ |
| 7415 | H | D | D | D | H | —CH$_3$ |
| 7416 | D | D | D | D | H | —CH$_3$ |
| 7417 | D | D | D | H | D | —CH$_3$ |
| 7418 | D | D | H | D | D | —CH$_3$ |
| 7419 | D | H | H | H | H | —CD$_3$ |
| 7420 | H | D | H | H | H | —CD$_3$ |
| 7421 | H | H | D | H | H | —CD$_3$ |
| 7422 | D | D | H | H | H | —CD$_3$ |
| 7423 | D | H | D | H | H | —CD$_3$ |
| 7424 | D | H | H | D | H | —CD$_3$ |
| 7425 | D | H | H | H | D | —CD$_3$ |
| 7426 | H | D | D | H | H | —CD$_3$ |
| 7427 | H | D | H | D | H | —CD$_3$ |
| 7428 | D | D | D | H | H | —CD$_3$ |
| 7429 | D | D | H | D | H | —CD$_3$ |
| 7430 | D | D | H | H | D | —CD$_3$ |
| 7431 | D | H | D | D | H | —CD$_3$ |
| 7432 | D | H | D | H | D | —CD$_3$ |
| 7433 | H | D | D | D | H | —CD$_3$ |
| 7434 | D | D | D | D | H | —CD$_3$ |
| 7435 | D | D | D | H | D | —CD$_3$ |
| 7436 | D | D | H | D | D | —CD$_3$ | or a pharmaceutically acceptable form thereof.

In some embodiments, the compounds provided herein, including any compound specifically provided in the tables above, have an enantiomeric excess of at least about 1%, about 5%, about 10%, about 20%, about 30%, about 40%, about 50%, about 75%, about 90%, about 95%, or about 99%. In one embodiment, the enantiomeric excess is at least 50%. In one embodiment, the enantiomeric excess is at least 75%. In one embodiment, the enantiomeric excess is at least 90%. In one embodiment, the enantiomeric excess is at least 95%. In one embodiment, the enantiomeric excess is at least 99%. In one embodiment, the compound is Compound 101. In one embodiment, the compound is Compound 201. In one embodiment, the compound is Compound 301. In one embodiment, the compound is Compound 401. In one embodiment, the compound is Compound 501. In one embodiment, the compound is Compound 601.

In another set of embodiments, provided herein are the corresponding R-enantiomers of the S-enantiomer compounds provided herein, including any compound specifically provided in the tables above.

In another set of embodiments, provided herein are the corresponding racemic mixtures of the S-enantiomer compounds provided herein, including any compound specifically provided in the tables above.

In some embodiments, for the compounds provided herein, including any compound specifically provided in the tables above, each position designated as deuterium independently has a minimum isotopic enrichment factor of at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom.

In one embodiment, for the compounds provided herein, including any compound specifically provided in the tables above, wherein $Y^1$ is designated as deuterium, $Y^1$ has a minimum isotopic enrichment factor of at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom. In one embodiment, the deuterium incorporation at $Y^1$ is at least 52.5%. In one embodiment, the deuterium incorporation at $Y^1$ is at least 75%. In one embodiment, the deuterium incorporation at $Y^1$ is at least 90%. In one embodiment, the deuterium incorporation at $Y^1$ is at least 95%. In one embodiment, the deuterium incorporation at $Y^1$ is at least 99%. In one embodiment, the compound is Compound 101. In one embodiment, the compound is Compound 201. In one embodiment, the compound is Compound 301. In one embodiment, the compound is Compound 401. In one embodiment, the compound is Compound 501. In one embodiment, the compound is Compound 601.

The synthesis of the compounds provided herein may be readily achieved by synthetic chemists of ordinary skill by reference to the exemplary synthesis and examples provided herein. Analogous procedures used for the preparation of certain non-deuterium enriched isoquinolinone and quinazolinone compounds are provided in International Application Publication Nos. WO 2015/051244 and WO 2015/143012, the entireties of which are incorporated herein by reference.

Methods of Treatment, Prevention and/or Management

In certain embodiments, provided herein is a composition (e.g., a pharmaceutical composition) comprising a compound described herein and a pharmaceutically acceptable excipient. In some embodiments, provided herein is a method of inhibiting a PI3 kinase, comprising contacting the PI3 kinase with an effective amount of a compound or a pharmaceutical composition described herein. In certain embodiments, a method is provided for inhibiting a PI3 kinase wherein said PI3 kinase is present in a cell. The inhibition can take place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, among others. In certain embodiments, a second therapeutic agent is administered to the subject.

In certain embodiments, a method is provided for selectively inhibiting a PI3 kinase gamma isoform over PI3 kinase alpha or beta isoform wherein the inhibition takes place in a cell. Non-limiting examples of the methods provided herein can comprise contacting PI3 kinase gamma isoform with an effective amount of a compound or a pharmaceutical composition provided herein. In an embodiment, such contact can occur in a cell.

In certain embodiments, a method is provided for selectively inhibiting a PI3 kinase gamma isoform over PI3 kinase alpha or beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase gamma isoform over PI3 kinase alpha or beta isoform by administering an amount of a compound or a pharmaceutical composition provided herein to said subject, wherein said amount is sufficient for selective modulation of PI3 kinase gamma isoform over PI3 kinase alpha or beta isoform.

In certain embodiments, a method is provided for selectively inhibiting a PI3 kinase delta isoform over PI3 kinase alpha or beta isoform wherein the inhibition takes place in a cell. Non-limiting examples of the methods provided herein can comprise contacting PI3 kinase delta isoform with an effective amount of a compound or a pharmaceutical composition provided herein. In an embodiment, such contact can occur in a cell.

In certain embodiments, a method is provided for selectively inhibiting a PI3 kinase delta isoform over PI3 kinase alpha or beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase delta isoform over PI3 kinase alpha or beta isoform by administering an amount of a compound or a pharmaceutical composition provided herein to said subject, wherein said amount is sufficient for selective modulation of PI3 kinase delta isoform over PI3 kinase alpha or beta isoform.

In certain embodiments, a method is provided for selectively inhibiting a PI3 kinase gamma isoform over PI3 kinase delta isoform wherein the inhibition takes place in a cell. Non-limiting examples of the methods provided herein can comprise contacting PI3 kinase gamma isoform with an effective amount of a compound or a pharmaceutical composition provided herein. In an embodiment, such contact can occur in a cell.

In certain embodiments, a method is provided for selectively inhibiting a PI3 kinase gamma isoform over PI3 kinase delta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase gamma isoform over PI3 kinase delta isoform by administering an amount of a compound or a pharmaceutical composition provided herein to said subject, wherein said amount is sufficient for selective modulation of PI3 kinase gamma isoform over PI3 kinase delta isoform.

In certain embodiments, provided herein is a method of inhibiting a PI3 kinase in a subject suffering from a disease or disorder, comprising administering to the subject an effective amount of a compound provided herein.

In certain embodiments, provided herein is a method of treating or preventing a PI3K mediated disease or disorder in a subject, comprising administering to the subject an effective amount of a compound provided herein. In certain embodiments, provided herein is a method of treating a PI3K mediated disease or disorder in a subject, comprising administering to the subject an effective amount of a compound provided herein.

In some embodiments, the disease or disorder is an inflammatory disease, an immune disease, or a respiratory disease, In certain embodiments, provided herein is a method of treating an inflammatory disease, an immune disease, or a respiratory disease, comprising administering to the subject an effective amount of a compound provided herein.

In some embodiments, the disorder treated by the methods or compounds provided herein is a cancer. In some embodiments, the cancer is a solid or soft tissue tumor (e.g., a carcinoid, carcinoma or sarcoma), a hematopoietic tissue tumor (e.g., a heme malignancy), or a metastatic lesion, e.g., a metastatic lesion of any of the cancers or tumors provided herein. In one embodiment, the cancer is metastatic cancer to the bone.

In one embodiment, the cancer treated by the methods or compounds provided herein is a a soft tissue tumor, a heme malignancy, or a hematological cancer. In one embodiment, the cancer is acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus type 1 (HTLV-1) leukemia/lymphoma, AIDS-related lymphoma, adult T-cell lymphoma, acute lymphoblastic leukemia (ALL), T-cell acute lymphoblastic leukemia, B-cell acute lymphoblastic leukemia, chronic lymphocytic leukemia, or multiple myeloma (MM). In one embodiment, the cancer is leukemia or lymphoma. In one embodiment, the leukemia is B-cell acute lymphoblastic leukemia (B-ALL), acute myeloid leukemia (AML), acute lymphoblastic leukemia, chronic myeloid leukemia, hairy cell leukemia, myeloproliferative disorders, acute myelogenous leukemia (AML), chronic myelogenous leukemia (CML), chronic lymphocytic leukemia (CLL), multiple myeloma (MM), myelodysplastic syndrome (MDS), or mast cell cancer. In one embodiment, the lymphoma is diffuse large B-cell lymphoma, B-cell immunoblastic lymphoma, small non-cleaved cell or Burkitt lymphoma, human lymphotropic virus-type 1 (HTLV-1) leukemia/lymphoma, adult T-cell lymphoma, Hodgkin disease, or non-Hodgkin lymphomas, or a metastatic lesion thereof.

In one embodiment, the cancer treated by the methods or compounds provided herein is a solid tumor (e.g., a carcinoid, carcinoma or sarcoma), or a metastatic lesion thereof. In one embodiment, the cancer is a lung cancer (e.g., non-small cell lung cancer or small cell lung cancer); a skin cancer; a melanoma; a prostate cancer; a glioblastoma; an endometrial cancer; a pancreatic cancer (e.g., pancreatic adenocarcinoma (e.g., pancreatic ductal adenocarcinoma (PDA)); a renal cell carcinoma; a colorectal cancer; a breast cancer (e.g., triple negative breast cancer); a thyroid cancer; a sarcoma, a liver or hepatocellular cancer (HCC), a head and neck cancer, a cervical or vulvar cancer, an esophageal cancer, a gastric cancer, an adrenal cancer, or an ovarian cancer, or a metastatic lesion thereof. In one embodiment, the solid tumor is prostate cancer, breast cancer, or a glioblastoma, or a metastatic lesion thereof.

In some embodiments, the cancer or tumor treated is a solid, fibrotic tumor chosen from one or more of pancreatic (e.g., pancreatic adenocarcinoma or pancreatic ductal adenocarcinoma), breast, colorectal, colon, lung (e.g., a small or non-small cell lung cancer), skin, ovarian, prostate, cervix, gastrointestinal (e.g., carcinoid or stromal), stomach, head and neck, kidney, brain cancer, or a metastatic lesion thereof.

In some embodiments, the cancer or tumor treated using the methods or compounds provided herein is a cancer or tumor chosen from one or more of the head, neck, nasal cavity, paranasal sinuses, nasopharynx, oral cavity, oropharynx, larynx, hypopharynx, salivary glands, paragangliomas, pancreas, stomach, skin, esophagus, endometrium, liver and biliary tree, bone, intestine, colon, rectum, ovaries, prostate, lung, breast, lymphatic system, blood, bone marrow central nervous system, brain, or a metastatic lesion thereof.

In some embodiments, the disorder treated by the methods or compounds provided herein is an inflammatory disease or an immune disease. In one embodiment, the inflammatory disease or the immune disease is asthma, emphysema, allergy, dermatitis, arthritis (e.g., rheumatoid arthritis), psoriasis, lupus erythematosus, graft versus host disease, inflammatory bowel disease, eczema, scleroderma, Crohn's disease, or multiple sclerosis. In one embodiment, the disorder is rheumatoid arthritis. In one embodiment, the disorder is rheumatoid arthritis, and the amount of the compound is effective to ameliorate one or more symptoms associated with rheumatoid arthritis, wherein the symptom associated with rheumatoid arthritis is independently a reduction in the swelling of the joints, a reduction in serum anti collagen levels, a reduction in bone resorption, a reduction in cartilage damage, a reduction in pannus, or a reduction in inflammation.

In some embodiments, the disorder treated by the methods or compounds provided herein is a respiratory disease. In one embodiment, the respiratory disease is asthma, chronic obstructive pulmonary disease (COPD), chronic bronchitis, emphysema, or bronchiectasis. In one embodiment, the disorder is asthma.

In certain embodiments, a method is provided for selectively inhibiting a PI3 kinase gamma isoform over PI3 kinase alpha or beta isoform wherein the inhibition takes place in a subject suffering from a respiratory disease. In one embodiment, the respiratory disease is asthma, chronic obstructive pulmonary disease (COPD), chronic bronchitis, emphysema, or bronchiectasis. In one embodiment, the respiratory disease is asthma. In one embodiment, the respiratory disease is COPD.

In one embodiment, provided herein is a method of inhibiting a PI3 kinase in a subject suffering from a cancer, comprising administering to the subject an effective amount of a compound provided herein. In one embodiment, the cancer is selected from acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus-type 1 (HTLV-1) leukemia/lymphoma, AIDS-related lymphoma, adult T-cell lymphoma, acute lymphoblastic leukemia (ALL), B-cell acute lymphoblastic leukemia, T-cell acute lymphoblastic leukemia, chronic lymphocytic leukemia, or multiple myeloma (MM). In one embodiment, the cancer is leukemia or lymphoma. In one embodiment, the leukemia is selected from B-cell acute lymphoblastic leukemia (B-ALL), acute lymphocytic leukemia, hairy cell leukemia, myelodysplasia, myeloproliferative disorders, acute myelogenous leukemia (AML), chronic myelogenous leukemia (CML), chronic lymphocytic leukemia (CLL), multiple myeloma (MM), myelodysplastic syndrome (MD S), or mast cell cancer. In one embodiment, the lymphoma is selected from diffuse large B-cell lymphoma, B-cell immunoblastic lymphoma, small non-cleaved cell or Burkitt lymphoma, human lymphotropic virus-type 1 (HTLV-1) leukemia/lymphoma, AIDS-related lymphoma, adult T-cell lymphoma, Hodgkin disease, or non-Hodgkin lymphomas. In one embodiment, the compound is administered in combination with one or more therapeutic agents provided herein.

In one embodiment, provided herein is a method of inhibiting a PI3 kinase in a subject suffering from an inflammatory disease or an immune disease, comprising administering to the subject an effective amount of a compound provided herein. In one embodiment, the inflammatory disease or immune disease is asthma, emphysema, allergy, dermatitis, rheumatoid arthritis, psoriasis, lupus erythematosus, graft versus host disease, inflammatory bowel disease, eczema, scleroderma, Crohn's disease, or multiple sclerosis. In one embodiment, the inflammatory disease or immune disease is rheumatoid arthritis. In one embodiment, the compound is administered in combination with one or more therapeutic agents provided herein.

In one embodiment, provided herein is a method of inhibiting a PI3 kinase in a subject suffering from a respiratory disease, comprising administering to the subject an effective amount of a compound provided herein. In one embodiment, the respiratory disease is asthma, chronic obstructive pulmonary disease (COPD), chronic bronchitis, emphysema, or bronchiectasis. In one embodiment, the respiratory disease is asthma. In one embodiment, the compound is administered in combination with one or more therapeutic agents provided herein.

In certain embodiments, provided herein is a method of inhibiting PI3K-γ in a subject, comprising administering to the subject an effective amount of a compound provided herein.

In some embodiments, a method is provided for treating a disease or disorder described herein, the method comprising administering a therapeutically effective amount of a compound or a pharmaceutical composition described herein to a subject.

In some embodiments, a method is provided for treating a PI3K mediated disorder in a subject, the method comprising administering a therapeutically effective amount of a compound or a pharmaceutical composition described herein to a subject.

In some embodiments, provided herein is a use of a compound or a pharmaceutical composition described herein for the treatment of a disease or disorder described herein in a subject.

In some embodiments, provided herein is a use of a compound or a pharmaceutical composition described herein for the treatment of a PI3K mediated disorder in a subject.

In some embodiments, provided herein is a use of a compound or a pharmaceutical composition described herein in the manufacture of a medicament for the treatment of a disease or disorder described herein in a subject.

In some embodiments, provided herein is use of a compound or a pharmaceutical composition described herein in the manufacture of a medicament for the treatment of a PI3K mediated disorder in a subject.

In one embodiment, the methods provided herein further comprise administration of one or more therapeutic agents selected from chemotherapeutic agents, cytotoxic agents, and radiation. In one embodiment, the compound is administered in combination with an mTOR inhibitor. In one embodiment, the compound is administered in combination with one or more of: an agent that inhibits IgE production or activity, 2-(4-(6-cyclohexyloxy-2-naphtyloxy)phenylacetamide)benzoic acid, an mTOR inhibitor, rapamycin, a TORC1 inhibitor, a TORC2 inhibitor, an anti-IgE antibody, prednisone, corticosteroid, a leukotriene inhibitor, XOLAIR, ADVAIR, SINGULAIR, or SPIRIVA. In one embodiment, the compound is administered in combination with one or more of: a mitotic inhibitor, an alkylating agent, an anti-metabolite, an intercalating antibiotic, a growth factor inhibitor, a cell cycle inhibitor, an enzyme, a topoisomerase inhibitor, an anti-hormone, an angiogenesis inhibitor, an anti-androgen, or an anti-receptor kinase antibody. In one embodiment, the compound is administered in combination with one or more of: Imatinib Mesylate, bortezomib, bicalutamide, gefitinib, ADRIAMYCIN, alkylating agents, alkyl sulfonates, ethylenimines, altretamine, triethylenemelamine, trietylenephosphoramide, triethylenethiophosphaoramide, trimethylolomelamine, nitrogen mustards, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, nitrosureas, antibiotics, anti-metabolites, denopterin, methotrexate, pteropterin, trimetrexate, 5-fluorouracil (5-FU), fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens, anti-adrenals, folic acid replenisher, arabinoside, cyclophosphamide, thiotepa, taxanes, anti-hormonal agents, anti-estrogens, tamoxifen, raloxifene, aromatase inhibiting 4(5)-imidazoles, 4-hydroxytamoxifen, trioxifene, keoxifene, onapristone, toremifene, anti-androgens, chlorambucil, gemcitabine, 6-thioguanine; mercaptopurine; cisplatin, carboplatin, vincristine; vinorelbine, vinblastin, ifosfamide, mitomycin C, daunorubicin, doxorubicin, mitoxantrone, HERCEPTIN, AVASTIN, ERBITUX, RITUXAN, TAXOL, ARIMIDEX, TAXOTERE, or an anti-receptor tyrosine kinase antibody selected from cetuximab, panitumumab, trastuzumab, anti CD20 antibody, rituximab, tositumomab, alemtuzumab, bevacizumab, obinutuzumab (GAZYVA), and gemtuzumab. In one embodiment, the compound is administered in combination with one or more of: bortezomib, ADRIAMYCIN, alkylating agents, anti-metabolites, denopterin, pteropterin, trimetrexate, a nitrogen mustard, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, methotrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens, cyclophosphamide, taxanes, antihormonal agents, gemcitabine; cisplatin, carboplatin, vincristine, vinorelbine, vinblastin, ifosfamide, mitomycin C, daunorubicin, doxorubicin, mitoxantrone, HERCEPTIN, AVASTIN, ERBITUX, RITUXAN, TAXOL, ARIMIDEX, or TAXOTERE. In one embodiment, the compound is administered in combination with one or more of: non-steroidal anti-inflammatory drugs (NSAIDs), corticosteroids, prednisone, chloroquine, hydroxychloroquine, azathioprine, cyclophosphamide, methotrexate, cyclosporine, anti-CD20 antibodies, ENBREL, REMICADE, HUMIRA, AVONEX, or REBIF.

In one embodiment, the subject is a mammal. In one embodiment, the mammal is a human. In one embodiment, the subject is a human.

Pharmaceutical Compositions and Dosage Forms

In some embodiments, provided herein are pharmaceutical compositions comprising a compound as provided herein, or an enantiomer, a mixture of enantiomers, or a mixture of two or more diastereomers thereof, or a pharmaceutically acceptable form thereof (e.g., pharmaceutically acceptable salts, hydrates, solvates, isomers, prodrugs, and isotopically labeled derivatives), and a pharmaceutically acceptable excipient, diluent, or carrier, including inert solid diluents and fillers, sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic).

1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as provided herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the pharmaceutical compositions provided herein is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v or v/v.

In some embodiments, the concentration of one or more of the compounds as provided herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v, or v/v.

In some embodiments, the concentration of one or more of the compounds as provided herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10%, w/w, w/v or v/v.

In some embodiments, the concentration of one or more of the compounds as provided herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9%, w/w, w/v or v/v.

In some embodiments, the amount of one or more of the compounds as provided herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of the compounds as provided herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as provided herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

1A. Formulations for Oral Administration

In some embodiments, provided herein are pharmaceutical compositions for oral administration containing a compound as provided herein, and a pharmaceutical excipient suitable for oral administration. In some embodiments, provided herein are pharmaceutical compositions for oral administration containing: (i) an effective amount of a compound provided herein; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds provided herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof, polyoxyethylated vitamins and derivatives thereof; polyoxyethylene-polyoxypropylene block copolymers; and mixtures thereof, polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylene diaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytouened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as provided herein, and a pharmaceutical excipient suitable for parenteral administration. In some embodiments, provided herein are pharmaceutical compositions for parenteral administration containing: (i) an effective amount of a compound provided herein; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the pharmaceutical compositions provided herein can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as provided herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as provided herein.

1C. Formulations for Topical Administration

In some embodiments, provided herein are pharmaceutical compositions for topical (e.g., transdermal) administration containing a compound as provided herein, and a pharmaceutical excipient suitable for topical administration. In some embodiments, provided herein are pharmaceutical compositions for topical administration containing: (i) an effective amount of a compound provided herein; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods provided herein employs transdermal delivery devices ("patches"). Such transdermal patches can be used to provide continuous or discontinuous infusion of a compound as provided herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001, 139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable excipients described herein.

1D. Formulations for Inhalation Administration

In some embodiments, provided herein are pharmaceutical compositions for inhalation administration containing a compound as provided herein, and a pharmaceutical excipient suitable for topical administration. In some embodiments, provided herein are pharmaceutical compositions for inhalation administration containing: (i) an effective amount of a compound provided herein; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

1E. Formulations for Ocular Administration

In some embodiments, the disclosure provides a pharmaceutical composition for treating ophthalmic disorders. The pharmaceutical composition can contain an effective amount of a compound as provided herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as provided herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

1F. Formulations for Controlled Release Administration

In some embodiments, provided herein are pharmaceutical compositions for controlled release administration containing a compound as provided herein, and a pharmaceutical excipient suitable for controlled release administration. In some embodiments, provided herein are pharmaceutical compositions for controlled release administration containing: (i) an effective amount of a compound provided herein; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided herein encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as provided herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, e.g., thus requiring only a fraction of the systemic dose (see, e.g., Goodson, *Medical Applications of Controlled Release*, 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

2. Dosage

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described herein. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg per day. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as provided herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as provided herein can continue as long as necessary. In some embodiments, an agent as provided herein is administered for more than about 1, about 2, about 3, about 4, about 5, about 6, about 7, about 14, or about 28 days. In some embodiments, an agent as provided herein is administered for less than about 28, about 14, about 7, about 6, about 5, about 4, about 3, about 2, or about 1 day. In some embodiments, an agent as provided herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day. In some embodiments, the dose is about 1 mg/kg, about 5 mg/kg, about 7.5 mg/kg, about 10 mg/kg, about 15 mg/kg, about 20 mg/kg, about 25 mg/kg, about 50 mg/kg, about 75 mg/kg, or about 100 mg/kg per day. In some embodiments, the dose is about 1 mg/kg, about 7.5 mg/kg, about 20 mg/kg, or about 50 mg/kg per day.

When a compound provided herein, is administered in a pharmaceutical composition that comprises one or more agents, and the agent has a shorter half-life than the compound provided herein unit dose forms of the agent and the compound provided herein can be adjusted accordingly.

3. Kits

In some embodiments, provided herein are kits. The kits can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as provided herein and the agent are provided as separate pharmaceutical compositions in separate containers within the kit. In some embodiments, the compound as provided herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

EXAMPLES

Chemical Examples

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours.

The terms "solvent," "organic solvent," and "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine, and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure, such as, for example, filtration, extraction, crystallization, column chromatography, thin-layer chromatography, or thick-layer chromatography, or a combination of these procedures. Specific illustrations of suitable separation and isolation procedures are given by reference to the examples herein below. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation. Further, atropisomers (i.e., stereoisomers from hindered rotation about single bonds) of compounds provided herein can be resolved or isolated by methods known to those skilled in the art. For example, certain B substituents with ortho or meta substituted phenyl may form atropisomers, where they may be separated and isolated.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, compounds provided herein can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the compounds and is not intended to limit the scope of reactions or reaction sequences that can be used in preparing the compounds provided herein.

General Synthetic Methods

The compounds herein being generally described, it will be more readily understood by reference to the following examples, which are included merely for purposes of illustration of certain aspects and embodiments, and are not intended to limit these aspects and embodiments.

It is to be understood that isotopically enriched compounds provided herein can be prepared by the general methods described herein when corresponding isotopically enriched (e.g., deuterium enriched) starting material, intermediate, and/or reagents are used.

(i) General Method for the Synthesis of Amine Cores:

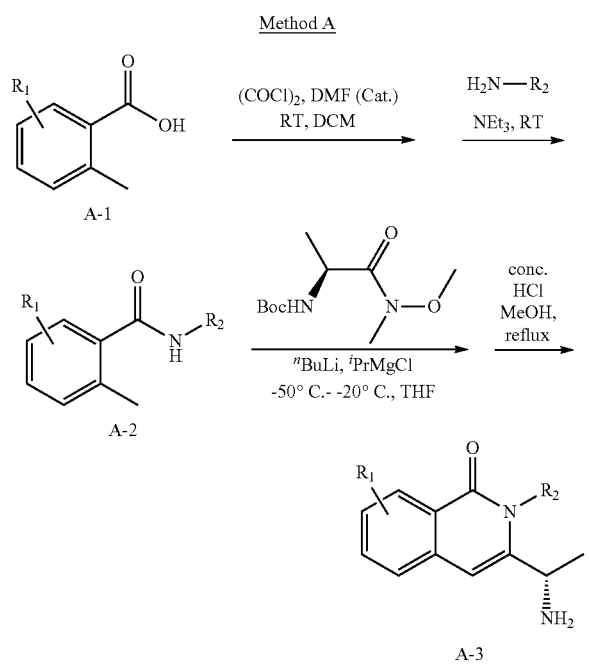

General conditions for the preparation of (S)-3-(1-aminoethyl)-isoquinolin-1(2H)-ones:

To a stirred mixture of a given o-methylbenzoic acid (A-1) (1.5 mol, 1 eq) and DMF (2 mL) in DCM (1275 mL) at RT, oxalyl chloride (1.65 mol, 1.1 eq) is added over 5 min and the resulting mixture is stirred at RT for 2 h. The mixture is then concentrated in vacuo. The residue is dissolved in DCM (150 mL) and the resulting solution (solution A) is used directly in the next step.

To a stirred mixture of aniline (1.58 mol, 1.05 eq) and triethylamine (3.15 mol, 2.1 eq) in DCM (1350 mL), the above solution A (150 mL) is added dropwise while the reaction temperature is maintained between 25° C. to 40° C. by an ice-water bath. The resulting mixture is stirred at RT for 2 h and then water (1000 mL) is added. The organic layers are separated and washed with water (2×1000 mL), dried over Na$_2$SO$_4$ and filtered. The filtrate is concentrated in vacuo. The product is suspended in n-heptanes (1000 mL) and stirred at RT for 30 min. The precipitate is collected by filtration, rinsed with heptanes (500 mL) and further dried in vacuo to afford the amide (A-2).

To a stirred mixture of amide (A-2) (173 mmol, 1 eq) in anhydrous THF (250 mL) at −30° C. under an argon atmosphere, a solution of n-butyllithium in hexanes (432 mol, 2.5 eq) is added dropwise over 30 min while keeping the inner temperature between −30° C. and −10° C. The resulting mixture is then stirred at −30° C. for 30 min.

To a stirred mixture of (S)-tert-butyl 1-(methoxy(methyl) amino)-1-oxopropan-2-ylcarbamate (260 mmol, 1.5 eq) in anhydrous THF (250 mL) at −30° C. under an argon atmosphere, a solution of isopropylmagnesium chloride in THF (286 mmol, 1.65 eq) is added dropwise over 30 min while keeping inner temperature between −30° C. and −10° C. The resulting mixture is stirred at −30° C. for 30 min. This solution is then slowly added to above reaction mixture while keeping inner temperature between −30° C. and −10° C. The resulting mixture is stirred at −15° C. for 1 h. The reaction mixture is quenched with water (50 mL) and then acidified with conc. HCl at −10° C. to 0° C. to adjust the pH to 1-3. The mixture is allowed to warm to RT and concentrated in vacuo. The residue is dissolved in MeOH (480 mL), and then conc. HCl (240 mL) is added quickly at RT. The resulting mixture is stirred at reflux for 1 h. The reaction mixture is concentrated in vacuo to reduce the volume to about 450 mL. The residue is extracted with a 2:1 mixture of heptane and ethyl acetate (2×500 mL). The aqueous layer is basified with concentrated ammonium hydroxide to adjust the pH value to 9-10 while keeping the inner temperature between −10° C. and 0° C. The mixture is then extracted with DCM (3×300 mL), washed with brine, dried over MgSO$_4$ and filtered. The filtrate is concentrated in vacuo and the residue is dissolved in MeOH (1200 mL) at RT. To this solution, D-(−)-tartaric acid (21 g, 140 mmol, 0.8 eq) is added in one portion at RT. After stirring at RT for 30 min, a white solid precipitates and the mixture is slurried at RT for 10 h. The solid is collected by filtration and rinsed with MeOH (3×50 mL). The collected solid is suspended in water (500 mL) and then neutralized with concentrated ammonium hydroxide solution at RT to adjust the pH to 9-10. The mixture is extracted with DCM (3×200 mL). The combined organic layers are washed with brine, dried over MgSO$_4$ and filtered. The filtrate is concentrated in vacuo to afford the (S)-3-(1-aminoethyl)-isoquinolin-1(2H)-ones (A-3).

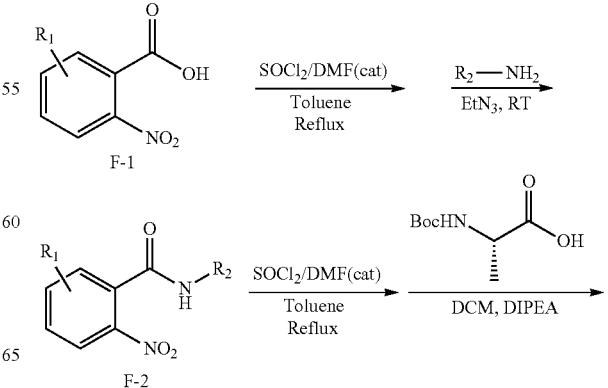

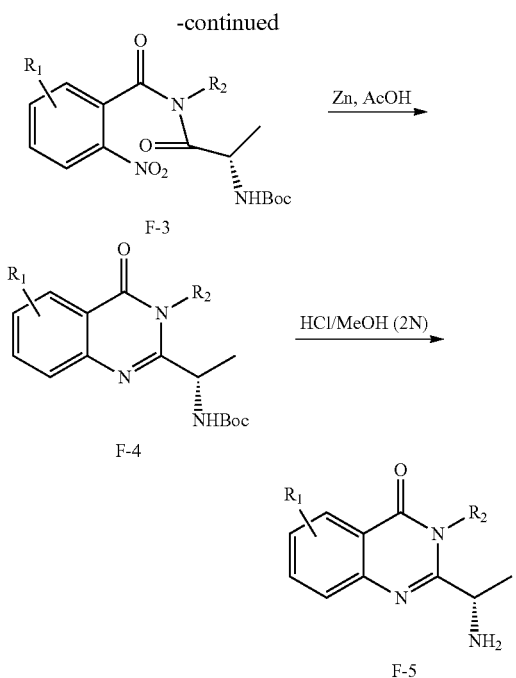

F-3

F-4

F-5

To a stirred mixture of nitrobenzoic acid (F-1) (1.0 mol, 1.0 eq) and DMF (2.0 mL) in toluene (800 mL), thionyl chloride (292 mL, 1.0 mol, 4.0 eq) is added dropwise (over 15 min) and the resulting mixture is stirred at reflux for 1.5 h. The mixture is allowed to cool to RT and then concentrated in vacuo. The residue is dissolved in DCM (100 mL) to form solution A, which is used directly in the next step.

To a stirred mixture of a given amine $R_2$—$NH_2$ (102.4 g, 1.1 mol, 1.1 eq) and triethylamine (280 mL, 2.0 mol, 2.0 eq) in DCM (700 mL), solution A is added dropwise while keeping the reaction temperature below 10° C. The resulting mixture is allowed to warm to RT and then stirred at RT overnight. The reaction mixture is diluted with ice-water (1.0 L) and stirred for 15 min. The precipitate is collected by filtration, rinsed with isopropyl ether (3×100 mL) and petroleum ether (3×100 mL), and then dried in vacuo to afford product amide (F-2).

A mixture of nitro-benzamide (F-2) (20.0 mmol, 1.0 eq) and DMF (cat.) in toluene (60 mL) at RT, thionyl chloride (12 mL, 164 mmol, 8.2 eq) is added dropwise (over 5 min) and the resulting mixture is stirred at reflux for 2 h. The mixture is allowed to cool to RT and then concentrated in vacuo. The residue is dissolved in DCM (10 mL) to form solution B, which is used directly in the next step.

To a stirred mixture of N-(tert-butoxycarbonyl)-L-alanine (16.0 mmol, 0.8 eq) and N,N-diisopropylethylamine (4.0 g, 31.0 mol, 1.5 eq) in DCM (20 mL), solution B is added dropwise while keeping the reaction temperature between 0-10° C. The resulting mixture is stirred at this temperature for 1 h and then stirred at RT overnight. The reaction mixture is quenched with ice-water (100 mL). The organic layer is separated and the aqueous layer is extracted with DCM (2×80 mL). The combined organic layers are washed with brine, dried over $Na_2SO_4$ and filtered. The filtrate is concentrated in vacuo and the residue is slurried in isopropyl ether (100 mL) for 15 min. The solid is collected by filtration and dried in vacuo to afford product (F-3).

To a suspension of zinc dust (7.2 g, 110 mmol, 10.0 eq) in glacial acetic acid (40 mL) at 15° C., a solution of (F-3) (11.0 mmol, 1.0 eq) in glacial acetic acid (40 mL) is added and the resulting mixture is stirred at RT for 4 h. The mixture is poured into ice-water (200 mL) and neutralized with saturated aqueous $NaHCO_3$ solution to adjust the pH to 8. The resulting mixture is extracted with DCM (3×150 mL). The combined organic layers are washed with brine, dried over $Na_2SO_4$ and filtered. The filtrate is concentrated in vacuo and the residue is purified by flash chromatography on silica gel (7% ethyl acetate-petroleum ether) to afford product (F-4).

Compound (F-4) (0.5 mmol, 1.0 eq) is dissolved in hydrochloric methanol solution (2N, 20 mL) and the resulting mixture is stirred at RT for 2 h. The mixture is concentrated in vacuo. The residue is diluted with water (30 mL) and then neutralized with saturated aqueous $NaHCO_3$ to adjust the pH to 8 while keeping the temperature below 5° C. The resulting mixture is extracted with DCM (3×30 mL). The combined organic layers are washed with brine, dried over $Na_2SO_4$ and filtered. The filtrate is concentrated in vacuo and the residue is slurried in petroleum ether (10 mL). The solid is collected by filtration and dried in vacuo to afford product (F-5).

The quinazolinone (F-5) can be used to synthesize compounds described herein using, for example, Method D to couple the amine to $W_d$ groups.

(ii) General Methods for Amide Synthesis:

Method D

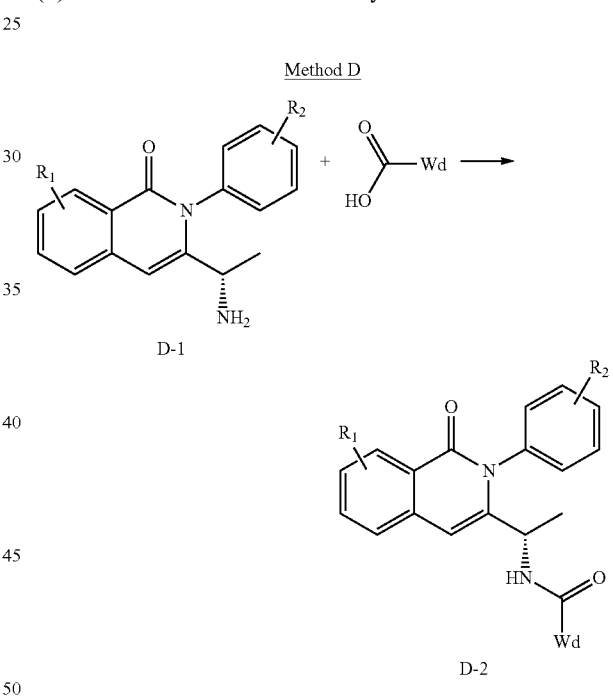

D-1

D-2

To a mixture of amine (D-1) (0.5 mmol, 1.0 eq), $W_d$—COOH carboxylic acid (0.55 mmol, 1.1 eq), and N,N-diisopropylethylamine (0.17 mL, 1.0 mmol, 2.0 eq) in anhydrous DMF (5 mL), 1-hydroxybenzotriazole hydrate (0.65 mmol, 1.3 eq) and EDC hydrochloride (0.65 mmol, 1.3 eq) are added sequentially and the resulting mixture is stirred at RT for 2-16 h. Ice-water or saturated sodium carbonate solution is added to the reaction mixture and then stirred for 10 min. The precipitate is collected by filtration, rinsed with water and dried in vacuo. The solid collected is further purified by flash column chromatography on silica gel (0-10% MeOH-DCM) to afford the product amide (D-2).

Method E

A solution of amine (D-1) (0.25 mmol, 1 eq), $W_d$—COOH carboxylic acid (1.1 eq), and 1-hydroxybenzotriazole hydrate (1.3 eq) in dimethylformamide (0.1 M) is treated with diisopropylethylamine (2 eq) and then EDC hydrochloride (63 mg, 1.3 eq). The reaction mixture is stirred at ambient temperature overnight. The reaction mixture is diluted with water (5× solvent) and acetic acid (1.5 eq) is added, then the mixture is stirred in an ice bath for 40 min. The resulting precipitate is collected by filtration, and washed with water (3×3 mL). The collected solid is dried in vacuo to afford amide (D-2).

(iii) General Methods for Alkyne Synthesis:

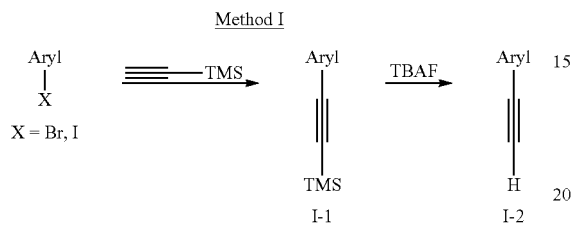

Method I

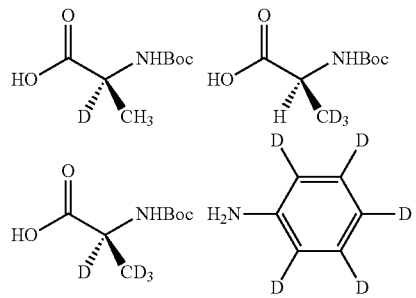

Synthesis of Deuterated Pyrazoles:

A sealed vessled is chared with PdCl$_2$(MeCN)$_2$ and X-Phos (3:1 ratio of X-Phos to PdCl$_2$(MeCN)$_2$, 5-15 mol % catalyst), cesium carbonate (1.5-3.0 equiv) and propionitrile (0.5 M). The mixture is stirred for 5 min after which the aryl bromide or aryl iodid substrate is added. After another 5 minutes of stirring TMS-acetylene (3.0 equiv) is added and the flask is sealed and heated at RT for 10 min follwed by 1 h of heating at 95° C. The reaction is allowed to cool after which it is concentrated directly onto silica gel and purified using flash silica gel chromatography (gradient of ethyl acetate/hexanes) to provide alkyne I-1.

Alkyne I-1 (1.0 equiv) is then dissolved in tetrahydrofuran (0.13 M) and charged with TBAF (1.1 equiv, 1.0 M in tetrahydrofuran). The resulting mixture is stirred at RT for 6 h after which it is poured into saturated bicarbonate solution and extracted with ethyl acetate. The organic layer is washed with brine and concentrated onto silica gel where it is purified directly by flash silica gel chromatography (gradient of ethyl acetate/hexanes) to provide aryl alkyne I-2.

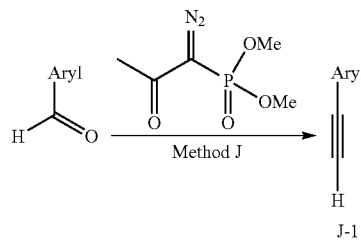

Aldehyde (1.0 equiv) is a dissolved in anhydrous methanol (0.2-0.5 mM) and charged with cesium carbonate (1.0 equiv) and cooled to 0-5° C. Dimethyl (1-diazo-2-oxopropyl)phosphonate (1.0 equiv) is added dropwise after which the reaction is allowed to stir for 1-18 h after which the crude mixture is concentrated onto silica gel and purified directly by flash silica gel chromatography to provide the desired alkyne J-1.

Deuterium Incorporation

Deuterium enriched building blocks that are commercially available (e.g., from Sigma-Aldrich or CDN Isotopes, Inc.) include, but are not limited to, the following:

4-Ethynyl-1-(methyl-d3)-1H-pyrazole is prepared from 4-bromo-1-(methyl-d3)-1H-pyrazole (commercially available from, e.g., CombiPhos Catalysis, Inc.) based on the routes described in Method I.

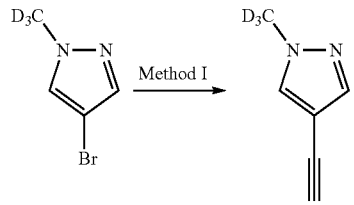

4-Ethynyl-1-(methyl-d3)-1H-pyrazole-3,5-d2 is prepared from 4-bromo-1-(methyl-d3)-1H-pyrazole-3,5-d2 (commercially available from, e.g., CombiPhos Catalysis, Inc.) based on the routes described in Method I.

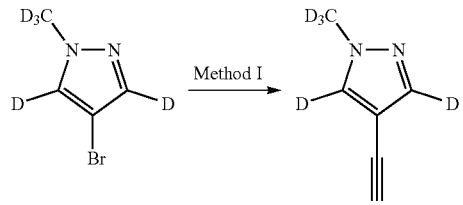

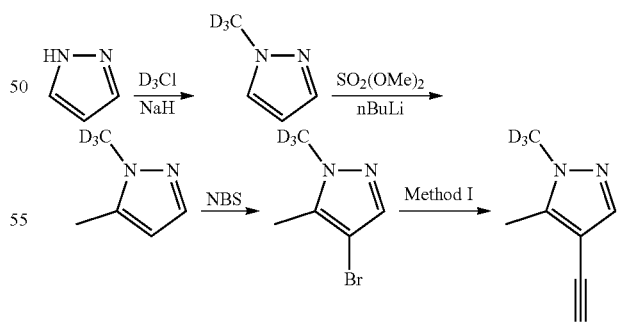

4-Bromo-1-(methyl-d3)-5-methyl-1H-pyrazole is prepared from pyrazole in three steps based on the routes described in WO 2015/066188, the entirety of which is incorporated herein by reference. 4-Ethynyl-1-(methyl-d3)-5-methyl-1H-pyrazole is prepared from 4-bromo-1-(methyl-d3)-5-methyl-1H-pyrazole based on the routes described in Method I.

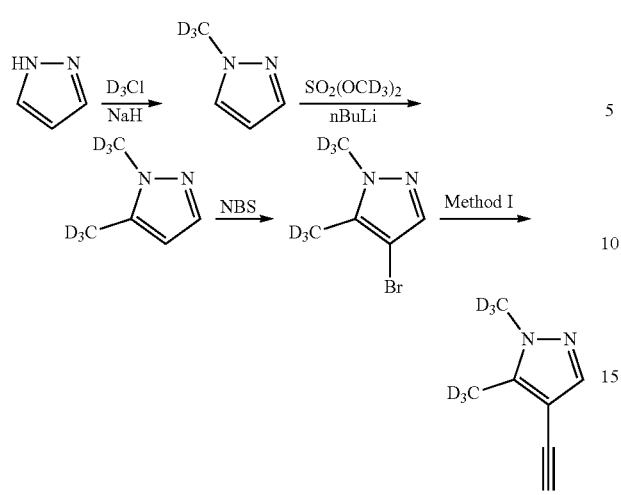

4-Bromo-1,5-(dimethyl-d6)-1H-pyrazole is prepared from pyrazole in three steps based on the routes described in WO 2015/066188, the entirety of which is incorporated herein by reference. 4-Ethynyl-1,5-(dimethyl-d6)-1H-pyrazole is prepared from 4-bromo-1,5-(dimethyl-d6)-1H-pyrazole based on the routes described in Method I.

Synthesis of Mono, Bi, Tri and Tetra-Substituted Deuterated Anilines:

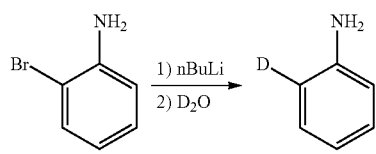 [SMILES: Nc1ccccc1Br ; [2H]c1ccccc1N]

Aniline-2-d is prepared from 2-bromoaniline based on the routes described in Chi et. al., *Organic Letters*, 2014, 16, 6274-6277, the entirety of which is incorporated herein by reference.

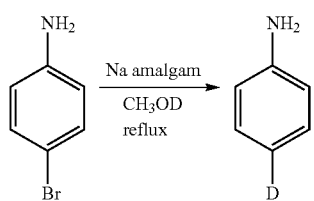

Aniline-4-d is prepared from 4-bromoaniline based on the routes described in Miura et. al., *J. Org. Chem.* 1997, 62, 1188-1190, the entirety of which is incorporated herein by reference.

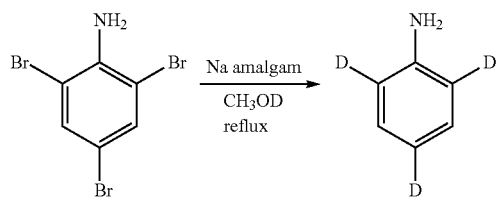 [SMILES: Nc1c(Br)cc(Br)cc1Br ; [2H]c1cc([2H])c(N)c([2H])c1]

Aniline-2,4,6-d3 is prepared from 2,4,6-tribromoaniline based on the routes described in Miura et. al., *J. Org. Chem.* 1997, 62, 1188-1190, the entirety of which is incorporated herein by reference.

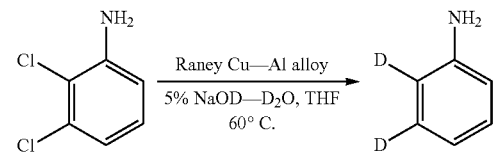 [SMILES: Nc1cccc(Cl)c1Cl ; [2H]c1cccc(N)c1[2H]]

Aniline-2,3-d2 is prepared from 2,3-dichloroaniline based on the routes described in Tashiro et al., *Journal of Labelled Compounds and Radiopharmaceuticals*, 1990, 28, 703-712, the entirety of which is incorporated herein by reference. Additional deuterated anilines are prepared from the following halogenated aniline using this method:

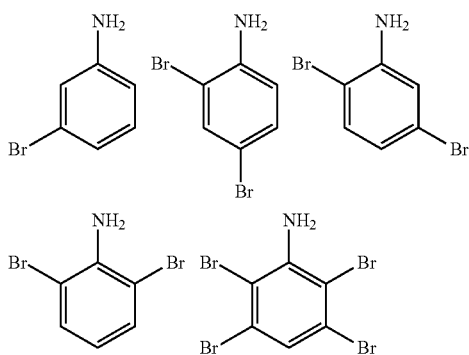

Incorporation of Deuterium into Quinoline:

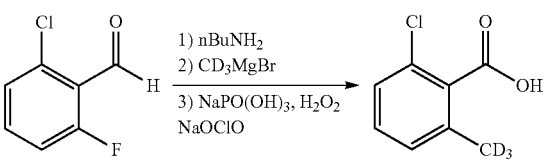 [SMILES: O=Cc1c(F)cccc1Cl ; [2H]C([2H])([2H])c1cccc(Cl)c1C(=O)O]

2-Chloro-6-(methyl-d3)benzoic acid is prepared from 2-chloro-6-fluorobenzaldehyde based on the routes described in Andrzej et. al., *Org. Process Research & Development*, 2002, 6, 220-224, the entirety of which is incorporated herein by reference. Synthesis of CD$_3$MgBr is described in Al-Afyouni et al., *J. Am. Chem. Soc.*, 2014, 136, 15457-15460, the entirety of which is incorporated herein by reference.

147

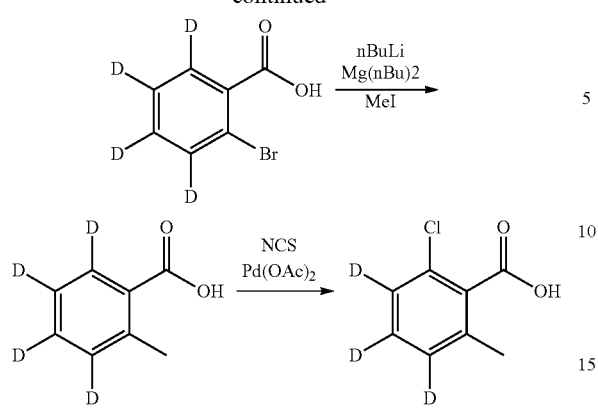

2-Chloro-6-methylbenzoic acid-3,4,5-d3 is prepared from 1-bromo-2-methylbenzene-3,4,5,6-d4 (commercially available from, e.g., CDN Isotopes, Inc.) based on the general routes described in (1) Courchay, et al., Organometallics, 2006, 25, 6074-6086, (2) WO 2003/101916, and (3) WO 2001/083421, the entirety of each of which is incorporated herein by reference.

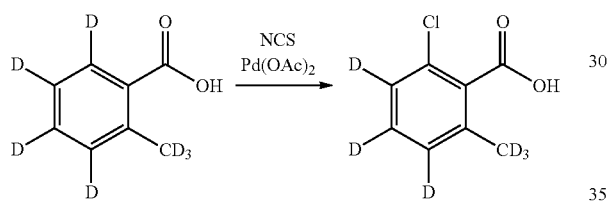

2-Chloro-6-(methyl-d3)-benzoic acid-3,4,5-d3 is prepared from 2-(methyl-d3)benzoic acid-3,4,5,6-d4 (commercially available from, e.g., CDN Isotopes, Inc.) based on the general routes described in WO 2001/083421, the entirety of which is incorporated herein by reference.

Incorporation of Deuterium into Pyrazolo[1,5-a]Pyrimidine Moiety:

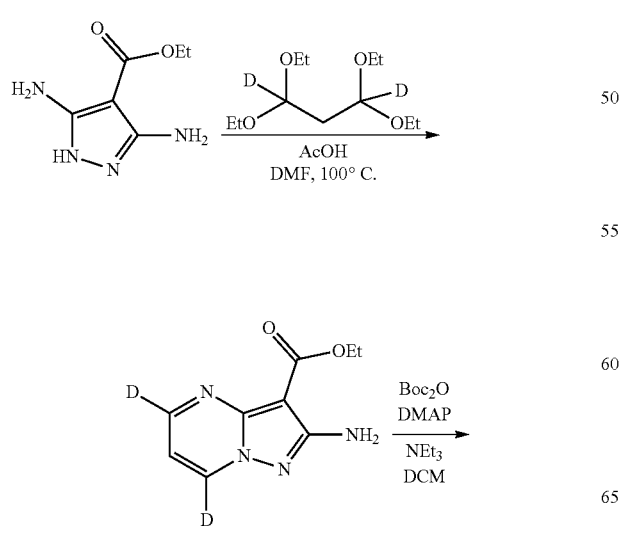

148

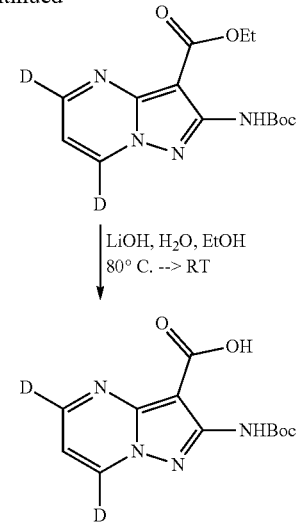

Synthesis of deuterated 2-((tert-butoxycarbonyl)amino)pyrazolo[1,5-a]pyrimidine-3-carboxylic acid from commercially available starting materials is accomplished using the analogous procedure from WO 2015/073267, the entirety of each of which is incorporated herein by reference, except that malonaldehyde-1,3-$d_2$ bis(diethyl acetal) (CDN Isotopes, Inc.) is used in place of 1,1,3,3-tetramethoxy propane.

Example 1: Synthesis of Compound 101

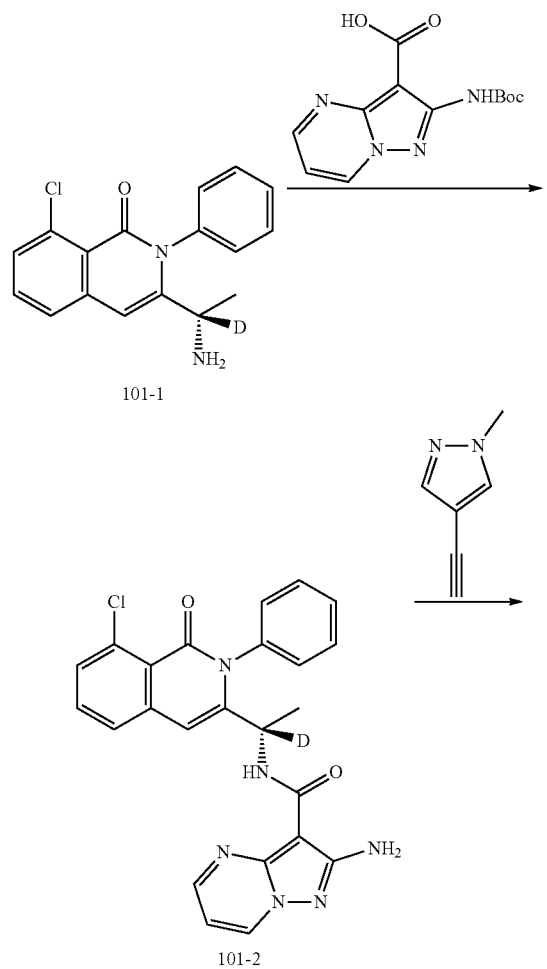

-continued

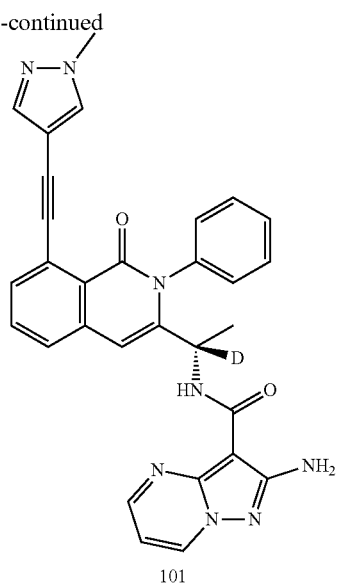

101

Compound 101-1 is prepared from 2-chloro-6-methylbenzoic acid based on the routes described in Method A, using

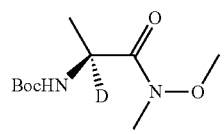 [SMILES: [2H][C@@](C)(NC(=O)OC(C)(C)C)C(=O)N(C)OC]

in place of

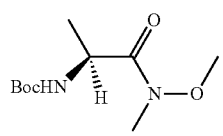

Compound 101-1 is coupled to 2-((tert-butoxycarbonyl)amino)pyrazolo[1,5-a]pyrimidine-3-carboxylic acid according to the following procedure: Compound A (27.4 mmol, 1.0 equiv), HOBt hydrate (1.2 equiv), 2-((tert-butoxycarbonyl)amino)pyrazolo[1,5-a]pyrimidine-3-carboxylic acid (1.05 equiv) and EDC (1.25 equiv) are added to a 200 mL round bottomed flask with a stir bar. N,N-Dimethylforamide (50 mL) is added and the suspension is stirred at RT for 2 min. Hunig's base (4.0 equiv) is added and after which the suspension becomes homogeneous and is stirred for 22 h resulting in the formation of a solid cake in the reaction flask. The solid mixture is added to water (600 mL) and stirred for 3 h. The resulting cream colored solid is filtered and washed with water (2×100 mL) and dried. The solid is then dissolved in methylene chloride (40 mL) after which trifluoroacetic acid (10 equiv, 20 mL) is added and the reaction is stirred for 30 min at RT after which there is no more starting material by LC/MS analysis. The solution is then concentrated and coevaporated with a mixture of methylene choride/ethanol (1:1 v/v) and then dried under high vacuum overnight. The resulting solid is tirturated into 60 mL of ethanol for 1 h and then collected via vacuum filtration. The beige solid is then neutralized with sodium carbonate solution (100 mL) and then transferred to a separatory funnel with methylene chloride (350 mL). The water layer is extracted with an additional 100 mL of methylene chloride. The combined organic layers are dried over sodium sulfate, filtered and concentrated under vacuum to provide a crude product that is purified using flash silica gel chromatrography to provide amide 101-2.

Amide 101-2 is placed in a sealed tube (0.67 mmol, 1.0 equiv) followed by dichlorobis(acetonitrile)palladium (15 mol %), X-Phos (45 mol %), and cesium carbonate (3.0 equiv) Propionitrile (5 mL) is added and the mixture is bubbled with Ar for 1 min. 4-Ethynyl-1-methyl-1H-pyrazole (1.24 equiv) is added and the resulting orange mixture is sealed and stirred in an oil bath at 85° C. for 1.5 h. The resulting mixture is allowed to cool at which point there is no more SM by LC/MS analysis. The mixture is then filtered through a short plug of cotton using acetonitrile and methylene chloride. The combined filtrates are concentrated onto silica gel and purified using flash silica gel chromatography. The resulting material is further purified by reverse phase HPLC to provide the desired compound 101.

Example 2: Synthesis of Compound 501

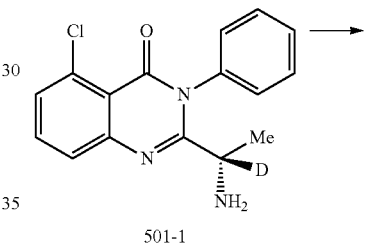

501-1

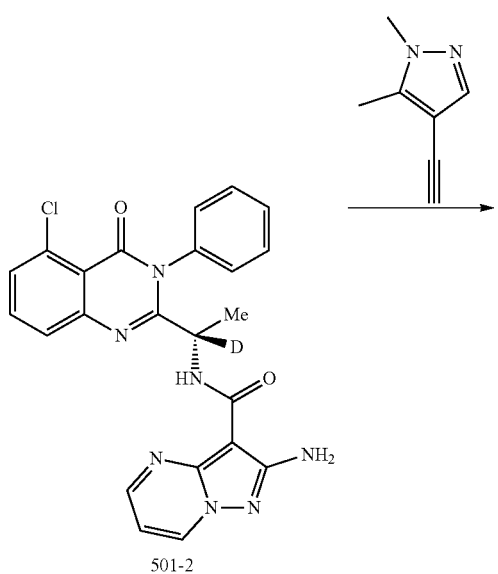

501-2

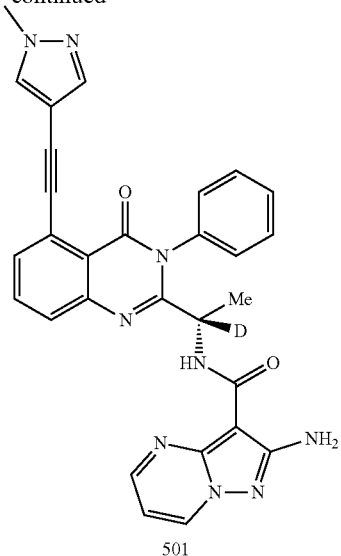

Compound 501-1 is prepared from 2-chloro-6-nitrobenzoic acid based on the routes described in Method F, using

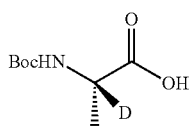

in place of

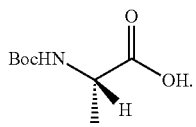

Compound 501-1 is converted to compound 501-2 using the analogous procedure for compound 101-2 in Example 1.

A suspension of Compound 501-2 (0.317 mmol), Cesium carbonate (198 mg, 0.608 mmol, 2 eq.), dichlorobis(acetonitrile)palladium (II) (15 mg, 0.058 mmol, 0.2 eq.) and Xphos (87 mg, 0.182 mmol, 0.6 eq.) in propionitrile (2 mL) is bubbled with argon for 5 minutes. The mixture is charged with 4-ethynyl-1,5-dimethyl-1H-pyrazole (73 mg, 0.6 mmol, 2 eq.), heated to 95° C. and stirred for 2 hr. The resulting mixture is cooled to RT, partitioned between Ethyl acetate and water. The organic phase is separated, washed with saturated aqueous sodium chloride solution, dried with sodium sulfate and concentrated. The residue is purified with silica gel chromatography to provide Compound 501.

Example 3: PI3-Kinase HTRF™ Assay

A PI3-Kinase HTRF® assay kit (cat No. 33-016) purchased from Millipore Corporation is used to screen compounds provided herein. This assay uses specific, high affinity binding of the GRP1 pleckstrin homology (PH) domain to PIP3, the product of a Class 1A or 1B PI3 Kinase acting on its physiological substrate PIP2. During the detection phase of the assay, a complex is generated between the GST-tagged PH domain and biotinylated short chain PIP3. The biotinylated PIP3 and the GST-tagged PH domain recruite fluorophores (Streptavidin-Allophycocyanin and Europium-labeled anti-GST respectively) to form the fluorescence resonance energy transfer (FRET) architecture, generating a stable time-resolved FRET signal. The FRET complex is disrupted in a competitive manner by non-biotinylated PIP3, a product formed in the PI3 Kinase assay.

PI3 Kinase α, β, γ or δ activity is assayed using the PI3 Kinase HTRF® assay kit (catalogue No. 33-016) purchased from Millipore Corporation. Purified recombinant PI3Kα (catalogue No. 14-602-K), PI3Kβ (catalogue No. 14-603-K), PI3Kγ (catalogue No. 14-558-K), and PI3Kδ (catalogue No. 14-604-K) are obtained from Millipore Corporation. Purified recombinant PI3K enzyme is used to catalyze the phosphorylation of phosphatidylinositol 4,5-bisphosphate (PIP2 at 10 μM) to phosphatidylinositol 3,4,5-trisphosphate (PIP3) in the presence of 10 μM ATP. The assay is carried out in 384-well format and detected using a Perkin Elmer EnVision Xcite Multilabel Reader. Emission ratios are converted into percent inhibitions and imported into GraphPad Prism software. The concentration necessary to achieve inhibition of enzyme activity by 50% ($IC_{50}$) is calculated using concentrations ranging from 20 μM to 0.1 nM (12-point curve). $IC_{50}$ values are determined using a nonlinear regression model available in GraphPad Prism 5.

Example 4: Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 μM stock solution to an aliquot of PBS (in duplicate) to give a final assay volume of 400 μL, containing 5 μM test compound and 1% DMSO (for half-life determination a total sample volume of 700 μL is prepared). Reactions are incubated, with shaking, for 24 hours at 37° C.; for half-life determination samples are incubated for 0, 2, 4, 6, and 24 hours. Reactions are stopped by adding immediately 100 μL of the incubation mixture to 100 μL of acetonitrile and vortexing for 5 minutes. The samples are then stored at −20° C. until analysis by HPLC-MS/MS. Where desired, a control compound or a reference compound such as chlorambucil (5 μM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 5: Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). $IC_{50}$ values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM $MgCl_2$), and freshly sonicated phosphatidylinositol (100 μg/ml). Reactions are initiated by the addition of ATP containing 10 μCi of γ-32P-ATP to a final concentration of 10 or 100 μM and allowed to proceed for 5 minutes at room temperature. For TLC analysis, reactions are then terminated by the addition of 105 μL 1N HCl followed by 160 μL $CHCl_3$:MeOH (1:1). The biphasic mixture is vortexed, briefly centrifuged, and the organic phase is transferred to a new tube using a gel loading pipette tip precoated with $CHCl_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, $IC_{50}$ determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including, but not limited to, PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 μL per well. In the first step, each well receives 2 μL of test compound in 20% dimethylsulphoxide resulting in a 2% DMSO final concentration. Next, approximately 14.5 μL of a kinase/PIP2 mixture (diluted in 1× reaction buffer) is added per well for a final concentration of 0.25-0.3 μg/mL kinase and 10 μM PIP2. The plate is sealed and incubated for 15 minutes at room temperature. To start the reaction, 3.5 μL of ATP (diluted in 1× reaction buffer) is added per well for a final concentration of 10 μM ATP. The plate is sealed and incubated for 1 hour at room temperature. The reaction is stopped by adding 5 μL of Stop Solution per well and then 5 μL of Detection Mix is added per well. The plate is sealed, incubated for 1 hour at room temperature, and then read on an appropriate plate reader. Data is analyzed and $IC_{50}$s are generated using GraphPad Prism 5.

Example 6: B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 μL at 50,000 cells/well in B Cell Media (RPMI+10% FBS+Penn/Strep+50 μM bME+5 mM HEPES). A compound provided herein is diluted in B Cell Media and added in a 10 μL volume. Plates are incubated for 30 min at 37° C. and 5% $CO_2$ (0.2% DMSO final concentration). A 50 μL B cell stimulation cocktail is then added containing either 10 μg/mL LPS or 5 μg/mL F(ab')2 Donkey anti-mouse IgM plus 2 ng/mL recombinant mouse IL4 in B Cell Media. Plates are incubated for 72 hours at 37° C. and 5% $CO_2$. A volume of 15 μL of Alamar Blue reagent is added to each well and plates are incubated for 5 hours at 37° C. and 5% $CO_2$. Alamar Blue fluoresce is read at 560Ex/590Em, and $IC_{50}$ or $EC_{50}$ values are calculated using GraphPad Prism 5.

Example 7: Tumor Cell Line Proliferation Assay

The ability of one or more subject compounds to inhibit tumor cell line proliferation can be determined according to standard procedures known in the art. For instance, an in vitro cellular proliferation assay can be performed to measure the metabolic activity of live cells. The assay is performed in a 96-well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 μL at 5,000 cells/well in Tumor Cell Media. A compound provided herein is diluted in Tumor Cell Media and added in a 10 μL volume. Plates are incubated for 72 hours at 37° C. and 5% $CO_2$. A volume of 10 μL of Alamar Blue reagent is added to each well and plates are incubated for 3 hours at 37° C. and 5% $CO_2$. Alamar Blue fluoresce is read at 560Ex/590Em, and $IC_{50}$ values are calculated using GraphPad Prism 5.

Example 8: Antitumor Activity In Vivo

The compounds described herein can be evaluated in a panel of human and murine tumor models.
Paclitaxel-Refractory Tumor Models
 1. Clinically-Derived Ovarian Carcinoma Model.
 This tumor model is established from a tumor biopsy of an ovarian cancer patient. Tumor biopsy is taken from the patient. The compounds described herein are administered to nude mice bearing staged tumors using an every 2 days×5 schedule.
 2. A2780Tax Human Ovarian Carcinoma Xenograft (Mutated Tubulin).
 A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days×5 schedule.
 3. HCT116/VM46 Human Colon Carcinoma Xenograft (Multi-Drug Resistant).
 HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days×5 schedule.
 4. M5076 Murine Sarcoma Model
 M5076 is a mouse fibrosarcoma that is inherently refractory to paclitaxel in vivo. The compounds described herein can be administered to mice bearing staged tumors on an every 2 days×5 schedule.

One or more compounds as provided herein can be used in combination with other therapeutic agents in vivo in the multidrug resistant human colon carcinoma xenografts HCT/VM46 or any other model known in the art including those described herein.

In one aspect, compounds provided herein may be evaluated in the following models according to methods known in the art. The dosage and schedule of administration may be varied depending on the model. The results may be evaluated with those of selective delta inhibitors, and combinations of delta and gamma inhibitors, and/or with antibodies that block specific inhibitory receptors.

Pancreatic Models

KPC model is a transgenic mouse model of pancreatic ductal adenocarcinoma (PDA), in which there is conditional expression of both mutant KrasG12D and p53R172H alleles in pancreatic cells. Tumors develop spontaneously in this mouse over a period of 3-6 months, and can be used to study prophylactic, as well as therapeutic efficacy with novel agents. Cells from these KPC tumors can also be adoptively transferred into syngeneic B6.129 hybrid mice, creating a model with a shorter latency period and allowing large number of animals with tumors to be synchronously established. See e.g., Cancer Cell 7:468 (2005).

Pan02 model: The murine pancreatic adenocarcinoma cell line Pan02 is a nonmetastatic tumor line, syngeneic to C57BL/6. It can be studied following s.c. injection into flank, or orthotopically following injection directly into the pancreas. See e.g., Cancer Res. 44: 717-726 (1984).

Lung Models

LLC Lewis Lung Adenocarcinoma model: LLC cells are derived from a spontaneous lung tumor from a C57BL/6 mouse and can be studied as a s.c. tumor when injected in the flank, or as an orthotopic tumor if injected i.v., following which it localizes to the lung.

LLC cells have also been modified to express a peptide from ovalbumin (LL2-OVA cells). Use of these cells, following either s.c. or i.v. injection, allows the tracking of OVA-specific CD8+ lymphocyctes and measurement of effects of therapy on the adaptive immune response against the tumor. See e.g., Science 330:827 (2010).

Breast Model

The 4T1 mammary carcinoma is a transplantable tumor cell line that grows in syngeneic BALB/c mice. It is highly tumorigenic and invasive and, unlike most tumor models, can spontaneously metastasize from the primary tumor in the mammary gland to multiple distant sites including lymph nodes, blood, liver, lung, brain, and bone. See e.g., Current Protocols in Immunology Unit 20.2 (2000).

Lymphoma Model

EL4 is a C57BL/6 T thymoma and EG7 is an OVA-expressing subclone of EL4. The parental EL4 line has been modified to constitutively express luciferase, which allows non-invasive imaging of tumor growth throughout the animal using the Xenogen imaging platform.

Melanoma Model

B16 murine melanoma cells are syngeneic with C57BL/6 mice and can be studied after s.c. or i.v. injection. Placement at either site will result in metastases to lung and other organs. This model has been extensively studied in terms of the role that inhibitory receptors play in the anti-tumor immune response. See e.g., PNAS 107:4275 (2010).

Example 9: Microsome Stability Assay

The stability of one or more subject compounds is determined according to standard procedures known in the art. For example, stability of one or more subject compounds is established by an in vitro assay. For example, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL of 10.0 mg/mL NADPH; 75 µL of 20.0 mg/mL mouse, rat or human liver microsome; 0.4 µL of 0.2 M phosphate buffer, and 425 µL of ddH$_2$O. Negative control (without NADPH) tube contains 75 µL of 20.0 mg/mL mouse, rat or human liver microsome; 0.4 µL of 0.2 M phosphate buffer, and 525 µL of ddH$_2$O. The reaction is started by adding 1.0 µL of 10.0 mM tested compound. The reaction tubes are incubated at 37° C. 100 µL sample is collected into new Eppendorf tube containing 300 µL cold methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 10: Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37 C, or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

In one embodiment, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims. Various publications, patents and patent applications are cited herein, the disclosures of which are incorporated by reference in their entireties.

What is claimed is:

1. A compound of Formula (AB'):

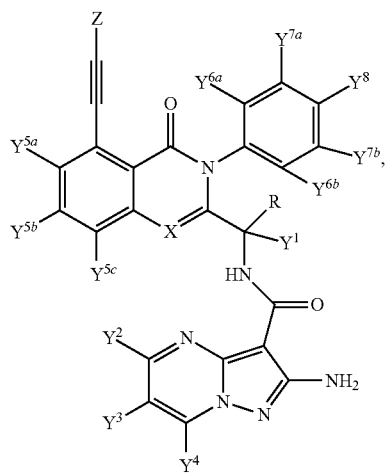

(AB')

or a pharmaceutically acceptable salt thereof, wherein

R is $C_1$-$C_3$ alkyl optionally substituted with one or more deuterium or halogen;

X is $CY^{5d}$ or N;

$Y^1$ is hydrogen or deuterium;

$Y^2$, $Y^3$, and $Y^4$ are each independently hydrogen or deuterium;

$Y^{5a}$, $Y^{5b}$, $Y^{5c}$, and $Y^{5d}$ are each independently hydrogen or deuterium;

$Y^{6a}$, $Y^{6b}$, $Y^{7a}$, $Y^{7b}$, and $Y^8$ are each independently hydrogen, deuterium, halogen, or $C_1$-$C_3$ alkyl, wherein each instance of the $C_1$-$C_3$ alkyl is independently optionally substituted with one or more deuterium or halogen;

Z is a pyrazolyl optionally substituted with one or more deuterium, halogen, or $C_1$-$C_3$ alkyl, wherein each instance of the $C_1$-$C_3$ alkyl is independently optionally substituted with one or more deuterium or halogen; and at least one of R, $Y^1$, $Y^2$, $Y^3$, $Y^4$, $Y^{5a}$, $Y^{5b}$, $Y^{5c}$, $Y^{5d}$, $Y^{6a}$, $Y^{6b}$, $Y^{7a}$, $Y^{7b}$, $Y^8$, and Z is or comprises a deuterium;

provided that, when $Y^{6a}$, $Y^{6b}$, $Y^{7a}$, $Y^{7b}$, and $Y^8$ are all deuterium, at least one of R, $Y^1$, $Y^2$, $Y^3$, $Y^4$, $Y^{5a}$, $Y^{5b}$, $Y^{5c}$, $Y^{5d}$, and Z is or comprises a deuterium.

2. The compound of claim 1, wherein the compound is a compound of Formula (AB), (A'), (A), (B'), or (B):

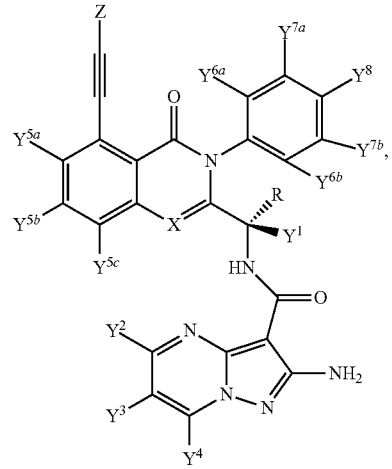

(AB)

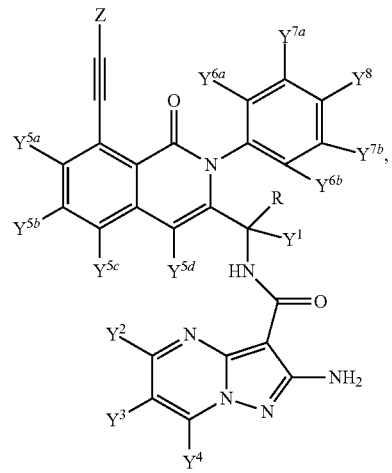

(A')

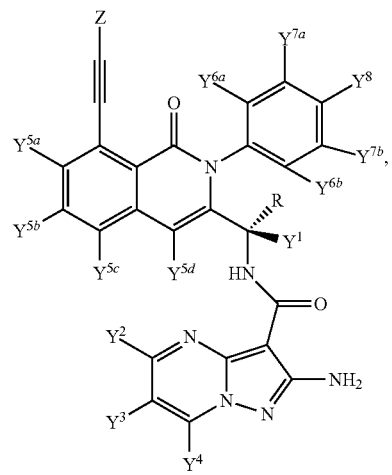

(A)

-continued

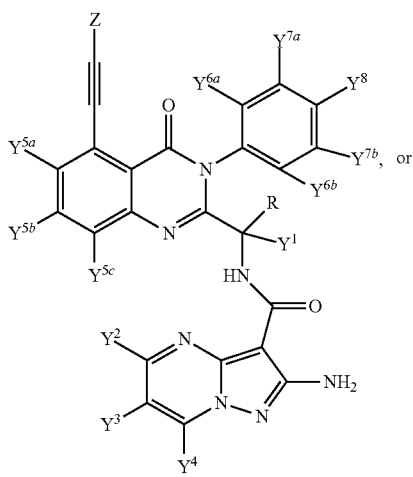
(B')

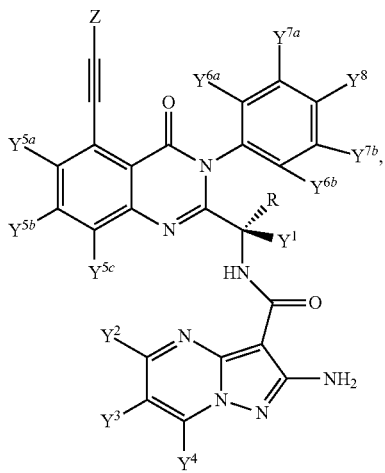
(B)

or a pharmaceutically acceptable salt thereof.

3. The compound of claim 1, wherein $Y^{5a}$ is deuterium; $Y^{5b}$ is deuterium; $Y^{5c}$ is deuterium; $Y^{5a}$, $Y^{5b}$, and $Y^{5c}$ are all hydrogen; or $Y^{5a}$, $Y^{5b}$, and $Y^{5c}$ are all deuterium.

4. The compound of claim 1, wherein $Y^{6a}$, $Y^{6b}$, $Y^{7a}$, $Y^{7b}$, and $Y^8$ are all hydrogen; $Y^{6a}$, $Y^{6b}$, $Y^{7a}$, $Y^{7b}$ and $Y^8$ are all deuterium; or one or more of $Y^{6a}$, $Y^{6b}$, $Y^{7a}$, $Y^{7b}$, and $Y^8$ are $C_1$-$C_3$ alkyl, wherein each instance of the $C_1$-$C_3$ alkyl is independently optionally substituted with one or more deuterium or halogen.

5. The compound of claim 1, wherein Z is a 4-pyrazolyl.

6. The compound of claim 1, wherein Z is substituted with one or more $C_1$-$C_3$ alkyl, wherein each instance of the $C_1$-$C_3$ alkyl is independently optionally substituted with one or more deuterium or halogen.

7. The compound of claim 6, wherein Z is substituted with one or two methyl, wherein each instance of the methyl is independently optionally substituted with one or more deuterium or halogen.

8. The compound of claim 1, wherein the compound is a compound of Formula (A-I), (A-II), (A-III), (B-I), (B-II), or (B-III):

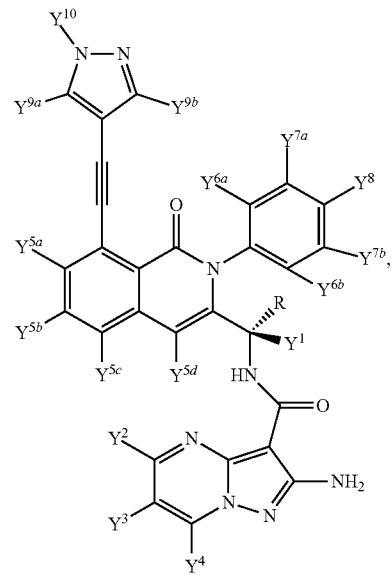
(A-I)

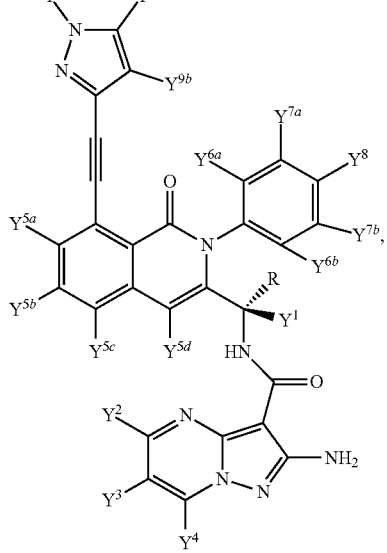
(A-II)

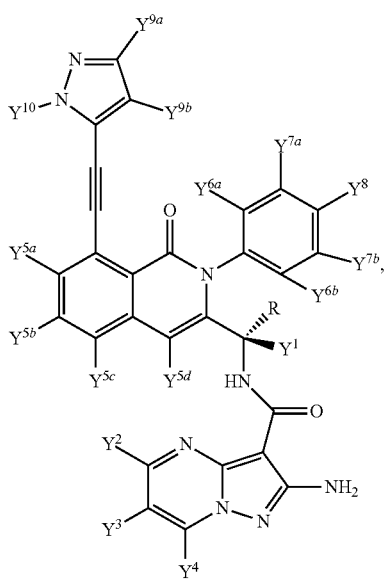

(A-III)

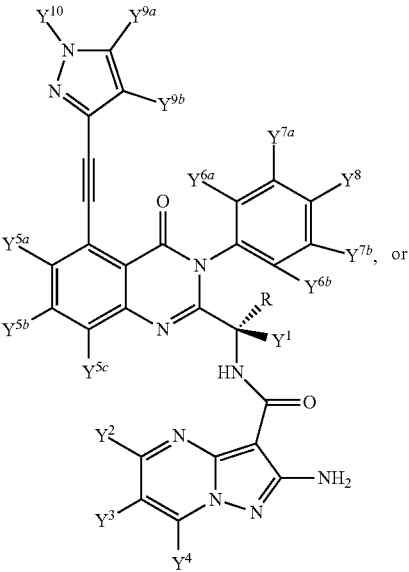

(B-II)

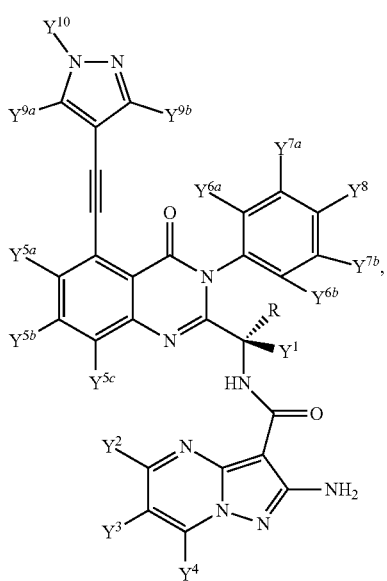

(B-I)

(B-III)

or a pharmaceutically acceptable salt thereof, wherein
$Y^{9a}$ and $Y^{9b}$ are each independently hydrogen, deuterium, or $C_1$-$C_3$ alkyl, wherein each instance of the $C_1$-$C_3$ alkyl is independently optionally substituted with one or more deuterium or halogen; and $Y^{10}$ is hydrogen or $C_1$-$C_3$ alkyl, wherein the $C_1$-$C_3$ alkyl itself is optionally substituted with one or more deuterium or halogen.

9. The compound of claim 8, wherein $Y^{9a}$ and $Y^{9b}$ are each independently hydrogen or deuterium; or $Y^{9a}$ and $Y^{9b}$ are both $C_1$-$C_3$ alkyl, wherein each instance of the $C_1$-$C_3$ alkyl is independently optionally substituted with one or more deuterium or halogen.

10. The compound of claim 8, wherein $Y^{10}$ is $C_1$-$C_3$ alkyl, wherein the $C_1$-$C_3$ alkyl itself is optionally substituted with one or more deuterium or halogen.

11. The compound of claim 10, wherein $Y^{10}$ is —$CD_3$.

12. The compound of claim 1, wherein R is $C_1$-$C_3$ alkyl optionally substituted with one or more deuterium.

13. The compound of claim 12, wherein R is —CD₃.
14. The compound of claim 1, wherein Y¹ is deuterium.
15. The compound of claim 1, wherein Y² is deuterium; Y³ is deuterium; Y⁴ is deuterium; Y², Y³, and Y⁴ are all hydrogen; or Y², Y³, and Y⁴ are all deuterium.
16. The compound of claim 1, wherein the compound is a compound of Formula (A-I-a), (A-I-b), (A-II-a), (B-I-a), (B-I-b), or (B-II-a):
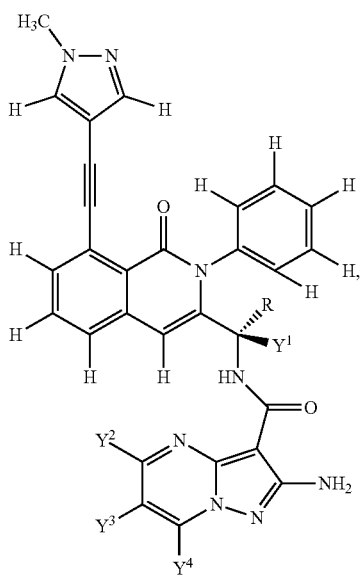
(A-I-a)
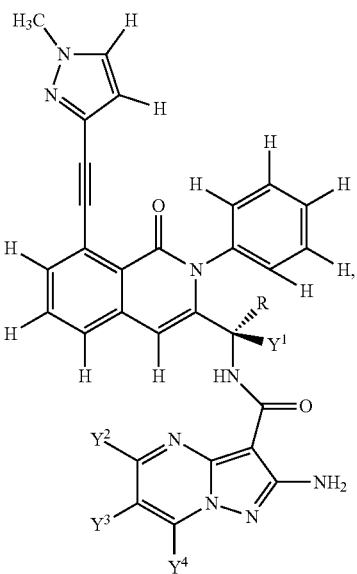
(A-II-a)
(A-I-b)
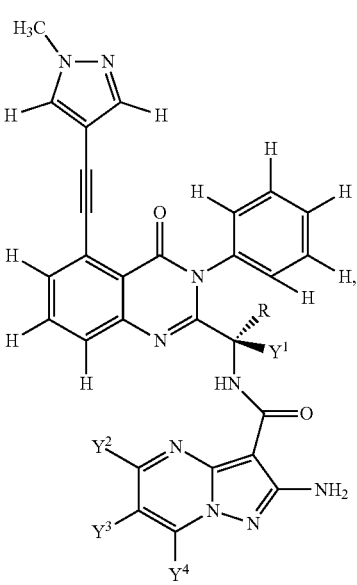
(B-I-a)

-continued (B-I-b)

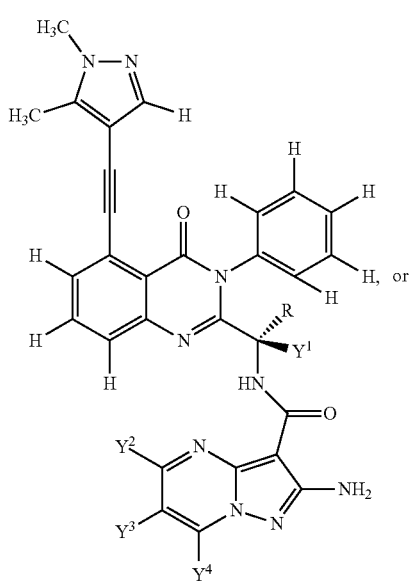

(B-II-a)

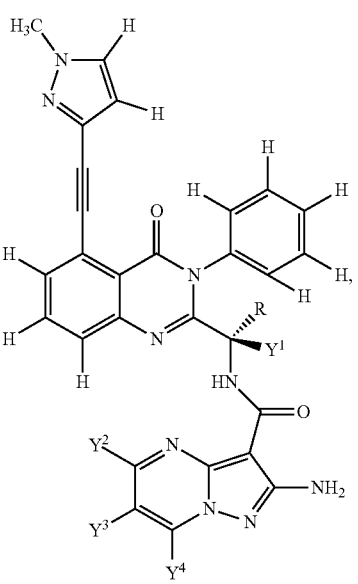

or a pharmaceutically acceptable salt thereof.

17. The compound of claim 1, which is selected from any one of the compounds in Tables 1 to 74, or a pharmaceutically acceptable salt thereof.

18. The compound of claim 8, wherein one of $Y^{9a}$ and $Y^{9b}$ is hydrogen or deuterium, and the other is $C_1$-$C_3$ alkyl, wherein the $C_1$-$C_3$ alkyl itself is optionally substituted with one or more deuterium or halogen.

19. The compound of claim 1, which is:

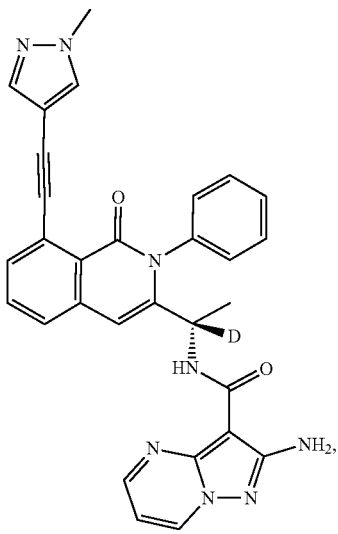 [SMILES: [2H][C@@](C)(NC(=O)c1c(N)nn2cccnc12)c1cc2cccc(C#Cc3cnn(C)c3)c2c(=O)n1-c1ccccc1]

or a pharmaceutically acceptable salt thereof.

20. The compound of claim 1, which is:

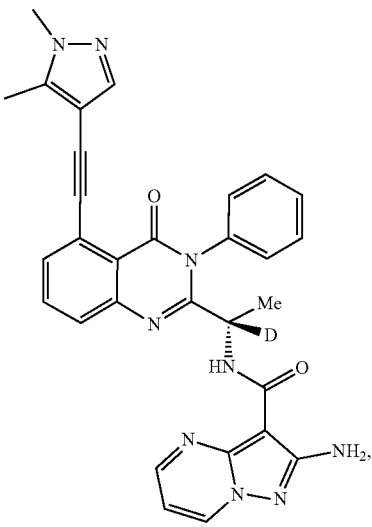 [SMILES: [2H][C@@](C)(NC(=O)c1c(N)nn2cccnc12)c1nc2cccc(C#Cc3cnn(C)c3C)c2c(=O)n1-c1ccccc1]

or a pharmaceutically acceptable salt thereof.

21. A pharmaceutical composition comprising a compound of claim 1, and a pharmaceutically acceptable excipient.

22. A method of inhibiting a PI3K in a subject, comprising administering a therapeutically effective amount of a compound of claim 1 to the subject.

* * * * *

UNITED STATES PATENT AND TRADEMARK OFFICE
CERTIFICATE OF CORRECTION

PATENT NO. : 10,759,806 B2
APPLICATION NO. : 16/085536
DATED : September 1, 2020
INVENTOR(S) : Evans Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 37 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*